(12) United States Patent
Dransfield et al.

(10) Patent No.: US 8,044,175 B2
(45) Date of Patent: Oct. 25, 2011

(54) PEPTIDES THAT SPECIFICALLY BIND HGF RECEPTOR (CMET) AND USES THEREOF

(75) Inventors: Daniel T. Dransfield, Hanson, MA (US); Aaron Sato, Richmond, CA (US); Robert Charles Ladner, Ijamsville, MD (US); Palaniappa Nanjappan, Princeton, NJ (US)

(73) Assignees: Dyax Corp., Cambridge, MA (US); Bracco Suisse SA, Manno (CH)

( * ) Notice: Subject to any disclaimer, the term of this patent is extended or adjusted under 35 U.S.C. 154(b) by 590 days.

(21) Appl. No.: 12/012,011

(22) Filed: Jan. 30, 2008

(65) Prior Publication Data

US 2010/0261875 A1    Oct. 14, 2010

Related U.S. Application Data

(62) Division of application No. 10/792,582, filed on Mar. 3, 2004, now abandoned.

(60) Provisional application No. 60/451,588, filed on Mar. 3, 2003.

(51) Int. Cl.
| A61K 38/00 | (2006.01) |
| A61K 38/02 | (2006.01) |
| C07K 7/08  | (2006.01) |
| C07K 1/00  | (2006.01) |
| A61K 51/00 | (2006.01) |

(52) U.S. Cl. ......... 530/326; 530/300; 530/333; 514/1.1; 424/1.69

(58) Field of Classification Search .................. None
See application file for complete search history.

(56) References Cited

U.S. PATENT DOCUMENTS

| 5,223,409 | A  | 6/1993  | Ladner et al.      |
| 5,316,921 | A  | 5/1994  | Godowski et al.    |
| 5,547,856 | A  | 8/1996  | Godowski et al.    |
| 5,686,292 | A  | 11/1997 | Schwall et al.     |
| 5,707,624 | A  | 1/1998  | Nickoloff et al.   |
| 5,766,860 | A  | 6/1998  | Terman et al.      |
| 5,769,080 | A  | 6/1998  | Unger et al.       |
| 5,773,024 | A  | 6/1998  | Unger et al.       |
| 5,871,959 | A  | 2/1999  | Rong et al.        |
| 5,876,973 | A  | 3/1999  | Marchionni         |
| 5,877,289 | A  | 3/1999  | Thorpe et al.      |
| 5,935,820 | A  | 8/1999  | Hu et al.          |
| 6,051,230 | A  | 4/2000  | Thorpe et al.      |
| 6,071,495 | A  | 6/2000  | Unger et al.       |
| 6,146,657 | A  | 11/2000 | Unger et al.       |
| 6,204,011 | B1 | 3/2001  | Kendall et al.     |
| 6,207,152 | B1 | 3/2001  | Schwall et al.     |
| 6,221,839 | B1 | 4/2001  | Alitalo et al.     |
| 6,245,530 | B1 | 6/2001  | Alitalo et al.     |
| 6,261,535 | B1 | 7/2001  | Thorpe et al.      |
| 6,261,537 | B1 | 7/2001  | Klaveness et al.   |
| 6,264,917 | B1 | 7/2001  | Klaveness et al.   |
| 6,331,289 | B1 | 12/2001 | Klaveness et al.   |
| 6,359,115 | B1 | 3/2002  | Kendall et al.     |
| 6,361,946 | B1 | 3/2002  | Alitalo et al.     |
| 6,403,088 | B1 | 6/2002  | Alitalo et al.     |
| 6,451,764 | B1 | 9/2002  | Lee et al.         |
| 6,521,211 | B1 | 2/2003  | Unger et al.       |
| 6,576,608 | B1 | 6/2003  | Lee et al.         |
| 6,645,933 | B1 | 11/2003 | Alitalo et al.     |
| 6,710,165 | B2 | 3/2004  | Lee et al.         |
| 7,199,100 | B2 | 4/2007  | Betz et al.        |
| 2002/0058619 | A1 | 5/2002 | Tchistiakova et al. |
| 2002/0065218 | A1 | 5/2002 | Achen et al.       |
| 2002/0068697 | A1 | 6/2002 | Tournaire et al.   |
| 2002/0086013 | A1 | 7/2002 | King               |
| 2002/0091082 | A1 | 7/2002 | Aiello             |
| 2002/0102260 | A1 | 8/2002 | Achen et al.       |
| 2002/0136721 | A1 | 9/2002 | Schwall et al.     |
| 2003/0082103 | A1 | 5/2003 | Wartchow et al.    |
| 2003/0091567 | A1 | 5/2003 | Alitalo et al.     |
| 2004/0018974 | A1 | 1/2004 | Arbogast et al.    |

FOREIGN PATENT DOCUMENTS

| EP | 0536350 A2   | 9/1992  |
| EP | 1166798 A1   | 1/2002  |
| EP | 1166799 A1   | 1/2002  |
| EP | 666868 B1    | 4/2002  |
| EP | 1238986 A2   | 9/2002  |
| EP | 1261370 A1   | 12/2002 |
| EP | 1268760 A1   | 1/2003  |
| EP | 1278771 A2   | 1/2003  |
| EP | 1292335 A2   | 3/2003  |
| EP | 848755 B1    | 6/2003  |
| EP | 1259248 A2   | 12/2004 |
| JP | 11-506327    | 6/1999  |
| JP | 2002-330772 A | 11/2002 |
| JP | 3398382 B2   | 4/2003  |
| WO | WO 94/10202 A1 | 5/1994 |
| WO | WO 96/38557 A2 | 12/1996 |
| WO | WO 96/40285 A1 | 12/1996 |
| WO | WO 97/17442 A1 | 5/1997 |
| WO | WO 98/18498 A2 | 5/1998 |
| WO | WO 98/18501 A2 | 5/1998 |
| WO | WO 98/47541 A1 | 10/1998 |

(Continued)

OTHER PUBLICATIONS

Bardelli et al., A peptide representing the carboxyl-terminal tail of the met receptor inhibits kinase activity and invasive growth. J Biol Chem. Oct. 8, 1999;274(41):29274-81.

Date et al., HGF/NK4 is a specific antagonist for pleiotrophic actions of hepatocyte growth factor. FEBS Lett. Dec. 22, 1997;420(1):1-6.

Hanessian et al., Synthesis of a Versatile Peptidomimetic Scaffold. Methods in Molecular Medicine 23: 161-174, 1999.

Hart et al., Cyclophilin Inhibition by a (Z)-Alkene cis-Proline Mimic. J Org Chem 64: 2998-2999, 1999.

Holmes et al., Site specific 1:1 opioid: albumin conjugate with in vitro activity and long in vivo duration. Bioconjug Chem 11: 439-444, 2000.

(Continued)

Primary Examiner — Maury Audet

(74) Attorney, Agent, or Firm — Wolf, Greenfield & Sacks, P.C.

(57) ABSTRACT

A polypeptide or multimeric polypeptide construct having the ability to bind to cMet or a complex comprising cMet and HGF, and methods for use are disclosed.

4 Claims, 24 Drawing Sheets

FOREIGN PATENT DOCUMENTS

| | | |
|---|---|---|
| WO | WO 99/29861 A1 | 6/1999 |
| WO | WO 99/40947 A2 | 8/1999 |
| WO | WO 99/58162 A2 | 11/1999 |
| WO | WO 00/27414 A2 | 5/2000 |
| WO | WO 00/45856 A2 | 8/2000 |
| WO | WO 01/16135 A2 | 3/2001 |
| WO | WO 01/42284 A2 | 6/2001 |
| WO | WO 01/54723 A1 | 8/2001 |
| WO | WO 01/62942 A2 | 8/2001 |
| WO | WO 01/64235 A1 | 8/2001 |
| WO | WO 01/70268 A1 | 9/2001 |
| WO | WO 01/70945 A1 | 9/2001 |
| WO | WO 01/82870 A2 | 11/2001 |
| WO | WO 01/83693 A2 | 11/2001 |
| WO | WO 01/97850 A2 | 12/2001 |
| WO | WO 02/07747 A1 | 1/2002 |
| WO | WO 02/28895 A2 | 4/2002 |
| WO | WO 02/057299 A2 | 7/2002 |
| WO | WO 02/060950 A2 | 8/2002 |
| WO | WO 02/083849 A2 | 10/2002 |
| WO | WO 03/000842 A2 | 1/2003 |
| WO | WO 03/000844 A2 | 1/2003 |
| WO | WO 03/028643 A2 | 4/2003 |
| WO | WO 03/094617 A2 | 11/2003 |

OTHER PUBLICATIONS

Parr et al., Hepatocyte growth factor activators, inhibitors and antagonists and their implication in cancer intervention. Histol Histopathol. Jan. 2001;16(1):251-68. Review.

Thomas et al., A peptide sequence on carcinoembryonic antigen binds to a 80kD protein on Kupffer cells. Biochem Biophys Res Commun 188: 671-677, 1992.

SEQUENCE LISTING

```
<160> NUMBER OF SEQ ID NOS: 619

<210> SEQ ID NO 1
<211> LENGTH: 16
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 1

Gly Ser Trp Ile Ile Cys Trp Trp Asp Asn Cys Gly Ser Ser Ala Pro
  1               5                  10                  15

<210> SEQ ID NO 2
<211> LENGTH: 16
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 2

Gly Ser Tyr Tyr Asp Cys Arg Glu Phe Gln Cys Asn Lys Pro Ala Pro
  1               5                  10                  15

<210> SEQ ID NO 3
<211> LENGTH: 16
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 3

Gly Ser Ser His Leu Cys Asn Pro Glu Phe Cys His Phe Thr Ala Pro
  1               5                  10                  15

<210> SEQ ID NO 4
<211> LENGTH: 16
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 4

Gly Ser Met Leu Met Cys Glu Leu Trp Trp Cys Arg Phe Leu Ala Pro
  1               5                  10                  15
```

```
<210> SEQ ID NO 5
<211> LENGTH: 16
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 5

Gly Ser Leu Ile Phe Cys Pro Tyr Gly Glu Cys Met Met Tyr Ala Pro
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 6

Gly Ser Glu Tyr Ser Cys Arg Thr Ser Arg Cys Ile Phe Ser Ala Pro
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 7

Gly Ser Phe Ile Leu Cys Trp Trp Thr Phe Cys Asp Thr Asn Ala Pro
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 8

Gly Ser Ser Thr Ile Cys Pro Gly Thr Ala Cys Val Asp His Ala Pro
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 9

Gly Ser Leu Ile Ile Cys Trp Trp Ser Trp Cys Asp Lys Gln Ala Pro
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 10
```

```
Gly Ser Phe Asn Ile Cys Pro Tyr Gln Trp Cys Thr Leu Trp Ala Pro
1               5                   10                  15

<210> SEQ ID NO 11
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 11

Ala Gly Gly Phe Ala Cys Gly Pro Pro Trp Asp Ile Cys Trp Met Phe
1               5                   10                  15

Gly Thr

<210> SEQ ID NO 12
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 12

Ala Gly Ala Trp Asn Cys Glu Tyr Pro Thr Phe Ile Cys Glu Trp Gln
1               5                   10                  15

Gly Ala

<210> SEQ ID NO 13
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 13

Ala Gly Asn Trp Ile Cys Asn Leu Ser Glu Met Arg Cys Tyr Pro Lys
1               5                   10                  15

Gly Thr

<210> SEQ ID NO 14
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 14

Ala Gly Asp Gly Trp Cys Met Ala Trp Pro Glu Ile Cys Glu Trp Leu
1               5                   10                  15

Gly Thr

<210> SEQ ID NO 15
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 15

Ala Gly Leu Tyr Leu Cys Asp Leu Ser Ile Met Tyr Cys Phe Phe Gln
```

```
                1               5                   10                  15

Gly Thr

<210> SEQ ID NO 16
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 16

Ala Gly Trp Trp Ser Cys Gln Trp Glu Leu Asn Val Cys Ile Trp Gln
1               5                   10                  15

Gly Thr

<210> SEQ ID NO 17
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 17

Ala Gly Tyr Tyr His Cys Ile Asp Asp Phe Pro Gln Cys Lys Trp Met
1               5                   10                  15

Gly Thr

<210> SEQ ID NO 18
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 18

Ala Gly Trp Phe Glu Cys Glu Phe Gly Phe Trp Gly Cys Asn Trp Leu
1               5                   10                  15

Gly Thr

<210> SEQ ID NO 19
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 19

Ala Gly Thr Val Tyr Cys Ser Trp Glu Ser Ser Glu Cys Trp Trp Val
1               5                   10                  15

Gly Thr

<210> SEQ ID NO 20
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 20

Ala Gly Val Trp Ile Cys Arg Val Trp Asp Asp Glu Cys Phe Phe Gln
```

```
                1               5                  10                  15

Gly Thr

<210> SEQ ID NO 21
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 21

Ala Gly Asp His Tyr Cys Trp Glu Glu Trp Trp Phe Cys Trp Asp Ser
  1               5                  10                  15

Gly Thr

<210> SEQ ID NO 22
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 22

Ala Gly Val Leu Gln Cys Ile Gly Phe Glu Trp Phe Cys Asp Ile Trp
  1               5                  10                  15

Gly Thr

<210> SEQ ID NO 23
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 23

Ala Gly Val Ile Val Cys Asn Leu Ser Met Met Tyr Cys Leu Tyr Pro
  1               5                  10                  15

Gly Thr

<210> SEQ ID NO 24
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 24

Ala Gly Tyr Pro Glu Cys Lys Asp Asn Tyr His Trp Cys Glu Trp Lys
  1               5                  10                  15

Gly Thr

<210> SEQ ID NO 25
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 25

Ala Gly Trp Thr Trp Cys Asp Leu Ser Met Met Ser Cys Ile Phe His
```

```
                1               5              10              15

Gly Thr

<210> SEQ ID NO 26
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 26

Ala Gly Val Thr Asn Cys Asn Leu Ser Thr Met Phe Cys Phe Leu His
 1               5                  10                  15

Gly Thr

<210> SEQ ID NO 27
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 27

Ala Gly Thr Leu Ser Cys Ser Glu Glu Tyr Lys Ser Cys Gln Leu Gln
 1               5                  10                  15

Gly Thr

<210> SEQ ID NO 28
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 28

Ala Gly Thr Ile Arg Cys Asn Leu Ala Met Met Val Cys Met Phe Glu
 1               5                  10                  15

Gly Thr

<210> SEQ ID NO 29
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 29

Ala Gly Gln Tyr Leu Cys Thr Gln Ala Ala Leu Gly Cys Pro Glu Trp
 1               5                  10                  15

Gly Thr

<210> SEQ ID NO 30
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 30

Ala Gly Gln Met Trp Cys Ala Glu Lys Asn Ser Lys Cys Tyr Gln Trp
```

```
                  1               5                  10                 15

Gly Thr

<210> SEQ ID NO 31
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 31

Ala Gly Gln Ala Val Cys Glu Trp Gly Pro Phe Trp Cys Gln Met Gln
  1               5                  10                 15

Gly Thr

<210> SEQ ID NO 32
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 32

Ala Gly Pro Tyr Ser Cys His Ser Glu Ser His Asp Cys Lys Leu Met
  1               5                  10                 15

Gly Thr

<210> SEQ ID NO 33
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 33

Ala Gly Pro Leu Phe Cys Phe Glu Trp Pro Ser Leu Cys His Trp Gly
  1               5                  10                 15

Gly Thr

<210> SEQ ID NO 34
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 34

Ala Gly Asn Leu Pro Cys His Trp Asn Met Ser Val Cys Asp His Gln
  1               5                  10                 15

Gly Thr

<210> SEQ ID NO 35
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 35

Ala Gly Met Asp Phe Cys Glu Gly Phe Trp Phe Leu Cys Ile Gly Asn
```

```
                    1               5              10              15
Ala Thr

<210> SEQ ID NO 36
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 36

Ala Gly Leu Leu Gly Cys Trp Asp Met Pro Met Glu Cys Thr Gly Glu
 1               5                  10                  15

Gly Thr

<210> SEQ ID NO 37
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 37

Ala Gly Lys Tyr Met Cys Glu Gly Phe Glu Trp Phe Cys Glu Met Trp
 1               5                  10                  15

Gly Thr

<210> SEQ ID NO 38
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 38

Ala Gly Lys Thr Val Cys Gln Lys Trp Glu Ser Val Cys Ser Gly Met
 1               5                  10                  15

Gly Thr

<210> SEQ ID NO 39
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 39

Ala Gly Lys Gln Trp Cys Val Val Trp Glu Glu Thr Cys Asp Gln Leu
 1               5                  10                  15

Gly Thr

<210> SEQ ID NO 40
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 40

Ala Gly Ile Trp Phe Cys Asn Asn Glu Glu Lys Ser Cys Trp Ala Tyr
```

```
                 1               5                  10                  15

Gly Thr

<210> SEQ ID NO 41
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 41

Ala Gly His Thr Ile Cys Gln His Lys Ala Leu Gly Cys Pro Ala Asn
 1               5                  10                  15

Gly Thr

<210> SEQ ID NO 42
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 42

Ala Gly His Phe Glu Cys Pro Lys His Gln Tyr Met Cys Asp Met Pro
 1               5                  10                  15

Gly Thr

<210> SEQ ID NO 43
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 43

Ala Gly Gly Asn Trp Cys Ser Phe Tyr Glu Glu Leu Cys Glu Trp Leu
 1               5                  10                  15

Gly Thr

<210> SEQ ID NO 44
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 44

Ala Gly Gly His Trp Cys Leu Glu Leu Lys His Leu Cys Pro Pro Tyr
 1               5                  10                  15

Gly Thr

<210> SEQ ID NO 45
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 45

Ala Gly Phe Trp Asp Cys Gly Trp Met Met Gln Asp Cys His Met His
```

```
<210> SEQ ID NO 46
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 46

Ala Asp Ala Trp Met Cys Glu Tyr Phe Gln Trp Asn Cys Gly Asp Lys
 1               5                  10                  15

Gly Thr

<210> SEQ ID NO 47
<211> LENGTH: 18
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 47

Gly Asp Gly Phe Leu Cys Arg Trp Glu Asn Gly Trp Cys Glu Phe Trp
 1               5                  10                  15

Asp Pro

<210> SEQ ID NO 48
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 48

Ala Gly Ser Ile Gln Cys Lys Gly Pro Pro Trp Phe Ser Cys Ala Met
 1               5                  10                  15

Tyr Gly Thr

<210> SEQ ID NO 49
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 49

Ala Gly Tyr Tyr Gly Cys Lys Gly Pro Pro Thr Phe Glu Cys Gln Trp
 1               5                  10                  15

Met Gly Thr

<210> SEQ ID NO 50
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 50

Ala Gly Gln Phe Lys Cys Ala Gly Pro Pro Ser Phe Ala Cys Trp Met
```

Thr Gly Thr

<210> SEQ ID NO 51
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 51

Ala Gly Trp Phe Gln Cys Lys Gly Pro Pro Ser Phe Glu Cys Glu Arg
1               5                   10                  15

His Gly Thr

<210> SEQ ID NO 52
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 52

Ala Gly Trp Thr His Cys Ile Gly Pro Pro Thr Phe Glu Cys Ile Pro
1               5                   10                  15

Met Gly Thr

<210> SEQ ID NO 53
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 53

Ala Gly Ser Phe Ala Cys Lys Gly Pro Pro Thr Phe Ala Cys Val Glu
1               5                   10                  15

Phe Gly Thr

<210> SEQ ID NO 54
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 54

Ala Gly Asn Tyr Phe Cys Ala Gly Ser Pro Ser Phe Ser Cys Tyr Phe
1               5                   10                  15

Met Gly Thr

<210> SEQ ID NO 55
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 55

Ala Gly Ser Trp His Cys Ala Gly Pro Pro Ser Phe Glu Cys Trp Glu

```
1               5                  10                 15

Phe Gly Thr

<210> SEQ ID NO 56
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 56

Ala Gly Trp Ile Ser Cys Ala Gly Pro Pro Thr Phe Ala Cys Trp Pro
1               5                  10                 15

Gly Gly Thr

<210> SEQ ID NO 57
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 57

Ala Gly Phe Val Asn Cys Lys Gly Pro Pro Thr Phe Glu Cys Ile Leu
1               5                  10                 15

Thr Gly Thr

<210> SEQ ID NO 58
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 58

Ala Gly Asp Trp Ile Cys His Gly Pro Pro Met Phe Glu Cys Glu Trp
1               5                  10                 15

Val Gly Thr

<210> SEQ ID NO 59
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 59

Ala Gly Tyr Thr Ser Cys Val Gly Pro Pro Ser Phe Glu Cys Thr Pro
1               5                  10                 15

Tyr Gly Thr

<210> SEQ ID NO 60
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 60

Ala Gly Tyr Phe Glu Cys Lys Gly Pro Pro Thr Phe Glu Cys Trp Leu
```

```
                 1               5                  10                  15
Ser Gly Thr

<210> SEQ ID NO 61
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 61

Ala Gly His Ala Trp Cys Ser Gly Pro Pro Arg Phe Glu Cys Trp Pro
 1               5                  10                  15
Pro Gly Thr

<210> SEQ ID NO 62
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 62

Ala Gly His Tyr Trp Cys Ala Gly Pro Pro Thr Phe Ile Cys Met Gly
 1               5                  10                  15
Pro Gly Thr

<210> SEQ ID NO 63
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 63

Ala Gly Glu Thr Thr Cys Leu Gly Trp Pro Thr Phe Val Cys Val Asp
 1               5                  10                  15
Tyr Gly Thr

<210> SEQ ID NO 64
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 64

Ala Gly His Gly Thr Cys Arg Gly Trp Pro Thr Phe Glu Cys Ile Tyr
 1               5                  10                  15
Phe Gly Thr

<210> SEQ ID NO 65
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 65

Ala Gly Asp Trp His Cys Gln Gly Pro Pro Ala Phe Met Cys Trp Met
```

```
                 1               5                  10                 15

Ile Gly Thr

<210> SEQ ID NO 66
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 66

Ala Gly Leu Pro Lys Cys Ser Gly Pro Pro Trp Phe Ser Cys Tyr Tyr
 1               5                  10                 15

Gly Gly Thr

<210> SEQ ID NO 67
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 67

Ala Gly Gly Trp Glu Cys Thr Gly Pro Pro Trp Phe Gln Cys Gly Tyr
 1               5                  10                 15

Tyr Gly Thr

<210> SEQ ID NO 68
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 68

Ala Gly Asp Ile Val Cys Thr Gly His Pro Tyr Phe Glu Cys Trp Ser
 1               5                  10                 15

Trp Gly Thr

<210> SEQ ID NO 69
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 69

Ala Gly Thr Trp His Cys Ala Gly Pro Pro Trp Phe Thr Cys Tyr Met
 1               5                  10                 15

Asp Gly Thr

<210> SEQ ID NO 70
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 70

Ala Gly Ser Trp Glu Cys Thr Gly Pro Pro Ser Phe His Cys Gln Trp
```

Tyr Gly Thr

```
<210> SEQ ID NO 71
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 71
```

Ala Gly His Trp Ile Cys Val Gly Pro Pro Thr Phe Ser Cys Gln Trp
 1               5                  10                  15

His Gly Thr

```
<210> SEQ ID NO 72
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 72
```

Ala Gly Glu Trp Trp Cys His Gly Pro Pro Glu Phe Leu Cys Tyr Trp
 1               5                  10                  15

Thr Gly Thr

```
<210> SEQ ID NO 73
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 73
```

Ala Gly Glu Thr Val Cys Tyr Trp Leu Asn Gly Trp Phe Cys Val Asp
 1               5                  10                  15

Asp Gly Thr

```
<210> SEQ ID NO 74
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 74
```

Ala Gly Ser Ile Gln Cys Val Gly Pro Pro Ser Phe Glu Cys Thr Pro
 1               5                  10                  15

Tyr Gly Thr

```
<210> SEQ ID NO 75
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 75
```

Ala Gly Tyr Ser Val Cys Lys Gly Tyr Pro Ser Phe Glu Cys Ala Phe

```
                   1               5                  10                  15
Phe Gly Thr

<210> SEQ ID NO 76
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 76

Ala Gly Val Asn Ser Cys Leu Gly Pro Pro Thr Phe Glu Cys Tyr Gln
1               5                   10                  15

Met Gly Thr

<210> SEQ ID NO 77
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 77

Ala Gly Tyr Trp His Cys Lys Gly Pro Pro His Phe Ala Cys Glu Phe
1               5                   10                  15

His Gly Thr

<210> SEQ ID NO 78
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 78

Ala Gly Asn Trp Ile Cys Thr Gly Pro Pro Ser Phe Gly Cys Trp Tyr
1               5                   10                  15

His Gly Thr

<210> SEQ ID NO 79
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 79

Ala Gly Tyr Trp Ser Cys Ala Gly Pro Pro Met Phe Met Cys Thr Trp
1               5                   10                  15

Gln Gly Thr

<210> SEQ ID NO 80
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 80

Ala Gly Tyr Trp Asp Cys Lys Gly Pro Pro His Phe Phe Cys Glu Trp
```

```
                1               5                  10                 15
His Gly Thr

<210> SEQ ID NO 81
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 81

Ala Gly Tyr Phe His Cys Ser Gly Ser Pro Trp Phe Gln Cys Asp Tyr
1               5                   10                  15

Tyr Gly Thr

<210> SEQ ID NO 82
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 82

Ala Gly Trp Tyr Asn Cys Ser Gly Glu Asn Phe Trp Asn Cys Lys Trp
1               5                   10                  15

Ile Gly Thr

<210> SEQ ID NO 83
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 83

Ala Gly Trp Ser Asp Cys Leu Gly Pro Pro Gln Phe Thr Cys Val His
1               5                   10                  15

Trp Gly Thr

<210> SEQ ID NO 84
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 84

Ala Gly Thr Met Tyr Cys Leu Gly Pro Pro Thr Phe Ile Cys Gln Gln
1               5                   10                  15

Tyr Gly Thr

<210> SEQ ID NO 85
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 85

Ala Gly Ser Tyr Trp Cys Ser Gly Pro Pro Thr Phe Met Cys Arg Tyr
```

```
                 1               5                  10                  15

Glu Gly Thr

<210> SEQ ID NO 86
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 86

Ala Gly Ser Thr Asp Cys Arg Gly His Pro Thr Phe Glu Cys Trp Gly
 1               5                  10                  15

Trp Gly Thr

<210> SEQ ID NO 87
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 87

Ala Gly Ser Ser Pro Cys Lys Gly Trp Pro Thr Phe Glu Cys Tyr Phe
 1               5                  10                  15

Tyr Gly Thr

<210> SEQ ID NO 88
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 88

Ala Gly Ser Ile Ala Cys Thr Gly Trp Pro Tyr Phe Ser Cys Ile Asp
 1               5                  10                  15

Leu Gly Thr

<210> SEQ ID NO 89
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 89

Ala Gly Gln Phe Tyr Cys Ser Gly Pro Pro Thr Phe Gln Cys Ile Met
 1               5                  10                  15

Ile Gly Thr

<210> SEQ ID NO 90
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 90

Ala Gly Pro Trp Lys Cys Thr Gly Pro Pro Thr Phe Ser Cys Ile Gln
```

Phe Gly Thr

<210> SEQ ID NO 91
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 91

Ala Gly Asn Tyr Trp Cys Ser Gly Pro Pro Ser Phe Ile Cys His Ala
1               5                   10                  15

Val Gly Thr

<210> SEQ ID NO 92
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 92

Ala Gly Met Thr Leu Cys Ala Gly Pro Pro Thr Phe Glu Cys Tyr Glu
1               5                   10                  15

Val Gly Thr

<210> SEQ ID NO 93
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 93

Ala Gly Glu Thr Lys Cys Ser Gly Pro Pro Tyr Phe Tyr Cys Trp Met
1               5                   10                  15

Glu Gly Thr

<210> SEQ ID NO 94
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 94

Ala Gly Glu Thr Phe Cys Val Gly Asn Pro Ser Phe Glu Cys Trp Ser
1               5                   10                  15

Trp Gly Thr

<210> SEQ ID NO 95
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 95

Ala Gly Glu Thr Phe Cys Ser Gly Trp Pro Thr Phe Glu Cys Met Gln

```
                 1               5                   10                  15
Trp Gly Thr

<210> SEQ ID NO 96
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 96

Ala Gly Glu Ile Phe Cys Val Gly Pro Pro Thr Phe Thr Cys Met Trp
 1               5                   10                  15
Thr Gly Thr

<210> SEQ ID NO 97
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 97

Ala Gly Asp Phe Ile Cys Gln Gly Pro Pro Ser Phe Val Cys Thr Asn
 1               5                   10                  15
Ile Gly Thr

<210> SEQ ID NO 98
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 98

Ala Gly Ala Phe Phe Cys Ser Gly Pro Pro Thr Phe Met Cys Ser Leu
 1               5                   10                  15
Tyr Gly Thr

<210> SEQ ID NO 99
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 99

Ala Gly Trp Gly Trp Cys Ser Gly Pro Pro Met Phe Met Cys Thr Glu
 1               5                   10                  15
Tyr Gly Thr

<210> SEQ ID NO 100
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 100

Gly Ser Glu Phe Glu Cys Thr Gly Trp Pro Glu Phe Arg Cys Tyr Glu
```

Tyr Ala Pro

<210> SEQ ID NO 101
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 101

Gly Ser Ile Leu Tyr Cys Ile Asn Arg Asn Asp Pro Gln Cys Pro Tyr
1               5                   10                  15

Thr Ala Pro

<210> SEQ ID NO 102
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 102

Ser Glu Thr Arg Pro Thr Glu Ala Gly Asp Leu Ile Cys Ser Gly Pro
1               5                   10                  15

Pro Thr Phe Ile Cys Thr Leu Tyr His Thr Glu Pro Thr Glu
            20                  25                  30

<210> SEQ ID NO 103
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 103

Ser Glu Thr Arg Pro Thr Gln Ala Val Arg Ser Gln Cys Ser Gly Pro
1               5                   10                  15

Pro Thr Phe Glu Cys Trp Tyr Phe Gly Thr Glu Pro Thr Glu
            20                  25                  30

<210> SEQ ID NO 104
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 104

Ser Glu Thr Arg Pro Thr Glu Gly Gly Ser Trp Tyr Cys Ser Gly Pro
1               5                   10                  15

Pro Ala Phe Glu Cys Trp Trp Tyr Gly Thr Glu Pro Thr Glu
            20                  25                  30

<210> SEQ ID NO 105
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

```
<400> SEQUENCE: 105

Ser Glu Thr Arg Pro Thr Val Ala Ser Arg Trp His Cys Asn Gly Pro
1               5                   10                  15

Pro Thr Phe Glu Cys Trp Arg Tyr Gly Thr Glu Pro Thr Glu
            20                  25                  30

<210> SEQ ID NO 106
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 106

Ser Glu Thr Arg Pro Thr Glu Ala Gly Thr Phe His Cys Ser Gly Pro
1               5                   10                  15

Pro Thr Phe Glu Cys Trp Ser Tyr Gly Pro Lys Pro Thr Glu
            20                  25                  30

<210> SEQ ID NO 107
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 107

Ser Glu Thr Arg Pro Thr Glu Ala Gly Ser Leu Trp Cys Met Gly Pro
1               5                   10                  15

Pro Trp Phe Cys Cys Val Ile Tyr Gly Thr Gln Pro Thr Glu
            20                  25                  30

<210> SEQ ID NO 108
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 108

Ser Glu Thr Arg Pro Thr Glu Ala Gly Ile Leu His Cys Ser Gly Pro
1               5                   10                  15

Pro Thr Phe Glu Cys Trp Trp Asn Tyr Thr Glu Pro Thr Glu
            20                  25                  30

<210> SEQ ID NO 109
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 109

Ser Glu Thr Arg Pro Thr Glu Ser Gly Arg Val His Cys Pro Gly Pro
1               5                   10                  15

Pro Trp Phe Arg Cys Ala Arg Asn Gly Thr Glu Pro Thr Glu
            20                  25                  30

<210> SEQ ID NO 110
<211> LENGTH: 30
<212> TYPE: PRT
```

-continued

```
<213> ORGANISM: Artificial Sequence
<220> FEATURE:
<223> OTHER INFORMATION: Synthetically generated cMet-binding peptide
      sequence

<400> SEQUENCE: 110

Ser Glu Thr Arg Pro Thr Ala Ala Gly Arg Ile Leu Cys Thr Gly Pro
1               5                   10                  15

Pro Trp Phe Ser Cys Ala Met Tyr Gly Thr Glu Pro Thr Glu
            20                  25                  30

<210> SEQ ID NO 111
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 111

Ser Glu Thr Arg Pro Thr Glu Ala Ala Asp Trp Leu Cys Ser Gly Pro
1               5                   10                  15

Pro Thr Phe Glu Cys Trp Trp Phe Gly Thr Glu Pro Thr Glu
            20                  25                  30

<210> SEQ ID NO 112
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 112

Ser Glu Thr Arg Pro Thr Gln Val Gly Arg Trp Gln Cys Asp Gly Pro
1               5                   10                  15

Pro Thr Phe Ala Cys Arg Ser Tyr Gly Thr Glu Pro Thr Glu
            20                  25                  30

<210> SEQ ID NO 113
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 113

Ser Glu Thr Arg Pro Thr Glu Ala Gly Ser Thr Lys Cys Ser Gly Pro
1               5                   10                  15

Pro Thr Phe Glu Cys Trp Trp Phe Asp Thr Glu Pro Thr Glu
            20                  25                  30

<210> SEQ ID NO 114
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 114

Ser Glu Thr Arg Pro Thr Val Ala Gly Ser Trp His Cys Ser Gly Pro
1               5                   10                  15

Pro Thr Phe Glu Cys Trp Trp Tyr Gly Thr Glu Pro Thr Glu
            20                  25                  30
```

<210> SEQ ID NO 115
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 115

Ser Glu Thr Arg Pro Thr Glu Ala Gly Arg Asn His Cys Lys Gly Pro
1               5                   10                  15

Pro Gly Phe Arg Cys Ala Met Thr Asp Thr Glu Pro Thr Glu
            20                  25                  30

<210> SEQ ID NO 116
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 116

Ser Glu Thr Arg Pro Thr Glu Thr Asp Phe Val Tyr Cys Arg Gly Pro
1               5                   10                  15

Pro Thr Phe Glu Cys Trp Trp Tyr Gly Thr Gly Pro Thr Glu
            20                  25                  30

<210> SEQ ID NO 117
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 117

Ser Glu Thr Arg Pro Thr Ser Ser Gly Ser Arg His Cys Lys Gly Pro
1               5                   10                  15

Pro Thr Phe Glu Cys Trp Gly Tyr Gly Thr Glu Pro Thr Glu
            20                  25                  30

<210> SEQ ID NO 118
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 118

Ser Glu Thr Arg Pro Thr Glu Ala Gly Ser Trp Arg Cys Ser Gly Pro
1               5                   10                  15

Pro Thr Phe Glu Cys Trp Trp Tyr Glu Thr Ser Pro Thr Glu
            20                  25                  30

<210> SEQ ID NO 119
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 119

```
Ser Glu Thr Arg Pro Thr Asp Ala Ile Arg Ser Tyr Cys Ser Gly Pro
1               5                   10                  15

Pro Thr Phe Glu Cys Trp Trp Phe Gly Thr Glu Pro Thr Glu
            20                  25                  30

<210> SEQ ID NO 120
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 120

Ser Glu Thr Arg Pro Thr Glu Ala Gly Ser Trp Asn Cys Ser Gly Pro
1               5                   10                  15

Pro Ala Phe Glu Cys Trp Trp Tyr Gly Ser Glu Pro Thr Glu
            20                  25                  30

<210> SEQ ID NO 121
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 121

Ser Glu Thr Arg Pro Thr Glu Ala Gly Ser Trp Gln Cys Ser Gly Pro
1               5                   10                  15

Pro Thr Phe Glu Cys Trp Ser Phe Gly Thr Glu Pro Thr Glu
            20                  25                  30

<210> SEQ ID NO 122
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 122

Ser Glu Thr Arg Pro Thr Glu Ala Gly Ser Trp His Cys Asn Gly Pro
1               5                   10                  15

Pro Thr Phe Glu Cys Trp Trp Tyr Asp Met Glu Pro Thr Glu
            20                  25                  30

<210> SEQ ID NO 123
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 123

Ser Glu Thr Arg Pro Thr Glu Ala Gly Arg Val Ser Cys Leu Gly Pro
1               5                   10                  15

Pro Thr Phe Glu Cys Trp Trp Phe Val Pro Glu Pro Thr Glu
            20                  25                  30

<210> SEQ ID NO 124
<211> LENGTH: 30
<212> TYPE: PRT
<213> ORGANISM: Artificial Sequence
<220> FEATURE:
```

<223> OTHER INFORMATION: Synthetically generated cMet-binding peptide
      sequence

<400> SEQUENCE: 124

Ser Glu Thr Arg Pro Thr Asp Ala Gly Ser Trp Arg Cys Ala Gly Pro
1               5                   10                  15

Pro Thr Phe Glu Cys Trp Trp Phe Gly Thr Glu Pro Thr Glu
            20                  25                  30

<210> SEQ ID NO 125
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 125

Ser Glu Thr Arg Pro Thr Glu Pro Val Thr Trp Gln Cys Thr Gly Pro
1               5                   10                  15

Pro Thr Phe Glu Cys Trp Trp Leu Gly Thr Glu Pro Thr Glu
            20                  25                  30

<210> SEQ ID NO 126
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 126

Ser Glu Thr Arg Pro Thr Asp Ala Val Ser Thr His Cys Asn Gly Pro
1               5                   10                  15

Pro Thr Phe Glu Cys Tyr Ile Tyr Gly Thr Glu Pro Thr Glu
            20                  25                  30

<210> SEQ ID NO 127
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 127

Ser Glu Thr Arg Pro Thr Val Ala Glu Ser Trp Tyr Cys Val Gly Pro
1               5                   10                  15

Pro Ser Phe Glu Cys Trp Trp Tyr Gly Thr Glu Pro Thr Glu
            20                  25                  30

<210> SEQ ID NO 128
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 128

Ser Glu Thr Arg Pro Thr Glu Ala Gly Ser Trp Asn Cys Ser Gly Pro
1               5                   10                  15

Pro Thr Phe Glu Cys Trp Ser Tyr Gln Thr Glu Pro Thr Glu
            20                  25                  30

```
<210> SEQ ID NO 129
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 129

Ser Glu Thr Arg Pro Thr Glu Ala Gly Ser Gly His Cys Asn Gly Pro
1               5                   10                  15

Pro Thr Phe Lys Cys Trp Trp Tyr Asp Met Glu Pro Thr Glu
            20                  25                  30

<210> SEQ ID NO 130
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 130

Ser Glu Thr Arg Pro Thr Asp Gln Asp Ser Trp Gln Cys Ser Gly Pro
1               5                   10                  15

Pro Thr Phe Glu Cys Trp Trp Tyr Gly Thr Glu Pro Thr Glu
            20                  25                  30

<210> SEQ ID NO 131
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 131

Ser Glu Thr Arg Pro Thr Glu Ser Thr Gln Val Gln Cys Ala Gly Pro
1               5                   10                  15

Pro Ser Phe Ala Cys Trp Met Thr Gly Thr Glu Pro Thr Glu
            20                  25                  30

<210> SEQ ID NO 132
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 132

Ser Glu Thr Arg Pro Thr Glu Val Glu Ser Trp His Cys Ser Gly Pro
1               5                   10                  15

Pro Thr Phe Glu Cys Trp Trp Tyr Gly Thr Glu Pro Thr Glu
            20                  25                  30

<210> SEQ ID NO 133
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 133

Ser Glu Thr Arg Pro Thr Glu Ala Gly Ser Phe His Cys Ser Gly Pro
1               5                   10                  15
```

```
Pro Thr Phe Glu Cys Trp Leu Tyr Trp Thr Asp Pro Thr Glu
            20                  25                  30

<210> SEQ ID NO 134
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 134

Ser Glu Thr Arg Pro Thr Glu Ala Gly Gln Phe Gly Cys Lys Gly Pro
1               5                   10                  15

Pro Pro Phe Glu Cys Lys Leu Met Gly Arg Val Pro Thr Glu
            20                  25                  30

<210> SEQ ID NO 135
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 135

Ser Glu Thr Arg Pro Thr Asp Thr Val Thr Trp His Cys Asn Gly Pro
1               5                   10                  15

Pro Thr Phe Glu Cys Trp Trp Tyr Gly Thr Glu Pro Thr Glu
            20                  25                  30

<210> SEQ ID NO 136
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 136

Ser Glu Thr Arg Pro Thr Glu Ala Asp Arg Trp His Cys Asp Gly Pro
1               5                   10                  15

Pro Thr Phe Glu Cys Trp Trp Tyr Gly Thr Glu Pro Thr Glu
            20                  25                  30

<210> SEQ ID NO 137
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 137

Ser Glu Thr Arg Pro Thr Glu Ala Gly Ser Ile Gln Cys Val Gly Pro
1               5                   10                  15

Pro Trp Phe Ser Cys Arg Met Tyr Val Thr Glu Pro Thr Glu
            20                  25                  30

<210> SEQ ID NO 138
<211> LENGTH: 30
<212> TYPE: PRT
<213> ORGANISM: Artificial Sequence
<220> FEATURE:
<223> OTHER INFORMATION: Synthetically generated cMet-binding peptide
      sequence
```

<400> SEQUENCE: 138

Ser Glu Thr Arg Pro Thr Val Ser Gly Ser Trp Gln Cys Val Gly Pro
1               5                   10                  15

Pro Thr Phe Glu Cys Trp Ser Tyr Gly Thr Glu Pro Thr Glu
            20                  25                  30

<210> SEQ ID NO 139
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 139

Ser Glu Thr Arg Pro Thr Glu Asn Gly Ser Trp His Cys Asn Gly Pro
1               5                   10                  15

Pro Thr Phe Glu Cys Trp Trp Tyr Gly Thr Glu Pro Thr Glu
            20                  25                  30

<210> SEQ ID NO 140
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 140

Ser Glu Thr Arg Pro Thr Glu Ala Gly Ser Trp His Cys Ser Gly Pro
1               5                   10                  15

Pro Ile Phe Glu Cys Trp Trp Tyr Asp Met Glu Pro Thr Glu
            20                  25                  30

<210> SEQ ID NO 141
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 141

Ser Glu Thr Arg Pro Thr Val Asp Gly Gly Trp His Cys Asn Gly Pro
1               5                   10                  15

Pro Thr Phe Glu Cys Trp Met Tyr Gly Thr Glu Pro Thr Glu
            20                  25                  30

<210> SEQ ID NO 142
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 142

Ser Glu Thr Arg Pro Thr Asp Ala Gly Thr Trp Asn Cys Thr Gly Pro
1               5                   10                  15

Pro Ser Phe Glu Cys Trp Trp Phe Gly Thr Glu Pro Thr Glu
            20                  25                  30

<210> SEQ ID NO 143
<211> LENGTH: 30

```
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 143

Ser Glu Thr Arg Pro Thr Trp Asp Gly Lys Trp His Cys Ser Gly Pro
1               5                   10                  15

Pro Thr Phe Glu Cys Trp Trp Tyr Gly Thr Glu Pro Thr Glu
            20                  25                  30

<210> SEQ ID NO 144
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 144

Ser Glu Thr Arg Pro Thr Glu Ala Gly Ser Trp Arg Cys Ser Gly Pro
1               5                   10                  15

Pro Thr Phe Glu Cys Trp Trp Tyr Tyr Thr Glu Pro Thr Glu
            20                  25                  30

<210> SEQ ID NO 145
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 145

Ser Glu Thr Arg Pro Thr Glu Ala Gly Asn Trp Leu Cys Ser Gly Pro
1               5                   10                  15

Pro Thr Phe Glu Cys Trp Trp Tyr Val Thr Gly Pro Thr Glu
            20                  25                  30

<210> SEQ ID NO 146
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 146

Ser Glu Thr Arg Pro Thr Glu Gly Gly Asn Trp His Cys Ser Gly Pro
1               5                   10                  15

Pro Thr Phe Glu Cys Trp Leu Tyr Gly Thr Glu Pro Thr Glu
            20                  25                  30

<210> SEQ ID NO 147
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 147

Ser Glu Thr Arg Pro Thr Glu Ala Gly Gly Trp His Cys Ser Gly Pro
1               5                   10                  15

Pro Thr Phe Glu Cys Trp Trp Phe Asn Met Glu Pro Thr Glu
```

<210> SEQ ID NO 148
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 148

Ser Glu Thr Arg Pro Thr Glu Val Ile Ser Trp His Cys Ser Gly Pro
1               5                   10                  15

Pro Thr Phe Glu Cys Tyr Arg Tyr Gly Thr Glu Pro Thr Glu
            20                  25                  30

<210> SEQ ID NO 149
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 149

Ser Glu Thr Arg Pro Thr Glu Val Gly Ser Trp His Cys Asn Gly Pro
1               5                   10                  15

Pro Thr Phe Glu Cys Trp Trp Tyr Gly Thr Glu Pro Thr Glu
            20                  25                  30

<210> SEQ ID NO 150
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 150

Ser Glu Thr Arg Pro Thr Leu Ala Ser Thr Trp Tyr Cys Ser Gly Pro
1               5                   10                  15

Pro Thr Phe Glu Cys Trp Trp Tyr Gly Thr Glu Pro Thr Glu
            20                  25                  30

<210> SEQ ID NO 151
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 151

Ser Glu Thr Arg Pro Thr Glu Ala Gly Gly Trp Tyr Cys Lys Gly Pro
1               5                   10                  15

Pro Thr Phe Glu Cys Trp Trp Asp Gly Thr Glu Pro Thr Glu
            20                  25                  30

<210> SEQ ID NO 152
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 152

```
Ser Glu Thr Arg Pro Thr Glu Ala Gly Gly Trp Phe Cys Ser Gly Pro
1               5                   10                  15

Pro Thr Phe Glu Cys Trp Trp Tyr Asp Thr Val Pro Thr Glu
            20                  25                  30

<210> SEQ ID NO 153
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 153

Ser Glu Thr Arg Pro Thr Glu Ala Ala Thr Trp Gln Cys Ser Gly Pro
1               5                   10                  15

Pro Thr Phe Glu Cys Trp Gly Tyr Gly Thr Glu Pro Thr Glu
            20                  25                  30

<210> SEQ ID NO 154
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 154

Ser Glu Thr Arg Pro Thr Glu Ala Gly Asp Tyr Val Cys Val Gly Pro
1               5                   10                  15

Pro Thr Phe Glu Cys Tyr Leu Met Asp Ala Glu Pro Thr Glu
            20                  25                  30

<210> SEQ ID NO 155
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 155

Ser Glu Thr Arg Pro Thr Glu Ala Gly Gly Trp Tyr Cys Ser Gly Pro
1               5                   10                  15

Pro Ser Phe Glu Cys Trp Ser Tyr Gly Thr Glu Pro Thr Glu
            20                  25                  30

<210> SEQ ID NO 156
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 156

Ser Glu Thr Arg Pro Thr Glu Ser Ser Trp His Cys Ser Gly Pro
1               5                   10                  15

Pro Thr Phe Glu Cys Trp Arg Phe Gly Thr Glu Pro Thr Glu
            20                  25                  30

<210> SEQ ID NO 157
<211> LENGTH: 30
<212> TYPE: PRT
<213> ORGANISM: Artificial Sequence
```

```
<220> FEATURE:
<223> OTHER INFORMATION: Synthetically generated cMet-binding peptide
      sequence

<400> SEQUENCE: 157

Ser Glu Thr Arg Pro Thr Glu Ala Gly Ser Trp Tyr Cys Ser Gly Pro
1               5                   10                  15

Pro Thr Phe Glu Cys Trp Trp Tyr Tyr Ala Glu Pro Thr Glu
            20                  25                  30

<210> SEQ ID NO 158
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 158

Ser Glu Thr Arg Pro Thr Leu Ala Gly Asn Trp Gln Cys Ser Gly Pro
1               5                   10                  15

Pro Thr Phe Glu Cys Trp Trp Tyr Gly Thr Glu Pro Thr Glu
            20                  25                  30

<210> SEQ ID NO 159
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 159

Ser Glu Thr Arg Pro Thr Glu Ala Gly Ser Trp His Cys Asn Gly Pro
1               5                   10                  15

Pro Thr Phe Glu Cys Trp Gln Tyr Gly Thr Glu Pro Thr Glu
            20                  25                  30

<210> SEQ ID NO 160
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 160

Ser Glu Thr Arg Pro Thr Glu Ala Gly Ser Trp Glu Cys His Gly Pro
1               5                   10                  15

Pro Ser Phe Glu Cys Trp Trp Tyr Gly Thr Glu Pro Thr Glu
            20                  25                  30

<210> SEQ ID NO 161
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 161

Ser Glu Thr Arg Pro Thr Glu Ala Gly Ser Trp Arg Cys Ser Gly Pro
1               5                   10                  15

Pro Thr Phe Glu Cys Trp Trp Tyr Asp Ala Glu Pro Thr Glu
            20                  25                  30
```

<210> SEQ ID NO 162
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 162

Ser Glu Thr Arg Pro Thr Glu Ala Gly Ser Trp Asn Cys Ala Gly Pro
1               5                   10                  15

Pro Thr Phe Glu Cys Trp Trp Tyr Gly Thr Glu Pro Thr Glu
            20                  25                  30

<210> SEQ ID NO 163
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 163

Ser Glu Thr Arg Pro Thr Glu Ala Gly Ser Phe Tyr Cys Ser Gly Pro
1               5                   10                  15

Pro Thr Phe Glu Cys Trp Gln Tyr Val Pro Glu Pro Thr Glu
            20                  25                  30

<210> SEQ ID NO 164
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 164

Ser Glu Thr Arg Pro Thr Glu Ala Gly Ser Trp Met Cys Ser Gly Pro
1               5                   10                  15

Pro Thr Phe Glu Cys Trp Gln Tyr Phe Thr Glu Pro Thr Glu
            20                  25                  30

<210> SEQ ID NO 165
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 165

Ser Glu Thr Arg Pro Thr Glu Ala Gly Ser Leu His Cys Ser Gly Pro
1               5                   10                  15

Pro Thr Phe Glu Cys Trp Trp Trp Glu Thr Glu Pro Thr Glu
            20                  25                  30

<210> SEQ ID NO 166
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 166

Ser Glu Thr Arg Pro Thr Glu Glu Gly Val Trp His Cys Asn Gly Pro

```
                1               5                  10                  15
Pro Thr Phe Glu Cys Trp Trp Tyr Gly Thr Glu Pro Thr Glu
                20                  25                  30

<210> SEQ ID NO 167
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 167

Ser Glu Thr Arg Pro Thr Glu Ala Gly Arg Trp Asn Cys Ser Gly Pro
1               5                   10                  15
Pro Thr Phe Glu Cys Trp Trp Tyr Ser Thr Glu Pro Thr Glu
                20                  25                  30

<210> SEQ ID NO 168
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 168

Ser Glu Thr Arg Pro Thr Glu Ala Gly Ser Trp Arg Cys Ser Gly Pro
1               5                   10                  15
Pro Thr Phe Glu Cys Trp Trp Phe Gly Thr Glu Pro Thr Glu
                20                  25                  30

<210> SEQ ID NO 169
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 169

Ser Glu Thr Arg Pro Thr Gln Ala Val Ser Ser Tyr Cys Ser Gly Pro
1               5                   10                  15
Pro Thr Phe Glu Cys Trp Ser Phe Gly Thr Glu Pro Thr Glu
                20                  25                  30

<210> SEQ ID NO 170
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 170

Ser Glu Thr Arg Pro Thr Glu Ala Gly Arg Ser Tyr Cys Ser Gly Pro
1               5                   10                  15
Pro Thr Phe Glu Cys Trp Trp Tyr Ala Thr Glu Pro Thr Glu
                20                  25                  30

<210> SEQ ID NO 171
<211> LENGTH: 30
<212> TYPE: PRT
<213> ORGANISM: Artificial Sequence
<220> FEATURE:
<223> OTHER INFORMATION: Synthetically generated cMet-binding peptide
```

-continued

<400> SEQUENCE: 171

Ser Glu Thr Arg Pro Thr Val Val Ala Lys Val His Cys Ala Gly Pro
1               5                   10                  15

Pro Thr Phe Glu Cys Trp Thr Tyr Gly Thr Glu Pro Thr Glu
            20                  25                  30

<210> SEQ ID NO 172
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 172

Ser Glu Thr Arg Pro Thr Glu Pro Gly Ser Trp His Cys Ser Gly Pro
1               5                   10                  15

Pro Thr Phe Val Cys Trp Trp Trp Gly Thr Glu Pro Thr Glu
            20                  25                  30

<210> SEQ ID NO 173
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 173

Ser Glu Thr Arg Pro Thr Glu Ala Gly Arg Trp His Cys Ser Gly Pro
1               5                   10                  15

Pro Thr Phe Glu Cys Trp Trp His Asp Thr Glu Pro Thr Glu
            20                  25                  30

<210> SEQ ID NO 174
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 174

Ser Glu Thr Arg Pro Thr Glu Ala Gly Ser Trp Gln Cys Thr Gly Pro
1               5                   10                  15

Pro Thr Phe Glu Cys Trp Gly Tyr Val Glu Glu Pro Thr Glu
            20                  25                  30

<210> SEQ ID NO 175
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 175

Ser Glu Thr Arg Pro Thr Glu Ala Gly Ser Trp Gln Cys Gly Gly Pro
1               5                   10                  15

Pro Thr Phe Glu Cys Trp Trp Tyr Tyr Thr Gly Pro Thr Glu
            20                  25                  30

<210> SEQ ID NO 176

```
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 176

Ser Glu Thr Arg Pro Thr Glu Ala Gly Ser Trp Tyr Cys Thr Gly Pro
1               5                   10                  15

Pro Thr Phe Glu Cys Trp Leu Tyr Glu Thr Tyr Pro Thr Glu
            20                  25                  30

<210> SEQ ID NO 177
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 177

Ser Glu Thr Arg Pro Thr Ala Ala Trp Ser Gly Ser Cys Ser Gly Pro
1               5                   10                  15

Pro Ser Phe Glu Cys Trp Asn Tyr Gly Thr Glu Pro Thr Glu
            20                  25                  30

<210> SEQ ID NO 178
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 178

Ser Glu Thr Arg Pro Thr Glu Ala Gly Ser Trp Gln Cys Ser Gly Pro
1               5                   10                  15

Pro Thr Phe Ala Cys Trp Trp Tyr Gly Thr Glu Pro Thr Glu
            20                  25                  30

<210> SEQ ID NO 179
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 179

Ser Glu Thr Arg Pro Thr Glu Ala Gly Ile Leu His Cys Ser Gly Pro
1               5                   10                  15

Pro Thr Phe Glu Cys Trp Trp Glu Val Met Glu Pro Thr Glu
            20                  25                  30

<210> SEQ ID NO 180
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 180

Ser Glu Thr Arg Pro Thr Glu Ala Gly Arg Val Ala Cys Ser Gly Pro
1               5                   10                  15
```

Pro Thr Phe Glu Cys Trp Ser Tyr Asp Glu Pro Thr Glu
            20                  25                  30

<210> SEQ ID NO 181
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 181

Ser Glu Thr Arg Pro Thr Glu Ala Gly Asn Trp Glu Cys Gln Gly Pro
1               5                   10                  15

Pro Thr Phe Glu Cys Trp Trp Phe Gly Thr Glu Pro Thr Glu
            20                  25                  30

<210> SEQ ID NO 182
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 182

Ser Glu Thr Arg Pro Thr Leu Ala Ser Asn Gly Tyr Cys Asn Gly Pro
1               5                   10                  15

Pro Thr Phe Glu Cys Trp His Tyr Gly Thr Glu Pro Thr Glu
            20                  25                  30

<210> SEQ ID NO 183
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 183

Ser Glu Thr Arg Pro Thr Glu Ala Gly Ser Phe His Cys Ser Gly Pro
1               5                   10                  15

Pro Thr Phe Glu Cys Ile Trp Tyr Gly Ser Glu Pro Thr Glu
            20                  25                  30

<210> SEQ ID NO 184
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 184

Ser Glu Thr Arg Pro Thr Glu Ala Gly Ser Trp Tyr Cys Ser Gly Pro
1               5                   10                  15

Pro Thr Phe Ala Cys Trp Trp Asp Gly Thr Glu Pro Thr Glu
            20                  25                  30

<210> SEQ ID NO 185
<211> LENGTH: 30
<212> TYPE: PRT
<213> ORGANISM: Artificial Sequence
<220> FEATURE:
<223> OTHER INFORMATION: Synthetically generated cMet-binding peptide
      sequence -continued

```
<400> SEQUENCE: 185

Ser Glu Thr Arg Pro Thr Gln Gly Asp Asn Trp Asn Cys Ser Gly Pro
1               5                   10                  15

Pro Thr Phe Glu Cys Trp Trp Tyr Gly Thr Glu Pro Thr Glu
            20                  25                  30

<210> SEQ ID NO 186
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 186

Ser Glu Thr Arg Pro Thr Glu Ala Gly Arg Trp His Cys Asn Gly Pro
1               5                   10                  15

Pro Thr Phe Glu Cys Trp Arg Tyr Asp Tyr Asp Pro Thr Glu
            20                  25                  30

<210> SEQ ID NO 187
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 187

Ser Glu Thr Arg Pro Thr Glu Ala Tyr Ser Trp Glu Cys Thr Gly Pro
1               5                   10                  15

Pro Met Phe Glu Cys Trp Trp Tyr Gly Thr Glu Pro Thr Glu
            20                  25                  30

<210> SEQ ID NO 188
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 188

Ser Glu Thr Arg Pro Thr Glu Val Val Asp Trp His Cys Ser Gly Pro
1               5                   10                  15

Pro Gln Phe Glu Cys Trp Trp Tyr Gly Thr Glu Pro Thr Glu
            20                  25                  30

<210> SEQ ID NO 189
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 189

Ser Glu Thr Arg Pro Thr Glu Ala Gly Ser Trp Asn Cys Ser Gly Pro
1               5                   10                  15

Pro Thr Phe Glu Cys Trp Trp Tyr Gly Ser Glu Pro Thr Glu
            20                  25                  30

<210> SEQ ID NO 190
<211> LENGTH: 30
<212> TYPE: PRT
```

```
<213> ORGANISM: Artificial Sequence
<220> FEATURE:
<223> OTHER INFORMATION: Synthetically generated cMet-binding peptide
      sequence

<400> SEQUENCE: 190

Ser Glu Thr Arg Pro Thr Ala Ser Gly Ser Trp His Cys Ser Gly Pro
1               5                   10                  15

Pro Thr Phe Glu Cys Trp Ile Phe Gly Thr Glu Pro Thr Glu
            20                  25                  30

<210> SEQ ID NO 191
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 191

Ser Glu Thr Arg Pro Thr Glu Ala Gly Ala Trp Tyr Cys Met Gly Pro
1               5                   10                  15

Pro Thr Phe Glu Cys Trp Trp Tyr Asp Arg Gly Pro Thr Glu
            20                  25                  30

<210> SEQ ID NO 192
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 192

Ser Glu Thr Arg Pro Thr Glu Ala Gly Gly Leu His Cys Ser Gly Pro
1               5                   10                  15

Pro Thr Phe Glu Cys Trp Trp Tyr Asp Thr Glu Pro Thr Glu
            20                  25                  30

<210> SEQ ID NO 193
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 193

Ser Glu Thr Arg Pro Thr Val Gly Gly Ser Trp Asp Cys Lys Gly Pro
1               5                   10                  15

Pro Thr Phe Glu Cys Trp Ser Tyr Gly Thr Glu Pro Thr Glu
            20                  25                  30

<210> SEQ ID NO 194
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 194

Ser Glu Thr Arg Pro Thr Glu Ala Gly Ala Trp Ser Cys Leu Gly Pro
1               5                   10                  15

Pro Thr Phe Glu Cys Trp Trp Tyr Gly Thr Glu Pro Thr Glu
            20                  25                  30
```

<210> SEQ ID NO 195
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 195

Ser Glu Thr Arg Pro Thr Glu Ala Gly Ser Leu His Cys Ser Gly Pro
1               5                   10                  15

Pro Thr Phe Glu Cys Trp Trp Phe Asp Thr Glu Pro Thr Glu
            20                  25                  30

<210> SEQ ID NO 196
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 196

Ser Glu Thr Arg Pro Thr Ala Gly Arg Ser Trp Glu Cys Ser Gly Pro
1               5                   10                  15

Pro Thr Phe Glu Cys Trp Val Phe Gly Thr Glu Pro Thr Glu
            20                  25                  30

<210> SEQ ID NO 197
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 197

Ser Glu Thr Arg Pro Thr Asp Asn Gly Ser Trp His Cys Asn Gly Pro
1               5                   10                  15

Pro Thr Phe Glu Cys Trp Trp Tyr Gly Thr Glu Pro Thr Glu
            20                  25                  30

<210> SEQ ID NO 198
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 198

Ser Glu Thr Arg Pro Thr Glu Ala Gly Ser Trp Gln Cys Lys Gly Pro
1               5                   10                  15

Pro Thr Phe Glu Cys Trp Trp Tyr Gly Thr Glu Pro Thr Glu
            20                  25                  30

<210> SEQ ID NO 199
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 199

```
Ser Glu Thr Arg Pro Thr Glu Val Gly Asn Tyr Lys Cys Ser Gly Pro
1               5                  10                 15

Pro Thr Phe Glu Cys Trp Trp Tyr Gly Thr Pro Thr Glu
            20                 25                 30

<210> SEQ ID NO 200
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 200

Ser Glu Thr Arg Pro Thr Glu Ala Gly Ser Trp His Cys Val Gly Pro
1               5                  10                 15

Pro Thr Phe Glu Cys Trp Gly Tyr Val Thr Glu Pro Thr Glu
            20                 25                 30

<210> SEQ ID NO 201
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 201

Ser Glu Thr Arg Pro Thr Glu Ala Gly Ser Phe Val Cys Lys Gly Pro
1               5                  10                 15

Pro Thr Phe Glu Cys Tyr Trp Phe Gly Gln Asp Pro Thr Glu
            20                 25                 30

<210> SEQ ID NO 202
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 202

Ser Glu Thr Arg Pro Thr Glu Ala Gly Ser Trp His Cys Ser Gly Pro
1               5                  10                 15

Pro Thr Phe Glu Cys Trp Trp Tyr Gly Pro Asp Pro Thr Glu
            20                 25                 30

<210> SEQ ID NO 203
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 203

Ser Glu Thr Arg Pro Thr Glu Ala Glu Arg Trp His Cys Ser Gly Pro
1               5                  10                 15

Pro Thr Phe Glu Cys Trp Trp Tyr Gly Thr Glu Pro Thr Glu
            20                 25                 30

<210> SEQ ID NO 204
<211> LENGTH: 30
<212> TYPE: PRT
<213> ORGANISM: Artificial Sequence
<220> FEATURE:
```

<223> OTHER INFORMATION: Synthetically generated cMet-binding peptide
      sequence

<400> SEQUENCE: 204

Ser Glu Thr Arg Pro Thr Glu Ala Gly Ser Trp His Cys Ser Gly Pro
1               5                   10                  15

Pro Thr Phe Glu Cys Trp Phe Tyr Val Lys Glu Pro Thr Glu
            20                  25                  30

<210> SEQ ID NO 205
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 205

Ser Glu Thr Arg Pro Thr Glu Ala Gly Ser Trp Asp Cys Ser Gly Pro
1               5                   10                  15

Pro Thr Phe Glu Cys Trp Trp Phe Gly Thr Glu Pro Thr Glu
            20                  25                  30

<210> SEQ ID NO 206
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 206

Ser Glu Thr Arg Pro Thr Glu Pro Ala Gly Trp Glu Cys Arg Gly Pro
1               5                   10                  15

Pro Ser Phe Glu Cys Leu Trp Tyr Gly Thr Glu Pro Thr Glu
            20                  25                  30

<210> SEQ ID NO 207
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 207

Ser Glu Thr Arg Pro Thr Asp Ala Gly Pro Trp Asn Cys Thr Gly Pro
1               5                   10                  15

Pro Ser Phe Glu Cys Trp Trp Tyr Gly Thr Glu Pro Thr Glu
            20                  25                  30

<210> SEQ ID NO 208
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 208

Ser Glu Thr Arg Pro Thr Glu Ala Arg Gly Trp His Cys Ser Gly Pro
1               5                   10                  15

Pro Thr Phe Glu Cys Trp Leu Trp Gly Thr Glu Pro Thr Glu
            20                  25                  30

-continued

```
<210> SEQ ID NO 209
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 209

Ser Glu Thr Arg Pro Thr Glu Ala Gly Arg Trp Asn Cys Ser Gly Pro
1               5                   10                  15

Pro Thr Phe Glu Cys Trp Gln Tyr Glu Met Asp Pro Thr Glu
            20                  25                  30

<210> SEQ ID NO 210
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 210

Ser Glu Thr Arg Pro Thr Glu Ala Gly Ser Trp Tyr Cys Ser Gly Pro
1               5                   10                  15

Pro Thr Phe Glu Cys Phe Trp Tyr Asp Thr Glu Pro Thr Glu
            20                  25                  30

<210> SEQ ID NO 211
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 211

Ser Glu Thr Arg Pro Thr Glu Ser Gly Ser Trp His Cys Ser Gly Pro
1               5                   10                  15

Pro Thr Phe Glu Cys Trp Trp Phe Gly Thr Glu Pro Thr Glu
            20                  25                  30

<210> SEQ ID NO 212
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 212

Ser Glu Thr Arg Pro Thr Glu Ala Gly Ser Trp Leu Cys Thr Gly Pro
1               5                   10                  15

Pro Thr Phe Glu Cys Trp Trp Phe Asp Thr Asp Pro Thr Glu
            20                  25                  30

<210> SEQ ID NO 213
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 213

Ser Glu Thr Arg Pro Thr Glu Pro Ser His Trp His Cys Val Gly Pro
1               5                   10                  15
```

```
Pro Thr Phe Ala Cys Trp Trp Tyr Val Thr Asp Pro Thr Glu
            20                  25                  30

<210> SEQ ID NO 214
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 214

Ser Glu Thr Arg Pro Thr Glu Ala Gly Ser Trp Tyr Cys Ser Gly Pro
1               5                   10                  15

Pro Met Phe Glu Cys Tyr Leu Phe Val Thr Glu Pro Thr Glu
            20                  25                  30

<210> SEQ ID NO 215
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 215

Ser Glu Thr Arg Pro Thr Glu Ala Val Asn Trp His Cys Leu Gly Pro
1               5                   10                  15

Pro Ser Phe Glu Cys Trp Gln Phe Gly Thr Glu Pro Thr Glu
            20                  25                  30

<210> SEQ ID NO 216
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 216

Ser Glu Thr Arg Pro Thr Glu Ala Gly Ser Trp His Cys Ser Gly Pro
1               5                   10                  15

Pro Thr Phe Glu Cys Trp Trp Tyr Gly Thr Asp Pro Thr Glu
            20                  25                  30

<210> SEQ ID NO 217
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 217

Ser Glu Thr Arg Pro Thr Glu Ala Gly Ser Trp His Cys Ser Gly Pro
1               5                   10                  15

Pro Thr Phe Glu Cys Trp Ser Phe Val Ser Leu Pro Thr Glu
            20                  25                  30

<210> SEQ ID NO 218
<211> LENGTH: 30
<212> TYPE: PRT
<213> ORGANISM: Artificial Sequence
<220> FEATURE:
<223> OTHER INFORMATION: Synthetically generated cMet-binding peptide
      sequence
```

<400> SEQUENCE: 218

Ser Glu Thr Arg Pro Thr Glu Gly Ser Glu Trp Ser Cys Ile Gly Pro
1               5                   10                  15

Pro Ser Phe Glu Cys Trp Trp Tyr Gly Thr Glu Pro Thr Glu
            20                  25                  30

<210> SEQ ID NO 219
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 219

Ser Glu Thr Arg Pro Thr Glu Asp Gly Tyr Trp Asn Cys Ser Gly Pro
1               5                   10                  15

Pro Thr Phe Glu Cys Trp Trp His Gly Thr Glu Pro Thr Glu
            20                  25                  30

<210> SEQ ID NO 220
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 220

Ser Glu Thr Arg Pro Thr Glu Ala Gly Ser Trp Ser Cys Ser Gly Pro
1               5                   10                  15

Pro Thr Phe Glu Cys Trp Pro Tyr Tyr Thr Glu Pro Thr Glu
            20                  25                  30

<210> SEQ ID NO 221
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 221

Ser Glu Thr Arg Pro Thr Glu Ala Gly Ser Trp Tyr Cys Ser Gly Pro
1               5                   10                  15

Pro Thr Phe Glu Cys Trp Trp Tyr Trp Pro Gly Pro Thr Glu
            20                  25                  30

<210> SEQ ID NO 222
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 222

Ser Glu Thr Arg Pro Thr Asp Asp Gly Arg Trp Ser Cys Ala Gly Pro
1               5                   10                  15

Pro Thr Phe Glu Cys Trp Arg Tyr Gly Thr Glu Pro Thr Glu
            20                  25                  30

<210> SEQ ID NO 223
<211> LENGTH: 30

```
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 223

Ser Glu Thr Arg Pro Thr Glu Gly Gly Ser Trp Ser Cys Gly Gly Pro
1               5                   10                  15

Pro Thr Phe Glu Cys Trp Trp Phe Gly Thr Glu Pro Thr Glu
            20                  25                  30

<210> SEQ ID NO 224
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 224

Ser Glu Thr Arg Pro Thr Val Thr Gly Ser Trp Tyr Cys Ser Gly Pro
1               5                   10                  15

Pro Thr Phe Glu Cys Trp Trp Tyr Gly Thr Glu Pro Thr Glu
            20                  25                  30

<210> SEQ ID NO 225
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 225

Ser Glu Thr Arg Pro Thr Glu Ala Ser Ser Trp Tyr Cys Thr Gly Pro
1               5                   10                  15

Pro Ala Phe Glu Cys Trp Trp Tyr Gly Thr Glu Pro Thr Glu
            20                  25                  30

<210> SEQ ID NO 226
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 226

Ser Glu Thr Arg Pro Thr Glu Ala Gly Ser Trp Leu Cys Ser Gly Pro
1               5                   10                  15

Pro Thr Phe Glu Cys Trp Trp Tyr Gly Thr Glu Pro Thr Glu
            20                  25                  30

<210> SEQ ID NO 227
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 227

Ser Glu Thr Arg Pro Thr Glu Ser Val Arg Trp Tyr Cys Ser Gly Pro
1               5                   10                  15

Pro Thr Phe Glu Cys Trp Trp Tyr Gly Thr Glu Pro Thr Glu
```

```
<210> SEQ ID NO 228
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 228

Ser Glu Thr Arg Pro Thr Glu Ala Gly Arg Leu Val Cys Ser Gly Pro
1               5                   10                  15

Pro Thr Phe Met Cys Arg Thr Tyr Ala Thr Asp Pro Thr Glu
            20                  25                  30

<210> SEQ ID NO 229
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 229

Ser Glu Thr Arg Pro Thr Glu Ala Gly Ser Trp Glu Cys Thr Gly Pro
1               5                   10                  15

Pro Trp Phe Val Cys Arg Gln Tyr Ala Ile Glu Pro Thr Glu
            20                  25                  30

<210> SEQ ID NO 230
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 230

Ser Glu Thr Arg Pro Thr Glu Ala Gly Tyr Leu Tyr Cys Ser Gly Pro
1               5                   10                  15

Pro Thr Phe Glu Cys Trp Trp Tyr Asp Thr Met Pro Thr Glu
            20                  25                  30

<210> SEQ ID NO 231
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 231

Ser Glu Thr Arg Pro Thr Glu Ala Gly Ser Trp His Cys Ser Gly Pro
1               5                   10                  15

Pro Thr Phe Glu Cys Trp Trp Phe Gly Thr Glu Pro Thr Glu
            20                  25                  30

<210> SEQ ID NO 232
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 232
```

Ser Glu Thr Arg Pro Thr Glu Ala Gly Asn Trp His Cys Leu Gly Pro
1               5                   10                  15

Pro Thr Phe Glu Cys Trp Trp Tyr Gly Thr Glu Pro Thr Glu
            20                  25                  30

<210> SEQ ID NO 233
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 233

Ser Glu Thr Arg Pro Thr Glu Ala Gly Ser Trp His Cys Ser Gly Pro
1               5                   10                  15

Pro Thr Phe Glu Cys Trp Trp Tyr Asp Thr Glu Pro Thr Glu
            20                  25                  30

<210> SEQ ID NO 234
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 234

Ser Glu Thr Arg Pro Thr Glu Ser Gly Gly Trp Tyr Cys Ser Gly Pro
1               5                   10                  15

Pro Ala Phe Glu Cys Trp Trp Tyr Gly Thr Glu Pro Thr Glu
            20                  25                  30

<210> SEQ ID NO 235
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 235

Ser Glu Thr Arg Pro Thr Val Ala Gly Ala Val Ser Cys Ser Gly Pro
1               5                   10                  15

Pro Thr Phe Glu Cys Trp Trp Tyr Gly Thr Glu Pro Thr Glu
            20                  25                  30

<210> SEQ ID NO 236
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 236

Ser Glu Thr Arg Pro Thr Glu Ala Gly Arg Trp Tyr Cys Ser Gly Pro
1               5                   10                  15

Pro Thr Phe Glu Cys Trp Trp Phe Leu Pro Asp Pro Thr Glu
            20                  25                  30

<210> SEQ ID NO 237
<211> LENGTH: 30
<212> TYPE: PRT
<213> ORGANISM: Artificial Sequence

```
<220> FEATURE:
<223> OTHER INFORMATION: Synthetically generated cMet-binding peptide
      sequence

<400> SEQUENCE: 237

Ser Glu Thr Arg Pro Thr Glu Ala Gly Gly Trp His Cys Ser Gly Pro
1               5                   10                  15

Pro Ser Phe Glu Cys Trp Trp Phe Asp Thr Val Pro Thr Glu
            20                  25                  30

<210> SEQ ID NO 238
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 238

Ser Glu Thr Arg Pro Thr Gly Val Gly Gly Trp Tyr Cys Ser Gly Pro
1               5                   10                  15

Pro Ser Phe Glu Cys Trp Leu Tyr Gly Thr Glu Pro Thr Glu
            20                  25                  30

<210> SEQ ID NO 239
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 239

Ser Glu Thr Arg Pro Thr Gln Ala Asp Tyr Leu His Cys Ser Gly Pro
1               5                   10                  15

Pro Thr Phe Glu Cys Phe Trp Tyr Gly Thr Glu Pro Thr Glu
            20                  25                  30

<210> SEQ ID NO 240
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 240

Ser Glu Thr Arg Pro Thr Gly Asp Gly Asn Trp His Cys Asn Gly Pro
1               5                   10                  15

Pro Thr Phe Glu Cys Trp Arg Phe Gly Thr Glu Pro Thr Glu
            20                  25                  30

<210> SEQ ID NO 241
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 241

Ser Glu Thr Arg Pro Thr Glu Ala Ser Asn Tyr His Cys Ile Gly Pro
1               5                   10                  15

Pro Thr Phe Glu Cys Phe Trp Tyr Gly Thr Glu Pro Thr Glu
            20                  25                  30
```

```
<210> SEQ ID NO 242
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 242

Ser Glu Thr Arg Pro Thr Glu Ala Gly Asp Trp Leu Cys Lys Gly Pro
 1               5                  10                  15

Pro Thr Phe Glu Cys Trp Trp Gln Val Thr Asp Pro Thr Glu
            20                  25                  30

<210> SEQ ID NO 243
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 243

Ser Glu Thr Arg Pro Thr Glu Ala Gly Ser Trp His Cys Asn Gly Pro
 1               5                  10                  15

Pro Thr Phe Glu Cys Trp Trp Tyr Ser Ser Asp Pro Thr Glu
            20                  25                  30

<210> SEQ ID NO 244
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 244

Ser Glu Thr Arg Pro Thr Glu Asp Gly Gly Trp Arg Cys Ser Gly Pro
 1               5                  10                  15

Pro Thr Phe Glu Cys Trp Trp Tyr Gly Thr Glu Pro Thr Glu
            20                  25                  30

<210> SEQ ID NO 245
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 245

Ser Glu Thr Arg Pro Thr Glu Ala Gly Arg Ile Glu Cys Lys Gly Pro
 1               5                  10                  15

Pro Trp Phe Ser Cys Val Ile Tyr Gly Thr Glu Pro Thr Glu
            20                  25                  30

<210> SEQ ID NO 246
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 246

Ser Glu Thr Arg Pro Thr Gly Gly Gly Ser Trp Asn Cys Ser Gly Pro
```

```
                1               5                  10                 15
Pro Thr Phe Glu Cys Trp Trp Tyr Gly Thr Glu Pro Thr Glu
                20                 25                 30

<210> SEQ ID NO 247
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 247

Ser Glu Thr Arg Pro Thr Glu Ala Gly Ser Leu Tyr Cys Ser Gly Pro
1               5                   10                  15
Pro Thr Phe Glu Cys Trp Trp Tyr Ile Thr His Pro Thr Glu
                20                  25                  30

<210> SEQ ID NO 248
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 248

Ser Glu Thr Arg Pro Thr Glu Ala Gly Arg Trp His Cys Ser Gly Pro
1               5                   10                  15
Pro Arg Phe Glu Cys Trp Trp Tyr Asp Thr Glu Pro Thr Glu
                20                  25                  30

<210> SEQ ID NO 249
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 249

Ser Glu Thr Arg Pro Thr Glu Tyr Gly Ser Trp His Cys Ser Gly Pro
1               5                   10                  15
Pro Thr Phe Glu Cys Trp Tyr His Gly Thr Glu Pro Thr Glu
                20                  25                  30

<210> SEQ ID NO 250
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 250

Ser Glu Thr Arg Pro Thr Glu Ala Gly Asn Trp His Cys Ser Gly Pro
1               5                   10                  15
Pro Ser Phe Glu Cys Trp Trp Tyr Ala Thr Glu Pro Thr Glu
                20                  25                  30

<210> SEQ ID NO 251
<211> LENGTH: 30
<212> TYPE: PRT
<213> ORGANISM: Artificial Sequence
<220> FEATURE:
<223> OTHER INFORMATION: Synthetically generated cMet-binding peptide
``` sequence

<400> SEQUENCE: 251

Ser Glu Thr Arg Pro Thr Glu Gln Gly Ser Trp His Cys Lys Gly Pro
1               5                   10                  15

Pro Thr Phe Glu Cys Trp Ser Tyr Gly Thr Glu Pro Thr Glu
            20                  25                  30

<210> SEQ ID NO 252
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 252

Ser Glu Thr Arg Pro Thr Asp Ala Ala Asn Tyr His Cys Ser Gly Pro
1               5                   10                  15

Pro Thr Phe Glu Cys Trp Trp Tyr Gly Thr Glu Pro Thr Glu
            20                  25                  30

<210> SEQ ID NO 253
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 253

Ser Glu Thr Arg Pro Thr Glu Ala Gly Ser Trp Tyr Cys Ser Gly Pro
1               5                   10                  15

Pro Met Phe Glu Cys Trp Trp Leu Ala Glu Glu Pro Thr Glu
            20                  25                  30

<210> SEQ ID NO 254
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 254

Ser Glu Thr Arg Pro Thr Glu Ala Gly Gly Trp Tyr Cys Ser Gly Pro
1               5                   10                  15

Pro Ala Phe Glu Cys Trp Trp Tyr Ala Thr Glu Pro Thr Glu
            20                  25                  30

<210> SEQ ID NO 255
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 255

Ser Glu Thr Arg Pro Thr Glu Ala Gly Ile Trp Ser Cys Ser Gly Pro
1               5                   10                  15

Pro Thr Phe Glu Cys Trp Trp Tyr Glu Ser Ser Pro Thr Glu
            20                  25                  30

<210> SEQ ID NO 256

```
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 256

Ser Glu Thr Arg Pro Thr Glu Glu Gly Leu Arg Val Cys Ser Gly Pro
1               5                   10                  15

Pro Thr Phe Glu Cys Trp Trp Tyr Gly Thr Glu Pro Thr Glu
            20                  25                  30

<210> SEQ ID NO 257
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 257

Ser Glu Thr Arg Pro Thr Glu Ala Gly Ser Trp Leu Cys Phe Gly Pro
1               5                   10                  15

Pro Thr Phe Glu Cys Trp Ser Phe Gly Thr Glu Pro Thr Glu
            20                  25                  30

<210> SEQ ID NO 258
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 258

Ser Glu Thr Arg Pro Thr Val Ala Gly Ser Trp Asp Cys Ser Gly Pro
1               5                   10                  15

Pro Thr Phe Glu Cys Trp Trp Tyr Gly Thr Glu Pro Thr Glu
            20                  25                  30

<210> SEQ ID NO 259
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 259

Ser Glu Thr Arg Pro Thr Lys Ala Asp Asn Trp His Cys Ser Gly Pro
1               5                   10                  15

Pro Thr Phe Glu Cys Trp Trp Tyr Gly Thr Glu Pro Thr Glu
            20                  25                  30

<210> SEQ ID NO 260
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 260

Ser Glu Thr Arg Pro Thr Glu Ala Gly Ile Val Tyr Cys Ser Gly Pro
1               5                   10                  15
```

Pro Thr Phe Glu Cys Trp Trp Phe Gly Thr Glu Pro Thr Glu
            20                  25                  30

<210> SEQ ID NO 261
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 261

Ser Glu Thr Arg Pro Thr Glu Ala Gly Tyr Trp His Cys Leu Gly Pro
1               5                   10                  15

Pro Thr Phe Glu Cys Trp Trp Tyr Val Lys Glu Pro Thr Glu
            20                  25                  30

<210> SEQ ID NO 262
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 262

Ser Glu Thr Arg Pro Thr Glu Pro Gly Leu Leu His Cys Ser Gly Pro
1               5                   10                  15

Pro Thr Phe Glu Cys Trp Trp Tyr Gly Thr Glu Pro Thr Glu
            20                  25                  30

<210> SEQ ID NO 263
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 263

Ser Glu Thr Arg Pro Thr Glu Ala Ser Ser Trp Tyr Cys Ser Gly Pro
1               5                   10                  15

Pro Ser Phe Glu Cys Trp Trp Tyr Gly Thr Glu Pro Thr Glu
            20                  25                  30

<210> SEQ ID NO 264
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 264

Ser Glu Thr Arg Pro Thr Glu Ala Gly Ser Trp His Cys Leu Gly Pro
1               5                   10                  15

Pro Thr Phe Glu Cys Trp Trp Tyr Val Lys Glu Pro Thr Glu
            20                  25                  30

<210> SEQ ID NO 265
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 265

Ser Glu Thr Arg Pro Thr Glu Ala Gly Ile Ile Leu Cys Lys Gly Pro
1               5                   10                  15

Pro Trp Phe Ser Cys Asp Ile Tyr Asp Thr Gly Pro Thr Glu
            20                  25                  30

<210> SEQ ID NO 266
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 266

Ser Glu Thr Arg Pro Thr Ala Ala Gly Asn Trp His Cys Ser Gly Pro
1               5                   10                  15

Pro Thr Phe Glu Cys Trp Ala Tyr Gly Thr Glu Pro Thr Glu
            20                  25                  30

<210> SEQ ID NO 267
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 267

Ser Glu Thr Arg Pro Thr Val Gly Gly Ser Trp Tyr Cys Ser Gly Pro
1               5                   10                  15

Pro Thr Phe Glu Cys Trp Ser Tyr Gly Thr Glu Pro Thr Glu
            20                  25                  30

<210> SEQ ID NO 268
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 268

Ser Glu Thr Arg Pro Thr Glu Asp Gly Trp Leu Asp Cys Lys Gly Pro
1               5                   10                  15

Pro Thr Phe Glu Cys Trp Trp Tyr Gly Thr Glu Pro Thr Glu
            20                  25                  30

<210> SEQ ID NO 269
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 269

Ser Glu Thr Arg Pro Thr Glu Asp Gly Asn Trp His Cys Ser Gly Pro
1               5                   10                  15

Pro Thr Phe Glu Cys Trp Ser Tyr Gly Thr Glu Pro Thr Glu
            20                  25                  30

<210> SEQ ID NO 270
<211> LENGTH: 30
<212> TYPE: PRT

```
<213> ORGANISM: Artificial Sequence
<220> FEATURE:
<223> OTHER INFORMATION: Synthetically generated cMet-binding peptide
      sequence

<400> SEQUENCE: 270

Ser Glu Thr Arg Pro Thr Glu Ala Gly Ser Trp His Cys Ser Gly Pro
1               5                   10                  15

Pro Thr Phe Glu Cys Trp Tyr Tyr Trp Pro Glu Pro Thr Glu
            20                  25                  30

<210> SEQ ID NO 271
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 271

Ser Glu Thr Arg Pro Thr Glu Ala Gly Ser Leu Tyr Cys Ser Gly Pro
1               5                   10                  15

Pro Met Phe Glu Cys Trp Trp Tyr Asp Trp Tyr Pro Thr Glu
            20                  25                  30

<210> SEQ ID NO 272
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 272

Ser Glu Thr Arg Pro Thr Glu Ala Gly Gly Trp Tyr Cys Met Gly Pro
1               5                   10                  15

Pro Ala Phe Glu Cys Trp Trp Tyr Ala Ser Glu Pro Thr Glu
            20                  25                  30

<210> SEQ ID NO 273
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 273

Ser Glu Thr Arg Pro Thr Asn Ala Gly Ser Trp Tyr Cys Ser Gly Pro
1               5                   10                  15

Pro Thr Phe Glu Cys Trp Trp Tyr Gly Thr Glu Pro Thr Glu
            20                  25                  30

<210> SEQ ID NO 274
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 274

Ser Glu Thr Arg Pro Thr Glu Ala Ser Arg Trp His Cys Asn Gly Pro
1               5                   10                  15

Pro Thr Phe Glu Cys Trp Trp Tyr Gly Thr Glu Pro Thr Glu
            20                  25                  30
```

<210> SEQ ID NO 275
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 275

Ser Glu Thr Arg Pro Thr Glu Ala Gly Ser Phe Val Cys Ser Gly Pro
1               5                   10                  15

Pro Thr Phe Glu Cys Trp Trp Tyr Asn Thr Gly Pro Thr Glu
            20                  25                  30

<210> SEQ ID NO 276
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 276

Ser Glu Thr Arg Pro Thr Glu Ala Gly Ser Trp His Cys Ser Gly Pro
1               5                   10                  15

Pro Thr Phe Glu Cys Trp Ser Tyr Gly Thr Glu Pro Thr Glu
            20                  25                  30

<210> SEQ ID NO 277
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 277

Ser Glu Thr Arg Pro Thr Glu Ser Asp Ile Trp Leu Cys Ser Gly Pro
1               5                   10                  15

Pro Thr Phe Glu Cys Trp Trp Tyr Gly Thr Glu Pro Thr Glu
            20                  25                  30

<210> SEQ ID NO 278
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 278

Ser Glu Thr Arg Pro Thr Asp Ala Asp Pro Trp His Cys Ser Gly Pro
1               5                   10                  15

Pro Thr Phe Glu Cys Trp Trp Phe Gly Thr Glu Pro Thr Glu
            20                  25                  30

<210> SEQ ID NO 279
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 279

```
Ser Glu Thr Arg Pro Thr Glu Ala Gly Val Val Leu Cys Ser Gly Pro
1               5                   10                  15

Pro Thr Phe Glu Cys Trp Trp Tyr Asp Thr Glu Pro Thr Glu
            20                  25                  30

<210> SEQ ID NO 280
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 280

Ser Glu Thr Arg Pro Thr Glu Val Gly Ser Val His Cys Ser Gly Pro
1               5                   10                  15

Pro Thr Phe Glu Cys Trp Trp Phe Gly Thr Glu Pro Thr Glu
            20                  25                  30

<210> SEQ ID NO 281
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 281

Ser Glu Thr Arg Pro Thr Glu Ala Gly Arg Trp Leu Cys Ser Gly Pro
1               5                   10                  15

Pro Thr Phe Glu Cys Trp Glu Tyr Asp Thr Glu Pro Thr Glu
            20                  25                  30

<210> SEQ ID NO 282
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 282

Ser Glu Thr Arg Pro Thr Asp Ala Gly Trp Leu Gln Cys Ser Gly Pro
1               5                   10                  15

Pro Thr Phe Glu Cys Trp Trp Tyr Gly Thr Glu Pro Thr Glu
            20                  25                  30

<210> SEQ ID NO 283
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 283

Ser Glu Thr Arg Pro Thr Glu Ala Ser Arg Arg His Cys Asn Gly Pro
1               5                   10                  15

Pro Thr Phe Glu Cys Trp Arg Tyr Gly Thr Glu Pro Thr Glu
            20                  25                  30

<210> SEQ ID NO 284
<211> LENGTH: 30
<212> TYPE: PRT
<213> ORGANISM: Artificial Sequence
<220> FEATURE:
```

<223> OTHER INFORMATION: Synthetically generated cMet-binding peptide
      sequence

<400> SEQUENCE: 284

Ser Glu Thr Arg Pro Thr Glu Ala Gly Arg Trp Tyr Cys Ser Gly Pro
1               5                   10                  15

Pro Thr Phe Glu Cys Trp Leu Phe Val Glu Glu Pro Thr Glu
            20                  25                  30

<210> SEQ ID NO 285
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 285

Ser Glu Thr Arg Pro Thr Ala Ala Asp Ser Trp Gln Cys Ser Gly Pro
1               5                   10                  15

Pro Thr Phe Glu Cys Trp Ser Phe Gly Thr Glu Pro Thr Glu
            20                  25                  30

<210> SEQ ID NO 286
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 286

Ser Glu Thr Arg Pro Thr Glu Ala Gly Ser Trp His Cys Gly Gly Pro
1               5                   10                  15

Pro Thr Phe Glu Cys Trp Met Tyr Val Thr Glu Pro Thr Glu
            20                  25                  30

<210> SEQ ID NO 287
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 287

Ser Glu Thr Arg Pro Thr Asp Asp Gly Ser Trp Tyr Cys Ser Gly Pro
1               5                   10                  15

Pro Thr Phe Glu Cys Trp Trp Tyr Gly Thr Glu Pro Thr Glu
            20                  25                  30

<210> SEQ ID NO 288
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 288

Ser Glu Thr Arg Pro Thr Glu Ala Gly Tyr Trp His Cys Leu Gly Pro
1               5                   10                  15

Pro Thr Phe Glu Cys Trp Trp Tyr Asp Met Glu Pro Thr Glu
            20                  25                  30

```
<210> SEQ ID NO 289
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 289

Ser Glu Thr Arg Pro Thr Glu Ala Gly Ile Leu Arg Cys Ser Gly Pro
1               5                   10                  15

Pro Thr Phe Glu Cys Trp Tyr Tyr Glu Thr Glu Pro Thr Glu
            20                  25                  30

<210> SEQ ID NO 290
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 290

Ser Glu Thr Arg Pro Thr Glu Asp Val Ser Val His Cys Ala Gly Pro
1               5                   10                  15

Pro Thr Phe Glu Cys Trp Leu Tyr Gly Thr Glu Pro Thr Glu
            20                  25                  30

<210> SEQ ID NO 291
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 291

Ser Glu Thr Arg Pro Thr Glu Glu Gly Val Phe Gln Cys Val Gly Pro
1               5                   10                  15

Pro Thr Phe Glu Cys Trp Trp Tyr Gly Thr Glu Pro Thr Glu
            20                  25                  30

<210> SEQ ID NO 292
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 292

Ser Glu Thr Arg Pro Thr Glu Asp Gly Gly Phe Phe Cys Ser Gly Pro
1               5                   10                  15

Pro Thr Phe Glu Cys Trp Trp Tyr Gly Thr Glu Pro Thr Glu
            20                  25                  30

<210> SEQ ID NO 293
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 293

Ser Glu Thr Arg Pro Thr Glu Pro Gly Ser Trp His Cys Ser Gly Pro
1               5                   10                  15
```

Pro Thr Phe Glu Cys Trp Trp Tyr Gly Thr Glu Pro Thr Glu
            20                  25                  30

<210> SEQ ID NO 294
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 294

Ser Glu Thr Arg Pro Thr Glu Ala Gly Ser Trp His Cys Ser Gly Pro
1               5                   10                  15

Pro Thr Phe Glu Cys Trp Trp Tyr Asp Arg Ala Pro Thr Glu
            20                  25                  30

<210> SEQ ID NO 295
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 295

Ser Glu Thr Arg Pro Thr Glu Ala Gly Thr Trp Tyr Cys Ser Gly Pro
1               5                   10                  15

Pro Thr Phe Glu Cys Trp Tyr Tyr Ala Thr Glu Pro Thr Glu
            20                  25                  30

<210> SEQ ID NO 296
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 296

Ser Glu Thr Arg Pro Thr Glu Ala Gly Ser Leu Tyr Cys Ser Gly Pro
1               5                   10                  15

Pro Ala Phe Glu Cys Tyr Trp Tyr Gly Thr Val Pro Thr Glu
            20                  25                  30

<210> SEQ ID NO 297
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 297

Ser Glu Thr Arg Pro Thr Asp Pro Gly Val Leu His Cys Ser Gly Pro
1               5                   10                  15

Pro Thr Phe Glu Cys Trp Trp Phe Gly Thr Glu Pro Thr Glu
            20                  25                  30

<210> SEQ ID NO 298
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 298

Ser Glu Thr Arg Pro Thr Glu Ala Gly Thr Trp Tyr Cys Leu Gly Pro
1               5                   10                  15

Pro Thr Phe Glu Cys Trp Ser Phe Trp Gln Asp Pro Thr Glu
            20                  25                  30

<210> SEQ ID NO 299
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 299

Ser Glu Thr Arg Pro Thr Glu Ala Gly Arg Trp Gly Cys Ser Gly Pro
1               5                   10                  15

Pro Thr Phe Glu Cys Trp Trp Tyr Val Ala Glu Pro Thr Glu
            20                  25                  30

<210> SEQ ID NO 300
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 300

Ser Glu Thr Arg Pro Thr Glu Ala Gly Ile Trp His Cys Ala Gly Pro
1               5                   10                  15

Pro Thr Phe Ile Cys Trp Leu Tyr Glu Thr Glu Pro Thr Glu
            20                  25                  30

<210> SEQ ID NO 301
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 301

Ser Glu Thr Arg Pro Thr Glu Ala Gly Ser Trp His Cys Ser Gly Pro
1               5                   10                  15

Pro Ser Phe Glu Cys Trp Gln Tyr Ser Thr Glu Pro Thr Glu
            20                  25                  30

<210> SEQ ID NO 302
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 302

Ser Glu Thr Arg Pro Thr Glu Ala Gly Ser Trp Gln Cys Ser Gly Pro
1               5                   10                  15

Pro Thr Phe Glu Cys Trp Val Tyr Glu Thr Glu Pro Thr Glu
            20                  25                  30

<210> SEQ ID NO 303
<211> LENGTH: 30

```
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 303

Ser Glu Thr Arg Pro Thr Glu Ala Gly Ser Trp Tyr Cys Ser Gly Pro
1               5                   10                  15

Pro Thr Phe Glu Cys Trp Trp Tyr Asp Val Gly Pro Thr Glu
            20                  25                  30

<210> SEQ ID NO 304
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 304

Ser Glu Thr Arg Pro Thr Asp Glu Val Ser Trp Glu Cys Arg Gly Pro
1               5                   10                  15

Pro Thr Phe Glu Cys Trp Trp Tyr Gly Thr Glu Pro Thr Glu
            20                  25                  30

<210> SEQ ID NO 305
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 305

Ser Glu Thr Arg Pro Thr Glu Gly Ser Trp Val Cys Ser Gly Pro
1               5                   10                  15

Pro Thr Phe Glu Cys Trp Trp Tyr Gly Thr Glu Pro Thr Glu
            20                  25                  30

<210> SEQ ID NO 306
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 306

Ser Glu Thr Arg Pro Thr Glu Tyr Gly Ser Trp Tyr Cys Ser Gly Pro
1               5                   10                  15

Pro Thr Phe Glu Cys Trp Trp Leu Gly Thr Glu Pro Thr Glu
            20                  25                  30

<210> SEQ ID NO 307
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 307

Ser Glu Thr Arg Pro Thr Glu Ala Gly Val Trp Leu Cys Ser Gly Pro
1               5                   10                  15

Pro Thr Phe Glu Cys Trp Trp Tyr Asp Thr Asp Pro Thr Glu
```

<210> SEQ ID NO 308
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 308

Ser Glu Thr Arg Pro Thr Met Ala Gly Ser Tyr Tyr Cys Ser Gly Pro
1               5                   10                  15

Pro Thr Phe Glu Cys Trp Val Tyr Gly Thr Glu Pro Thr Glu
            20                  25                  30

<210> SEQ ID NO 309
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 309

Ser Glu Thr Arg Pro Thr Glu Ala Gly Tyr Val Gln Cys Tyr Gly Pro
1               5                   10                  15

Pro Ser Phe Val Cys His Pro Met Val Pro Asp Pro Thr Glu
            20                  25                  30

<210> SEQ ID NO 310
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 310

Ser Glu Thr Arg Pro Thr Glu Asp Gly Phe Val Leu Cys Lys Gly Pro
1               5                   10                  15

Pro Trp Phe Ser Cys Glu Met Tyr Gly Thr Glu Pro Thr Glu
            20                  25                  30

<210> SEQ ID NO 311
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 311

Ser Glu Thr Arg Pro Thr Glu Ala Gly Gly Trp Asn Cys Ser Gly Pro
1               5                   10                  15

Pro Thr Phe Glu Cys Trp Trp Tyr Val Thr Glu Pro Thr Glu
            20                  25                  30

<210> SEQ ID NO 312
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 312

```
Ser Glu Thr Arg Pro Thr Glu Asp Gly Ser Trp Glu Cys Phe Gly Pro
 1               5                  10                  15

Pro Thr Phe Glu Cys Trp Ser Tyr Gly Thr Glu Pro Thr Glu
             20                  25                  30

<210> SEQ ID NO 313
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 313

Ser Glu Thr Arg Pro Thr Asp Ala Val Ser Tyr Val Cys Lys Gly Pro
 1               5                  10                  15

Pro Thr Phe Glu Cys Trp Trp Tyr Gly Thr Glu Pro Thr Glu
             20                  25                  30

<210> SEQ ID NO 314
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 314

Ser Glu Thr Arg Pro Thr Glu Ala Arg Ser Trp His Cys Ser Gly Pro
 1               5                  10                  15

Pro Thr Phe Glu Cys Trp Trp Tyr Gly Thr Glu Pro Thr Glu
             20                  25                  30

<210> SEQ ID NO 315
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 315

Ser Glu Thr Arg Pro Thr Ala Ser Val Ser Trp His Cys Ser Gly Pro
 1               5                  10                  15

Pro Thr Phe Glu Cys Trp Ser Tyr Gly Thr Glu Pro Thr Glu
             20                  25                  30

<210> SEQ ID NO 316
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 316

Ser Glu Thr Arg Pro Thr Glu Ala Gly Ser Trp Tyr Cys Ser Gly Pro
 1               5                  10                  15

Pro Thr Phe Glu Cys Trp Tyr Tyr Asp Met Asp Pro Thr Glu
             20                  25                  30

<210> SEQ ID NO 317
<211> LENGTH: 30
<212> TYPE: PRT
<213> ORGANISM: Artificial Sequence
```

```
<220> FEATURE:
<223> OTHER INFORMATION: Synthetically generated cMet-binding peptide
      sequence

<400> SEQUENCE: 317

Ser Glu Thr Arg Pro Thr Glu Ala Gly Ser Trp Leu Cys Ser Gly Pro
1               5                  10                  15

Pro Thr Phe Glu Cys Trp Trp Phe Gly Thr Glu Pro Thr Glu
            20                  25                  30

<210> SEQ ID NO 318
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 318

Ser Glu Thr Arg Pro Thr Gly Asp Gly Ser Trp Tyr Cys Ser Gly Pro
1               5                  10                  15

Pro Thr Phe Glu Cys Trp Trp Leu Gly Thr Glu Pro Thr Glu
            20                  25                  30

<210> SEQ ID NO 319
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 319

Ser Glu Thr Arg Pro Thr Glu Ala Gly Ser Trp Tyr Cys Ser Gly Pro
1               5                  10                  15

Pro Thr Phe Glu Cys Trp Trp Tyr Phe Leu Asp Pro Thr Glu
            20                  25                  30

<210> SEQ ID NO 320
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 320

Ser Glu Thr Arg Pro Thr Glu Ala Gly Gly Trp Tyr Cys Ser Gly Pro
1               5                  10                  15

Pro Thr Phe Glu Cys Trp Trp Phe Ala Thr Glu Pro Thr Glu
            20                  25                  30

<210> SEQ ID NO 321
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 321

Ser Glu Thr Arg Pro Thr Glu Ala Gly Asp Leu Asp Cys Leu Gly Pro
1               5                  10                  15

Pro Thr Phe Ile Cys Arg Ile Tyr Gly Thr Glu Pro Thr Glu
            20                  25                  30
```

```
<210> SEQ ID NO 322
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 322

Ser Glu Thr Arg Pro Thr Glu Ala Gly Ser Trp Gln Cys Val Gly Pro
  1               5                  10                  15

Pro Thr Phe Glu Cys Trp Ser Phe Gly Thr Glu Pro Thr Glu
             20                  25                  30

<210> SEQ ID NO 323
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 323

Ser Glu Thr Arg Pro Thr Glu Ala Asp Ser Trp Tyr Cys Ser Gly Pro
  1               5                  10                  15

Pro Thr Phe Glu Cys Trp Leu Phe Gly Thr Glu Pro Thr Glu
             20                  25                  30

<210> SEQ ID NO 324
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 324

Ser Glu Thr Arg Pro Thr Gln Ala Asp Ser Trp Tyr Cys Ser Gly Pro
  1               5                  10                  15

Pro Thr Phe Glu Cys Trp Trp Trp Gly Thr Glu Pro Thr Glu
             20                  25                  30

<210> SEQ ID NO 325
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 325

Ser Glu Thr Arg Pro Thr Glu Ala Phe Ser Trp Asp Cys Ser Gly Pro
  1               5                  10                  15

Pro Thr Phe Glu Cys Trp Trp Phe Gly Thr Glu Pro Thr Glu
             20                  25                  30

<210> SEQ ID NO 326
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 326

Ser Glu Thr Arg Pro Thr Glu Ala Gly Ser Trp Gln Cys Ser Gly Pro
```

```
                1               5                  10                  15
Pro Val Phe Glu Cys Trp Trp Tyr Asp Thr Glu Pro Thr Glu
                20                  25                  30

<210> SEQ ID NO 327
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 327

Ser Glu Thr Arg Pro Thr Glu Ala Gly Asn Val Gln Cys Ser Gly Pro
1               5                  10                  15
Pro Thr Phe Glu Cys Trp Trp Phe Asp Thr Glu Pro Thr Glu
                20                  25                  30

<210> SEQ ID NO 328
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 328

Ser Glu Thr Arg Pro Thr Glu Ala Gly Ser Val Val Cys Ser Gly Pro
1               5                  10                  15
Pro Arg Phe Glu Cys Trp Ala Phe Val Thr Glu Pro Thr Glu
                20                  25                  30

<210> SEQ ID NO 329
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 329

Ser Glu Thr Arg Pro Thr Glu Asp Gly Thr Leu His Cys Ser Gly Pro
1               5                  10                  15
Pro Thr Phe Ala Cys Trp Trp Tyr Gly Thr Glu Pro Thr Glu
                20                  25                  30

<210> SEQ ID NO 330
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 330

Ser Glu Thr Arg Pro Thr Asp Ala Glu Val Trp Val Cys Asn Gly Pro
1               5                  10                  15
Pro Thr Phe Glu Cys Trp Trp Tyr Gly Thr Glu Pro Thr Glu
                20                  25                  30

<210> SEQ ID NO 331
<211> LENGTH: 30
<212> TYPE: PRT
<213> ORGANISM: Artificial Sequence
<220> FEATURE:
<223> OTHER INFORMATION: Synthetically generated cMet-binding peptide
```

-continued sequence

<400> SEQUENCE: 331

Ser Glu Thr Arg Pro Thr Glu Asp Val Thr Phe His Cys Ser Gly Pro
1               5                   10                  15

Pro Thr Phe Glu Cys Trp Leu Tyr Gly Thr Glu Pro Thr Glu
            20                  25                  30

<210> SEQ ID NO 332
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 332

Ser Glu Thr Arg Pro Thr Ser Asp Phe Asp Trp His Cys Lys Gly Pro
1               5                   10                  15

Pro Thr Phe Glu Cys Trp Ser Tyr Gly Thr Glu Pro Thr Glu
            20                  25                  30

<210> SEQ ID NO 333
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 333

Ser Glu Thr Arg Pro Thr Glu Ala Asp Ser Trp Tyr Cys Ser Gly Pro
1               5                   10                  15

Pro Thr Phe Glu Cys Trp Trp Tyr Val Pro Glu Pro Thr Glu
            20                  25                  30

<210> SEQ ID NO 334
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 334

Ser Glu Thr Arg Pro Thr Asp Asp Gly Asn Trp Tyr Cys Ser Gly Pro
1               5                   10                  15

Pro Thr Phe Glu Cys Trp Trp Tyr Gly Thr Glu Pro Thr Glu
            20                  25                  30

<210> SEQ ID NO 335
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 335

Ser Glu Thr Arg Pro Thr Glu Ala Gly Ser Trp Tyr Cys Ser Gly Pro
1               5                   10                  15

Pro Thr Phe Glu Cys Trp Arg Tyr Asp Thr Asp Pro Thr Glu
            20                  25                  30

<210> SEQ ID NO 336

```
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 336

Ser Glu Thr Arg Pro Thr Glu Ala Gly Pro Trp Ser Cys Ser Gly Pro
1               5                   10                  15

Pro Thr Phe Glu Cys Trp Trp Phe Asp Thr Glu Pro Thr Glu
            20                  25                  30

<210> SEQ ID NO 337
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 337

Ser Glu Thr Arg Pro Thr Glu Ala Gly Met Phe Leu Cys Ser Gly Pro
1               5                   10                  15

Pro Ala Phe Glu Cys Trp Trp Tyr Asp Thr Glu Pro Thr Glu
            20                  25                  30

<210> SEQ ID NO 338
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 338

Ser Glu Thr Arg Pro Thr Glu Ala Gly Ser Leu Tyr Cys Ser Gly Pro
1               5                   10                  15

Pro Thr Phe Glu Cys Trp Leu Tyr Asp Val Glu Pro Thr Glu
            20                  25                  30

<210> SEQ ID NO 339
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 339

Ser Glu Thr Arg Pro Thr Glu Ala Gly Gln Trp Asn Cys Ser Gly Pro
1               5                   10                  15

Pro Thr Phe Glu Cys Trp Trp Tyr Asp Ile Glu Pro Thr Glu
            20                  25                  30

<210> SEQ ID NO 340
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 340

Ser Glu Thr Arg Pro Thr Glu Ala Gly Ser Trp Tyr Cys Ser Gly Pro
1               5                   10                  15
```

Pro Thr Phe Glu Cys Trp Trp Phe Glu Thr Glu Pro Thr Glu
            20                  25                  30

<210> SEQ ID NO 341
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 341

Ser Glu Thr Arg Pro Thr Glu Ala Gly Ser Phe Val Cys Ser Gly Pro
1               5                   10                  15

Pro Thr Phe Glu Cys Trp Gly Tyr Val Thr Glu Pro Thr Glu
            20                  25                  30

<210> SEQ ID NO 342
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 342

Ser Glu Thr Arg Pro Thr Gln Asp Gly Thr Trp Phe Cys Ser Gly Pro
1               5                   10                  15

Pro Thr Phe Glu Cys Trp Trp Tyr Gly Thr Glu Pro Thr Glu
            20                  25                  30

<210> SEQ ID NO 343
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 343

Ser Glu Thr Arg Pro Thr Glu Gly Asp Ser Trp His Cys Ala Gly Pro
1               5                   10                  15

Pro Thr Phe Glu Cys Trp Trp Tyr Gly Thr Glu Pro Thr Glu
            20                  25                  30

<210> SEQ ID NO 344
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 344

Ser Glu Thr Arg Pro Thr Glu Ala Gly Ser Trp Ser Cys Ser Gly Pro
1               5                   10                  15

Pro Thr Phe Glu Cys Trp Ser Tyr Gly Thr Glu Pro Thr Glu
            20                  25                  30

<210> SEQ ID NO 345
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 345

Ser Glu Thr Arg Pro Thr Glu Ala Gly Arg Ile Gln Cys Ser Gly Pro
1               5                   10                  15

Pro Thr Phe Glu Cys Trp Trp Tyr Asp Glu Glu Pro Thr Glu
            20                  25                  30

<210> SEQ ID NO 346
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 346

Ser Glu Thr Arg Pro Thr Glu Ala Gly Thr Ile Val Cys Lys Gly Pro
1               5                   10                  15

Pro Trp Phe Ser Cys Glu Ile Tyr Glu Thr Glu Pro Thr Glu
            20                  25                  30

<210> SEQ ID NO 347
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 347

Ser Glu Thr Arg Pro Thr Glu Ala Gly Asp Trp Tyr Cys Ser Gly Pro
1               5                   10                  15

Pro Ala Phe Glu Cys Trp Glu Tyr Leu Gly Glu Pro Thr Glu
            20                  25                  30

<210> SEQ ID NO 348
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 348

Ser Glu Thr Arg Pro Thr Glu Ala Gly Ser Trp Phe Cys Ser Gly Pro
1               5                   10                  15

Pro Ser Phe Glu Cys Trp Ser Tyr Val Thr Glu Pro Thr Glu
            20                  25                  30

<210> SEQ ID NO 349
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 349

Ser Glu Thr Arg Pro Thr Glu Ala Gly Ser Trp His Cys Ser Gly Pro
1               5                   10                  15

Pro Ala Phe Glu Cys Trp Trp Tyr Asp Asn Glu Pro Thr Glu
            20                  25                  30

<210> SEQ ID NO 350
<211> LENGTH: 30
<212> TYPE: PRT

<213> ORGANISM: Artificial Sequence
<220> FEATURE:
<223> OTHER INFORMATION: Synthetically generated cMet-binding peptide
      sequence

<400> SEQUENCE: 350

Ser Glu Thr Arg Pro Thr Glu Ala Gly Arg Trp Thr Cys Ser Gly Pro
1               5                   10                  15

Pro Thr Phe Glu Cys Trp Trp Tyr Val Ser Asp Pro Thr Glu
            20                  25                  30

<210> SEQ ID NO 351
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 351

Ser Glu Thr Arg Pro Thr Glu Ala Gly Glu Trp Tyr Cys Gly Gly Pro
1               5                   10                  15

Pro Thr Phe Glu Cys Trp Trp Phe Asp Thr Ala Pro Thr Glu
            20                  25                  30

<210> SEQ ID NO 352
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 352

Ser Glu Thr Arg Pro Thr Glu Ala Gly Ser Trp His Cys Ser Gly Pro
1               5                   10                  15

Pro Ser Phe Glu Cys Trp Trp Phe Asp Thr Gly Pro Thr Glu
            20                  25                  30

<210> SEQ ID NO 353
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 353

Ser Glu Thr Arg Pro Thr Glu Ala Gly Ser Phe Ile Cys Ser Gly Pro
1               5                   10                  15

Pro Thr Phe Glu Cys Trp Trp Tyr Gly Thr Glu Pro Thr Glu
            20                  25                  30

<210> SEQ ID NO 354
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 354

Ser Glu Thr Arg Pro Thr Glu Asp Val Arg Trp Tyr Cys Ser Gly Pro
1               5                   10                  15

Pro Thr Phe Glu Cys Trp Trp Phe Gly Thr Glu Pro Thr Glu
            20                  25                  30

<210> SEQ ID NO 355
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 355

Ser Glu Thr Arg Pro Thr Glu Ala Gly Ser Trp Tyr Cys Ser Gly Pro
1               5                   10                  15

Pro Thr Phe Glu Cys Trp Trp Tyr Val Pro Glu Pro Thr Glu
            20                  25                  30

<210> SEQ ID NO 356
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 356

Ser Glu Thr Arg Pro Thr Glu Ala Gly Asn Trp Leu Cys Ser Gly Pro
1               5                   10                  15

Pro Ala Phe Glu Cys Trp Trp Phe Val Ala Glu Pro Thr Glu
            20                  25                  30

<210> SEQ ID NO 357
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 357

Ser Glu Thr Arg Pro Thr Glu Ala Gly Ser Trp Tyr Cys Ser Gly Pro
1               5                   10                  15

Pro Thr Phe Glu Cys Trp Trp Tyr Gly Thr Glu Pro Thr Glu
            20                  25                  30

<210> SEQ ID NO 358
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 358

Ser Glu Thr Arg Pro Thr Glu Ala Gly Asp Trp Leu Cys Ala Gly Pro
1               5                   10                  15

Pro Thr Phe Glu Cys Trp Trp Trp Gly Thr Asp Pro Thr Glu
            20                  25                  30

<210> SEQ ID NO 359
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 359

-continued

```
Ser Glu Thr Arg Pro Thr Glu Ala Gly Ser Trp His Cys Val Gly Pro
1               5                   10                  15

Pro Thr Phe Glu Cys Trp Trp Phe Asp Thr Glu Pro Thr Glu
            20                  25                  30

<210> SEQ ID NO 360
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 360

Ser Glu Thr Arg Pro Thr Glu Ala Gly Glu Trp Ser Cys Ser Gly Pro
1               5                   10                  15

Pro Thr Phe Glu Cys Trp Trp Trp Asp Met Glu Pro Thr Glu
            20                  25                  30

<210> SEQ ID NO 361
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 361

Ser Glu Thr Arg Pro Thr Tyr Tyr Val Ser Trp Tyr Cys Ser Gly Pro
1               5                   10                  15

Pro Thr Phe Glu Cys Trp Ser Tyr Gly Thr Glu Pro Thr Glu
            20                  25                  30

<210> SEQ ID NO 362
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 362

Ser Glu Thr Arg Pro Thr Glu Asp Gly Ser Trp Tyr Cys Ser Gly Pro
1               5                   10                  15

Pro Thr Phe Glu Cys Trp Trp Tyr Gly Thr Glu Pro Thr Glu
            20                  25                  30

<210> SEQ ID NO 363
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 363

Ser Glu Thr Arg Pro Thr Glu Asp Gly Thr Trp Tyr Cys Ser Gly Pro
1               5                   10                  15

Pro Thr Phe Glu Cys Trp Trp Tyr Gly Thr Glu Pro Thr Glu
            20                  25                  30

<210> SEQ ID NO 364
<211> LENGTH: 30
<212> TYPE: PRT
<213> ORGANISM: Artificial Sequence
<220> FEATURE:
```

<223> OTHER INFORMATION: Synthetically generated cMet-binding peptide
      sequence

<400> SEQUENCE: 364

Ser Glu Thr Arg Pro Thr Glu Thr Asp Ser Trp Val Cys Ser Gly Pro
1               5                   10                  15

Pro Thr Phe Glu Cys Trp Trp Tyr Gly Thr Glu Pro Thr Glu
            20                  25                  30

<210> SEQ ID NO 365
<211> LENGTH: 20
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 365

Gly Ser Trp Arg Phe Cys Gly Gly Glu Tyr Ser Phe Gln Val Cys Gln
1               5                   10                  15

Asp Val Ala Pro
            20

<210> SEQ ID NO 366
<211> LENGTH: 20
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 366

Gly Ser His His Thr Cys Leu Asp Gly Phe Ala Gly Trp Arg Cys Thr
1               5                   10                  15

Glu Val Ala Pro
            20

<210> SEQ ID NO 367
<211> LENGTH: 20
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 367

Gly Ser Phe Ala Pro Cys Gly Trp Pro Ser Phe Ala Ile Asp Cys Ile
1               5                   10                  15

Ala Glu Ala Pro
            20

<210> SEQ ID NO 368
<211> LENGTH: 20
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 368

Gly Ser Thr Lys Val Cys His Glu Lys Trp Asn Gln Leu Phe Cys His
1               5                   10                  15

Asn Gln Ala Pro
            20

```
<210> SEQ ID NO 369
<211> LENGTH: 20
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 369

Gly Ser Pro Glu Met Cys Met Met Phe Pro Phe Leu Tyr Pro Cys Asn
1               5                   10                  15

His His Ala Pro
            20

<210> SEQ ID NO 370
<211> LENGTH: 20
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 370

Gly Ser Phe Phe Pro Cys Trp Arg Ile Asp Arg Phe Gly Tyr Cys His
1               5                   10                  15

Ala Asn Ala Pro
            20

<210> SEQ ID NO 371
<211> LENGTH: 21
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 371

Gly Ser Gln Gln Ile Cys Asp Arg Lys Glu Tyr Arg Phe Gln Ala Cys
1               5                   10                  15

Leu Ser Asp Ala Pro
            20

<210> SEQ ID NO 372
<211> LENGTH: 21
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 372

Gly Ser Thr Met Ser Cys Trp Arg Trp Gly Arg Asp Ala Tyr Ser Cys
1               5                   10                  15

Asn Gln Met Ala Pro
            20

<210> SEQ ID NO 373
<211> LENGTH: 21
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 373

Gly Ser Ser Gln Ile Cys Ala Val Tyr Leu Asp Asp Thr His Asn Cys
1               5                   10                  15
```

Glu Arg His Ala Pro
            20

<210> SEQ ID NO 374
<211> LENGTH: 20
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 374

Gly Ser Ser His Cys Asn Gln Met Ile Thr Pro Trp Gln Asn Cys Gly
1               5                   10                  15

Met Arg Ala Pro
            20

<210> SEQ ID NO 375
<211> LENGTH: 21
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 375

Gly Ser Ser Ala Arg Cys Asp Glu Leu Ile Asn Asp Phe His Ser Cys
1               5                   10                  15

Leu Val Met Ala Pro
            20

<210> SEQ ID NO 376
<211> LENGTH: 21
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 376

Gly Ser Arg Phe His Cys Trp Gln Gly Asp Leu Met Gln Thr Tyr Cys
1               5                   10                  15

Met Pro Met Ala Pro
            20

<210> SEQ ID NO 377
<211> LENGTH: 21
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 377

Gly Ser Gln Asn Asn Cys Glu Tyr Gly Ser Arg Gly Ser Ser Phe Cys
1               5                   10                  15

Leu Ala Met Ala Pro
            20

<210> SEQ ID NO 378
<211> LENGTH: 21
<212> TYPE: PRT
<213> ORGANISM: Artificial Sequence
<220> FEATURE:
<223> OTHER INFORMATION: Synthetically generated cMet-binding peptide
      sequence

```
<400> SEQUENCE: 378

Gly Ser Met Asn Met Cys Asp Thr Thr Asp Glu Ile Ser Pro Thr Cys
1               5                   10                  15

His Pro Ser Ala Pro
            20

<210> SEQ ID NO 379
<211> LENGTH: 21
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 379

Gly Ser Met Leu Gly Cys Leu Phe Glu His Gln Asn Lys Tyr Asp Cys
1               5                   10                  15

Tyr Val Leu Ala Pro
            20

<210> SEQ ID NO 380
<211> LENGTH: 21
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 380

Gly Ser Leu Tyr Arg Cys Leu Gly Glu Ala Ser Pro Thr Pro Pro Cys
1               5                   10                  15

Ala Tyr Glu Ala Pro
            20

<210> SEQ ID NO 381
<211> LENGTH: 21
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 381

Gly Ser Gly Met Gly Cys His Gln Val Asn Ile Ser Thr Gly Asp Cys
1               5                   10                  15

Ala Glu Asp Ala Pro
            20

<210> SEQ ID NO 382
<211> LENGTH: 21
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 382

Gly Ser Gly Asp Pro Cys Ser Pro Gly Pro Ser Ile Asn Gly His Cys
1               5                   10                  15

Ser Val Met Ala Pro
            20

<210> SEQ ID NO 383
<211> LENGTH: 21
```

```
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 383

Gly Ser Phe Trp Asn Cys Thr Thr Asp Leu Gly Ala Met Ser Asp Cys
1               5                   10                  15

Gly Phe Phe Ala Pro
            20

<210> SEQ ID NO 384
<211> LENGTH: 21
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 384

Gly Ser Phe Thr Ala Cys Asn Lys Thr Ser Thr Thr Arg Gln Pro Cys
1               5                   10                  15

Asn Pro Tyr Ala Pro
            20

<210> SEQ ID NO 385
<211> LENGTH: 21
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 385

Gly Ser Glu Leu Phe Cys Phe Tyr His His Gln Gly Tyr Glu Gly Cys
1               5                   10                  15

Asp Val Leu Ala Pro
            20

<210> SEQ ID NO 386
<211> LENGTH: 21
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 386

Gly Ser Asp Met Asn Cys Thr Val Leu Ala Gln Asp Gln Ile Phe Cys
1               5                   10                  15

Phe Arg Glu Ala Pro
            20

<210> SEQ ID NO 387
<211> LENGTH: 21
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 387

Gly Ser Ala Gly Trp Cys Tyr Thr Met Asn Tyr Val Asp Gln Leu Cys
1               5                   10                  15

Thr Tyr Met Ala Pro
```

<210> SEQ ID NO 388
<211> LENGTH: 30
<212> TYPE: PRT
<213> ORGANISM: Artificial Sequence
<220> FEATURE:
<223> OTHER INFORMATION: Synthetically generated cMet-binding peptide sequence

<400> SEQUENCE: 388

Ser Glu Thr Arg Pro Thr Glu Ala Gly Met Cys Ala Cys Arg Gly Pro
1               5                   10                  15

Pro Ala Phe Val Cys Gln Trp Tyr Gly Ser Glu Pro Thr Glu
            20                  25                  30

<210> SEQ ID NO 389
<211> LENGTH: 30
<212> TYPE: PRT
<213> ORGANISM: Artificial Sequence
<220> FEATURE:
<223> OTHER INFORMATION: Synthetically generated cMet-binding peptide sequence

<400> SEQUENCE: 389

Ser Glu Thr Arg Pro Thr Glu Ala Gly Ser Cys His Cys Ser Gly Pro
1               5                   10                  15

Pro Thr Phe Glu Cys Trp Ser Tyr Val Thr Glu Pro Thr Glu
            20                  25                  30

<210> SEQ ID NO 390
<211> LENGTH: 22
<212> TYPE: PRT
<213> ORGANISM: Artificial Sequence
<220> FEATURE:
<223> OTHER INFORMATION: Synthetically generated cMet-binding peptide sequence

<400> SEQUENCE: 390

Gly Asp Tyr Asp Tyr Cys Asp Phe Asp Leu Glu Thr Tyr Ile Pro Glu
1               5                   10                  15

Cys His Ser Tyr Asp Pro
            20

<210> SEQ ID NO 391
<211> LENGTH: 22
<212> TYPE: PRT
<213> ORGANISM: Artificial Sequence
<220> FEATURE:
<223> OTHER INFORMATION: Synthetically generated cMet-binding peptide sequence

<400> SEQUENCE: 391

Gly Asp Asp Phe His Cys Glu Phe Ile Asp Asp Tyr Gln Ser Glu Ile
1               5                   10                  15

Cys Tyr Phe Asn Asp Pro
            20

<210> SEQ ID NO 392
<211> LENGTH: 22
<212> TYPE: PRT
<213> ORGANISM: Artificial Sequence
<220> FEATURE:
<223> OTHER INFORMATION: Synthetically generated cMet-binding peptide sequence

<400> SEQUENCE: 392

-continued

```
Gly Asp Leu Leu Val Cys Lys Phe Asp Lys Phe Trp Thr Glu Thr
1               5                   10                  15

Cys Glu Trp Ala Asp Pro
            20

<210> SEQ ID NO 393
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 393

Gly Asp Ser Tyr Asn Cys Ser Trp Asp Ser Lys Thr Phe Glu Val Thr
1               5                   10                  15

Cys Leu Tyr Ala Asp Pro
            20

<210> SEQ ID NO 394
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 394

Gly Asp Ala Ser Trp Cys Asp Glu Asn Ser Pro Ala Ala Trp Phe Tyr
1               5                   10                  15

Cys Glu Leu Trp Asp Pro
            20

<210> SEQ ID NO 395
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 395

Gly Asp Leu Leu Gly Cys Gly Tyr Gln Glu Lys Gly Gly Glu Tyr Lys
1               5                   10                  15

Cys Arg Phe Asn Asp Pro
            20

<210> SEQ ID NO 396
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 396

Gly Asp Pro Trp Trp Cys Phe Glu Lys Asp Ser Phe Ile Pro Phe Ala
1               5                   10                  15

Cys Trp His His Asp Pro
            20

<210> SEQ ID NO 397
<211> LENGTH: 22
<212> TYPE: PRT
<213> ORGANISM: Artificial Sequence
```

```
<220> FEATURE:
<223> OTHER INFORMATION: Synthetically generated cMet-binding peptide
      sequence

<400> SEQUENCE: 397

Gly Asp Tyr Tyr Gln Cys Gln Phe Ser Lys Asp Met Tyr Ser Glu Arg
1               5                   10                  15

Cys Trp Pro Tyr Asp Pro
            20

<210> SEQ ID NO 398
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 398

Gly Asp Asn Arg Phe Cys Ser Trp Val Tyr Asn Val Asp Asp Trp Trp
1               5                   10                  15

Cys Val Asp Asn Asp Pro
            20

<210> SEQ ID NO 399
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 399

Gly Asp Tyr Ser Glu Cys Phe Phe Glu Pro Asp Ser Phe Glu Val Lys
1               5                   10                  15

Cys Tyr Asp Arg Asp Pro
            20

<210> SEQ ID NO 400
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 400

Gly Asp Tyr Arg Met Cys Gln Ile Ser Asp Met Trp Gly Asn Tyr Glu
1               5                   10                  15

Cys Ser Ser Asp Asp Pro
            20

<210> SEQ ID NO 401
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 401

Gly Asp Pro Asp Glu Cys Gln Leu Asn Arg Glu Thr Phe Glu Val Trp
1               5                   10                  15

Cys Pro Trp His Asp Pro
            20
```

```
<210> SEQ ID NO 402
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 402

Gly Asp His Arg Lys Cys Glu Ile Ser Ala Lys Thr His Glu Val Thr
1               5                   10                  15

Cys Tyr Asp Asn Asp Pro
            20

<210> SEQ ID NO 403
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 403

Gly Asp His Leu Thr Cys Glu Phe Arg Asp Asp Gly Trp Lys Glu His
1               5                   10                  15

Cys Trp Trp Ser Asp Pro
            20

<210> SEQ ID NO 404
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 404

Gly Asp Ala Ser Met Cys Tyr Asp Gly Leu Ala Leu Arg Trp Asp Gln
1               5                   10                  15

Cys Trp Pro His Asp Pro
            20

<210> SEQ ID NO 405
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 405

Ser Glu Thr Arg Pro Thr Glu Ala Gly Ser Cys His Cys Ser Gly Pro
1               5                   10                  15

Pro Thr Phe Gln Cys Trp Cys Tyr Glu Val Pro Thr Glu
            20                  25                  30

<210> SEQ ID NO 406
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 406

Ser Glu Thr Arg Pro Thr Glu Ala Gly Ser Cys His Cys Ser Gly Pro
1               5                   10                  15
```

```
                1               5                  10                  15
Pro Thr Phe Glu Cys Trp Cys Tyr Gly Thr Glu Pro Thr Glu
            20                  25                  30

<210> SEQ ID NO 407
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 407

Ser Glu Thr Arg Pro Thr Gly Glu Ser Asp Cys His Cys Ser Gly Pro
1               5                  10                  15
Pro Thr Phe Glu Cys Tyr Cys Tyr Gly Thr Glu Pro Thr Glu
            20                  25                  30

<210> SEQ ID NO 408
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 408

Ser Glu Thr Arg Pro Thr Glu Ser Gly Asn Cys Tyr Cys Ser Gly Pro
1               5                  10                  15
Pro Trp Phe Glu Cys Trp Cys Tyr Gly Thr Glu Pro Thr Glu
            20                  25                  30

<210> SEQ ID NO 409
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 409

Ser Glu Thr Arg Pro Thr Glu Ala Gly Ala Cys Arg Cys Ser Gly Pro
1               5                  10                  15
Pro Thr Phe Glu Cys Tyr Cys Tyr Asp Met Ala Pro Thr Glu
            20                  25                  30

<210> SEQ ID NO 410
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 410

Ser Glu Thr Arg Pro Thr Glu Ala Gly Ser Cys Tyr Cys Ser Gly Pro
1               5                  10                  15
Pro Arg Phe Glu Cys Trp Cys Tyr Glu Thr Glu Pro Thr Glu
            20                  25                  30

<210> SEQ ID NO 411
<211> LENGTH: 30
<212> TYPE: PRT
<213> ORGANISM: Artificial Sequence
<220> FEATURE:
<223> OTHER INFORMATION: Synthetically generated cMet-binding peptide
``` sequence

<400> SEQUENCE: 411

Ser Glu Thr Arg Pro Thr Glu Ala Gly Ser Cys His Cys Ser Gly Pro
1               5                   10                  15

Pro Ser Phe Glu Cys Trp Cys Phe Gly Thr Glu Pro Thr Glu
            20                  25                  30

<210> SEQ ID NO 412
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 412

Ser Glu Thr Arg Pro Thr Val Ser Val Ser Cys Ser Cys Gly Gly Pro
1               5                   10                  15

Pro Thr Phe Glu Cys Trp Cys Phe Gly Thr Glu Pro Thr Glu
            20                  25                  30

<210> SEQ ID NO 413
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 413

Ser Glu Thr Arg Pro Thr Glu Ala Gly Ser Cys His Cys Asn Gly Pro
1               5                   10                  15

Pro Thr Phe Glu Cys Phe Cys Phe Gly Thr Glu Pro Thr Glu
            20                  25                  30

<210> SEQ ID NO 414
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 414

Ser Glu Thr Arg Pro Thr Glu Ala Gly Ser Cys Tyr Cys Gly Gly Pro
1               5                   10                  15

Pro Ser Phe Glu Cys Trp Cys Tyr Gly Thr Glu Pro Thr Glu
            20                  25                  30

<210> SEQ ID NO 415
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 415

Ser Glu Thr Arg Pro Thr Glu Ala Gly Ser Cys His Cys Ser Gly Pro
1               5                   10                  15

Pro Thr Phe Glu Cys Trp Cys Tyr Gly Ser Asn Pro Thr Glu
            20                  25                  30

<210> SEQ ID NO 416

-continued

```
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 416

Ser Glu Thr Arg Pro Thr Glu Ala Gly Ser Cys His Cys Ser Gly Pro
1               5                   10                  15

Pro Ala Phe Glu Cys Trp Cys Tyr Arg Ala Glu Pro Thr Glu
            20                  25                  30

<210> SEQ ID NO 417
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 417

Ser Glu Thr Arg Pro Thr Glu Ala Gly Ser Cys Asp Cys Ser Gly Pro
1               5                   10                  15

Pro Thr Phe Glu Cys Trp Cys Phe Gly Thr Glu Pro Thr Glu
            20                  25                  30

<210> SEQ ID NO 418
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 418

Ser Glu Thr Arg Pro Thr Glu Ala Gly Lys Cys His Cys Gly Gly Pro
1               5                   10                  15

Pro Ser Phe Glu Cys Trp Cys Tyr Ala Thr Glu Pro Thr Glu
            20                  25                  30

<210> SEQ ID NO 419
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 419

Ser Glu Thr Arg Pro Thr Glu Ala Gly Lys Cys His Cys Ser Gly Pro
1               5                   10                  15

Pro Thr Phe Glu Cys Thr Cys Tyr His Thr Asp Pro Thr Glu
            20                  25                  30

<210> SEQ ID NO 420
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 420

Ser Glu Thr Arg Pro Thr Glu Ala Gly Phe Cys Gln Cys Ser Gly Pro
1               5                   10                  15
```

Pro Ala Phe Glu Cys Trp Cys Tyr Asp Thr Glu Pro Thr Glu
            20                  25                  30

<210> SEQ ID NO 421
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 421

Ser Glu Thr Arg Pro Thr Glu Ala Val Ser Cys Glu Cys Lys Gly Pro
1               5                   10                  15

Pro Thr Phe Glu Cys Trp Cys Phe Gly Thr Glu Pro Thr Glu
            20                  25                  30

<210> SEQ ID NO 422
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 422

Ser Glu Thr Arg Pro Thr Glu Ala Gly Asp Cys His Cys Ser Gly Pro
1               5                   10                  15

Pro Thr Phe Glu Cys Trp Cys Tyr Gly Thr Glu Pro Thr Glu
            20                  25                  30

<210> SEQ ID NO 423
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 423

Ser Glu Thr Arg Pro Thr Glu Ala Gly Ala Cys Asp Cys Ile Gly Pro
1               5                   10                  15

Pro Thr Phe Glu Cys Trp Cys Tyr Asp Thr Tyr Pro Thr Glu
            20                  25                  30

<210> SEQ ID NO 424
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 424

Ser Glu Thr Arg Pro Thr Glu Ala Gly Asn Cys Leu Cys Ser Gly Pro
1               5                   10                  15

Pro Thr Phe Glu Cys Ala Cys Tyr His Ser Glu Pro Thr Glu
            20                  25                  30

<210> SEQ ID NO 425
<211> LENGTH: 30
<212> TYPE: PRT
<213> ORGANISM: Artificial Sequence
<220> FEATURE:
<223> OTHER INFORMATION: Synthetically generated cMet-binding peptide
      sequence -continued

```
<400> SEQUENCE: 425

Ser Glu Thr Arg Pro Thr Glu Ala Gly Ser Cys His Cys Ser Gly Pro
1               5                   10                  15

Pro Thr Phe Gln Cys Trp Cys Tyr Ser Thr Glu Pro Thr Glu
            20                  25                  30

<210> SEQ ID NO 426
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 426

Ser Glu Thr Arg Pro Thr Glu Ala Gly Ile Cys His Cys Ser Gly Pro
1               5                   10                  15

Pro Thr Phe Glu Cys Trp Cys Tyr Ala Thr Glu Pro Thr Glu
            20                  25                  30

<210> SEQ ID NO 427
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 427

Ser Glu Thr Arg Pro Thr Glu Glu Gly Ser Cys His Cys Ser Gly Pro
1               5                   10                  15

Pro Thr Phe Glu Cys Trp Cys Phe Gly Thr Glu Pro Thr Glu
            20                  25                  30

<210> SEQ ID NO 428
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 428

Ser Glu Thr Arg Pro Thr Glu Ala Gly Ile Cys Asn Cys Ser Gly Pro
1               5                   10                  15

Pro Thr Phe Glu Cys Trp Cys Tyr Ser Met Gly Pro Thr Glu
            20                  25                  30

<210> SEQ ID NO 429
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 429

Ser Glu Thr Arg Pro Thr Gln Gly Gly Asn Cys His Cys Ser Gly Pro
1               5                   10                  15

Pro Thr Phe Glu Cys Trp Cys Tyr Gly Thr Glu Pro Thr Glu
            20                  25                  30

<210> SEQ ID NO 430
<211> LENGTH: 30
<212> TYPE: PRT
```

```
<213> ORGANISM: Artificial Sequence
<220> FEATURE:
<223> OTHER INFORMATION: Synthetically generated cMet-binding peptide
      sequence

<400> SEQUENCE: 430

Ser Glu Thr Arg Pro Thr Glu Ala Gly Ser Cys Asn Cys Ser Gly Pro
 1               5                  10                  15

Pro Thr Phe Glu Cys Tyr Cys Tyr Thr Leu Asp Pro Thr Glu
            20                  25                  30

<210> SEQ ID NO 431
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 431

Ser Glu Thr Arg Pro Thr Asp Asn Gly Ser Cys Gln Cys Ser Gly Pro
 1               5                  10                  15

Pro Thr Phe Glu Cys Trp Cys Phe Gly Thr Glu Pro Thr Glu
            20                  25                  30

<210> SEQ ID NO 432
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 432

Ser Glu Thr Arg Pro Thr Glu Ser Gly Ser Cys His Cys Ser Gly Pro
 1               5                  10                  15

Pro Thr Phe Glu Cys Trp Cys Tyr Gly Thr Glu Pro Thr Glu
            20                  25                  30

<210> SEQ ID NO 433
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 433

Ser Glu Thr Arg Pro Thr Glu Ala Gly Ser Cys Asn Cys Ser Gly Pro
 1               5                  10                  15

Pro Ser Phe Glu Cys Trp Cys Tyr Val Thr Glu Pro Thr Glu
            20                  25                  30

<210> SEQ ID NO 434
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 434

Ser Glu Thr Arg Pro Thr Glu Gly Gly Ser Cys Tyr Cys Gly Gly Pro
 1               5                  10                  15

Pro Thr Phe Glu Cys Trp Cys Tyr Gly Thr Glu Pro Thr Glu
            20                  25                  30
```

<210> SEQ ID NO 435
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 435

Ser Glu Thr Arg Pro Thr Glu Ala Gly Arg Cys His Cys Ser Gly Pro
1               5                   10                  15

Pro Thr Phe Glu Cys Trp Cys Tyr Val Gln Glu Pro Thr Glu
            20                  25                  30

<210> SEQ ID NO 436
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 436

Ser Glu Thr Arg Pro Thr Glu Ser Gly Ser Cys Leu Cys Ser Gly Pro
1               5                   10                  15

Pro Gln Phe Glu Cys Trp Cys Tyr Gly Thr Glu Pro Thr Glu
            20                  25                  30

<210> SEQ ID NO 437
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 437

Ser Glu Thr Arg Pro Thr Glu Thr Asp Ser Cys His Cys Ile Gly Pro
1               5                   10                  15

Pro Thr Phe Glu Cys Trp Cys Tyr Gly Thr Glu Pro Thr Glu
            20                  25                  30

<210> SEQ ID NO 438
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 438

Ser Glu Thr Arg Pro Thr Glu Ala Gly Phe Cys Arg Cys Ser Gly Pro
1               5                   10                  15

Pro Thr Phe Glu Cys Trp Cys Tyr Asp Thr Glu Pro Thr Glu
            20                  25                  30

<210> SEQ ID NO 439
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 439

```
Ser Glu Thr Arg Pro Thr Glu His Gly Ser Cys Asn Cys Tyr Gly Pro
1               5                   10                  15

Pro Thr Phe Glu Cys Trp Cys Tyr Gly Thr Glu Pro Thr Glu
            20                  25                  30

<210> SEQ ID NO 440
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 440

Ser Glu Thr Arg Pro Thr Ala Leu Gly Gly Cys Leu Cys Ser Gly Pro
1               5                   10                  15

Pro Thr Phe Glu Cys Trp Cys Tyr Gly Thr Glu Pro Thr Glu
            20                  25                  30

<210> SEQ ID NO 441
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 441

Ser Glu Thr Arg Pro Thr Glu Gly Gly Ser Cys Glu Cys Ser Gly Pro
1               5                   10                  15

Pro Thr Phe Glu Cys Trp Cys Tyr Gly Thr Glu Pro Thr Glu
            20                  25                  30

<210> SEQ ID NO 442
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 442

Ser Glu Thr Arg Pro Thr Glu Glu Gly Ser Cys His Cys Ser Gly Pro
1               5                   10                  15

Pro Ala Phe Glu Cys Trp Cys Tyr Gly Thr Glu Pro Thr Glu
            20                  25                  30

<210> SEQ ID NO 443
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 443

Ser Glu Thr Arg Pro Thr Glu Ala Gly Thr Cys Tyr Cys Ser Gly Pro
1               5                   10                  15

Pro Thr Phe Glu Cys Trp Cys Tyr Gly Thr Glu Pro Thr Glu
            20                  25                  30

<210> SEQ ID NO 444
<211> LENGTH: 30
<212> TYPE: PRT
<213> ORGANISM: Artificial Sequence
<220> FEATURE:
```

<223> OTHER INFORMATION: Synthetically generated cMet-binding peptide
      sequence

<400> SEQUENCE: 444

Ser Glu Thr Arg Pro Thr Glu Asp Gly Ser Cys His Cys Ser Gly Pro
1               5                   10                  15

Pro Arg Phe Glu Cys Trp Cys Tyr Gly Thr Glu Pro Thr Glu
            20                  25                  30

<210> SEQ ID NO 445
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 445

Ser Glu Thr Arg Pro Thr Glu Ala Gly Ser Cys His Cys Ser Gly Pro
1               5                   10                  15

Pro Thr Phe Glu Cys Trp Cys Tyr Ser Thr Glu Pro Thr Glu
            20                  25                  30

<210> SEQ ID NO 446
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 446

Ser Glu Thr Arg Pro Thr Glu Ala Gly Ser Cys Tyr Cys Ser Gly Pro
1               5                   10                  15

Pro Thr Phe Glu Cys Trp Cys Tyr Ala Glu Glu Pro Thr Glu
            20                  25                  30

<210> SEQ ID NO 447
<211> LENGTH: 30
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 447

Ser Glu Thr Arg Pro Thr Glu Ala Gly Ser Cys His Cys Ser Gly Pro
1               5                   10                  15

Pro Thr Phe Glu Cys Trp Cys Phe Glu Pro Glu Pro Thr Glu
            20                  25                  30

<210> SEQ ID NO 448
<211> LENGTH: 28
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 448

Ser Glu Tyr Pro Thr Trp Val Ser Lys Glu Phe His Glu Cys Ala Gly
1               5                   10                  15

Glu Leu Val Ala Met Gln Gly Gly Ser Gly Thr Glu
            20                  25

```
<210> SEQ ID NO 449
<211> LENGTH: 21
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 449

Ala Gln Gln Ala Ser Arg Phe Thr Phe Thr Asp Gly Asp Ser Tyr Trp
1               5                   10                  15

Trp Phe Glu Asp Phe
            20

<210> SEQ ID NO 450
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 450

Ala Gln Ile Gln Gly Ile Gln Lys Thr Glu Gln Gly Glu Phe Tyr Trp
1               5                   10                  15

Phe Asn Trp Phe Pro Ala
            20

<210> SEQ ID NO 451
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 451

Ala Gln Arg Glu Val Glu Glu Pro Tyr Trp Tyr Leu Asp Phe Leu Ser
1               5                   10                  15

Ser Trp Arg Met His Glu
            20

<210> SEQ ID NO 452
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 452

Ala Gln Arg Pro Glu Ala His Tyr Lys Leu Ala Met Ser Tyr Pro Ile
1               5                   10                  15

Ile Pro Arg Thr Lys Thr
            20

<210> SEQ ID NO 453
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 453

Ala Gln Arg Trp Ser Ser Pro Gly Met Ser Gln Ser Phe Val Leu Glu
1               5                   10                  15
```

Trp Lys Trp Asn Asp Asn
            20

<210> SEQ ID NO 454
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 454

Ala Gln Tyr Asp Thr Trp Val Phe Gln Phe Ile His Glu Val Pro Gly
1               5                   10                  15

Glu Leu Val Ala Met Gln
            20

<210> SEQ ID NO 455
<211> LENGTH: 20
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 455

Ala Gln Met Tyr Gln Thr Pro Asp Gly Val Ile Gly Lys Phe Val Asp
1               5                   10                  15

Trp Met Phe Asn
            20

<210> SEQ ID NO 456
<211> LENGTH: 20
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 456

Ala Gln Val Gly Ser Pro Met Leu Pro Ser Trp Phe Ser Phe Glu Ala
1               5                   10                  15

Asn Trp Ser Ser
            20

<210> SEQ ID NO 457
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 457

Ala Gln Asn Ala Val Val Pro Pro Pro Met Leu Trp Ser Ile Tyr Trp
1               5                   10                  15

Asp Tyr Gly Arg Glu Gly
            20

<210> SEQ ID NO 458
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 458

Ala Gln Pro Tyr Tyr Glu Leu Gln Asp Ala Asp Met Leu Leu Val Val
1               5                   10                  15

Ala Leu Leu Ser Thr Gly
            20

<210> SEQ ID NO 459
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 459

Ala Gln Val Gly Thr Ala Glu Ala Ile Met Phe Ser Asp Val Glu Asp
1               5                   10                  15

Thr Gly Val His Lys Phe
            20

<210> SEQ ID NO 460
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 460

Ala Gln Phe Pro Leu Glu Phe Asp Val Pro Asn Phe Ser Tyr His Trp
1               5                   10                  15

Leu Val Ser Phe Asn Pro
            20

<210> SEQ ID NO 461
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 461

Ala Gln Asp Leu Lys Pro Trp Thr Ala Gly Trp Glu Pro Pro Trp Leu
1               5                   10                  15

Trp Thr Asp Arg Gly Pro
            20

<210> SEQ ID NO 462
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 462

Ala Gln His Gln Tyr Gly Gln Met Met Val Leu His Ile Gln Tyr Asp
1               5                   10                  15

Met Gly Glu Phe Ile Pro
            20

<210> SEQ ID NO 463
<211> LENGTH: 22

```
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 463

Ala Gln Ser Pro Tyr Ile Phe Pro Ile Asp Asp Ser Gly Arg Gln Ile
1               5                   10                  15

Phe Val Ile Gln Trp Gly
            20

<210> SEQ ID NO 464
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 464

Ala Gln Val Pro Asp Trp Leu Ser Ala Val Val Ile Glu Lys Leu Ile
1               5                   10                  15

Glu Tyr Gly Met Met Val
            20

<210> SEQ ID NO 465
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 465

Ala Gln Phe Asp Arg Tyr Trp His Phe Ala Trp Met Asp Val Ser Phe
1               5                   10                  15

Ser Ser Gly Gln Ser Gly
            20

<210> SEQ ID NO 466
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 466

Ala Gln Lys Glu Thr Trp Glu Phe Phe Asp Ile Val Tyr Gly Ser Gly
1               5                   10                  15

Trp Lys Phe Asn Ser Pro
            20

<210> SEQ ID NO 467
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 467

Ala Gln His Ser Val Gln Arg Gln Met Asp Val Trp Met Pro Val Gln
1               5                   10                  15

Phe Met Ala Gly Phe Thr
```

20

<210> SEQ ID NO 468
<211> LENGTH: 21
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 468

Ala Gln Glu Trp Gln Thr Trp Thr Trp Asn Met Ile Glu Val Ile Ser
1               5                   10                  15

Glu Asn Lys Thr Pro
            20

<210> SEQ ID NO 469
<211> LENGTH: 20
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 469

Ala Gln Gly Phe Glu Leu Trp Val Asp His Thr Arg Asn Phe Phe Ile
1               5                   10                  15

Ala Ile Ser Pro
            20

<210> SEQ ID NO 470
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 470

Ala Gln Ala Tyr Glu Trp Trp Ala Asp Glu Ser Ile Phe Asn His Gly
1               5                   10                  15

Tyr Tyr Trp Gly His Gln
            20

<210> SEQ ID NO 471
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 471

Ala Gln Asp Pro Gly Phe Ser Lys His Ser Met Gly His Gly Tyr Pro
1               5                   10                  15

Ser Lys Met Asn Trp Gly
            20

<210> SEQ ID NO 472
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 472

Ala Gln Glu Trp Glu Arg Glu Tyr Phe Val Asp Gly Phe Trp Gly Ser
1               5                   10                  15

Trp Phe Gly Ile Pro His
                20

<210> SEQ ID NO 473
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 473

Ala Gln Met Gly His His Trp Asp Val Gln Trp Asp Tyr Lys Leu Phe
1               5                   10                  15

His Val Ala Arg Gly Asp
                20

<210> SEQ ID NO 474
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 474

Ala Gln Glu Leu Phe Gln Ile Leu Glu Lys Gln Met Trp Ser Asp Phe
1               5                   10                  15

Met Glu Trp Ala Thr Pro
                20

<210> SEQ ID NO 475
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 475

Ala Gln His Trp Asp Tyr Asp Ser Gly Ser Asp Phe Trp Phe Pro Val
1               5                   10                  15

Phe Phe Leu Glu His His
                20

<210> SEQ ID NO 476
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 476

Ala Gln His Gly Tyr Leu Ser Pro Leu Lys Gly Tyr Gln Met Ser His
1               5                   10                  15

Val Glu Phe Trp Thr Tyr
                20

<210> SEQ ID NO 477
<211> LENGTH: 22
<212> TYPE: PRT
<213> ORGANISM: Artificial Sequence

```
<220> FEATURE:
<223> OTHER INFORMATION: Synthetically generated cMet-binding peptide
      sequence

<400> SEQUENCE: 477

Ala Gln Phe Ser Gly Leu Val Met Tyr Gly Arg Thr His Glu Val Gln
1               5                   10                  15

Trp Thr Phe Gly Ser Met
            20

<210> SEQ ID NO 478
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 478

Ala Gln Ala Glu Trp Val Ile Thr Ser Glu Glu Phe Tyr Trp Lys Met
1               5                   10                  15

Ala Asp Phe Gly Pro Pro
            20

<210> SEQ ID NO 479
<211> LENGTH: 19
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 479

Ala Gln Trp Pro His Asp Gly Leu Val His Trp Gly Glu Val Ile Met
1               5                   10                  15

Leu Arg Phe

<210> SEQ ID NO 480
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 480

Ala Gln Trp Asn Gln Trp Asp Glu Phe Met Trp Phe Leu Asn Pro Pro
1               5                   10                  15

Pro Ile Gly Leu Met Trp
            20

<210> SEQ ID NO 481
<211> LENGTH: 21
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 481

Ala Gln Asp Asn Thr Ala Asp Gln Met Phe Asn Gly Phe His Val Leu
1               5                   10                  15

Ala Met Tyr Met Val
            20
```

-continued

```
<210> SEQ ID NO 482
<211> LENGTH: 21
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 482

Ala Gln Ser Asp His Asp His Ala His Trp Gly Val Lys His Trp Pro
 1               5                  10                  15

Phe Arg Arg Tyr Gln
            20

<210> SEQ ID NO 483
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 483

Ala Gln Leu Phe Gln Tyr Leu Trp His Asp Asp Pro Gln Gly Ala Phe
 1               5                  10                  15

Phe Gln Leu Ser Met Trp
            20

<210> SEQ ID NO 484
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 484

Ala Gln His Val Val Thr Leu Thr Leu Ile Gln Met Pro Phe Ala Phe
 1               5                  10                  15

Asn Phe Glu Pro Arg Met
            20

<210> SEQ ID NO 485
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 485

Ala Gln Val Gly Glu Ser Leu Asp Asp Gly Trp Thr Phe Phe Ser Asp
 1               5                  10                  15

Lys Trp Phe Asp Phe Phe
            20

<210> SEQ ID NO 486
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 486

Ala Gln Phe Met Tyr Glu Lys Glu His Tyr Val Met Ser Ile Ser Leu
 1               5                  10                  15
```

Pro Gly Leu Trp Phe Tyr
            20

<210> SEQ ID NO 487
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 487

Ala Gln His Met Asp Pro Ala Glu Trp Asp Trp Phe Ile Arg Ile Tyr
 1               5                  10                  15

Ser Pro Val Val Asn Pro
            20

<210> SEQ ID NO 488
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 488

Ala Gln Met Trp His Arg Val His Asp Pro Gly Tyr Thr Phe Glu Val
 1               5                  10                  15

Thr Trp Leu Trp Asp Asn
            20

<210> SEQ ID NO 489
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 489

Ala Gln Trp Asn Trp Asp Met Gly Phe Met Trp Thr Thr Asp Ser Ala
 1               5                  10                  15

Gln Val Gln Pro Ser Met
            20

<210> SEQ ID NO 490
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 490

Ala Gln Lys Thr Trp Phe Leu Glu Ala Asp Leu Phe Gln Met Phe Gln
 1               5                  10                  15

Glu Val Thr Trp Gln Phe
            20

<210> SEQ ID NO 491
<211> LENGTH: 22
<212> TYPE: PRT
<213> ORGANISM: Artificial Sequence
<220> FEATURE:
<223> OTHER INFORMATION: Synthetically generated cMet-binding peptide
      sequence -continued

<400> SEQUENCE: 491

Ala Gln Trp Gly Ala Val Asp Asn Asp Trp Tyr Asp Trp Glu Met Glu
1               5                   10                  15

Gln Ile Trp Met Phe Glu
            20

<210> SEQ ID NO 492
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 492

Ala Gln Val Glu Asp Met Ala Thr Val His Phe Lys Phe Asn Pro Ala
1               5                   10                  15

Thr His Glu Val Ile Trp
            20

<210> SEQ ID NO 493
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 493

Ala Gln Arg Asp Tyr Leu Phe Tyr Trp Asn Asp Gly Ser Tyr Gln Pro
1               5                   10                  15

Trp Gln Val Phe Val Gly
            20

<210> SEQ ID NO 494
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 494

Ala Gln Gln Trp Met Phe Gln Ile His Gln Ser Met Ala Trp Pro Tyr
1               5                   10                  15

Glu Trp Ile Asp Ser Tyr
            20

<210> SEQ ID NO 495
<211> LENGTH: 22
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 495

Ala Gln Gly Ile Ala Trp Gln Leu Glu Trp Ser Tyr Met Pro Gln Ser
1               5                   10                  15

Pro Pro Ser Phe Asp Arg
            20

<210> SEQ ID NO 496
<211> LENGTH: 21

```
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 496

Ala Gln Gly Gly Arg Tyr Pro Phe Tyr Asp Thr Asp Trp Phe Lys Trp
1               5                   10                  15

Glu Met Tyr Val Leu
            20

<210> SEQ ID NO 497
<211> LENGTH: 28
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 497

Ser Glu Glu Asp Thr Trp Leu Phe Trp Gln Ile Ile Glu Val Pro Val
1               5                   10                  15

Gly Gln Val Leu Met Gln Gly Gly Ser Gly Thr Glu
            20                  25

<210> SEQ ID NO 498
<211> LENGTH: 28
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 498

Ser Glu Tyr Asp Thr Leu Leu Phe Gln Arg Thr Gly Glu Val Val Gly
1               5                   10                  15

Lys Leu Gly Ser Met Gln Gly Gly Ser Gly Thr Glu
            20                  25

<210> SEQ ID NO 499
<211> LENGTH: 28
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 499

Ser Glu Tyr Asp Thr Trp Val Phe Gln Phe Met Leu Glu Val Pro Gly
1               5                   10                  15

Ser Trp Met Ala Arg Leu Gly Gly Ser Gly Thr Glu
            20                  25

<210> SEQ ID NO 500
<211> LENGTH: 28
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 500

Ser Glu Tyr Asp Thr Trp Ile Phe Gln Phe Tyr Arg Glu Val Pro Gly
1               5                   10                  15

Val Pro Gly Ala Met Gln Gly Gly Ser Gly Thr Glu
```

<210> SEQ ID NO 501
<211> LENGTH: 28
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 501

Ser Glu Val Asp Thr Gly Val Gln Leu Leu Thr His Glu Gly Pro Gly
1               5                   10                  15

Glu Leu Val Ala Met Gln Gly Gly Ser Gly Thr Glu
            20                  25

<210> SEQ ID NO 502
<211> LENGTH: 28
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 502

Ser Glu Ser Asp Thr Trp Val Phe Gln Leu Ile His Glu Val Pro Ala
1               5                   10                  15

Ser Val Val Ala Met Gln Gly Gly Ser Gly Thr Glu
            20                  25

<210> SEQ ID NO 503
<211> LENGTH: 28
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 503

Ser Glu Tyr Asp Thr Trp Val Phe Gln Phe Arg His Gly Val Lys Ala
1               5                   10                  15

Gln Leu Val Ala Met Arg Gly Gly Ser Gly Thr Glu
            20                  25

<210> SEQ ID NO 504
<211> LENGTH: 28
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 504

Ser Glu Tyr Asp Ser Arg Val Phe Gln Tyr Ala Pro Glu Val Ala Gly
1               5                   10                  15

Gln Val Glu Ala Met Gln Gly Gly Ser Gly Thr Glu
            20                  25

<210> SEQ ID NO 505
<211> LENGTH: 28
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 505

```
Ser Glu Asp Glu Ser Arg Val Val Gln Phe Gln His Glu Val Ser Gly
1               5                   10                  15

Glu Leu Val Ala Met Gln Gly Gly Ser Gly Thr Glu
            20                  25

<210> SEQ ID NO 506
<211> LENGTH: 28
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 506

Ser Glu Gln Asp Thr Phe Val Phe Met Tyr Asn Gly Glu Val Ser Gly
1               5                   10                  15

Asp Met Val Ala Met Gln Gly Gly Ser Gly Thr Glu
            20                  25

<210> SEQ ID NO 507
<211> LENGTH: 28
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 507

Ser Glu Tyr Asp Thr Trp Val Phe Gln Phe Arg Arg Gln Val Pro Gly
1               5                   10                  15

Val Leu Glu Thr Met Leu Gly Gly Ser Gly Thr Glu
            20                  25

<210> SEQ ID NO 508
<211> LENGTH: 28
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 508

Ser Glu Gln Glu Thr Leu Val Phe Ala Val Ile Asp Gly Asp Pro Gly
1               5                   10                  15

Glu Leu Val Ala Met Gln Gly Gly Ser Gly Thr Glu
            20                  25

<210> SEQ ID NO 509
<211> LENGTH: 28
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 509

Ser Glu Tyr Asp Thr Trp Val Phe Gln Phe Ile His Val Ala Arg Gly
1               5                   10                  15

Glu Met Glu Gly Thr Leu Gly Gly Ser Gly Thr Glu
            20                  25

<210> SEQ ID NO 510
<211> LENGTH: 28
<212> TYPE: PRT
<213> ORGANISM: Artificial Sequence
```

```
<220> FEATURE:
<223> OTHER INFORMATION: Synthetically generated cMet-binding peptide
      sequence

<400> SEQUENCE: 510

Ser Glu Asp Glu Ser Arg Val Val Gln Phe Gln His Glu Val Ser Gly
 1               5                  10                  15

Glu Leu Val Ala Met Gln Gly Gly Ser Gly Thr Glu
            20                  25

<210> SEQ ID NO 511
<211> LENGTH: 28
<212> TYPE: PRT
<213> ORGANISM: Artificial Sequence
<220> FEATURE:
<223> OTHER INFORMATION: Synthetically generated cMet-binding peptide
      sequence

<400> SEQUENCE: 511

Ser Glu Gln Asp Thr Phe Val Phe Met Tyr Asn Gly Glu Val Ser Gly
 1               5                  10                  15

Asp Met Val Ala Met Gln Gly Gly Ser Gly Thr Glu
            20                  25

<210> SEQ ID NO 512
<211> LENGTH: 9
<212> TYPE: PRT
<213> ORGANISM: Artificial Sequence
<220> FEATURE:
<223> OTHER INFORMATION: Consensus motif
<220> FEATURE:
<221> NAME/KEY: VARIANT
<222> LOCATION: 2, 6, 8
<223> OTHER INFORMATION: Xaa = any amino acid

<400> SEQUENCE: 512

Cys Xaa Gly Pro Pro Xaa Phe Xaa Cys
 1               5

<210> SEQ ID NO 513
<211> LENGTH: 4
<212> TYPE: PRT
<213> ORGANISM: Artificial Sequence
<220> FEATURE:
<223> OTHER INFORMATION: Linker

<400> SEQUENCE: 513

Gly Gly Gly Lys
 1

<210> SEQ ID NO 514
<211> LENGTH: 24
<212> TYPE: PRT
<213> ORGANISM: Artificial Sequence
<220> FEATURE:
<223> OTHER INFORMATION: Synthetically generated peptide

<400> SEQUENCE: 514

Gly Ser Pro Glu Met Cys Met Met Phe Pro Phe Leu Tyr Pro Cys Asn
 1               5                  10                  15

His His Ala Pro Gly Gly Gly Lys
            20

<210> SEQ ID NO 515
<211> LENGTH: 24
<212> TYPE: PRT
<213> ORGANISM: Artificial Sequence
```

```
<220> FEATURE:
<223> OTHER INFORMATION: Synthetically generated peptide

<400> SEQUENCE: 515

Gly Ser Phe Phe Pro Cys Trp Arg Ile Asp Arg Phe Gly Tyr Cys His
1               5                   10                  15

Ala Asn Ala Pro Gly Gly Gly Lys
            20

<210> SEQ ID NO 516
<211> LENGTH: 26
<212> TYPE: PRT
<213> ORGANISM: Artificial Sequence
<220> FEATURE:
<223> OTHER INFORMATION: Synthetically generated peptide

<400> SEQUENCE: 516

Ala Gln Glu Trp Glu Arg Glu Tyr Phe Val Asp Gly Phe Trp Gly Ser
1               5                   10                  15

Trp Phe Gly Ile Pro His Gly Gly Gly Lys
            20                  25

<210> SEQ ID NO 517
<211> LENGTH: 26
<212> TYPE: PRT
<213> ORGANISM: Artificial Sequence
<220> FEATURE:
<223> OTHER INFORMATION: Synthetically generated peptide

<400> SEQUENCE: 517

Gly Asp Tyr Ser Glu Cys Phe Phe Glu Pro Asp Ser Phe Glu Val Lys
1               5                   10                  15

Cys Tyr Asp Arg Asp Pro Gly Gly Gly Lys
            20                  25

<210> SEQ ID NO 518
<211> LENGTH: 142
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (18)...(123)
<220> FEATURE:
<221> NAME/KEY: misc_feature
<222> LOCATION: 45,47, 48, 51, 52, 55, 58, 59, 67, 80, 84, 85, 91, 92,
      94 95
<223> OTHER INFORMATION: n = j =  0.12a + 0.12c + 0.64g + 0.12t
<220> FEATURE:
<221> NAME/KEY: misc_feature
<222> LOCATION: 46, 54, 61, 66, 78, 85, 97
<223> OTHER INFORMATION: n = e = 0.64a + 0.12c + 0.12g + 0.12t
<220> FEATURE:
<221> NAME/KEY: misc_feature
<222> LOCATION: 50, 53, 56, 57, 62, 68, 90, 93, 96, 98
<223> OTHER INFORMATION: n = z = 0.12a + 0.12c + 0.12g + 0.64t
<220> FEATURE:
<221> NAME/KEY: misc_feature
<222> LOCATION: 49, 60, 69, 70, 79
<223> OTHER INFORMATION: n = q = 0,12a + 0.64c + 0.12g + 0.12t

<400> SEQUENCE: 518
ctcagcagtc actgtct tcc atg ggt tct gaa act cgc cct aca nnn nnn         50
                   Ser Met Gly Ser Glu Thr Arg Pro Thr Glu Ala
                    1               5                   10 nnn nnn nnn nnn tgt nnn ggt cct cct nnn ttc nnn tgc nnn nnn nnn        98
Gly Ser Trp His Cys Ser Gly Pro Pro Thr Phe Glu Cys Trp Trp Tyr
            15                  20                  25
```

```
gga acg gag ccg act gaa gct agc g tgactctgac agtctctgt          142
Gly Thr Glu Pro Thr Glu Ala Ser
            30                  35

<210> SEQ ID NO 519
<211> LENGTH: 151
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (18)...(131)
<220> FEATURE:
<221> NAME/KEY: misc_feature
<222> LOCATION: 54, 61, 66, 78, 85, 97, 102, 106
<223> OTHER INFORMATION: n = e = 0.64a + 0.12c + 0.12g + 0.12t
<220> FEATURE:
<221> NAME/KEY: misc_feature
<222> LOCATION: 55, 58, 59, 67, 80, 84, 86, 91, 92, 94, 95, 99, 100,
      104, 105, 107
<223> OTHER INFORMATION: n = j =  0.12a + 0.12c + 0.64g + 0.12t
<220> FEATURE:
<221> NAME/KEY: misc_feature
<222> LOCATION: 56, 57, 62,, 68, 90, 93, 96, 98, 101
<223> OTHER INFORMATION: n = z = 0.12a + 0.12c + 0.12g + 0.64t
<220> FEATURE:
<221> NAME/KEY: misc_feature
<222> LOCATION: 60, 79, 88, 103
<223> OTHER INFORMATION: n = q = 0,12a + 0.64c + 0.12g + 0.12t

<400> SEQUENCE: 519
ctcagcagtc actgtct tcc atg ggt tct gaa act cgc cct aca gag gct     50
                   Ser Met Gly Ser Glu Thr Arg Pro Thr Glu Ala
                    1               5                  10 ggt nnn nnn nnn tgt nnn ggt cct cct nnn ttc nnn tgc nnn nnn nnn    98
Gly Ser Trp His Cys Ser Gly Pro Pro Thr Phe Glu Cys Trp Trp Tyr
            15                  20                  25 nnn nnn nnn ccg act gaa cgt cct agt gct agc gtgactctga cagtctctgt 151
Xaa Xaa Xaa Pro Thr Glu Arg Pro Ser Ala Ser
            30                  35

<210> SEQ ID NO 520
<211> LENGTH: 142
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (18)...(122)
<220> FEATURE:
<221> NAME/KEY: misc_feature
<222> LOCATION: 45, 47, 48, 51, 52, 55, 62, 68, 79, 80, 85, 90, 92, 95,
<223> OTHER INFORMATION: n = j =  0.12a + 0.12c + 0.64g + 0.12t
<220> FEATURE:
<221> NAME/KEY: misc_feature
<222> LOCATION: 46, 54, 57, 61, 66, 67, 84, 93,97
<223> OTHER INFORMATION: n = e = 0.64a + 0.12c + 0.12g + 0.12t
<220> FEATURE:
<221> NAME/KEY: misc_feature
<222> LOCATION: 50, 53, 56, 58, 59, 78, 86, 94, 96, 98
<223> OTHER INFORMATION: n = z = 0.12a + 0.12c + 0.12g + 0.64t
<220> FEATURE:
<221> NAME/KEY: misc_feature
<222> LOCATION: 49, 60, 91
<223> OTHER INFORMATION: n = q = 0,12a + 0.64c + 0.12g + 0.12t

<400> SEQUENCE: 520
ctcagcagtc actgtct tcc atg ggt tct gaa act cgc cct aca nnn nnn    50
                   Ser Met Gly Ser Glu Thr Arg Pro Thr Glu Ala
                    1               5                  10
```

```
nnn nnn nnn nnn tgc nnn ggt cct cct nnn ttc nnn tgt nnn nnn nnn        98
Gly Ser Ile Gln Cys Lys Gly Pro Pro Trp Phe Ser Cys Ala Met Tyr
            15                  20                  25 gga acg gag ccg act gaa gct agc gtgactctga cagtctctgt                 142
Gly Thr Glu Pro Thr Glu Ala Ser
        30                  35

<210> SEQ ID NO 521
<211> LENGTH: 151
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (18)...(131)
<220> FEATURE:
<221> NAME/KEY: misc_feature
<222> LOCATION: 54, 57, 61, 66, 67, 84, 93, 97, 102, 106
<223> OTHER INFORMATION: n = e = 0.64a + 0.12c + 0.12g + 0.12t
<220> FEATURE:
<221> NAME/KEY: misc_feature
<222> LOCATION: 55, 62, 68, 79, 80, 85, 90, 92, 95, 99, 100, 104, 105,
      107
<223> OTHER INFORMATION: n = j =  0.12a + 0.12c + 0.64g + 0.12t
<220> FEATURE:
<221> NAME/KEY: misc_feature
<222> LOCATION: 56, 58, 59, 78, 86, 94, 96, 98, 101
<223> OTHER INFORMATION: n = z = 0.12a + 0.12c + 0.12g + 0.64t
<220> FEATURE:
<221> NAME/KEY: misc_feature
<222> LOCATION: 60, 91, 103
<223> OTHER INFORMATION: n = q = 0,12a + 0.64c + 0.12g + 0.12t

<400> SEQUENCE: 521
ctcagcagtc actgtgtct tcc atg ggt tct gaa act cgc cct aca gag gcc      50
                    Ser Met Gly Ser Glu Thr Arg Pro Thr Glu Ala
                     1               5                  10 ggt nnn nnn nnn tgc nnn ggt cct cct nnn ttc nnn tgt nnn nnn nnn       98
Gly Ser Ile Gln Cys Lys Gly Pro Pro Trp Phe Ser Cys Ala Met Tyr
            15                  20                  25 nnn nnn nnn ccg act gaa cgt cct agt gct agc gtgactctga cagtctctgt    151
Gly Thr Glu Pro Thr Glu Arg Pro Ser Ala Ser
        30                  35

<210> SEQ ID NO 522
<211> LENGTH: 151
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (18)...(131)
<220> FEATURE:
<221> NAME/KEY: misc_feature
<222> LOCATION: 54, 56, 57, 59, 62, 80, 93, 97, 101
<223> OTHER INFORMATION: n = z= 0.12A + 0.12C + 0.12G + 0.64T
<220> FEATURE:
<221> NAME/KEY: misc_feature
<222> LOCATION: 55, 58, 66, 67, 78, 85, 91, 92, 96, 102, 106
<223> OTHER INFORMATION: n = e= 0.64A + 0.12C + 0.12G + 0.12T
<220> FEATURE:
<221> NAME/KEY: misc_feature
<222> LOCATION: 60, 61, 68, 84, 86, 94, 95, 98, 99, 100, 104, 105, 107
<223> OTHER INFORMATION: n = j = 0.12A + 0.12C + 0.64G + 0.12T
<220> FEATURE:
<221> NAME/KEY: misc_feature
<222> LOCATION: 79, 90, 103
<223> OTHER INFORMATION: n = q = 0.12A + 0.64C + 0.12G + 0.12T

<400> SEQUENCE: 522
ctcagcagtc actgtgtct tcc atg ggt tct gaa act cgc cct aca gag gct      50
```

```
                Ser Met Gly Ser Glu Thr Arg Pro Thr Glu Ala
                  1               5                  10 ggt nnn nnn nnn tgc nnn ggt cct cct nnn ttc nnn tgt nnn nnn nnn      98
Gly Tyr tyr Gly Cys Lys Gly Pro Pro Thr Phe Glu Cys Gln Trp Met
             15                  20                  25 nnn nnn nnn ccg act gaa cgt cct agt gct agc gtgactctga cagtctctgt   151
Gly Thr Glu Pro Thr Glu Arg Pro Ser Ala Ser
         30                  35
```

<210> SEQ ID NO 523
<211> LENGTH: 151
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (18)...(131)
<220> FEATURE:
<221> NAME/KEY: misc_feature
<222> LOCATION: 54, 74, 86, 91, 99, 100, 104, 105, 107
<223> OTHER INFORMATION: n = j = 0.12A + 0.12C + 0.64G + 0.12T
<220> FEATURE:
<221> NAME/KEY: misc_feature
<222> LOCATION: 55,59,62, 67, 72, 73, 79, 92, 93, 103
<223> OTHER INFORMATION: n = q = 0.12A + 0.64C + 0.12G + 0.12T
<220> FEATURE:
<221> NAME/KEY: misc_feature
<222> LOCATION: 56-58, 60, 61, 66, 68, 80, 85, 94-96, 98, 101
<223> OTHER INFORMATION: n = z = 0.12A + 0.12C + 0.12G + 0.64T
<220> FEATURE:
<221> NAME/KEY: misc_feature
<222> LOCATION: 78, 84, 90, 97, 102, 106
<223> OTHER INFORMATION: n = e = 0.64A + 0.12C + 0.12G + 0.12T

<400> SEQUENCE: 523

```
ctcagcagtc actgtct tcc atg ggt tct gaa act cgc cct aca gag gct       50
                    Ser Met Gly Ser Glu Thr Arg Pro Thr Glu Ala
                      1               5                  10 ggt nnn nnn nnn tgt nnn ggt nnn cct nnn ttc nnn tgc nnn nnn nnn      98
Gly Ala Phe Phe Cys Ser Gly Pro Pro Thr Phe Met Cys Ser Leu Tyr
             15                  20                  25 nnn nnn nnn ccg act gaa cgt cct agt gct agc gtgactctga cagtctctgt   151
Gly Thr Glu Pro Thr Glu Arg Pro Ser Ala Ser
         30                  35
```

<210> SEQ ID NO 524
<211> LENGTH: 142
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (18)...(122)
<220> FEATURE:
<221> NAME/KEY: misc_feature
<222> LOCATION: 45, 47, 48, 51, 52, 56, 62, 66, 74, 79, 84, 91, 92, 95
<223> OTHER INFORMATION: n = j = 0.12A + 0.12C + 0.64G + 0.12T
<220> FEATURE:
<221> NAME/KEY: misc_feature
<222> LOCATION: 46, 55, 60, 61, 78, 93, 96
<223> OTHER INFORMATION: n = e = 0.64A + 0.12C + 0.12G + 0.12T
<220> FEATURE:
<221> NAME/KEY: misc_feature
<222> LOCATION: 49, 54, 59, 67, 72, 73, 77, 85, 86, 97, 98
<223> OTHER INFORMATION: n = q = 0.12A + 0.64C + 0.12G + 0.12T
<220> FEATURE:
<221> NAME/KEY: misc_feature
<222> LOCATION: 50, 53, 57, 58, 68, 90, 94
<223> OTHER INFORMATION: n = z = 0.12A + 0.12C + 0.12G + 0.64T

<400> SEQUENCE: 524

-continued

```
ctcagcagtc actgtct tcc atg ggt tct gaa act cgc cct aca nnn nnn       50
                Ser Met Gly Ser Glu Thr Arg Pro Thr Glu Ala
                 1               5                  10 nnn nnn nnn nnn tgt nnn ggt nnn ccg nnn ttc nnn tgt nnn nnn nnn      98
Gly Gln Phe Lys Cys Ala Gly Pro Pro Ser Phe Ala Cys Trp Met Thr
            15              20              25 gga acg gag ccg act gaa gct agc gtgactctga cagtctctgt              142
Gly Thr Glu Pro Thr Glu Ala Ser
         30              35
```

<210> SEQ ID NO 525
<211> LENGTH: 19
<212> TYPE: PRT
<213> ORGANISM: Artificial Sequence
<220> FEATURE:
<223> OTHER INFORMATION: Consensus motif
<220> FEATURE:
<221> NAME/KEY: VARIANT
<222> LOCATION: 3
<223> OTHER INFORMATION: Xaa = Phe, Leu, Ser, Trp or Tyr
<220> FEATURE:
<221> NAME/KEY: VARIANT
<222> LOCATION: 4
<223> OTHER INFORMATION: Xaa = Ile, Tyr, His, or Thr
<220> FEATURE:
<221> NAME/KEY: VARIANT
<222> LOCATION: 5
<223> OTHER INFORMATION: Xaa = Ile, Leu, Met, Phe, or Ser, prferably Ile
<220> FEATURE:
<221> NAME/KEY: VARIANT
<222> LOCATION: 7
<223> OTHER INFORMATION: Xaa = Pro, Arg, Trp, or Glu, preferably Trp or
     Pro
<220> FEATURE:
<221> NAME/KEY: VARIANT
<222> LOCATION: 8
<223> OTHER INFORMATION: Xaa = Trp, Tyr, Glu, Pro, Leu, Thr, or Gly
<220> FEATURE:
<221> NAME/KEY: VARIANT
<222> LOCATION: 9
<223> OTHER INFORMATION: Xaa = Ser, Thr, Asp, Phe,Glu, Trp, Gly, or Gln
<220> FEATURE:
<221> NAME/KEY: VARIANT
<222> LOCATION: 10
<223> OTHER INFORMATION: Xaa =Phe, Trp, Asn, Gln, Glu, Arg, or Ala
<220> FEATURE:
<221> NAME/KEY: VARIANT
<222> LOCATION: 12
<223> OTHER INFORMATION: Xaa =Gly, Asn, His, Arg, Met, Ile, Asp, Val, or
     Thr
<220> FEATURE:
<221> NAME/KEY: VARIANT
<222> LOCATION: 13
<223> OTHER INFORMATION: Xaa = Ser, Lys, Phe, Met, Thr, Asp, or Leu
<220> FEATURE:
<221> NAME/KEY: VARIANT
<222> LOCATION: 14
<223> OTHER INFORMATION: Xaa = Ser, Pro, Thr, Leu, Tyr, Asn, His, Gln,
     or Trp

<400> SEQUENCE: 525

```
Gly Ser Xaa Xaa Xaa Cys Xaa Xaa Xaa Cys Xaa Xaa Xaa Ala Pro
 1               5                  10                  15

Gly Gly Lys
```

<210> SEQ ID NO 526
<211> LENGTH: 22
<212> TYPE: PRT
<213> ORGANISM: Artificial Sequence
<220> FEATURE:
<223> OTHER INFORMATION: Consensus motif
<220> FEATURE:
<221> NAME/KEY: VARIANT

```
<222> LOCATION: 3
<223> OTHER INFORMATION: Xaa = any amino acid other than Cys, preferably
      Gly, Val, Trp, Thr, Lys, Gln
<220> FEATURE:
<221> NAME/KEY: VARIANT
<222> LOCATION: 4
<223> OTHER INFORMATION: Xaa = any amino acid other than Cys, preferably
      Trp, Tyr, Leu, Phe, Thr
<220> FEATURE:
<221> NAME/KEY: VARIANT
<222> LOCATION: 5
<223> OTHER INFORMATION: Xaa = any amino acid other than Cys, preferably
      Trp, Glu, Phe, Ile, Leu, Ser
<220> FEATURE:
<221> NAME/KEY: VARIANT
<222> LOCATION: 7
<223> OTHER INFORMATION: Xaa = any amino acid other than Cys, preferably
      Glu, Asn, Gln
<220> FEATURE:
<221> NAME/KEY: VARIANT
<222> LOCATION: 8
<223> OTHER INFORMATION: Xaa = any amino acid other than Cys, preferably
      Trp, Leu, Glu
<220> FEATURE:
<221> NAME/KEY: VARIANT
<222> LOCATION: 9
<223> OTHER INFORMATION: Xaa = any amino acid other than Cys, preferably
      Glu, Ser, Tyr
<220> FEATURE:
<221> NAME/KEY: VARIANT
<222> LOCATION: 10
<223> OTHER INFORMATION: Xaa = any amino acid other than Cys, preferably
      Glu, Met, Pro
<220> FEATURE:
<221> NAME/KEY: VARIANT
<222> LOCATION: 11
<223> OTHER INFORMATION: Xaa = any amino acid other than Cys, preferably
      Met, Ser, Trp
<220> FEATURE:
<221> NAME/KEY: VARIANT
<222> LOCATION: 12
<223> OTHER INFORMATION: Xaa = any amino acid other than Cys, preferably
      Phe, Leu, Val
<220> FEATURE:
<221> NAME/KEY: VARIANT
<222> LOCATION: 14
<223> OTHER INFORMATION: Xaa = any amino acid other than Cys, preferably
      Glu, Asp, Trp
<220> FEATURE:
<221> NAME/KEY: VARIANT
<222> LOCATION: 15
<223> OTHER INFORMATION: Xaa = any amino acid other than Cys, preferably
      Trp, Phe, Met
<220> FEATURE:
<221> NAME/KEY: VARIANT
<222> LOCATION: 16
<223> OTHER INFORMATION: Xaa = any amino acid other than C, preferably
      Gln, Trp, Leu

<400> SEQUENCE: 526

Ala Gly Xaa Xaa Xaa Cys Xaa Xaa Xaa Xaa Xaa Xaa Cys Xaa Xaa Xaa
  1               5                  10                  15

Gly Thr Gly Gly Gly Lys
            20

<210> SEQ ID NO 527
<211> LENGTH: 18
<212> TYPE: PRT
<213> ORGANISM: Artificial Sequence
<220> FEATURE:
<223> OTHER INFORMATION: Consensus motif
<220> FEATURE:
<221> NAME/KEY: VARIANT
<222> LOCATION: 2
<223> OTHER INFORMATION: Xaa = any amino acid other than Cys, preferably
      Glu, Ser, Tyr, or Trp
<220> FEATURE:
```

-continued

```
<221> NAME/KEY: VARIANT
<222> LOCATION: 3
<223> OTHER INFORMATION: Xaa = any amino acid other than Cys, preferably
      Trp, Thr, or Phe
<220> FEATURE:
<221> NAME/KEY: VARIANT
<222> LOCATION: 4
<223> OTHER INFORMATION: Xaa = any amino acid other than Cys, preferably
      Trp, His, or Phe
<220> FEATURE:
<221> NAME/KEY: VARIANT
<222> LOCATION: 6
<223> OTHER INFORMATION: Xaa = any amino acid other than Cys, preferably
      Ala, Lys, Ser, or Thr
<220> FEATURE:
<221> NAME/KEY: VARIANT
<222> LOCATION: 8
<223> OTHER INFORMATION: Xaa = any amino acid other than Cys, preferably
      Pro or Trp
<220> FEATURE:
<221> NAME/KEY: VARIANT
<222> LOCATION: 10
<223> OTHER INFORMATION: Xaa = any amino acid other than Cys, preferably
      Thr or Ser
<220> FEATURE:
<221> NAME/KEY: VARIANT
<222> LOCATION: 12
<223> OTHER INFORMATION: Xaa = any amino acid other than Cys, preferably
      Glu or Ser
<220> FEATURE:
<221> NAME/KEY: VARIANT
<222> LOCATION: 14
<223> OTHER INFORMATION: Xaa = any amino acid other than Cys, preferably
      Trp,Tyr, or Ile
<220> FEATURE:
<221> NAME/KEY: VARIANT
<222> LOCATION: 15
<223> OTHER INFORMATION: Xaa = any amino acid other than Cys, preferably
      Trp, Tyr, Met, or Glu
<220> FEATURE:
<221> NAME/KEY: VARIANT
<222> LOCATION: 16
<223> OTHER INFORMATION: Xaa = any amino acid other than Cys, preferably
      Tyr

<400> SEQUENCE: 527

Gly Xaa Xaa Xaa Cys Xaa Gly Xaa Pro Xaa Phe Xaa Cys Xaa Xaa Xaa
 1               5                  10                  15

Gly Thr

<210> SEQ ID NO 528
<211> LENGTH: 22
<212> TYPE: PRT
<213> ORGANISM: Artificial Sequence
<220> FEATURE:
<223> OTHER INFORMATION: Consensus motif
<220> FEATURE:
<221> NAME/KEY: VARIANT
<222> LOCATION: 2
<223> OTHER INFORMATION: Xaa = any amino acid other than Cys, preferably
      Ser, Arg, Ile, Asp, or Asn
<220> FEATURE:
<221> NAME/KEY: VARIANT
<222> LOCATION: 3
<223> OTHER INFORMATION: Xaa = any amino acid other than Cys, preferably
      Trp, Lew, Phe, Val, or Ile
<220> FEATURE:
<221> NAME/KEY: VARIANT
<222> LOCATION: 4
<223> OTHER INFORMATION: Xaa = any amino acid other than Cys, preferably
      His, Tyr, Leu, Gln, Asn, or Val
<220> FEATURE:
<221> NAME/KEY: VARIANT
<222> LOCATION: 6
<223> OTHER INFORMATION: Xaa = any amino acid other than Cys, preferably
      Ser, Lys, or Leu
<220> FEATURE:
```

```
<221> NAME/KEY: VARIANT
<222> LOCATION: 10
<223> OTHER INFORMATION: Xaa = any amino acid other than Cys, preferably
      Thr, Ser, Ala, or Trp
<220> FEATURE:
<221> NAME/KEY: VARIANT
<222> LOCATION: 12
<223> OTHER INFORMATION: Xaa = any amino acid other than Cys, preferably
      Glu or Ser
<220> FEATURE:
<221> NAME/KEY: VARIANT
<222> LOCATION: 14
<223> OTHER INFORMATION: Xaa = any amino acid other than Cys, preferably
      Trp
<220> FEATURE:
<221> NAME/KEY: VARIANT
<222> LOCATION: 15
<223> OTHER INFORMATION: Xaa = any amino acid other than Cys, preferably
      Trp, Ser, or Leu
<220> FEATURE:
<221> NAME/KEY: VARIANT
<222> LOCATION: 16
<223> OTHER INFORMATION: Xaa = any amino acid other than Cys, preferably
      Tyr or Phe
<220> FEATURE:
<221> NAME/KEY: VARIANT
<222> LOCATION: 17
<223> OTHER INFORMATION: Xaa = any amino acid other than Cys, preferably
      Asp, Gly, Val, or Glu
<220> FEATURE:
<221> NAME/KEY: VARIANT
<222> LOCATION: 18
<223> OTHER INFORMATION: Xaa = any amino acid other than Cys, preferably
      Thr, Pro, Met , or Ser
<220> FEATURE:
<221> NAME/KEY: VARIANT
<222> LOCATION: 19
<223> OTHER INFORMATION: Xaa = any amino acid other than Cys, preferably
      Glu or Gly

<400> SEQUENCE: 528

Gly Xaa Xaa Xaa Cys Xaa Gly Pro Pro Xaa Phe Xaa Cys Xaa Xaa Xaa
 1               5                  10                  15

Xaa Xaa Xaa Pro Thr Glu
            20

<210> SEQ ID NO 529
<211> LENGTH: 20
<212> TYPE: PRT
<213> ORGANISM: Artificial Sequence
<220> FEATURE:
<223> OTHER INFORMATION: Consensus motif
<220> FEATURE:
<221> NAME/KEY: VARIANT
<222> LOCATION: 2
<223> OTHER INFORMATION: Xaa = any amino acid other than Cys, preferably
      Glu, Asp, or Val
<220> FEATURE:
<221> NAME/KEY: VARIANT
<222> LOCATION: 3
<223> OTHER INFORMATION: Xaa = any amino acid other than Cys, preferably
      Ala, Asp, Gly, Ser, or Val
<220> FEATURE:
<221> NAME/KEY: VARIANT
<222> LOCATION: 4
<223> OTHER INFORMATION: Xaa = any amino acid other than Cys, preferably
      Gly, Val, Asp, or Ser
<220> FEATURE:
<221> NAME/KEY: VARIANT
<222> LOCATION: 5
<223> OTHER INFORMATION: Xaa = any amino acid other than Cys, preferably
      Ser, Asn, Arg, Thr, or Gly
<220> FEATURE:
<221> NAME/KEY: VARIANT
<222> LOCATION: 6
<223> OTHER INFORMATION: Xaa = any amino acid other than Cys, preferably
      Trp
```

```
<220> FEATURE:
<221> NAME/KEY: VARIANT
<222> LOCATION: 7
<223> OTHER INFORMATION: Xaa = any amino acid other than Cys, preferably
      His or Gln
<220> FEATURE:
<221> NAME/KEY: VARIANT
<222> LOCATION: 9
<223> OTHER INFORMATION: Xaa = any amino acid other than Cys, preferably
      Ser, Asn, or Lys
<220> FEATURE:
<221> NAME/KEY: VARIANT
<222> LOCATION: 13
<223> OTHER INFORMATION: Xaa = any amino acid other than Cys, preferably
      Thr
<220> FEATURE:
<221> NAME/KEY: VARIANT
<222> LOCATION: 15
<223> OTHER INFORMATION: Xaa = any amino acid other than Cys, preferably
      Glu
<220> FEATURE:
<221> NAME/KEY: VARIANT
<222> LOCATION: 17
<223> OTHER INFORMATION: Xaa = any amino acid other than Cys, preferably
      Trp
<220> FEATURE:
<221> NAME/KEY: VARIANT
<222> LOCATION: 18
<223> OTHER INFORMATION: Xaa = any amino acid other than Cys, preferably
      Trp or Ser
<220> FEATURE:
<221> NAME/KEY: VARIANT
<222> LOCATION: 19
<223> OTHER INFORMATION: Xaa = any amino acid other than Cys, preferably
      Tyr or Phe

<400> SEQUENCE: 529

Thr Xaa Xaa Xaa Xaa Xaa Xaa Cys Xaa Gly Pro Pro Xaa Phe Xaa Cys
 1               5                  10                  15

Xaa Xaa Xaa Gly
            20

<210> SEQ ID NO 530
<211> LENGTH: 19
<212> TYPE: PRT
<213> ORGANISM: Artificial Sequence
<220> FEATURE:
<223> OTHER INFORMATION: Consensus motif
<220> FEATURE:
<221> NAME/KEY: VARIANT
<222> LOCATION: 2
<223> OTHER INFORMATION: Xaa = Trp, His, Phe, Thr, or Pro
<220> FEATURE:
<221> NAME/KEY: VARIANT
<222> LOCATION: 3
<223> OTHER INFORMATION: Xaa = Arg, His, Ala, Lys, Glu, or Phe
<220> FEATURE:
<221> NAME/KEY: VARIANT
<222> LOCATION: 4
<223> OTHER INFORMATION: Xaa = Phe, Thr, Pro, Val, or Met
<220> FEATURE:
<221> NAME/KEY: VARIANT
<222> LOCATION: 6
<223> OTHER INFORMATION: Xaa = Phe, Leu, His, Met, or Trp
<220> FEATURE:
<221> NAME/KEY: VARIANT
<222> LOCATION: 7
<223> OTHER INFORMATION: Xaa = Gly, Asp, Trp, Glu, Met, or Arg
<220> FEATURE:
<221> NAME/KEY: VARIANT
<222> LOCATION: 8
<223> OTHER INFORMATION: Xaa = Glu, Gly, Pro, Lys, Phe, or Ile
<220> FEATURE:
<221> NAME/KEY: VARIANT
<222> LOCATION: 9
<223> OTHER INFORMATION: Xaa = Tyr, Phe, Ser, Trp, Pro, or Asp
<220> FEATURE:
```

```
<221> NAME/KEY: VARIANT
<222> LOCATION: 10
<223> OTHER INFORMATION: Xaa = Ser, Ala, Phe, Asn, or Arg
<220> FEATURE:
<221> NAME/KEY: VARIANT
<222> LOCATION: 11
<223> OTHER INFORMATION: Xaa = Phe, Gly, Ala, Gln, or Leu
<220> FEATURE:
<221> NAME/KEY: VARIANT
<222> LOCATION: 12
<223> OTHER INFORMATION: Xaa = Gln, Trp, Ile, Leu, Tyr, or Gly
<220> FEATURE:
<221> NAME/KEY: VARIANT
<222> LOCATION: 13
<223> OTHER INFORMATION: Xaa = Val, Arg, Asp, Phe, Pro, or Tyr
<220> FEATURE:
<221> NAME/KEY: VARIANT
<222> LOCATION: 15
<223> OTHER INFORMATION: Xaa = Gln, Thr, Ile, His, or Asn
<220> FEATURE:
<221> NAME/KEY: VARIANT
<222> LOCATION: 16
<223> OTHER INFORMATION: Xaa = Asp, Glu, Ala, Asn, or His
<220> FEATURE:
<221> NAME/KEY: VARIANT
<222> LOCATION: 17
<223> OTHER INFORMATION: Xaa = Val, Glu, Gln, His, or Asn

<400> SEQUENCE: 530

Ser Xaa Xaa Xaa Cys Xaa Xaa Xaa Xaa Xaa Xaa Xaa Cys Xaa Xaa
 1               5                   10                  15

Xaa Ala Pro

<210> SEQ ID NO 531
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 531

Tyr Tyr Gly Cys Lys Gly Pro Pro Thr Phe Glu Cys Gln Trp Met
 1               5                   10                  15

<210> SEQ ID NO 532
<211> LENGTH: 20
<212> TYPE: PRT
<213> ORGANISM: Artificial Sequence
<220> FEATURE:
<223> OTHER INFORMATION: Consensus motif
<220> FEATURE:
<221> NAME/KEY: VARIANT
<222> LOCATION: 2
<223> OTHER INFORMATION: Xaa = any amino acid other than Cys, preferably
      Ser, Phe, Gly, Met, or Gln
<220> FEATURE:
<221> NAME/KEY: VARIANT
<222> LOCATION: 3
<223> OTHER INFORMATION: Xaa = any amino acid other than Cys, preferably
      Met, Leu, Asn, or Gln
<220> FEATURE:
<221> NAME/KEY: VARIANT
<222> LOCATION: 4
<223> OTHER INFORMATION: Xaa = any amino acid other than Cys, preferably
      Asn, Gly, His, Ile, or Arg
<220> FEATURE:
<221> NAME/KEY: VARIANT
<222> LOCATION: 6
<223> OTHER INFORMATION: Xaa = any amino acid other than Cys, preferably
      Asp, Leu, Asn, Thr, or Trp
<220> FEATURE:
<221> NAME/KEY: VARIANT
<222> LOCATION: 7
<223> OTHER INFORMATION: Xaa = any amino acid other than Cys, preferably
      Gln, Thr, Arg, Val, or Tyr
```

```
<220> FEATURE:
<221> NAME/KEY: VARIANT
<222> LOCATION: 8
<223> OTHER INFORMATION: Xaa = any amino acid other than Cys, preferably
      Gly, Glu, Leu, Met, or Thr
<220> FEATURE:
<221> NAME/KEY: VARIANT
<222> LOCATION: 9
<223> OTHER INFORMATION: Xaa = any amino acid other than Cys, preferably
      Ala, Asp, His, Ile, Leu, Asn, or Ser
<220> FEATURE:
<221> NAME/KEY: VARIANT
<222> LOCATION: 10
<223> OTHER INFORMATION: Xaa = any amino acid other than Cys, preferably
      Gln, Arg, Ser, Thr, or Tyr
<220> FEATURE:
<221> NAME/KEY: VARIANT
<222> LOCATION: 11
<223> OTHER INFORMATION: Xaa = any amino acid other than Cys, preferably
      Asp, Gly, Ile, or Pro
<220> FEATURE:
<221> NAME/KEY: VARIANT
<222> LOCATION: 12
<223> OTHER INFORMATION: Xaa = any amino acid other than Cys, preferably
      Thr, Phe, or Gln
<220> FEATURE:
<221> NAME/KEY: VARIANT
<222> LOCATION: 13
<223> OTHER INFORMATION: Xaa = any amino acid other than Cys, preferably
      Gln, Phe, His, Pro, Ser, or Tyr
<220> FEATURE:
<221> NAME/KEY: VARIANT
<222> LOCATION: 14
<223> OTHER INFORMATION: Xaa = any amino acid other than Cys, preferably
      Asp, Phe, Asn, Pro, or Ser
<220> FEATURE:
<221> NAME/KEY: VARIANT
<222> LOCATION: 16
<223> OTHER INFORMATION: Xaa = any amino acid other than Cys, preferably
      Leu, Ala, Gly, Asn, or Ser
<220> FEATURE:
<221> NAME/KEY: VARIANT
<222> LOCATION: 17
<223> OTHER INFORMATION: Xaa = any amino acid other than Cys, preferably
      Val, Pro, Arg, or Tyr
<220> FEATURE:
<221> NAME/KEY: VARIANT
<222> LOCATION: 18
<223> OTHER INFORMATION: Xaa = any amino acid other than Cys, preferably
      Met, Asp, Glu, or Leu

<400> SEQUENCE: 532

Ser Xaa Xaa Xaa Cys Xaa Xaa Xaa Xaa Xaa Xaa Xaa Xaa Xaa Cys Xaa
 1               5                  10                  15

Xaa Xaa Ala Pro
         20

<210> SEQ ID NO 533
<211> LENGTH: 21
<212> TYPE: PRT
<213> ORGANISM: Artificial Sequence
<220> FEATURE:
<223> OTHER INFORMATION: Consensus motif
<220> FEATURE:
<221> NAME/KEY: VARIANT
<222> LOCATION: 2
<223> OTHER INFORMATION: Xaa = any amino acid other than Cys, preferably
      Tyr, Ala, His, Leu, or Pro
<220> FEATURE:
<221> NAME/KEY: VARIANT
<222> LOCATION: 3
<223> OTHER INFORMATION: Xaa = any amino acid other than Cys, preferably
      Leu, Arg, Ser, Asp, or Tyr
<220> FEATURE:
<221> NAME/KEY: VARIANT
<222> LOCATION: 4
<223> OTHER INFORMATION: Xaa = any amino acid other than Cys, preferably
```

```
            Glu, Met, or Trp
<220> FEATURE:
<221> NAME/KEY: VARIANT
<222> LOCATION: 6
<223> OTHER INFORMATION: Xaa = any amino acid other than Cys, preferably
      Glu, Gln, Asp, Phe, or Ser
<220> FEATURE:
<221> NAME/KEY: VARIANT
<222> LOCATION: 7
<223> OTHER INFORMATION: Xaa = any amino acid other than Cys, preferably
      Phe, Ile, Trp, or Glu
<220> FEATURE:
<221> NAME/KEY: VARIANT
<222> LOCATION: 8
<223> OTHER INFORMATION: Xaa = any amino acid other than Cys, preferably
      Asp, Ser, or Asn
<220> FEATURE:
<221> NAME/KEY: VARIANT
<222> LOCATION: 9
<223> OTHER INFORMATION: Xaa = any amino acid other than Cys, preferably
      Asp, Ser, or Leu
<220> FEATURE:
<221> NAME/KEY: VARIANT
<222> LOCATION: 10
<223> OTHER INFORMATION: Xaa = any amino acid other than Cys, preferably
      Asp, Lys, or Glu
<220> FEATURE:
<221> NAME/KEY: VARIANT
<222> LOCATION: 11
<223> OTHER INFORMATION: Xaa = any amino acid other than Cys, preferably
      Thr, Phe, or Gly
<220> FEATURE:
<221> NAME/KEY: VARIANT
<222> LOCATION: 12
<223> OTHER INFORMATION: Xaa = any amino acid other than Cys, preferably
      Phe, Trp, Tyr, or Gly
<220> FEATURE:
<221> NAME/KEY: VARIANT
<222> LOCATION: 13
<223> OTHER INFORMATION: Xaa = any amino acid other than Cys, preferably
      Glu, Ser, or Trp
<220> FEATURE:
<221> NAME/KEY: VARIANT
<222> LOCATION: 14
<223> OTHER INFORMATION: Xaa = any amino acid other than Cys, preferably
      Glu, Val, Phe, or Tyr
<220> FEATURE:
<221> NAME/KEY: VARIANT
<222> LOCATION: 15
<223> OTHER INFORMATION: Xaa = any amino acid other than Cys, preferably
      Thr, Glu, Lys, or Val
<220> FEATURE:
<221> NAME/KEY: VARIANT
<222> LOCATION: 17
<223> OTHER INFORMATION: Xaa = any amino acid other than Cys, preferably
      Trp or Glu
<220> FEATURE:
<221> NAME/KEY: VARIANT
<222> LOCATION: 18
<223> OTHER INFORMATION: Xaa = any amino acid other than Cys, preferably
      Asp, Trp, Phe, Pro, or Ser
<220> FEATURE:
<221> NAME/KEY: VARIANT
<222> LOCATION: 19
<223> OTHER INFORMATION: Xaa = any amino acid other than C, preferably
      Asn, Ile, or Ala

<400> SEQUENCE: 533

Asp Xaa Xaa Xaa Cys Xaa Xaa Xaa Xaa Xaa Xaa Xaa Xaa Xaa Xaa Cys
 1               5                  10                  15

Xaa Xaa Xaa Asp Pro
            20

<210> SEQ ID NO 534
<211> LENGTH: 20
<212> TYPE: PRT
<213> ORGANISM: Artificial Sequence
```

```
<220> FEATURE:
<223> OTHER INFORMATION: Exemplary motif
<220> FEATURE:
<221> NAME/KEY: VARIANT
<222> LOCATION: 2
<223> OTHER INFORMATION: Xaa = any amino acid other than Cys, preferably
      Ser
<220> FEATURE:
<221> NAME/KEY: VARIANT
<222> LOCATION: 4
<223> OTHER INFORMATION: Xaa = any amino acid other than Cys, preferably
      His, Tyr, or Asn
<220> FEATURE:
<221> NAME/KEY: VARIANT
<222> LOCATION: 6
<223> OTHER INFORMATION: Xaa = any amino acid other than Cys, preferably
      Ser or Gly
<220> FEATURE:
<221> NAME/KEY: VARIANT
<222> LOCATION: 10
<223> OTHER INFORMATION: Xaa = any amino acid other than Cys, preferably
      Thr
<220> FEATURE:
<221> NAME/KEY: VARIANT
<222> LOCATION: 12
<223> OTHER INFORMATION: Xaa = any amino acid other than Cys, preferably
      Glu
<220> FEATURE:
<221> NAME/KEY: VARIANT
<222> LOCATION: 14
<223> OTHER INFORMATION: Xaa = any amino acid other than Cys, preferably
      Trp
<220> FEATURE:
<221> NAME/KEY: VARIANT
<222> LOCATION: 16
<223> OTHER INFORMATION: Xaa = any amino acid other than Cys, preferably
      Tyr
<220> FEATURE:
<221> NAME/KEY: VARIANT
<222> LOCATION: 17
<223> OTHER INFORMATION: Xaa = any amino acid other than Cys, preferably
      Gly, Asp, Ala, Glu, or Ser
<220> FEATURE:
<221> NAME/KEY: VARIANT
<222> LOCATION: 18
<223> OTHER INFORMATION: Xaa = any amino acid other than Cys, preferably
      Thr or Ser
<220> FEATURE:
<221> NAME/KEY: VARIANT
<222> LOCATION: (9
<223> OTHER INFORMATION: Xaa = any amino acid other than Cys, preferably
      Glu or Asp

<400> SEQUENCE: 534

Gly Xaa Cys Xaa Cys Xaa Gly Pro Pro Xaa Phe Xaa Cys Xaa Cys Xaa
 1               5                  10                  15

Xaa Xaa Xaa Pro
            20

<210> SEQ ID NO 535
<211> LENGTH: 20
<212> TYPE: PRT
<213> ORGANISM: Artificial Sequence
<220> FEATURE:
<223> OTHER INFORMATION: Exemplary motif
<220> FEATURE:
<221> NAME/KEY: VARIANT
<222> LOCATION: 2
<223> OTHER INFORMATION: Xaa = any amino acid other than Cys, preferably
      Glu
<220> FEATURE:
<221> NAME/KEY: VARIANT
<222> LOCATION: 3
<223> OTHER INFORMATION: Xaa = any amino acid other than Cys preferably
      Ala, Ser, Glu, or Gly
<220> FEATURE:
<221> NAME/KEY: VARIANT
```

```
<222> LOCATION: 4
<223> OTHER INFORMATION: Xaa = any amino acid other than Cys, preferably
      Gly
<220> FEATURE:
<221> NAME/KEY: VARIANT
<222> LOCATION: 5
<223> OTHER INFORMATION: Xaa = any amino acid other than Cys, preferably
      Ser
<220> FEATURE:
<221> NAME/KEY: VARIANT
<222> LOCATION: 7
<223> OTHER INFORMATION: Xaa = any amino acid other than Cys, preferably
      His
<220> FEATURE:
<221> NAME/KEY: VARIANT
<222> LOCATION: 9
<223> OTHER INFORMATION: Xaa = any amino acid other than Cys, preferably
      Ser
<220> FEATURE:
<221> NAME/KEY: VARIANT
<222> LOCATION: 13
<223> OTHER INFORMATION: Xaa = any amino acid other than Cys, preferably
      Thr
<220> FEATURE:
<221> NAME/KEY: VARIANT
<222> LOCATION: 17
<223> OTHER INFORMATION: Xaa = any amino acid other than Cys, preferably
      Trp, Tyr, or Phe
<220> FEATURE:
<221> NAME/KEY: VARIANT
<222> LOCATION: 19
<223> OTHER INFORMATION: Xaa = any amino acid other than Cys, preferably
      Tyr or Phe

<400> SEQUENCE: 535

Thr Xaa Xaa Xaa Xaa Cys Xaa Cys Xaa Gly Pro Pro Xaa Phe Glu Cys
1               5                   10                  15

Xaa Cys Xaa Gly
         20

<210> SEQ ID NO 536
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 536

Ala Phe Phe Cys Ser Gly Pro Pro Thr Phe Met Cys Ser Leu Tyr
1               5                   10                  15

<210> SEQ ID NO 537
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 537

Ser Ile Gln Cys Lys Gly Pro Pro Trp Phe Ser Cys Ala Met Tyr
1               5                   10                  15

<210> SEQ ID NO 538
<211> LENGTH: 12
<212> TYPE: PRT
<213> ORGANISM: Artificial Sequence
<220> FEATURE:
<223> OTHER INFORMATION: Exemplary motif
<220> FEATURE:
<221> NAME/KEY: VARIANT
<222> LOCATION: 1
<223> OTHER INFORMATION: Xaa = Phe, Leu, Ser, Trp, Tyr or Met
<220> FEATURE:
```

```
<221> NAME/KEY: VARIANT
<222> LOCATION: 2
<223> OTHER INFORMATION: Xaa = Ile, Tyr, His, Thr or Asn
<220> FEATURE:
<221> NAME/KEY: VARIANT
<222> LOCATION: 3
<223> OTHER INFORMATION: Xaa = Ile, Leu, Asp, Met, Phe or Ser
<220> FEATURE:
<221> NAME/KEY: VARIANT
<222> LOCATION: 5
<223> OTHER INFORMATION: Xaa = Arg, Asn, Glu, Pro or Trp
<220> FEATURE:
<221> NAME/KEY: VARIANT
<222> LOCATION: 6
<223> OTHER INFORMATION: Xaa = Glu, Gly, Leu, Pro, Thr, Trp or Tyr
<220> FEATURE:
<221> NAME/KEY: VARIANT
<222> LOCATION: 7
<223> OTHER INFORMATION: Xaa = Asp, Gln, Glu, Gly, Phe, Ser, Thr, or Trp
<220> FEATURE:
<221> NAME/KEY: VARIANT
<222> LOCATION: 8
<223> OTHER INFORMATION: Xaa = Ala, Arg, Asn, Gln, Glu, Gly, Phe or Trp
<220> FEATURE:
<221> NAME/KEY: VARIANT
<222> LOCATION: 10
<223> OTHER INFORMATION: Xaa = Gly, Asn, His, Arg, Met, Ile, Asp, Val,
      or Thr
<220> FEATURE:
<221> NAME/KEY: VARIANT
<222> LOCATION: 11
<223> OTHER INFORMATION: Xaa = Ser, Lys, Phe, Met, Thr, Asp or Leu
<220> FEATURE:
<221> NAME/KEY: VARIANT
<222> LOCATION: 12
<223> OTHER INFORMATION: Xaa = Ser, Pro, Thr, Leu, Tyr, Asn, His, Glu or
      Trp

<400> SEQUENCE: 538

Xaa Xaa Xaa Cys Xaa Xaa Xaa Xaa Cys Xaa Xaa Xaa
 1               5                  10

<210> SEQ ID NO 539
<211> LENGTH: 14
<212> TYPE: PRT
<213> ORGANISM: Artificial Sequence
<220> FEATURE:
<223> OTHER INFORMATION: Exemplary motif
<220> FEATURE:
<221> NAME/KEY: VARIANT
<222> LOCATION: 1
<223> OTHER INFORMATION: Xaa = Gly, Val, Trp, Thr, Lys or Gln
<220> FEATURE:
<221> NAME/KEY: VARIANT
<222> LOCATION: 2
<223> OTHER INFORMATION: Xaa = Trp, Tyr, Leu, Phe or Thr
<220> FEATURE:
<221> NAME/KEY: VARIANT
<222> LOCATION: 3
<223> OTHER INFORMATION: Xaa =  Trp, Glu, Phe, Ile, Leu or Ser
<220> FEATURE:
<221> NAME/KEY: VARIANT
<222> LOCATION: 5
<223> OTHER INFORMATION: Xaa = Asn, Gln or Glu
<220> FEATURE:
<221> NAME/KEY: VARIANT
<222> LOCATION: 6
<223> OTHER INFORMATION: Xaa = Leu, Glu or Trp
<220> FEATURE:
<221> NAME/KEY: VARIANT
<222> LOCATION: 7
<223> OTHER INFORMATION: Xaa = Glu, Ser or Tyr
<220> FEATURE:
<221> NAME/KEY: VARIANT
<222> LOCATION: 8
<223> OTHER INFORMATION: Xaa = Glu, Met or Pro
<220> FEATURE:
<221> NAME/KEY: VARIANT
```

```
<222> LOCATION: 9
<223> OTHER INFORMATION: Xaa = Met, Ser or Trp
<220> FEATURE:
<221> NAME/KEY: VARIANT
<222> LOCATION: 10
<223> OTHER INFORMATION: Xaa = Leu, Phe or Val
<220> FEATURE:
<221> NAME/KEY: VARIANT
<222> LOCATION: 12
<223> OTHER INFORMATION: Xaa = Asp, Glu or Trp
<220> FEATURE:
<221> NAME/KEY: VARIANT
<222> LOCATION: 13
<223> OTHER INFORMATION: Xaa =  Met, Phe or Trp
<220> FEATURE:
<221> NAME/KEY: VARIANT
<222> LOCATION: 14
<223> OTHER INFORMATION: Xaa = Gln, Leu, or Trp

<400> SEQUENCE: 539

Xaa Xaa Xaa Cys Xaa Xaa Xaa Xaa Xaa Xaa Cys Xaa Xaa Xaa
 1               5                  10

<210> SEQ ID NO 540
<211> LENGTH: 14
<212> TYPE: PRT
<213> ORGANISM: Artificial Sequence
<220> FEATURE:
<223> OTHER INFORMATION: Exemplary motif
<220> FEATURE:
<221> NAME/KEY: VARIANT
<222> LOCATION: 1
<223> OTHER INFORMATION: Xaa = Glu, Ser, or Trp
<220> FEATURE:
<221> NAME/KEY: VARIANT
<222> LOCATION: 2
<223> OTHER INFORMATION: Xaa = Phe-Thr or Trp
<220> FEATURE:
<221> NAME/KEY: VARIANT
<222> LOCATION: 3
<223> OTHER INFORMATION: Xaa = His, Phe or Trp
<220> FEATURE:
<221> NAME/KEY: VARIANT
<222> LOCATION: 5
<223> OTHER INFORMATION: Xaa = Ala, Lys, Ser or Thr
<220> FEATURE:
<221> NAME/KEY: VARIANT
<222> LOCATION: 7
<223> OTHER INFORMATION: Xaa = Pro or Trp
<220> FEATURE:
<221> NAME/KEY: VARIANT
<222> LOCATION: 9
<223> OTHER INFORMATION: Xaa = Ser or Thr
<220> FEATURE:
<221> NAME/KEY: VARIANT
<222> LOCATION: 11
<223> OTHER INFORMATION: Xaa = Glu or Ser
<220> FEATURE:
<221> NAME/KEY: VARIANT
<222> LOCATION: 13
<223> OTHER INFORMATION: Xaa = Ile, Trp or Tyr
<220> FEATURE:
<221> NAME/KEY: VARIANT
<222> LOCATION: 14
<223> OTHER INFORMATION: Xaa = Glu, Met or Tyr

<400> SEQUENCE: 540

Xaa Xaa Xaa Cys Xaa Gly Xaa Pro Xaa Phe Xaa Cys Xaa Xaa
 1               5                  10

<210> SEQ ID NO 541
<211> LENGTH: 18
<212> TYPE: PRT
<213> ORGANISM: Artificial Sequence
<220> FEATURE:
<223> OTHER INFORMATION: Exemplary motif
```

```
<220> FEATURE:
<221> NAME/KEY: VARIANT
<222> LOCATION: 1
<223> OTHER INFORMATION: Xaa = Arg, Asp, Asn, Ile or Ser
<220> FEATURE:
<221> NAME/KEY: VARIANT
<222> LOCATION: 2
<223> OTHER INFORMATION: Xaa = Leu, Ile, Phe, Trp or Val
<220> FEATURE:
<221> NAME/KEY: VARIANT
<222> LOCATION: 3
<223> OTHER INFORMATION: Xaa = Asn, Gln, His, Leu, Tyr or Val
<220> FEATURE:
<221> NAME/KEY: VARIANT
<222> LOCATION: 5
<223> OTHER INFORMATION: Xaa = Leu, Lys or Ser
<220> FEATURE:
<221> NAME/KEY: VARIANT
<222> LOCATION: 9
<223> OTHER INFORMATION: Xaa = Ala, Ser, Thr or Trp
<220> FEATURE:
<221> NAME/KEY: VARIANT
<222> LOCATION: 11
<223> OTHER INFORMATION: Xaa = Glu or Ser
<220> FEATURE:
<221> NAME/KEY: VARIANT
<222> LOCATION: 14
<223> OTHER INFORMATION: Xaa = Leu, Ser or Trp
<220> FEATURE:
<221> NAME/KEY: VARIANT
<222> LOCATION: 15
<223> OTHER INFORMATION: Xaa = Phe or Tyr
<220> FEATURE:
<221> NAME/KEY: VARIANT
<222> LOCATION: 16
<223> OTHER INFORMATION: Xaa = Asp, Glu, Gly or Val
<220> FEATURE:
<221> NAME/KEY: VARIANT
<222> LOCATION: 17
<223> OTHER INFORMATION: Xaa = Met, Pro, Thr or Ser
<220> FEATURE:
<221> NAME/KEY: VARIANT
<222> LOCATION: 18
<223> OTHER INFORMATION: Xaa = Glu or Gly

<400> SEQUENCE: 541

Xaa Xaa Xaa Cys Xaa Gly Pro Pro Xaa Phe Xaa Cys Trp Xaa Xaa Xaa
 1               5                  10                  15

Xaa Xaa

<210> SEQ ID NO 542
<211> LENGTH: 18
<212> TYPE: PRT
<213> ORGANISM: Artificial Sequence
<220> FEATURE:
<223> OTHER INFORMATION: Exemplary motif
<220> FEATURE:
<221> NAME/KEY: VARIANT
<222> LOCATION: 1
<223> OTHER INFORMATION: Xaa = Asp, Glu or Val
<220> FEATURE:
<221> NAME/KEY: VARIANT
<222> LOCATION: 2
<223> OTHER INFORMATION: Xaa = Ala, Asp, Gly, Ser or Val
<220> FEATURE:
<221> NAME/KEY: VARIANT
<222> LOCATION: 3
<223> OTHER INFORMATION: Xaa = Asp, Gly, Ser or Val
<220> FEATURE:
<221> NAME/KEY: VARIANT
<222> LOCATION: 4
<223> OTHER INFORMATION: Xaa = Arg, Asn, Gly, Ser or Thr
<220> FEATURE:
<221> NAME/KEY: VARIANT
<222> LOCATION: 6
<223> OTHER INFORMATION: Xaa = Gln or His
<220> FEATURE:
```

```
<221> NAME/KEY: VARIANT
<222> LOCATION: 8
<223> OTHER INFORMATION: Xaa = Asn, Lys or Ser
<220> FEATURE:
<221> NAME/KEY: VARIANT
<222> LOCATION: 17
<223> OTHER INFORMATION: Xaa = Ser or Trp
<220> FEATURE:
<221> NAME/KEY: VARIANT
<222> LOCATION: 18
<223> OTHER INFORMATION: Xaa = Phe or Tyr

<400> SEQUENCE: 542

Xaa Xaa Xaa Xaa Trp Xaa Cys Xaa Gly Pro Pro Thr Phe Glu Cys Trp
 1               5                  10                  15

Xaa Xaa

<210> SEQ ID NO 543
<211> LENGTH: 16
<212> TYPE: PRT
<213> ORGANISM: Artificial Sequence
<220> FEATURE:
<223> OTHER INFORMATION: Exemplary motif
<220> FEATURE:
<221> NAME/KEY: VARIANT
<222> LOCATION: 1
<223> OTHER INFORMATION: Xaa = His, Phe, Pro, Thr or Trp
<220> FEATURE:
<221> NAME/KEY: VARIANT
<222> LOCATION: 2
<223> OTHER INFORMATION: Xaa = Ala, Arg, Glu, His, Lys or Phe
<220> FEATURE:
<221> NAME/KEY: VARIANT
<222> LOCATION: 3
<223> OTHER INFORMATION: Xaa = Met, Phe, Pro, Thr or Val
<220> FEATURE:
<221> NAME/KEY: VARIANT
<222> LOCATION: 5
<223> OTHER INFORMATION: Xaa = His, Leu, Met, Phe or Trp
<220> FEATURE:
<221> NAME/KEY: VARIANT
<222> LOCATION: 6
<223> OTHER INFORMATION: Xaa = Arg, Asp, Glu, Gly, Met or Trp
<220> FEATURE:
<221> NAME/KEY: VARIANT
<222> LOCATION: 7
<223> OTHER INFORMATION: Xaa = Glu, Gly, Ile, Lys, Phe or Pro
<220> FEATURE:
<221> NAME/KEY: VARIANT
<222> LOCATION: 8
<223> OTHER INFORMATION: Xaa = Asp, Phe, Pro, Ser, Trp or Tyr
<220> FEATURE:
<221> NAME/KEY: VARIANT
<222> LOCATION: 9
<223> OTHER INFORMATION: Xaa = Ala, Arg, Asn, Phe or Ser
<220> FEATURE:
<221> NAME/KEY: VARIANT
<222> LOCATION: 10
<223> OTHER INFORMATION: Xaa = Ala, Gln, Gly, Leu or Phe
<220> FEATURE:
<221> NAME/KEY: VARIANT
<222> LOCATION: 11
<223> OTHER INFORMATION: Xaa = Gln, Gly, Ile, Leu, Trp or Tyr
<220> FEATURE:
<221> NAME/KEY: VARIANT
<222> LOCATION: 12
<223> OTHER INFORMATION: Xaa = Arg, Asp, Phe, Pro, Tyr or Val
<220> FEATURE:
<221> NAME/KEY: VARIANT
<222> LOCATION: 14
<223> OTHER INFORMATION: Xaa = Asn, Gln, His, Ile or Thr
<220> FEATURE:
<221> NAME/KEY: VARIANT
<222> LOCATION: 15
<223> OTHER INFORMATION: Xaa = Ala, Asn, Asp, Glu or His
<220> FEATURE:
<221> NAME/KEY: VARIANT
```

```
<222> LOCATION: 16
<223> OTHER INFORMATION: Xaa = Asn, Gln, Glu, His or Val

<400> SEQUENCE: 543

Xaa Xaa Xaa Cys Xaa Xaa Xaa Xaa Xaa Xaa Xaa Xaa Cys Xaa Xaa Xaa
 1               5                  10                  15

<210> SEQ ID NO 544
<211> LENGTH: 17
<212> TYPE: PRT
<213> ORGANISM: Artificial Sequence
<220> FEATURE:
<223> OTHER INFORMATION: Exemplary motif
<220> FEATURE:
<221> NAME/KEY: VARIANT
<222> LOCATION: 1
<223> OTHER INFORMATION: Xaa = Gln, Gly, Met, Phe or Ser
<220> FEATURE:
<221> NAME/KEY: VARIANT
<222> LOCATION: 2
<223> OTHER INFORMATION: Xaa = Asn, Gln, Leu or Met
<220> FEATURE:
<221> NAME/KEY: VARIANT
<222> LOCATION: 3
<223> OTHER INFORMATION: Xaa = Arg, Asn, Gly, His or Ile
<220> FEATURE:
<221> NAME/KEY: VARIANT
<222> LOCATION: 5
<223> OTHER INFORMATION: Xaa = Asn, Asp, Leu, Thr or Trp
<220> FEATURE:
<221> NAME/KEY: VARIANT
<222> LOCATION: 6
<223> OTHER INFORMATION: Xaa = Arg, Gln, Thr, Tyr or Val
<220> FEATURE:
<221> NAME/KEY: VARIANT
<222> LOCATION: 7
<223> OTHER INFORMATION: Xaa = Glu, Gly, Leu, Met or Thr
<220> FEATURE:
<221> NAME/KEY: VARIANT
<222> LOCATION: 8
<223> OTHER INFORMATION: Xaa = Ala, Asn, Asp, His, Ile, Leu, or Ser
<220> FEATURE:
<221> NAME/KEY: VARIANT
<222> LOCATION: 9
<223> OTHER INFORMATION: Xaa = Arg, Gln, Ser, Thr or Tyr
<220> FEATURE:
<221> NAME/KEY: VARIANT
<222> LOCATION: 10
<223> OTHER INFORMATION: Xaa = Asp, Gly, Ile or Phe
<220> FEATURE:
<221> NAME/KEY: VARIANT
<222> LOCATION: 11
<223> OTHER INFORMATION: Xaa = Gln, Phe or Thr
<220> FEATURE:
<221> NAME/KEY: VARIANT
<222> LOCATION: 12
<223> OTHER INFORMATION: Xaa = Gln, His, Phe, Pro, Ser or Tyr
<220> FEATURE:
<221> NAME/KEY: VARIANT
<222> LOCATION: 13
<223> OTHER INFORMATION: Xaa = Asn, Asp, Phe, Pro or Ser
<220> FEATURE:
<221> NAME/KEY: VARIANT
<222> LOCATION: 15
<223> OTHER INFORMATION: Xaa = Ala, Asn, Gly, Leu or Ser
<220> FEATURE:
<221> NAME/KEY: VARIANT
<222> LOCATION: 16
<223> OTHER INFORMATION: Xaa = Arg, Pro, Ser or Val
<220> FEATURE:
<221> NAME/KEY: VARIANT
<222> LOCATION: 17
<223> OTHER INFORMATION: Xaa = Asp, Glu, Leu or Met

<400> SEQUENCE: 544

Xaa Xaa Xaa Cys Xaa Xaa Xaa Xaa Xaa Xaa Xaa Xaa Xaa Cys Xaa Xaa
 1               5                  10                  15
```

Xaa

<210> SEQ ID NO 545
<211> LENGTH: 18
<212> TYPE: PRT
<213> ORGANISM: Artificial Sequence
<220> FEATURE:
<223> OTHER INFORMATION: Exemplary motif
<220> FEATURE:
<221> NAME/KEY: VARIANT
<222> LOCATION: 1
<223> OTHER INFORMATION: Xaa = Ala, His, Leu, Pro or Tyr
<220> FEATURE:
<221> NAME/KEY: VARIANT
<222> LOCATION: 2
<223> OTHER INFORMATION: Xaa = Arg, Asp, Leu, Ser or Tyr
<220> FEATURE:
<221> NAME/KEY: VARIANT
<222> LOCATION: 3
<223> OTHER INFORMATION: Xaa = Glu, Met or Trp
<220> FEATURE:
<221> NAME/KEY: VARIANT
<222> LOCATION: 5
<223> OTHER INFORMATION: Xaa = Asp, Gln, Glu, Phe or Ser
<220> FEATURE:
<221> NAME/KEY: VARIANT
<222> LOCATION: 6
<223> OTHER INFORMATION: Xaa = Glu, Ile, Phe or Trp
<220> FEATURE:
<221> NAME/KEY: VARIANT
<222> LOCATION: 7
<223> OTHER INFORMATION: Xaa = Asn, Asp or Ser
<220> FEATURE:
<221> NAME/KEY: VARIANT
<222> LOCATION: 8
<223> OTHER INFORMATION: Xaa = Asn, Asp or Leu
<220> FEATURE:
<221> NAME/KEY: VARIANT
<222> LOCATION: 9
<223> OTHER INFORMATION: Xaa = Asp, Glu or Lys
<220> FEATURE:
<221> NAME/KEY: VARIANT
<222> LOCATION: 10
<223> OTHER INFORMATION: Xaa = Gly, Phe or Thr
<220> FEATURE:
<221> NAME/KEY: VARIANT
<222> LOCATION: 11
<223> OTHER INFORMATION: Xaa = Gly, Phe, Trp or Tyr
<220> FEATURE:
<221> NAME/KEY: VARIANT
<222> LOCATION: 12
<223> OTHER INFORMATION: Xaa = Glu, Ser or Trp
<220> FEATURE:
<221> NAME/KEY: VARIANT
<222> LOCATION: 13
<223> OTHER INFORMATION: Xaa = Glu, Phe, Tyr or Val
<220> FEATURE:
<221> NAME/KEY: VARIANT
<222> LOCATION: 14
<223> OTHER INFORMATION: Xaa = Glu, Lys, Thr or Val
<220> FEATURE:
<221> NAME/KEY: VARIANT
<222> LOCATION: 16
<223> OTHER INFORMATION: Xaa = Glu or Trp
<220> FEATURE:
<221> NAME/KEY: VARIANT
<222> LOCATION: 17
<223> OTHER INFORMATION: Xaa = Asp, Phe, Pro, Ser or Trp
<220> FEATURE:
<221> NAME/KEY: VARIANT
<222> LOCATION: 18
<223> OTHER INFORMATION: Xaa = Ala, Asn or Ile

<400> SEQUENCE: 545

Xaa Xaa Xaa Cys Xaa Xaa Xaa Xaa Xaa Xaa Xaa Xaa Xaa Xaa Cys Xaa
 1               5                   10                  15

```
<210> SEQ ID NO 546
<211> LENGTH: 18
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 3
<223> OTHER INFORMATION: Xaa = Asn, His or Tyr
<220> FEATURE:
<221> NAME/KEY: VARIANT
<222> LOCATION: 5
<223> OTHER INFORMATION: Xaa = Gly or Ser
<220> FEATURE:
<221> NAME/KEY: VARIANT
<222> LOCATION: 16
<223> OTHER INFORMATION: Xaa = Ala, Asp, Glu, Gly or Ser
<220> FEATURE:
<221> NAME/KEY: VARIANT
<222> LOCATION: 17
<223> OTHER INFORMATION: Xaa = Ser or Thr
<220> FEATURE:
<221> NAME/KEY: VARIANT
<222> LOCATION: 18
<223> OTHER INFORMATION: Xaa = Asp or Glu

<400> SEQUENCE: 546

Ser Cys Xaa Cys Xaa Gly Pro Pro Thr Phe Glu Cys Trp Cys Tyr Xaa
 1               5                  10                  15

Xaa Xaa

<210> SEQ ID NO 547
<211> LENGTH: 18
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 2
<223> OTHER INFORMATION: Xaa = Ala, Glu, Gly or Ser
<220> FEATURE:
<221> NAME/KEY: VARIANT
<222> LOCATION: 16
<223> OTHER INFORMATION: Xaa = Phe, Trp or Tyr
<220> FEATURE:
<221> NAME/KEY: VARIANT
<222> LOCATION: 18
<223> OTHER INFORMATION: Xaa = Phe or Tyr

<400> SEQUENCE: 547

Glu Xaa Gly Ser Cys His Cys Ser Gly Pro Pro Thr Phe Glu Cys Xaa
 1               5                  10                  15

Cys Xaa

<210> SEQ ID NO 548
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 548

Cys Lys Gly Pro Pro Thr Phe Glu Cys
 1               5

<210> SEQ ID NO 549
<211> LENGTH: 9
```

```
<212> TYPE: PRT
<213> ORGANISM: Artificial Sequence
<220> FEATURE:
<223> OTHER INFORMATION: Synthetically generated peptide

<400> SEQUENCE: 549

Cys Ser Gly Pro Pro Thr Phe Met Cys
 1               5

<210> SEQ ID NO 550
<211> LENGTH: 119
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 25, 27, 30, 33-34, 38, 40-42, 46-48, 50-51, 54, 59
<223> OTHER INFORMATION: n = z = 0.12A + 0.12C + 0.12G + 0.64T
<220> FEATURE:
<221> NAME/KEY: misc_feature
<222> LOCATION: 26, 29, 31, 44, 49, 53, 56
<223> OTHER INFORMATION: n = e = 0.64A + 0.12C + 0.12G + 0.12T
<220> FEATURE:
<221> NAME/KEY: misc_feature
<222> LOCATION: 28, 35-37, 39, 45, 55, 57-58, 60, 63
<223> OTHER INFORMATION: n = j = 0.12A + 0.12C + 0.64G + 0.12T
<220> FEATURE:
<221> NAME/KEY: misc_feature
<222> LOCATION: 32, 43, 52, 61-62
<223> OTHER INFORMATION: n = q = 0.12A + 0.64C + 0.12G + 0.12T
<220> FEATURE:
<221> NAME/KEY: CDS
<222> LOCATION: (10)...(108)

<400> SEQUENCE: 550 tcactgtct tcc atg ggt tct gaa nnn nnn nnn nnn nnn nnn nnn nnn nnn    51
           Ser Met Gly Ser Glu Tyr Asp Thr Trp Val Phe Gln Phe Ile
            1               5                  10 nnn nnn nnn nnn ggt gag ctg gtt gct atg cag ggt ggt agt ggt act       99
His Glu Val Pro Gly Glu Leu Val Ala Met Gln Gly Gly Ser Gly Thr
 15              20                  25                  30 gaa gct agc gtgactctga c                                             119
Glu Ala Ser <210> SEQ ID NO 551
<211> LENGTH: 119
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (10)...(108)
<220> FEATURE:
<221> NAME/KEY: misc_feature
<222> LOCATION: 25, 27, 34, 38, 46-48, 50-51, 54, 66, 71, 74
<223> OTHER INFORMATION: N = z = 0.12A + 0.12C + 0.12G + 0.64T
<220> FEATURE:
<221> NAME/KEY: misc_feature
<222> LOCATION: 26, 44, 49, 53, 68
<223> OTHER INFORMATION: n = e = 0.64A + 0.12C + 0.12G + 0.12T
<220> FEATURE:
<221> NAME/KEY: misc_feature
<222> LOCATION: 35-37, 39, 45, 63-65, 67, 69, 72-73, 75-76, 78
<223> OTHER INFORMATION: n = j = 0.12A + 0.12C + 0.64G + 0.12T
<220> FEATURE:
<221> NAME/KEY: misc_feature
<222> LOCATION: 43, 52, 61-62, 70, 77
<223> OTHER INFORMATION: n = q = 0.12A + 0.64C + 0.12G + 0.12T

<400> SEQUENCE: 551 tcactgtct tcc atg ggt tct gaa nnn gat act nnn nnn ttt nnn nnn nnn    51
```

```
            Ser Met Gly Ser Glu Tyr Asp Thr Trp Val Phe Gln Phe Ile
              1               5                  10
nnn gag gtt nnn nnn nnn nnn nnn nnn atg caa ggt ggt agt ggt act      99
His Glu Val Pro Gln Glu Leu Val Ala Met Gln Gly Gly Ser Gly Thr
 15                  20                  25                  30 gaa gct agc gtgactctga c                                            119
Glu Ala Ser
```

<210> SEQ ID NO 552
<211> LENGTH: 119
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (10)...(108)
<220> FEATURE:
<221> NAME/KEY: misc_feature
<222> LOCATION: 49, 53, 56, 68, 79,
<223> OTHER INFORMATION: n = e = 0.64A + 0.12C + 0.12G + 0.12T
<220> FEATURE:
<221> NAME/KEY: misc_feature
<222> LOCATION: 50-51, 54, 59-60, 66, 71, 74, 80, 83-84
<223> OTHER INFORMATION: n = z = 0.12A + 0.12C + 0.12G + 0.64T
<220> FEATURE:
<221> NAME/KEY: misc_feature
<222> LOCATION: 52, 61-62, 70, 77, 82
<223> OTHER INFORMATION: n = q = 0.12A + 0.64C + 0.12G + 0.12T
<220> FEATURE:
<221> NAME/KEY: misc_feature
<222> LOCATION: 55, 57-58, 63-65, 67, 69, 72-73, 75-76, 78, 81
<223> OTHER INFORMATION: n = j = 0.12A + 0.12C + 0.64G + 0.12T

<400> SEQUENCE: 552

```
tcactgtctt tcc atg ggt tct gaa tat gat act tgg gtt ttt caa ttt nnn   51
            Ser Met Gly Ser Glu Tyr Asp Thr Trp Val Phe Gln Phe Ile
              1               5                  10
nnn nnn nnn nnn nnn nnn nnn nnn nnn nnn ggt ggt agt ggt act          99
His Glu Val Pro Gly Glu Leu Val Ala Met Gln Gly Gly Ser Gly Thr
 15                  20                  25                  30 gaa gct agc gtgactctga c                                            119
Glu Ala Ser
```

<210> SEQ ID NO 553
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 553
tcactgtctt ccatgggttc tgaa                                           24

<210> SEQ ID NO 554
<211> LENGTH: 36
<212> TYPE: DNA
<213> ORGANISM: Artificial Sequence
<220> FEATURE:
<223> OTHER INFORMATION: Synthetically generated oligonucleotide

<400> SEQUENCE: 554
tcactgtctt ccatgggttc tgaaactcgc cctaca                              36

<210> SEQ ID NO 555
<211> LENGTH: 22
<212> TYPE: DNA
<213> ORGANISM: Artificial Sequence
<220> FEATURE:

-continued

```
<223> OTHER INFORMATION: Synthetically generated oligonucleotide

<400> SEQUENCE: 555
ctcagcagtc actgtcttcc at                                              22

<210> SEQ ID NO 556
<211> LENGTH: 44
<212> TYPE: DNA
<213> ORGANISM: Artificial Sequence
<220> FEATURE:
<223> OTHER INFORMATION: Synthetically generated oligonucleotide

<400> SEQUENCE: 556
ctcagcagtc actgtcttcc atgggttctg aaactcgccc taca                      44

<210> SEQ ID NO 557
<211> LENGTH: 93
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 19, 21-22, 25-26, 29, 32-33, 41, 54, 58, 60, 65-66,
      68-69
<223> OTHER INFORMATION: n = j = 0.12A + 0.12C + 0.64G + 0.12T
<220> FEATURE:
<221> NAME/KEY: misc_feature
<222> LOCATION: 20, 28, 35, 40, 52, 59, 71
<223> OTHER INFORMATION: n = e = 0.64A + 0.12C + 0.12G + 0.12T
<220> FEATURE:
<221> NAME/KEY: misc_feature
<222> LOCATION: 23, 34, 53
<223> OTHER INFORMATION: n = q = 0.12A + 0.64C + 0.12G + 0.12T
<220> FEATURE:
<221> NAME/KEY: misc_feature
<222> LOCATION: 24, 27, 30-31, 36,42, 64, 67, 70, 72
<223> OTHER INFORMATION: n = z = 0.12A + 0.12C + 0.12G + 0.64T

<400> SEQUENCE: 557
tctgaaactc gccctacann nnnnnnnnnn nnnnnntgtn nnggtcctcc tnnnttcnnn      60
tgcnnnnnnn nnggaacgga gccgactgaa gct                                  93

<210> SEQ ID NO 558
<211> LENGTH: 44
<212> TYPE: DNA
<213> ORGANISM: Artificial Sequence
<220> FEATURE:
<223> OTHER INFORMATION: Synthetic construct

<400> SEQUENCE: 558
ggaacggagc cgactgaagc tagcgtgact ctgacagtct ctgt                      44

<210> SEQ ID NO 559
<211> LENGTH: 22
<212> TYPE: DNA
<213> ORGANISM: Artificial Sequence
<220> FEATURE:
<223> OTHER INFORMATION: Synthetic construct

<400> SEQUENCE: 559
cagtgactct gacagtctct gt                                              22

<210> SEQ ID NO 560
<211> LENGTH: 35
<212> TYPE: DNA
<213> ORGANISM: Artificial Sequence
<220> FEATURE:
<223> OTHER INFORMATION: Synthetic construct
```

<400> SEQUENCE: 560
ggaacggagc cgactgaagc tagcgtgact ctgac                       35

<210> SEQ ID NO 561
<211> LENGTH: 23
<212> TYPE: DNA
<213> ORGANISM: Artificial Sequence
<220> FEATURE:
<223> OTHER INFORMATION: Synthetic construct

<400> SEQUENCE: 561
actgaagcta gcgtgactct gac                                    23

<210> SEQ ID NO 562
<211> LENGTH: 22
<212> TYPE: DNA
<213> ORGANISM: Artificial Sequence
<220> FEATURE:
<223> OTHER INFORMATION: Synthetic construct

<400> SEQUENCE: 562
ctcagcagtc actgtcttcc at                                     22

<210> SEQ ID NO 563
<211> LENGTH: 44
<212> TYPE: DNA
<213> ORGANISM: Artificial Sequence
<220> FEATURE:
<223> OTHER INFORMATION: Synthetic construct

<400> SEQUENCE: 563
ctcagcagtc actgtcttcc atgggttctg aaactcgccc taca             44

<210> SEQ ID NO 564
<211> LENGTH: 100
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 28,35, 40, 52, 59, 71, 76, 80
<223> OTHER INFORMATION: n = e = 0.64A + 0.12C + 0.12G + 0.12T
<220> FEATURE:
<221> NAME/KEY: misc_feature
<222> LOCATION: 29, 32-33, 41, 54, 58, 60, 65-66, 68-69, 73-74, 78-79,
      81
<223> OTHER INFORMATION: n = j = 0.12A + 0.12C + 0.64G + 0.12T
<220> FEATURE:
<221> NAME/KEY: misc_feature
<222> LOCATION: 30-31, 36, 42, 64, 67, 70, 72, 75
<223> OTHER INFORMATION: n = z = 0.12A + 0.12C + 0.12G + 0.64T
<220> FEATURE:
<221> NAME/KEY: misc_feature
<222> LOCATION: 34, 53, 77
<223> OTHER INFORMATION: n = q = 0.12A + 0.64C + 0.12G + 0.12T

<400> SEQUENCE: 564
tctgaaactc gccctacaga ggctggtnnn nnnnnntgtn nnggtcctcc tnnnttcnnn    60
tgcnnnnnnn nnnnnnnnnn nccgactgaa cgtcctagtg                          100

<210> SEQ ID NO 565
<211> LENGTH: 44
<212> TYPE: DNA
<213> ORGANISM: Artificial Sequence
<220> FEATURE:
<223> OTHER INFORMATION: Synthetic construct -continued

```
<400> SEQUENCE: 565
ccgactgaac gtcctagtgc tagcgtgact ctgacagtct ctgt                    44

<210> SEQ ID NO 566
<211> LENGTH: 22
<212> TYPE: DNA
<213> ORGANISM: Artificial Sequence
<220> FEATURE:
<223> OTHER INFORMATION: Synthetic construct

<400> SEQUENCE: 566
cagtgactct gacagtctct gt                                            22

<210> SEQ ID NO 567
<211> LENGTH: 35
<212> TYPE: DNA
<213> ORGANISM: Artificial Sequence
<220> FEATURE:
<223> OTHER INFORMATION: Synthetic construct

<400> SEQUENCE: 567
ccgactgaac gtcctagtgc tagcgtgact ctgac                              35

<210> SEQ ID NO 568
<211> LENGTH: 22
<212> TYPE: DNA
<213> ORGANISM: Artificial Sequence
<220> FEATURE:
<223> OTHER INFORMATION: Synthetic construct

<400> SEQUENCE: 568
ctagtgctag cgtgactctg ac                                            22

<210> SEQ ID NO 569
<211> LENGTH: 22
<212> TYPE: DNA
<213> ORGANISM: Artificial Sequence
<220> FEATURE:
<223> OTHER INFORMATION: Synthetic construct

<400> SEQUENCE: 569
ctcagcagtc actgtcttcc at                                            22

<210> SEQ ID NO 570
<211> LENGTH: 44
<212> TYPE: DNA
<213> ORGANISM: Artificial Sequence
<220> FEATURE:
<223> OTHER INFORMATION: Synthetic construct

<400> SEQUENCE: 570
ctcagcagtc actgtcttcc atgggttctg aaactcgccc taca                    44

<210> SEQ ID NO 571
<211> LENGTH: 92
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 19, 21-22, 25-26, 29, 36, 42, 53-54, 59, 64, 66, 69
<223> OTHER INFORMATION: n = j = 0.12A + 0.12C + 0.64G + 0.12T
<220> FEATURE:
<221> NAME/KEY: misc_feature
<222> LOCATION: 20, 28, 31, 35, 40-41, 58, 67, 71
<223> OTHER INFORMATION: n = e =0.64A + 0.12C + 0.12G + 0.12T
<220> FEATURE:
```

```
<221> NAME/KEY: misc_feature
<222> LOCATION: 23, 34, 65
<223> OTHER INFORMATION: n = q = 0.12A + 0.64C + 0.12G + 0.12T
<220> FEATURE:
<221> NAME/KEY: misc_feature
<222> LOCATION: 24, 27, 30, 32-33, 52, 60, 68, 70, 72
<223> OTHER INFORMATION: n = z = 0.12A + 0.12C + 0.12G + 0.64T

<400> SEQUENCE: 571
tctgaaactc gccctacann nnnnnnnnnn nnnnnntgcn nnggtcctcc tnnnttcnnn    60 tgtnnnnnnnn nnggaacgga gccgactgaa gc                                 92

<210> SEQ ID NO 572
<211> LENGTH: 44
<212> TYPE: DNA
<213> ORGANISM: Artificial Sequence
<220> FEATURE:
<223> OTHER INFORMATION: Synthetic construct

<400> SEQUENCE: 572
ggaacggagc cgactgaagc tagcgtgact ctgacagtct ctgt                     44

<210> SEQ ID NO 573
<211> LENGTH: 22
<212> TYPE: DNA
<213> ORGANISM: Artificial Sequence
<220> FEATURE:
<223> OTHER INFORMATION: Synthetic construct

<400> SEQUENCE: 573
cagtgactct gacagtctct gt                                             22

<210> SEQ ID NO 574
<211> LENGTH: 22
<212> TYPE: DNA
<213> ORGANISM: Artificial Sequence
<220> FEATURE:
<223> OTHER INFORMATION: Synthetic construct

<400> SEQUENCE: 574
ctcagcagtc actgtcttcc at                                             22

<210> SEQ ID NO 575
<211> LENGTH: 44
<212> TYPE: DNA
<213> ORGANISM: Artificial Sequence
<220> FEATURE:
<223> OTHER INFORMATION: Synthetic construct

<400> SEQUENCE: 575
ctcagcagtc actgtcttcc atgggttctg aaactcgccc taca                     44

<210> SEQ ID NO 576
<211> LENGTH: 101
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 28, 31, 35, 40-41, 58, 67, 71, 76, 80
<223> OTHER INFORMATION: n = e = 0.64A + 0.12C + 0.12G + 0.12T
<220> FEATURE:
<221> NAME/KEY: misc_feature
<222> LOCATION: 29, 36, 42, 53-54, 59, 64, 66, 69, 73-74, 78-79, 81
<223> OTHER INFORMATION: n = j = 0.12A + 0.12C + 0.64G + 0.12T
<220> FEATURE:
<221> NAME/KEY: misc_feature
<222> LOCATION: 30,32-33, 52, 60, 68, 70, 72, 75
```

<223> OTHER INFORMATION: n = z = 0.12A + 0.12C + 0.12G + 0.64T
<220> FEATURE:
<221> NAME/KEY: misc_feature
<222> LOCATION: 34, 65, 77
<223> OTHER INFORMATION: n = q = 0.12A + 0.64C + 0.12G + 0.12T

<400> SEQUENCE: 576
tctgaaactc gccctacaga ggccggtnnn nnnnnntgcn nnggtcctcc tnnnttcnnn    60
tgtnnnnnnn nnnnnnnnnn nccgactgaa cgtcctagtg c                       101

<210> SEQ ID NO 577
<211> LENGTH: 44
<212> TYPE: DNA
<213> ORGANISM: Artificial Sequence
<220> FEATURE:
<223> OTHER INFORMATION: Synthetic construct

<400> SEQUENCE: 577
ccgactgaac gtcctagtgc tagcgtgact ctgacagtct ctgt                    44

<210> SEQ ID NO 578
<211> LENGTH: 22
<212> TYPE: DNA
<213> ORGANISM: Artificial Sequence
<220> FEATURE:
<223> OTHER INFORMATION: Synthetic construct

<400> SEQUENCE: 578
cagtgactct gacagtctct gt                                            22

<210> SEQ ID NO 579
<211> LENGTH: 22
<212> TYPE: DNA
<213> ORGANISM: Artificial Sequence
<220> FEATURE:
<223> OTHER INFORMATION: Synthetic construct

<400> SEQUENCE: 579
ctcagcagtc actgtcttcc at                                            22

<210> SEQ ID NO 580
<211> LENGTH: 44
<212> TYPE: DNA
<213> ORGANISM: Artificial Sequence
<220> FEATURE:
<223> OTHER INFORMATION: Synthetic construct

<400> SEQUENCE: 580
ctcagcagtc actgtcttcc atgggttctg aaactcgccc taca                    44

<210> SEQ ID NO 581
<211> LENGTH: 101
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 28,30-31, 33, 36, 54, 67, 71, 75
<223> OTHER INFORMATION: n = z = 0.12A + 0.12C + 0.12G + 0.64T
<220> FEATURE:
<221> NAME/KEY: misc_difference
<222> LOCATION: 29, 32, 40-41, 52, 59, 65-66, 70, 76, 80
<223> OTHER INFORMATION: n = e = 0.64A + 0.12C + 0.12G + 0.12T
<220> FEATURE:
<221> NAME/KEY: misc_feature
<222> LOCATION: 34-35, 42, 58, 60, 68-69, 72-74, 78-79, 81
<223> OTHER INFORMATION: n = j = 0.12A + 0.12C + 0.64G + 0.12T
<220> FEATURE:

```
<221> NAME/KEY: misc_feature
<222> LOCATION: 53, 64, 77
<223> OTHER INFORMATION: n = q = 0.12A + 0.64C + 0.12G + 0.12T

<400> SEQUENCE: 581
tctgaaactc gccctacaga ggctggtnnn nnnnnntgcn nnggtcctcc tnnnttcnnn      60
tgtnnnnnnn nnnnnnnnnn nccgactgaa cgtcctagtg c                        101

<210> SEQ ID NO 582
<211> LENGTH: 44
<212> TYPE: DNA
<213> ORGANISM: Artificial Sequence
<220> FEATURE:
<223> OTHER INFORMATION: Synthetic construct

<400> SEQUENCE: 582
ccgactgaac gtcctagtgc tagcgtgact ctgacagtct ctgt                      44

<210> SEQ ID NO 583
<211> LENGTH: 22
<212> TYPE: DNA
<213> ORGANISM: Artificial Sequence
<220> FEATURE:
<223> OTHER INFORMATION: Synthetic construct

<400> SEQUENCE: 583
cagtgactct gacagtctct gt                                              22

<210> SEQ ID NO 584
<211> LENGTH: 22
<212> TYPE: DNA
<213> ORGANISM: Artificial Sequence
<220> FEATURE:
<223> OTHER INFORMATION: Synthetic construct

<400> SEQUENCE: 584
ctcagcagtc actgtcttcc at                                              22

<210> SEQ ID NO 585
<211> LENGTH: 44
<212> TYPE: DNA
<213> ORGANISM: Artificial Sequence
<220> FEATURE:
<223> OTHER INFORMATION: Synthetic construct

<400> SEQUENCE: 585
ctcagcagtc actgtcttcc atgggttctg aaactcgccc taca                      44

<210> SEQ ID NO 586
<211> LENGTH: 101
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 28, 48, 60, 65, 73-74, 78-79, 81
<223> OTHER INFORMATION: n = j = 0.12A + 0.12C + 0.64G + 0.12T
<220> FEATURE:
<221> NAME/KEY: misc_feature
<222> LOCATION: 29, 33, 36, 41, 46-47, 53, 66-67, 77
<223> OTHER INFORMATION: n = q = 0.12A + 0.64C + 0.12G + 0.12T
<220> FEATURE:
<221> NAME/KEY: misc_feature
<222> LOCATION: 30-32, 34-35, 40, 42, 54, 59, 68-70, 72, 75
<223> OTHER INFORMATION: n = z = 0.12A + 0.12C + 0.12G + 0.64T
<220> FEATURE:
<221> NAME/KEY: misc_feature
<222> LOCATION: 52, 58, 64, 71, 76, 80
```

-continued

<223> OTHER INFORMATION: n = e = 0.64A + 0.12C + 0.12G + 0.12T

<400> SEQUENCE: 586
tctgaaactc gccctacaga ggctggtnnn nnnnnntgtn nnggtnnncc tnnnttcnnn    60
tgcnnnnnnn nnnnnnnnnn nccgactgaa cgtcctagtg c                      101

<210> SEQ ID NO 587
<211> LENGTH: 44
<212> TYPE: DNA
<213> ORGANISM: Artificial Sequence
<220> FEATURE:
<223> OTHER INFORMATION: Synthetic construct

<400> SEQUENCE: 587
ccgactgaac gtcctagtgc tagcgtgact ctgacagtct ctgt                    44

<210> SEQ ID NO 588
<211> LENGTH: 22
<212> TYPE: DNA
<213> ORGANISM: Artificial Sequence
<220> FEATURE:
<223> OTHER INFORMATION: Synthetic construct

<400> SEQUENCE: 588
cagtgactct gacagtctct gt                                            22

<210> SEQ ID NO 589
<211> LENGTH: 22
<212> TYPE: DNA
<213> ORGANISM: Artificial Sequence
<220> FEATURE:
<223> OTHER INFORMATION: Synthetic construct

<400> SEQUENCE: 589
ctcagcagtc actgtcttcc at                                            22

<210> SEQ ID NO 590
<211> LENGTH: 44
<212> TYPE: DNA
<213> ORGANISM: Artificial Sequence
<220> FEATURE:
<223> OTHER INFORMATION: Synthetic construct

<400> SEQUENCE: 590
ctcagcagtc actgtcttcc atgggttctg aaactcgccc taca                    44

<210> SEQ ID NO 591
<211> LENGTH: 92
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 19, 21-22, 25-26, 30, 36, 40, 48, 53, 58, 65-66, 69,
<223> OTHER INFORMATION: n = j = 0.12A + 0.12C + 0.64G + 0.12T
<220> FEATURE:
<221> NAME/KEY: misc_feature
<222> LOCATION: 20, 29, 34-35, 52, 67, 70
<223> OTHER INFORMATION: n = e = 0.64A + 0.12C + 0.12G + 0.12T
<220> FEATURE:
<221> NAME/KEY: misc_feature
<222> LOCATION: 23, 28, 33, 41, 46-47, 57, 59-60, 71-72
<223> OTHER INFORMATION: n = q = 0.12A + 0.64C + 0.12G + 0.12T
<220> FEATURE:
<221> NAME/KEY: misc_feature
<222> LOCATION: 24, 27, 31-32, 42, 54-56, 64, 68
<223> OTHER INFORMATION: n = z = 0.12A + 0.12C + 0.12G + 0.64T

<400> SEQUENCE: 591
tctgaaactc gccctacann nnnnnnnnnn nnnnnntgtn nnggtnnncc gnnnnnnnnn    60
tgtnnnnnnn nnggaacgga gccgactgaa gc                                  92

<210> SEQ ID NO 592
<211> LENGTH: 44
<212> TYPE: DNA
<213> ORGANISM: Artificial Sequence
<220> FEATURE:
<223> OTHER INFORMATION: Synthetic construct

<400> SEQUENCE: 592
ggaacggagc cgactgaagc tagcgtgact ctgacagtct ctgt                     44

<210> SEQ ID NO 593
<211> LENGTH: 22
<212> TYPE: DNA
<213> ORGANISM: Artificial Sequence
<220> FEATURE:
<223> OTHER INFORMATION: Synthetic construct

<400> SEQUENCE: 593
cagtgactct gacagtctct gt                                             22

<210> SEQ ID NO 594
<211> LENGTH: 24
<212> TYPE: DNA
<213> ORGANISM: Artificial Sequence
<220> FEATURE:
<223> OTHER INFORMATION: Synthetic construct

<400> SEQUENCE: 594
tcactgtctt ccatgggttc tgaa                                           24

<210> SEQ ID NO 595
<211> LENGTH: 105
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 25,27, 30, 33-34, 38, 40-42, 46-48, 50-51, 54, 59
<223> OTHER INFORMATION: n = z = 0.12A + 0.12C + 0.12G + 0.64T
<220> FEATURE:
<221> NAME/KEY: misc_feature
<222> LOCATION: 26,29, 31, 44, 49, 53, 56
<223> OTHER INFORMATION: n = e = 0.64A + 0.12C + 0.12G + 0.12T
<220> FEATURE:
<221> NAME/KEY: misc_feature
<222> LOCATION: 28, 35-37, 39, 45, 55, 57-58, 60, 63
<223> OTHER INFORMATION: n = j = 0.12A + 0.12C + 0.64G + 0.12T
<220> FEATURE:
<221> NAME/KEY: misc_feature
<222> LOCATION: 32, 43, 52, 61-62
<223> OTHER INFORMATION: n = q = 0.12A + 0.64C + 0.12G + 0.12T

<400> SEQUENCE: 595
tcactgtctt ccatgggttc tgaannnnnn nnnnnnnnnn nnnnnnnnnn nnnnnnnnnn    60
nnnggtgagc tggttgctat gcagggtggt agtggtactg aagct                   105

<210> SEQ ID NO 596
<211> LENGTH: 32
<212> TYPE: DNA
<213> ORGANISM: Artificial Sequence
<220> FEATURE:
<223> OTHER INFORMATION: Synthetic construct

<400> SEQUENCE: 596
ggtggtagtg gtactgaagc tagcgtgact ct                              32

<210> SEQ ID NO 597
<211> LENGTH: 24
<212> TYPE: DNA
<213> ORGANISM: Artificial Sequence
<220> FEATURE:
<223> OTHER INFORMATION: Synthetic construct

<400> SEQUENCE: 597
tcactgtctt ccatgggttc tgaa                                       24

<210> SEQ ID NO 598
<211> LENGTH: 105
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 25, 27, 34, 38, 46-48, 50-51, 54, 66, 71, 74
<223> OTHER INFORMATION: n = z = 0.12A + 0.12C + 0.12G + 0.64T
<220> FEATURE:
<221> NAME/KEY: misc_feature
<222> LOCATION: 26, 44, 49, 53, 68
<223> OTHER INFORMATION: n = e = 0.64A + 0.12C + 0.12G + 0.12T
<220> FEATURE:
<221> NAME/KEY: misc_feature
<222> LOCATION: 35-37, 39, 45, 63-65, 67, 69, 72-73, 75-76, 78
<223> OTHER INFORMATION: n = j = 0.12A + 0.12C + 0.64G + 0.12T
<220> FEATURE:
<221> NAME/KEY: misc_feature
<222> LOCATION: 43, 52, 61-62, 70, 77
<223> OTHER INFORMATION: n = q = 0.12A + 0.64C + 0.12G + 0.12T

<400> SEQUENCE: 598
tcactgtctt ccatgggttc tgaannngat actnnnnnnt ttnnnnnnnn nnnngaggtt   60
nnnnnnnnnn nnnnnnnnat gcaaggtggt agtggtactg aagct                 105

<210> SEQ ID NO 599
<211> LENGTH: 32
<212> TYPE: DNA
<213> ORGANISM: Artificial Sequence
<220> FEATURE:
<223> OTHER INFORMATION: Synthetic construct

<400> SEQUENCE: 599
ggtggtagtg gtactgaagc tagcgtgact ct                              32

<210> SEQ ID NO 600
<211> LENGTH: 24
<212> TYPE: DNA
<213> ORGANISM: Artificial Sequence
<220> FEATURE:
<223> OTHER INFORMATION: Synthetic construct

<400> SEQUENCE: 600
tcactgtctt ccatgggttc tgaa                                       24

<210> SEQ ID NO 601
<211> LENGTH: 105
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 49, 53, 56, 68, 79

<223> OTHER INFORMATION: n = e = 0.64A + 0.12C + 0.12G + 0.12T
<220> FEATURE:
<221> NAME/KEY: misc_feature
<222> LOCATION: 50-51, 54, 59-60, 66, 71, 74, 80, 83-84
<223> OTHER INFORMATION: n = z = 0.64A + 0.12C + 0.12G + 0.12T
<220> FEATURE:
<221> NAME/KEY: misc_feature
<222> LOCATION: 52, 61-62, 70, 77, 82
<223> OTHER INFORMATION: n = q = 0.12A + 0.64C + 0.12G + 0.12T
<220> FEATURE:
<221> NAME/KEY: misc_feature
<222> LOCATION: 55, 57-58, 63-65, 67, 69, 72-73, 75-76, 78, 81
<223> OTHER INFORMATION: n = j = 0.12A + 0.12C + 0.64G + 0.12T

<400> SEQUENCE: 601
tcactgtctt ccatgggttc tgaatatgat acttgggttt ttcaatttnn nnnnnnnnn    60 nnnnnnnnnn nnnnnnnnnn nnnnggtggt agtggtactg aagct                 105

<210> SEQ ID NO 602
<211> LENGTH: 32
<212> TYPE: DNA
<213> ORGANISM: Artificial Sequence
<220> FEATURE:
<223> OTHER INFORMATION: Synthetic construct

<400> SEQUENCE: 602
ggtggtagtg gtactgaagc tagcgtgact ct                                32

<210> SEQ ID NO 603
<211> LENGTH: 585
<212> TYPE: PRT
<213> ORGANISM: Homo sapiens

<400> SEQUENCE: 603

Asp Ala His Lys Ser Glu Val Ala His Arg Phe Lys Asp Leu Gly Glu
 1               5                  10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro

```
                210                 215                 220
Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Arg Leu Ala Lys Thr
            340                 345                 350

Tyr Lys Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Arg Ala Ala Leu Gly Leu
            580                 585

<210> SEQ ID NO 604
<211> LENGTH: 27
<212> TYPE: PRT
<213> ORGANISM: Artificial Sequence
<220> FEATURE:
<223> OTHER INFORMATION: Synthetically generated peptide

<400> SEQUENCE: 604
```

Gly Ser Phe Phe Pro Cys Trp Arg Ile Asp Arg Phe Gly Tyr Cys His
1               5                   10                  15

Ala Asn Ala Pro Gly Ser Gly Ser Gly Gly
            20                  25

<210> SEQ ID NO 605
<211> LENGTH: 25
<212> TYPE: PRT
<213> ORGANISM: Artificial Sequence
<220> FEATURE:
<223> OTHER INFORMATION: Synthetically generated peptide

<400> SEQUENCE: 605

Gly Ser Gly Gly Glu Gly Gly Ser Gly Ser Trp Ile Ile Cys Trp
1               5                   10                  15

Trp Asp Asn Cys Gly Ser Ser Ala Pro
            20                  25

<210> SEQ ID NO 606
<211> LENGTH: 637
<212> TYPE: PRT
<213> ORGANISM: Artificial Sequence
<220> FEATURE:
<223> OTHER INFORMATION: Synthetically generated peptide

<400> SEQUENCE: 606

Gly Ser Phe Phe Pro Cys Trp Arg Ile Asp Arg Phe Gly Tyr Cys His
1               5                   10                  15

Ala Asn Ala Pro Gly Ser Gly Ser Gly Gly Asp Ala His Lys Ser
            20                  25                  30

Glu Val Ala His Arg Phe Lys Asp Leu Gly Glu Glu Asn Phe Lys Ala
            35                  40                  45

Leu Val Leu Ile Ala Phe Ala Gln Tyr Leu Gln Gln Cys Pro Phe Glu
        50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190

Thr Glu Cys Cys Gln Ala Ala Asp Lys Ala Ala Cys Leu Leu Pro Lys
        195                 200                 205

Leu Asp Glu Leu Arg Asp Glu Gly Lys Ala Ser Ser Ala Lys Gln Arg
    210                 215                 220

Leu Lys Cys Ala Ser Leu Gln Lys Phe Gly Glu Arg Ala Phe Lys Ala
225                 230                 235                 240

Trp Ala Val Ala Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
              260                 265                 270

Cys His Gly Asp Leu Leu Glu Cys Ala Asp Asp Arg Ala Asp Leu Ala
              275                 280                 285

Lys Tyr Ile Cys Glu Asn Gln Asp Ser Ile Ser Ser Lys Leu Lys Glu
              290                 295                 300

Cys Cys Glu Lys Pro Leu Leu Glu Lys Ser His Cys Ile Ala Glu Val
305                 310                 315                 320

Glu Asn Asp Glu Met Pro Ala Asp Leu Pro Ser Leu Ala Ala Asp Phe
              325                 330                 335

Val Glu Ser Lys Asp Val Cys Lys Asn Tyr Ala Glu Ala Lys Asp Val
              340                 345                 350

Phe Leu Gly Met Phe Leu Tyr Glu Tyr Ala Arg Arg His Pro Asp Tyr
              355                 360                 365

Ser Val Val Leu Leu Leu Arg Leu Ala Lys Thr Tyr Lys Thr Thr Leu
              370                 375                 380

Glu Lys Cys Cys Ala Ala Ala Asp Pro His Glu Cys Tyr Ala Lys Val
385                 390                 395                 400

Phe Asp Glu Phe Lys Pro Leu Val Glu Glu Pro Gln Asn Leu Ile Lys
              405                 410                 415

Gln Asn Cys Glu Leu Phe Glu Gln Leu Gly Glu Tyr Lys Phe Gln Asn
              420                 425                 430

Ala Leu Leu Val Arg Tyr Thr Lys Lys Val Pro Gln Val Ser Thr Pro
              435                 440                 445

Thr Leu Val Glu Val Ser Arg Asn Leu Gly Lys Val Gly Ser Lys Cys
              450                 455                 460

Cys Lys His Pro Glu Ala Lys Arg Met Pro Cys Ala Glu Asp Tyr Leu
465                 470                 475                 480

Ser Val Val Leu Asn Gln Leu Cys Val Leu His Glu Lys Thr Pro Val
              485                 490                 495

Ser Asp Arg Val Thr Lys Cys Cys Thr Glu Ser Leu Val Asn Arg Arg
              500                 505                 510

Pro Cys Phe Ser Ala Leu Glu Val Asp Glu Thr Tyr Val Pro Lys Glu
              515                 520                 525

Phe Asn Ala Glu Thr Phe Thr Phe His Ala Asp Ile Cys Thr Leu Ser
              530                 535                 540

Glu Lys Glu Arg Gln Ile Lys Lys Gln Thr Ala Leu Val Glu Leu Val
545                 550                 555                 560

Lys His Lys Pro Lys Ala Thr Lys Glu Gln Leu Lys Ala Val Met Asp
              565                 570                 575

Asp Phe Ala Ala Phe Val Glu Lys Cys Cys Lys Ala Asp Asp Lys Glu
              580                 585                 590

Thr Cys Phe Ala Glu Glu Gly Lys Lys Leu Val Ala Ala Ser Arg Ala
              595                 600                 605

Ala Leu Gly Leu Gly Ser Gly Gly Glu Gly Gly Ser Gly Gly Ser Trp
              610                 615                 620

Ile Ile Cys Trp Trp Asp Asn Cys Gly Ser Ser Ala Pro
625                 630                 635

<210> SEQ ID NO 607
<211> LENGTH: 6
<212> TYPE: PRT
<213> ORGANISM: Artificial Sequence
<220> FEATURE:
<223> OTHER INFORMATION: Fragment from human source

```
<400> SEQUENCE: 607

Tyr Pro Glu Leu Pro Lys
 1               5

<210> SEQ ID NO 608
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 608

Arg Val Tyr Pro Glu Leu Pro Lys Pro Ser Gly Gly Gly
 1               5                  10

<210> SEQ ID NO 609
<211> LENGTH: 10
<212> TYPE: PRT
<213> ORGANISM: Artificial Sequence
<220> FEATURE:
<223> OTHER INFORMATION: Syntheticaly generated peptide

<400> SEQUENCE: 609

Arg Val Tyr Pro Glu Leu Pro Lys Pro Ser
 1               5                  10

<210> SEQ ID NO 610
<211> LENGTH: 4
<212> TYPE: PRT
<213> ORGANISM: Artificial Sequence
<220> FEATURE:
<223> OTHER INFORMATION: Linker sequence

<400> SEQUENCE: 610

Gly Ser Gly Lys
 1

<210> SEQ ID NO 611
<211> LENGTH: 5
<212> TYPE: PRT
<213> ORGANISM: Artificial Sequence
<220> FEATURE:
<223> OTHER INFORMATION: Linker sequence

<400> SEQUENCE: 611

Gly Ser Gly Ser Lys
 1               5

<210> SEQ ID NO 612
<211> LENGTH: 12
<212> TYPE: PRT
<213> ORGANISM: Artificial Sequence
<220> FEATURE:
<223> OTHER INFORMATION: A template sequence
<220> FEATURE:
<221> NAME/KEY: VARIANT
<222> LOCATION: 2-3, 5-8, 10-11
<223> OTHER INFORMATION: Xaa = any amino acid except Cys
<220> FEATURE:
<221> NAME/KEY: VARIANT
<222> LOCATION: 1, 12
<223> OTHER INFORMATION: Xaa = any amino acid except Cys, Glu, Ile, Lys,
      Met and Thr

<400> SEQUENCE: 612

Xaa Xaa Xaa Cys Xaa Xaa Xaa Xaa Cys Xaa Xaa Xaa
 1               5                  10
```

```
<210> SEQ ID NO 613
<211> LENGTH: 13
<212> TYPE: PRT
<213> ORGANISM: Artificial Sequence
<220> FEATURE:
<223> OTHER INFORMATION: A template sequence
<220> FEATURE:
<221> NAME/KEY: VARIANT
<222> LOCATION: 1-3, 5-9, 11-13
<223> OTHER INFORMATION: Xaa = any amino acid except Cys

<400> SEQUENCE: 613

Xaa Xaa Xaa Cys Xaa Xaa Xaa Xaa Xaa Cys Xaa Xaa Xaa
 1               5                  10

<210> SEQ ID NO 614
<211> LENGTH: 14
<212> TYPE: PRT
<213> ORGANISM: Artificial Sequence
<220> FEATURE:
<223> OTHER INFORMATION: A template sequence
<220> FEATURE:
<221> NAME/KEY: VARIANT
<222> LOCATION: 1-3, 5-10, 12-14
<223> OTHER INFORMATION: Xaa = any amino acid except Cys

<400> SEQUENCE: 614

Xaa Xaa Xaa Cys Xaa Xaa Xaa Xaa Xaa Xaa Cys Xaa Xaa Xaa
 1               5                  10

<210> SEQ ID NO 615
<211> LENGTH: 15
<212> TYPE: PRT
<213> ORGANISM: Artificial Sequence
<220> FEATURE:
<223> OTHER INFORMATION: A template sequence
<220> FEATURE:
<221> NAME/KEY: VARIANT
<222> LOCATION: 1-3, 5-11, 13-15
<223> OTHER INFORMATION: Xaa = any amino acid  except Cys

<400> SEQUENCE: 615

Xaa Xaa Xaa Cys Xaa Xaa Xaa Xaa Xaa Xaa Xaa Cys Xaa Xaa Xaa
 1               5                  10                  15

<210> SEQ ID NO 616
<211> LENGTH: 16
<212> TYPE: PRT
<213> ORGANISM: Artificial Sequence
<220> FEATURE:
<223> OTHER INFORMATION: A template sequence
<220> FEATURE:
<221> NAME/KEY: VARIANT
<222> LOCATION: 1,  2, 15, 16
<223> OTHER INFORMATION: Xaa = Asp, Phe, His, Leu, Asn, Pro, Arg, Ser,
     Trp, or Tyr
<220> FEATURE:
<221> NAME/KEY: VARIANT
<222> LOCATION: 3, 14
<223> OTHER INFORMATION: Xaa = Ala, Asp,Phe, Gly, His, Leu, Asn, Pro,
     Gln,Arg, Ser, Val, Trp, or Tyr
<220> FEATURE:
<221> NAME/KEY: VARIANT
<222> LOCATION: 5-12
<223> OTHER INFORMATION: Xaa = any amino acid except Cys

<400> SEQUENCE: 616

Xaa Xaa Xaa Cys Xaa Xaa Xaa Xaa Xaa Xaa Xaa Xaa Cys Xaa Xaa Xaa
 1               5                  10                  15

<210> SEQ ID NO 617
```

```
<211> LENGTH: 17
<212> TYPE: PRT
<213> ORGANISM: Artificial Sequence
<220> FEATURE:
<223> OTHER INFORMATION: A template sequence
<220> FEATURE:
<221> NAME/KEY: VARIANT
<222> LOCATION: 1-3, 5-13, 15-17
<223> OTHER INFORMATION: Xaa = any amino acid except Cys

<400> SEQUENCE: 617

Xaa Xaa Xaa Cys Xaa Xaa Xaa Xaa Xaa Xaa Xaa Xaa Xaa Cys Xaa Xaa
 1               5                   10                  15

Xaa

<210> SEQ ID NO 618
<211> LENGTH: 18
<212> TYPE: PRT
<213> ORGANISM: Artificial Sequence
<220> FEATURE:
<223> OTHER INFORMATION: A template sequence
<220> FEATURE:
<221> NAME/KEY: VARIANT
<222> LOCATION: 1, 2, 17, 18
<223> OTHER INFORMATION: Xaa = Ala, Asp, Phe, Gly, His, Leu, Asn, Pro,
      Arg, Ser,Trp, or Tyr
<220> FEATURE:
<221> NAME/KEY: VARIANT
<222> LOCATION: 3, 55-14, 16
<223> OTHER INFORMATION: Xaa = any amino acid  Except Cys

<400> SEQUENCE: 618

Xaa Xaa Xaa Cys Xaa Xaa Xaa Xaa Xaa Xaa Xaa Xaa Xaa Xaa Cys Xaa
 1               5                   10                  15

Xaa Xaa

<210> SEQ ID NO 619
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 1, 2, 3, 4
<223> OTHER INFORMATION: Xaa = any amino acid

<400> SEQUENCE: 619

Cys Xaa Gly Xaa Pro Xaa Phe Xaa Cys
 1               5
```

PEPTIDES THAT SPECIFICALLY BIND HGF RECEPTOR (CMET) AND USES THEREOF

This application is a continuation of U.S. application Ser. No. 10/792,582, filed Mar. 3, 2004, which claims priority under 35 USC §119(e) to U.S. Provisional Patent Application Ser. No. 60/451,588, filed on Mar. 3, 2003, the entire contents of both of which are hereby incorporated by reference.

BACKGROUND OF THE INVENTION

Hepatocyte growth factor (also known as scatter factor) is a multi-functional growth factor involved in various physiological processes such as embryogenesis, wound healing and angiogenesis. It has become apparent that HGF, through interactions with its high affinity receptor (cMet), is involved in tumor growth, invasion and metastasis. In fact, dysregulated cMet expression (for example, the overexpression of cMet in neoplastic epithelium of colorectal adenomas and in other carcinomas as compared to normal mucosa) and/or activity, as well as hyperactivity of the cMet receptor through an autocrine stimulatory loop with HGF, has been demonstrated in a variety of tumor tissues and induces oncogenic transformation of specific cell lines.

In general, HGF is produced by the stromal cells, which form part of many epithelial tumors; however, it is believed that the production of HGF by tumor cells themselves comprises the main pathway leading to the hyperproliferation of specific tumors. HGF/cMet autocrine stimulatory loops have been detected in gliomas, osteosarcomas, and mammary, prostate, breast, lung and other carcinomas.

Interrupting the HGF interaction with the cMet receptor slows tumor progression in animal models. In addition to stimulating proliferation of certain cancer cells through activation of cMet, HGF also protects against DNA-damaging agent-induced cytotoxicity in a variety of cell lines susceptible to hyperproliferative phenotypes (e.g., breast cancer). Therefore, preventing HGF from binding to cMet could predispose certain cancer cells to the cytotoxicity of certain drugs.

In addition to hyperproliferative disorders, cMet also has been linked to angiogenesis. For example, stimulation of cMet leads to the production of vascular endothelial growth factor (VEGF), which, in turn, stimulates angiogenesis. Additionally, stimulation of cMet also has been implicated in promoting wound healing.

In addition to identifying the cMet receptor as a therapeutic target for hyperproliferative disorders, angiogenesis and wound healing, the large discrepancy between expression levels of neoplastic and corresponding normal tissues indicates that cMet is an attractive target for imaging applications directed to hyperproliferative disorders.

SUMMARY OF THE INVENTION

The present invention relates to peptides, peptide complexes and compositions having the ability to bind to cMet and antagonize hepatocyte growth factor (HGF) activity by preventing HGF from binding to cMet. In addition, this invention relates to such peptides, peptide complexes and compositions having the ability to bind to cMet for the purpose of detecting and targeting this receptor, inhibiting cMet activity independent of HGF antagonistic properties, and for the purpose of diagnostic imaging. The involvement of the HGF/cMet axis in a variety of cellular functions including cellular proliferation, wound healing and angiogenesis, leading to hyperproliferative diseases such as cancer, make the present invention particularly useful for interrupting HGF-mediated physiological events, for targeting substances, e.g., therapeutics, including radiotherapeutics, to such sites, and for imaging important sites of cellular hyperproliferation.

In answer to the need for improved materials and methods for detecting, localizing, imaging, measuring and possibly inhibiting or affecting, e.g., hyperproliferation and/or angiogenesis, it has been surprisingly discovered that twelve classes of non-naturally occurring polypeptides bind specifically to cMet. Appropriate labeling of such polypeptides provides detectable imaging agents that can bind, e.g., at high concentration, to cMet-expressing cells or cells exhibiting HGF/cMet complexes, providing specific imaging agents for sites of cellular proliferation and/or angiogenesis. The cMet binding polypeptides of the instant invention can thus be used in the detection and diagnosis of such hyperproliferative-related and/or angiogenesis-related disorders. Conjugation or fusion of such polypeptides with effective agents such as cMet inhibitors or tumoricidal agents also can be used to treat pathogenic tumors, e.g., by causing the conjugate or fusion to "home" to the site of active proliferation and/or angiogenesis, thereby providing an effective means for treating pathogenic conditions associated with hyperproliferation and/or angiogenesis.

This invention pertains to cMet binding polypeptides, and includes use of a single binding polypeptide as a monomer or in a multimeric or polymeric construct as well as use of more than one binding polypeptide of the invention in multimeric or polymeric constructs. Binding polypeptides according to this invention are useful in any application where binding, inhibiting, detecting or isolating cMet, or fragments thereof retaining the polypeptide binding site, is advantageous. A particularly important aspect of such binding polypeptides is the inhibition of cMet activity, either through competition with HGF for cMet binding, or by directly inhibiting cMet activity irrespective of whether HGF is bound or not. For example, in some cases, cMet signaling can occur in the absence of HGF binding, in such situations, a binding polypeptide that inhibits cMet signaling activity irrespective of whether HGF is bound, would be useful in inhibiting cMet signaling.

Another particularly advantageous use of the binding polypeptides disclosed herein is in a method of imaging cellular proliferation and/or angiogenesis in vivo. The method entails the use of specific binding polypeptides according to the invention for detecting a site of cellular proliferation and/or angiogenesis, where the binding polypeptides have been detectably labeled for use as imaging agents, including magnetic resonance imaging (MRI) contrast agents, x-ray imaging agents, radiopharmaceutical imaging agents, ultrasound imaging agents, and optical imaging agents.

Yet another advantageous use of the cMet binding polypeptides disclosed herein is to target therapeutic agents, (including compounds capable of providing a therapeutic, radiotherapeutic or cytotoxic effect) or delivery vehicles for therapeutics (including drugs, genetic material, etc.) to sites of hyperproliferation and/or angiogenesis or other tissue expressing cMet.

The cMet receptor is part of the receptor tyrosine kinase family of signaling molecules. For the purposes of the present invention, receptor tyrosine kinase function can include any one of: oligomerization of the receptor, receptor phosphorylation, kinase activity of the receptor, recruitment of downstream signaling molecules, induction of genes, induction of cell proliferation, induction of cell migration, or combination thereof. "Heteromeric" molecules, used herein to refer to molecules containing more than one cMet binding peptide as described herein, such that each binding peptide of the heteromeric molecule binds to a different site, e.g., "epitope", of cMet, also are encompassed by the present invention. For example, heteromeric constructs of binding polypeptides provided herein could, for example, bind, via one binding peptide, to, for example, the HGF binding site of cMet, while another binding peptide of the heteromeric molecule binds to a different high affinity binding site of cMet. Targeting two or more distinct epitopes on cMet with a single binding construct can greatly improve the ability of the construct to inhibit HGF binding and/or receptor function (such inhibition can occur by direct inhibition of cMet irrespective of HGF binding). Even binding peptides with weak ability to block receptor activity can be used to generate heteromeric constructs having improved ability to block HGF-dependent and HGF-independent receptor function.

Therefore, the present invention is drawn to constructs comprising means for producing multimeric molecules comprising two or more binding polypeptides, at least one of which binds cMet. In one embodiment, the multimeric constructs comprise two or more copies of a single binding polypeptide or nucleotide sequence that encode two or more copies of a single binding polypeptide. In another embodiment, the multimeric constructs of the present invention comprise two or more binding polypeptides or nucleotide sequence that encode two or more binding polypeptides, such that at least two of the binding polypeptides in the construct are specific for different epitopes of cMet. These constructs also are referred to herein as "heteromeric constructs", "heteromultimers", etc. The constructs of the present invention also can include unrelated, or control peptide. The constructs can include two or more, three or more, or four or more binding polypeptides or the nucleotide sequences that encode such polypeptides. Based on the teachings provided herein, one of ordinary skill in the art is able to assemble the binding polypeptides provided herein into multimeric constructs and to select multimeric constructs having improved properties, such as improved ability to bind the target molecule, or improved ability to inhibit receptor tyrosine kinase function. Such multimeric constructs having improved properties are included in the present invention.

Consensus sequences from the screen of the cyclic/linear peptide libraries have been determined based on the twelve classes of specific cMet binding polypeptides shown in Table 6. In specific embodiments, cMet binding polypeptides of the invention comprise one or more of these sequences. Such preferred cMet binding polypeptides include polypeptides with the potential to form a cyclic or loop structure between invariant cysteine residues comprising.

The polypeptides described herein can have additional amino acids attached at either or both of the—and C-terminal ends. In preferred embodiments, binding polypeptides according to the invention can be prepared having N-terminal and/or C-terminal flanking peptides of one or more, preferably two, amino acids corresponding to the flanking peptides of the display construct of the phage selectant from which the binding polypeptides were isolated. Preferred N-terminal flanking peptides include Gly-Ser- (most preferably for TN6 sequences), Ala-Gly- (most preferably for TN8 and TN9 sequences), Gly-Ser- (most preferably for TN10 and TN11 sequences), Gly-Asp-(most preferably for TN12 sequences), Ala-Gln- (most preferably for linear sequences). Preferred C-terminal flanking peptides include -Ala-Pro (most preferably for TN6 sequences), -Gly-Thr (most preferably for TN8 and TN9 sequences), -Ala-Pro (most preferably for TN10 and TN11 sequences), -Asp-Pro (most preferably for TN12 sequences), -Asp-Phe (most preferably for linear sequences).

Single terminal amino acids also can be added to the binding polypeptides of the invention, and preferred terminal amino acids will correspond to the parental phage display construct, e.g., most preferably, N-terminal amino acids will be selected from Gly- (most preferably for TN6, TN8 and TN9 sequences), Ser- (most preferably for TN10 and TN11 sequences), Asp- (most preferably for TN12 sequences), and Gln- (most preferably for linear sequences), and most preferably C-terminal amino acids will be selected from -Gly (most preferably for TN6, TN8 and TN9, and linear sequences), -Ala (most preferably for TN10 and TN11 sequences), and -Asp (most preferably for TN12 sequences). Conservative substitutions (i.e., substitute amino acids selected within the following groups: {Arg, His, Lys}, {Glu, Asp}, {Asn, Cys, Glu, Gly, Ser, Thr, Tyr}, {Ala, Ile, Leu, Met, Phe, Pro, Trp, Val}) for such flanking amino acids also are contemplated.

Examination of the sequence information and binding data from the isolates of libraries containing polypeptides with the potential to form loop structures (e.g., libraries designated TN6, TN8, TN9, TN10, TN11 and TN12; the number refers to the number of amino acids in the sequence from cysteine to cysteine; additionally, the linear display library, LN20, also was screened) identifies an additional series of cMet binding polypeptides. A consensus motif was obtained from this initial screen of a TN9 library (CxGpPxFxC; SEQ ID NO:512). The consensus sequence was derived from the sequences listed in Table 6. This consensus sequence along with sequence trends in the cMet binding peptides identified from the linear peptide library was used to design a second generation library that was used in a secondary screen; Sequences from both screens were used to identify twelve classes of cMet binding motifs listed in Table 6.

Another aspect of the present invention relates to modifications of the polypeptides of the invention to provide specific cellular proliferation and/or angiogenesis imaging agents by detectably labeling a polypeptide or multimeric polypeptide construct according to the present invention. Such detectable labeling can involve radiolabeling, enzymatic labeling, or labeling with MR paramagnetic chelates or microparticles; incorporation into ultrasound bubbles, microparticles, microspheres, emulsions, or liposomes; or conjugation with optical dyes.

In another aspect of the present invention, methods for isolating cMet-expressing cells using the present binding polypeptides or multimeric polypeptide construct are provided.

Additionally, the cMet binding polypeptides or multimeric polypeptide construct of the invention can be used as therapeutic agents, either alone in a pharmaceutically acceptable composition or conjugated to (or in combination with) other therapeutic agents. The compositions can be used to treat diseases or conditions involving cellular proliferation, angiogenesis and/or wound healing.

When used as therapeutic agents, it may be advantageous to enhance the serum residence time of the peptides. This can be accomplished by: a) conjugating to the peptide a moiety, such as maleimide, that reacts with free sulfhydryl groups on serum proteins, such as serum albumin, b) conjugating to the peptide a moiety, such as a fatty acid, that binds non-covalently to serum proteins, especially serum albumin, c) conjugating to the peptide a polymer, such as polyethylene glycol (PEG), that is known to enhance serum residence time, and d) fusing DNA that encodes the cMet-binding peptide to DNA that encodes a serum protein such as human serum albumin or an antibody and expressing the encoded fusion protein.

In another aspect of the invention, methods of screening polypeptides identified by phage display for their ability to bind to cells expressing the target are provided. These methods permit rapid screening of the binding ability of polypeptides, including polypeptides with monomeric affinities that are too low for evaluation in standard cell-binding assays. Additionally, these methods can be used to rapidly assess the stability of the peptides in the presence of serum.

In one embodiment, the present invention is directed to a polypeptide or multimeric polypeptide construct having the ability to bind to cMet or a complex comprising cMet and HGF comprising an amino acid sequence comprising Cys-$X_1$-Gly-$X_2$-Pro-$X_3$-Phe-$X_4$-Cys (SEQ ID NO:619), wherein $X_1$, $X_2$, $X_3$ and $X_4$ can be any amino acid. In a particular embodiment, $X_2$ is Pro.

In another embodiment, the polypeptides of the invention further comprises N-terminal and/or C-terminal flanking peptides of one or more amino acids. For example, the polypeptide can comprise a modification selected from the group consisting of: an amino acid substitution, and amide bond substitution, a D-amino acid substitution, a glycosylated amino acid, a disulfide mimetic substitution, an amino acid translocation, a retro-inverso peptide, a peptoid, a retro-inverso peptoid and a synthetic peptide. In another embodiment, any of the polypeptides described herein can be conjugated to a detectable label or a therapeutic agent, optionally further comprising a linker or spacer between the polypeptide and the detectable label or the therapeutic agent. In a particular embodiment, the detectable label or the therapeutic agent is selected from the group consisting of: an enzyme, a fluorescent compound, a liposome, an optical dye, a paramagnetic metal ion, an ultrasound contrast agent and a radionuclide. In a particular embodiment, the therapeutic agent or detectable label comprises a radionuclide. For example, the radionuclide can be one or more selected from the group consisting of: $^{18}F$, $^{124}I$, $^{125}I$, $^{131}I$, $^{123}I$, $^{77}Br$, $^{76}Br$, $^{99m}Tc$, $^{51}Cr$, $^{67}Ga$, $^{68}Ga$, $^{47}Sc$, $^{51}Cr$, $^{167}Tm$, $^{141}Ce$, $^{111}In$, $^{168}Yb$, $^{175}Yb$, $^{140}La$, $^{90}Y$, $^{88}Y$, $^{153}Sm$, $^{166}Ho$, $^{165}Dy$, $^{166}Dy$, $^{62}Cu$, $^{64}Cu$, $^{67}Cu$, $^{97}Ru$, $^{103}Ru$, $^{186}Re$, $^{188}Re$, $^{203}Pb$, $^{211}Bi$, $^{212}Bi$, $^{213}Bi$, $^{214}Bi$, $^{105}Rh$, $^{109}Pd$, $^{117m}Sn$, $^{149}Pm$, $^{161}Tb$, $^{177}Lu$, $^{198}Au$ and $^{199}Au$. In another embodiment, the therapeutic agent or detectable label further comprises a chelator. For example, the chelator can comprise a compound selected from the group consisting of: formula 20, 21, 22, 23a, 23b, 24a, 24b and 25. In a particular embodiment, the radionuclide is $^{99m}Tc$ or $^{111}In$. In another embodiment, the radionuclide is selected from the group consisting of: $^{177}Lu$, $^{90}Y$, $^{153}Sm$ and $^{166}Ho$. In another embodiment, the detectable label comprises an ultrasound contrast agent. For example, the ultrasound contrast agent can comprise a phospholipid stabilized microbubble or a microballoon comprising a gas, e.g., a fluorinated gas. In another embodiment, the detectable label comprises a paramagnetic metal ion and a chelator. Another aspect of the invention is directed to any of the polypeptides of the invention, wherein the therapeutic agent is selected from the group consisting of: a bioactive agent, a cytotoxic agent, a drug, a chemotherapeutic agent or a radiotherapeutic agent. In other embodiments, the polypeptide has an apparent $K_D$ for cMet of cMet/HGF complex of less than about 10 μM, less than about 1.0 μM, less than about 0.1 μM or less than about 1 nM.

In one embodiment, the present invention is directed to a polypeptide or multimeric polypeptide construct having the ability to bind to cMet or a complex comprising cMet and HGF comprising an amino acid sequence of one of the following classes: Class 1: $X_1$-$X_2$-$X_3$-Cys-$X_4$-$X_5$-$X_6$-$X_7$-Cys-$X_8$-$X_9$-$X_{10}$ (TN6) (SEQ ID NO:538), wherein $X_1$ is Phe, Leu, Ser, Trp, Tyr or Met; $X_2$ is Ile, Tyr, His, Thr or Asn; $X_3$ is Ile, Leu, Asp, Met, Phe or Ser; $X_4$ is Arg, Asn, Glu, Pro or Trp; $X_5$ is Glu, Gly, Leu, Pro, Thr, Trp or Tyr; $X_6$ is Asp, Gln, Glu Gly, Phe, Ser, Thr or Trp; $X_7$ is Ala, Arg, Asn, Gln, Glu, Gly, Phe, or Trp; $X_8$ is Gly, Asn, His, Arg, Met, Ile, Asp, Val or Thr; $X_9$ is Ser, Lys, Phe, Met, Thr, Asp or Leu; and $X_{10}$ is Ser, Pro, Thr, Leu, Tyr, Asn, His, Glu or Trp; or Class II: $X_1$-$X_2$-$X_3$-Cys-$X_4$-$X_5$-$X_6$-$X_7$-$X_8$-$X_9$-Cys-$X_{10}$-$X_{11}$-$X_{12}$ (TN8) (SEQ ID NO:539), wherein $X_1$ is Gly, Val, Trp, Thr, Lys or Gln; $X_2$ is Trp, Tyr, Leu, Phe or Thr; $X_3$ is Trp, Glu, Phe, Ile, Leu and Ser; $X_4$ is Asn, Gln or Glu; $X_5$ is Leu, Glu or Trp; $X_6$ is Glu, Ser or Tyr; $X_7$ is Glu, Met or Pro; $X_8$ is Met, Ser or Trp; $X_9$ is Leu, Phe or Val; $X_{10}$ is Asp, Glu or Trp; $X_{11}$ is Met, Phe or Trp; and $X_{12}$ is Gln, Leu or Trp; or Class III: $X_1$-$X_2$-$X_3$-Cys-$X_4$-Gly-$X_5$-Pro-$X_6$-Phe-$X_7$-Cys-$X_8$-$X_0$ (TN9) (SEQ ID NO:540), wherein $X_1$ is Glu, Ser, Trp or Tyr; $X_2$ is Phe, Thr or Trp; $X_3$ is His, Phe or Trp; $X_4$ is Ala, Lys, Ser or Thr; $X_5$ is Pro or Trp; $X_6$ is Ser or Thr; $X_7$ is Glu or Ser; $X_8$ is Ile, Trp or Tyr; and $X_9$ is Glu, Met, Trp or Tyr; or Class IV-1: $X_1$-$X_2$-$X_3$-Cys-$X_4$-Gly-Pro-Pro-$X_5$-Phe-$X_6$-Cys-Trp-$X_7$-$X_8$-$X_0$-$X_{10}$-$X_{11}$ (TN9) (SEQ ID NO:541), wherein $X_1$ is Arg, Asp, Asn, Ile or Ser; $X_2$ is Leu, Ile, Phe, Trp or Val; $X_3$ is Asn, Gln, His, Leu, Tyr or Val; $X_4$ is Leu, Lys or Ser; $X_5$ is Ala, Ser, Thr or Trp; $X_6$ is Leu, Ser or Trp; $X_7$ is Leu, Ser or Trp; $X_8$ is Phe or Tyr; $X_9$ is Asp, Glu, Gly or Val; $X_{10}$ is Met, Pro, Thr or Ser; and $X_{11}$ is Glu or Gly; or Class IV-2: $X_1$-$X_2$-$X_3$-$X_4$-Trp-$X_5$-Cys-$X_6$-Gly-Pro-Pro-Thr-Phe-Glu-Cys-Trp-$X_7$-$X_8$ (TN9) (SEQ ID NO:542), wherein $X_1$ is Asp, Glu or Val; $X_2$ is Ala, Asp, Gly, Ser or Val; $X_3$ is Asp, Gly, Ser or Val; $X_4$ is Arg, Asn, Gly, Ser or Thr; $X_5$ is Gln or His; $X_6$ is Asn, Lys or Ser; $X_7$ is Ser or Trp; and $X_8$ is Phe or Tyr; or Class V: $X_1$-$X_2$-$X_3$-Cys-$X_4$-$X_5$-$X_6$-$X_7$-$X_8$-$X_9$-$X_{10}$-$X_{11}$-Cys-$X_{12}$-$X_{13}$-$X_{14}$ (TN10) (SEQ ID NO:543), wherein $X_1$ is His, Phe, Pro, Thr or Trp; $X_2$ is Ala, Arg, Glu, His, Lys or Phe; $X_3$ is Met, Phe, Pro, Thr or Val; $X_4$ is His, Leu, Met, Phe or Trp; $X_5$ is Arg, Asp, Glu, Gly, Met or Trp; $X_6$ is Glu, Gly, Ile, Lys, Phe or Pro; $X_7$ is Asp, Phe, Pro, Ser, Trp or Tyr; $X_8$ is Ala, Arg, Asn, Phe or Ser; $X_9$ is Ala, Gln, Gly, Leu or Phe; $X_{10}$ is Gln, Gly, Ile, Leu, Trp or Tyr; $X_{11}$ is Arg, Asp, Phe, Pro, Tyr or Val; $X_{12}$ is Asn, Gln, His, Ile or Thr; $X_{13}$ is Ala, Asn, Asp, Glu or His; and $X_{14}$ is Asn, Gln, His or Val; or Class VI: $X_1$-$X_2$-$X_3$-Cys-$X_4$-$X_5$-$X_6$-$X_7$-$X_8$-$X_9$-$X_{10}$-$X_{11}$-$X_{12}$-Cys-$X_{13}$-$X_{14}$-$X_{15}$ (SEQ ID NO:544), wherein $X_1$ is Gln, Gly, Met, Phe or Ser; $X_2$ is Asn, Gln, Leu or Met; $X_3$ is Arg, Asn, Gly, His or Ile; $X_4$ is Asn, Asp, Leu, Thr or Trp; $X_5$ is Arg, Gln, Thr, Tyr or Val; $X_6$ is Glu, Gly, Leu, Met or Thr; $X_7$ is Ala, Asn, Asp, His, Ile, Leu or Ser; $X_8$ is Arg, Gln, Ser, Thr or Tyr; $X_9$ is Asp, Gly, Ile or Phe; $X_{10}$ is Gln, Phe or Thr; $X_{11}$ is Gln, His, Phe, Pro, Ser or Tyr; $X_{12}$ is Asn, Asp, Phe, Pro or Ser; $X_{13}$ is Ala, Asn, Gly, Leu or Ser; $X_{14}$ is Arg, Pro, Ser or Val; and $X_{15}$ is Asp, Glu, Leu or Met; or Class VIII: $X_1$-$X_2$-$X_3$-Cys-$X_4$-$X_5$-$X_6$-$X_7$-$X_8$-$X_9$-$X_{10}$-$X_{11}$-$X_{12}$-$X_{13}$-Cys-$X_{14}$-$X_{15}$-$X_{16}$ (SEQ ID NO:545), wherein $X_1$ is Ala, His, Leu, Phe or Tyr; $X_2$ is Arg, Asp, Leu, Ser or Tyr; $X_3$ is Glu, Met or Trp; $X_4$ is Asp, Gln, Glu, Phe or Ser; $X_5$ is Glu, Ile, Phe or Trp; $X_6$ is Asn, Asp or Ser; $X_7$ is Asn, Asp or Leu; $X_8$ is Asp, Glue or Lys; $X_9$ is Gly, Phe or Thr; $X_{10}$ is Gly, Phe, Trp or Tyr; $X_{11}$ is Glu, Ser or Trp; $X_{12}$ is Glu, Phe, Tyr or Val; $X_{13}$ is Glu, Lys, Thr or Val; $X_{14}$ is Glu or Trp; $X_{15}$ is Asp, Phe, Pro, Ser or Trp; and $X_{16}$ is Ala, Asn or Ile; or Class IX-1: Ser-Cys-$X_1$-Cys-$X_2$-Gly-Pro-Pro-Thr-Phe-Glu-Cys-Trp-Cys-Tyr-$X_3$-$X_4$-$X_5$ (SEQ ID NO:546), wherein $X_1$ is Asn, His or Tyr; $X_2$ is Gly or Ser; $X_3$ is Ala, Asp, Glu, Gly or Ser; $X_4$ is Ser or Thr; and $X_5$ is Asp or Glu; or Class IX-2: Glu-$X_1$-Gly-Ser-Cys-His-Cys-Ser-Gly-Pro-Pro-Thr-Phe-Glu-Cys-$X_2$-Cys-$X_3$ (SEQ ID NO:547), wherein $X_1$ is Ala, Glu, Gly or Ser; $X_2$ is Phe, Trp or Tyr; and $X_3$ is Phe or Tyr.

In another embodiment, the invention is directed to a polypeptide or multimeric polypeptide construct having the ability to bind to cMet or a complex comprising cMet and HGF comprising an amino acid sequence, wherein the amino acid sequence comprises at least six amino acids out of a contiguous stretch of nine amino acids from a sequence selected from the group consisting of SEQ ID NOS:1-511. In a particular embodiment, the polypeptide, used as either a monomer or in a multimeric construct, can be selected from the group consisting of SEQ ID NOS:1-511, SEQ ID NOS:1-10, SEQ ID NOS:11-47, SEQ ID NOS:48-101, SEQ ID NOS:102-364, SEQ ID NOS:365-370, SEQ ID NOS:371-387, SEQ ID NO:388 or SEQ ID NO:399, SEQ ID NOS:390-404, SEQ ID NOS:405-447, SEQ ID NO:448, SEQ ID NOS:449-496 and SEQ ID NOS:497-511.

In another embodiment, the invention is directed to a method for isolating phage that bind cMet or a complex comprising cMet and HGF, comprising the steps of: immobilizing cMet or a complex comprising cMet and HGF on a solid support; contacting a library of potential cMet or cMet/HGF complex binding phage with the solid support to bind cMet or cMet/HGF binding phage in the library; and removing the unbound portion of the phage library from the solid support, thereby isolating phage that bind cMet or a complex comprising cMet and HGF.

In another embodiment, the invention is directed to a method of detecting cMet or a complex comprising cMet and HGF in an animal or human subject and optionally imaging at least a portion of the animal or human subject comprising the steps of: detectably labeling a polypeptide or multimeric polypeptide construct having the ability to bind to cMet or a complex comprising cMet and HGF comprising an amino acid sequence comprising Cys-$X_1$-Gly-$X_2$-Pro-$X_3$-Phe-$X_4$-Cys (SEQ ID NO:619), wherein $X_1$, $X_2$, $X_3$ and $X_4$ can be any amino acid; administering to the subject the labeled polypeptide or multimeric polypeptide construct; and, detecting the labeled polypeptide or construct in the subject, and, optionally, constructing an image, thereby detecting cMet or a complex comprising cMet and HGF.

In a particular embodiments, the methods of the invention encompass methods wherein the label is selected from the group consisting of: an enzyme, a fluorescent compound, an ultrasound contrast agent, a liposome and an optical dye, wherein the label optionally further comprises a linker and/or a spacer. In particular embodiment, the ultrasound contrast agent is a phospholipid stabilized microbubble or a microballoon comprising a gas, e.g., a fluorinated gas. In other embodiments, the label is a radioactive label or a paramagnetic metal atom, and optionally further comprises a linker or a spacer. In another embodiment, the radioactive label comprises a radionuclide selected from the group consisting of: $^{18}$F, $^{124}$I, $^{125}$I, $^{131}$I, $^{123}$I, $^{77}$Br, $^{76}$Br, $^{99m}$Tc, $^{51}$Cr, $^{67}$Ga, $^{68}$Ga, $^{47}$Sc, $^{51}$Cr, $^{167}$Tm, $^{141}$Ce, $^{111}$In, $^{168}$Yb, $^{175}$Yb, $^{175}$Yb, $^{140}$La, $^{90}$Y, $^{88}$Y, $^{153}$Sm, $^{166}$Ho, $^{165}$Dy, $^{166}$Dy, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{105}$Rh, $^{109}$Pd, $^{117m}$Sn, $^{149}$Pm, $^{161}$Tb, $^{177}$Lu, $^{198}$Au and $^{199}$Au. In another embodiment, the radioactive label further comprises a chelator, e.g., chelators selected from the group consisting of: formula 20, 21, 22, 23a, 23b, 24a, 24b and 25. In another embodiment, the radionuclide is $^{99m}$Tc or $^{111}$In. In a particular embodiment, the paramagnetic label comprises a paramagnetic metal atom selected from the group consisting of: $Mn^{2+}$, $Cu^{2+}$, $Fe^{1+}$, $Co^{2+}$, $Ni^{2+}$, $Gd^{3+}$, $Eu^{3+}$, $Dy^{3+}$, $Pr^{3+}$, $Cr^{3+}$, $Co^{3+}$, $Fe^{3+}$, $Ti^{3+}$, $Tb^{3+}$, $Nd^{3+}$, $Sm^{3+}$, $Ho^{3+}$, $Er^{3+}$, $Pa^{4+}$ and $Eu^{2+}$. In another embodiment, the paramagnetic label further comprises a chelator, e.g., a chelator is selected from the group consisting of: DTPA, DO3A, DOTA, EDTA, TETA, EHPG, HBED, NOTA, DOTMA, TETMA, PDTA, TTHA, LICAM, and MECAM. In particular embodiments, detection of the labeled polypeptide or multimeric polypeptide construct is indicative of a hyperproliferative disorder. In other embodiments, detection of the labeled polypeptide or multimeric polypeptide construct is indicative of angiogenesis or neovascularization. In particular embodiments, the label is an ultrasound contrast agent that comprises a fluorinated gas selected from the group of: $SF_6$ freons, $CF_4$, $C_2F_6$, $C_3F_8$, $C_4F_{10}$, $CBrF_3$, $CCI_2F_2$, $C_2CIF_5$, $CBrCIF_2$ and perfluorocarbons. In particular embodiments, the ultrasound contrast agent comprises a perfluorocarbon gas having the formula $C_nF_{n+2}$ wherein n is from 1 to 12.

In another embodiment, the invention is directed to a method of detecting cMet or a complex comprising cMet and HGF in an animal or human subject and optionally imaging at least a portion of the animal or human subject comprising the steps of: detectably labeling a polypeptide or multimeric polypeptide construct having the ability to bind to cMet or a complex comprising cMet and HGF comprising an amino acid sequence, wherein the amino acid sequence comprises at least six amino acids out of a contiguous stretch of nine amino acids from a sequence selected from the group consisting of SEQ ID NOS:1-511; administering to the subject the labeled polypeptide or construct; and, detecting the labeled polypeptide or construct in the subject, and, optionally, constructing an image, thereby detecting cMet or a complex comprising cMet and HGF.

In another embodiment, the invention is directed to a method of treating a condition involving activation of cMet, comprising administering to an animal or human subject in need of treatment for such a condition a composition comprising a polypeptide or multimeric polypeptide construct having the ability to bind to cMet or a complex comprising cMet and HGF comprising an amino acid sequence comprising Cys-$X_1$-Gly-$X_2$-Pro-$X_3$-Phe-$X_4$-Cys (SEQ ID NO:619), wherein $X_1$, $X_2$, $X_3$ and $X_4$ can be any amino acid. In another embodiment, the invention is directed to a method of treating a condition involving activation of cMet, comprising administering to an animal or human subject in need of treatment for such a condition a composition comprising a polypeptide or multimeric polypeptide construct having the ability to bind to cMet or a complex comprising cMet and HGF comprising an amino acid sequence, wherein the amino acid sequence comprises at least six amino acids out of a contiguous stretch of nine amino acids from a sequence selected from the group consisting of SEQ ID NOS:1-511. In a particular embodiment, the condition is solid tumor growth, e.g., wherein the tumor is selected from the group consisting of breast, thyroid, glioblastoma, prostate, malignant mesothelioma, colorectal, hepatocellular, hepatobiliary, renal, osteosarcoma and cervical. In a particular embodiment, the polypeptide or multimeric polypeptide construct can be conjugated to a tumoricidal agent.

In another embodiment, the invention is directed to a recombinant bacteriophage displaying any one or more of the polypeptides or multimeric polypeptide construct described herein or having any one or more of the consensus sequences described herein, such that the phage has the ability to bind to cMet or a complex comprising cMet and HGF, and wherein the polypeptide is displayed on the surface of the recombinant bacteriophage.

In another embodiment, the invention is directed to a magnetic resonance imaging contrast agent comprising a composition comprising a polypeptide having the ability to bind to cMet or a complex comprising cMet and HGF comprising an amino acid sequence comprising Cys-$X_1$-Gly-$X_2$-Pro-$X_3$-Phe-$X_4$-Cys (SEQ ID NO:619), wherein $X_1$, $X_2$, $X_3$ and $X_4$ can be any amino acid, or wherein the amino acid sequence comprises at least six amino acids out of a contiguous stretch of nine amino acids from a sequence selected from the group consisting of SEQ ID NOS:1-511. In a particular embodiment, the magnetic resonance imaging contrast agent further comprises at least one paramagnetic metal atom, e.g., at least one chelator selected from the group consisting of: DTPA, DOTA, EDTA, TETA, EHPG, HBED, NOTA, DOTMA, TETMA, PDTA, TTHA, LICAM, and MECAM. In particular embodiments, the chelator is selected from the group consisting of: diethylenetriamine, tetraazacyclododecane and a carboxymethyl-substituted derivative thereof. In other embodiments, the paramagnetic metal atom is selected from the group consisting of: $Mn^{2+}$, $Cu^{2+}$, $Fe^{2+}$, $Co^{2+}$, $Ni^{2+}$, $Gd^{3+}$, $Eu^{3+}$, $Dy^{3+}$, $Pr^{3+}$, $Cr^{3+}$, $Co^{3+}$, $Fe^{3+}$, $Ti^{3+}$, $Tb^{3+}$, $Nd^{3+}$, $Sm^{3+}$, $Ho^{3+}$, $Er^{3+}$, $Pa^{4+}$ and $Eu^{2+}$. In a particular embodiment, the multivalent cation is $Gd^{3+}$.

In another embodiment, the invention is directed to a method for identifying cMet or cMet/HGF complex binding compounds comprising the steps of: utilizing a cMet or cMet/HGF complex binding polypeptide or multimeric polypeptide construct having the ability to bind to cMet or a complex comprising cMet and HGF comprising an amino acid sequence comprising Cys-$X_1$-Gly-$X_2$-Pro-$X_3$-Phe-$X_4$-Cys (SEQ ID NO:619), wherein $X_1$, $X_2$, $X_3$ and $X_4$ can be any amino acid, to form a complex with a cMet or cMet/HGF complex target; contacting the complex with one or more potential cMet or cMet/HGF complex binding compounds; and determining whether the potential cMet or cMet/HGF complex binding compound competes with the cMet or cMet/HGF complex binding polypeptide to form a complex with the cMet or cMet/HGF complex target.

In one embodiment, the invention is directed to a diagnostic imaging contrast agent comprising a polypeptide or multimeric polypeptide construct having the ability to bind to cMet or a complex comprising cMet and HGF comprising an amino acid sequence comprising Cys-$X_1$-Gly-$X_2$-Pro-$X_3$-Phe-$X_4$-Cys (SEQ ID NO:619), wherein $X_1$, $X_2$, $X_3$ and $X_4$ can be any amino acid, or wherein the amino acid sequence comprises at least six amino acids out of a contiguous stretch of nine amino acids from a sequence selected from the group consisting of SEQ ID NOS:1-511.

In another embodiment, the invention is directed to a method of medical imaging comprising the steps of administering to an animal or human subject a pharmaceutical preparation of a contrast agent comprising at least one polypeptide or multimeric polypeptide construct having the ability to bind to cMet or a complex comprising cMet and HGF comprising an amino acid sequence comprising Cys-$X_1$-Gly-$X_2$-Pro-$X_3$-Phe-$X_4$-Cys (SEQ ID NO:619), wherein $X_1$, $X_2$, $X_3$ and $X_4$ can be any amino acid, and imaging the contrast agent by a method selected from the group consisting of: magnetic resonance imaging, ultrasound imaging, optical imaging, sonoluminescence imaging, photoacoustic imaging, and nuclear imaging. In another embodiment, the amino acid sequence comprises at least six amino acids out of a contiguous stretch of nine amino acids from a sequence selected from the group consisting of SEQ ID NOS:1-511, and imaging the contrast agent by a method selected from the group consisting of: magnetic resonance imaging, ultrasound imaging, optical imaging, sonoluminescence imaging, photoacoustic imaging, and nuclear imaging.

In another embodiment, the invention is directed to a method of radiotherapy comprising administering to an animal or human subject in need of such therapy a compound comprising at least one polypeptide or multimeric polypeptide construct having the ability to bind to cMet or a complex comprising cMet and HGF comprising an amino acid sequence comprising Cys-$X_1$-Gly-$X_2$-Pro-$X_3$-Phe-$X_4$-Cys (SEQ ID NO:619), wherein $X_1$, $X_2$, $X_3$ and $X_4$ can be any amino acid, or wherein the amino acid sequence comprises at least six amino acids out of a contiguous stretch of nine amino acids from a sequence selected from the group consisting of SEQ ID NOS:1-511, conjugated to a radionuclide useful for radiotherapy. In a particular embodiment, the compound further comprises a chelator, e.g., a compound selected from the group consisting of: formula 20, 21, 22, 23a, 23b, 24a, 24b and 25. In another embodiment, the compound further comprises a spacer or linker. In a particular embodiment, the radionuclide can be $^{186}Re$, $^{188}Re$, $^{177}Lu$, $^{90}Y$, $^{153}Sm$ or $^{166}Ho$.

In another embodiment, the invention is directed to a kit for preparation of a radiopharmaceutical comprising a polypeptide or multimeric polypeptide construct having the ability to bind to cMet or a complex comprising cMet and HGF comprising an amino acid sequence comprising Cys-$X_1$-Gly-$X_2$-Pro-$X_3$-Phe-$X_4$-Cys (SEQ ID NO:619), wherein $X_1$, $X_2$, $X_3$ and $X_4$ can be any amino acid, or wherein the amino acid sequence comprises at least six amino acids out of a contiguous stretch of nine amino acids from a sequence selected from the group consisting of SEQ ID NOS:1-511, a chelator for a radionuclide, and a reducing agent.

In another embodiment, the invention is directed to a method of targeting genetic material to cMet-expressing cells comprising administering to an animal or a human in need of such genetic material a polypeptide or multimeric polypeptide construct having the ability to bind to cMet or a complex comprising cMet and HGF comprising an amino acid sequence comprising Cys-$X_1$-Gly-$X_2$-Pro-$X_3$-Phe-$X_4$-Cys (SEQ ID NO:619), wherein $X_1$, $X_2$, $X_3$ and $X_4$ can be any amino acid, or wherein the amino acid sequence comprises at least six amino acids out of a contiguous stretch of nine amino acids from a sequence selected from the group consisting of SEQ ID NOS:1-511, conjugated to or associated with the genetic material or a delivery vehicle containing such genetic material.

In another embodiment, the invention is directed to a method of screening binding polypeptides identified by phage display for their ability to bind to cells expressing the cMet or cMet/HGF target comprising the steps of preparing multimeric constructs including one or more binding polypeptides; contacting the multimeric constructs with cells expressing the target and assessing the ability of the multimeric constructs to bind to the target. In a particular embodiment, the cells can be engineered by recombinant DNA technology to express the target. In another embodiment, the multimeric constructs can be detectably labeled. In another embodiment, the ability of the multimeric constructs to bind to the target is assessed in the presence of serum. In another embodiment, the multimeric construct can comprise biotinylated binding polypeptides complexed with avidin, streptavidin or neutravidin.

BRIEF DESCRIPTION OF THE DRAWINGS

FIG. 13A shows SEQ ID NO:514 linked to SEQ ID NO:515 (Ac-GSPEMCMMFPFLYPCNHHAPGGGK{PnAO6-Glut-K[Ac-GSFFPCWRIDRFGYCHANAPGGGKJJ-Glut]-NH2}-NH2); FIG. 13B shows SEQ ID NO:515 linked to SEQ ID NO:516 (Ac-GSFFPCWRIDRFGYCHANAPGGGK{PnAO6-Glut-K[Ac-AQEWEREYFVDGFWGSWFGIPHGGGK(JJ-Glut)-NH2]}-NH2); and FIG. 13C shows SEQ ID NO:514 linked to SEQ ID NO:517 (Ac-GSPEMCMMFPFLYPCNHHAPGGGK{PnAO6-Glut-K[Ac-GDYSECFFEPDSFEVKCYDRDPGGGK(JJ-Glut)-NH2]}-NH2).

DETAILED DESCRIPTION OF THE INVENTION

Figure 1A:
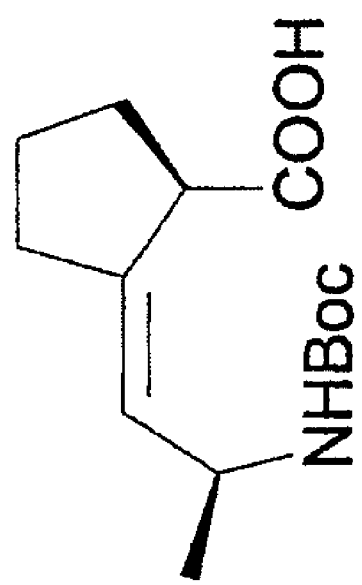
FIGS. 1A-1C are representations of mimics, which can be employed to mimic structural motifs and turn features in a peptide and simultaneously provide stability to proteolysis and enhance other properties (structure 1A: Hart, S, and Etzkorn, F., 1999. *J. Org. Chem.*, 64:2998-2999; structure 1B: Hanessian, S, and McNaughton-Smith, G., "Synthesis of a Versatile Peptidomimetic Scaffold" in *Methods in Molecular Medicine, Vol. 23: Peptidomimetics Protocols*, W. Kazmierski, Ed. (Humana Press Inc., Totowa, N.J., 1999), Chapter 10, pp. 161-174; structure 1C: WO 01/16135.

A description of preferred embodiments of the invention follows.

The present invention provides novel binding moieties that bind to the hepatocyte growth factor receptor ("HGFr" or "cMet"). Such binding moieties make possible the efficient detection, imaging and localization of activated cells exhibiting upregulated cMet expression and binding of HGF to cMet. Such activated cells are initiators of cellular proliferation, and therefore the polypeptides described herein provide a means of detecting, monitoring and localizing sites of proliferation. In particular, the binding moieties of this invention, which include polypeptides and multimeric polypeptide constructs, when appropriately labeled, are useful for detecting, imaging and localizing tumors or other proliferative disorders that result from dysregulated cellular proliferation (e.g., cancer). Thus, the binding polypeptides and multimeric polypeptide constructs of the invention can be used to form a variety of diagnostic and therapeutic agents for diagnosing and treating neoplastic tumor growth or other proliferative disorders. In addition, the binding polypeptides and multimeric polypeptide constructs can themselves be used as therapeutic agents.

Specific cMet binding polypeptides according to the present invention were isolated initially by screening of phage display libraries, that is, populations of recombinant bacteriophage transformed to express an exogenous peptide on their surface. In order to isolate new polypeptide binding moieties for a particular target, such as cMet, screening of large peptide libraries, for example using phage display techniques, is especially advantageous, in that very large numbers (e.g., $5 \times 10^9$) of potential binders can be tested and successful binders isolated in a short period of time.

In order to prepare a phage library of displaying polypeptides to screen for binding polypeptides such as cMet binding polypeptides and/or polypeptides that bind to a complex comprising HGF bound to cMet, a candidate binding domain is selected to serve as a structural template for the peptides to be displayed in the library. The phage library is made up of a multiplicity of analogues of the parental domain or template. The binding domain template can be a naturally occurring or synthetic protein, or a region or domain of a protein. The binding domain template can be selected based on knowledge of a known interaction between the binding domain template and the binding target, but this is not critical. In fact, it is not essential for the selected domain to act as a template for the library or have any affinity for the target at all; its purpose is to provide a structure from which a multiplicity (library) of similarly structured polypeptides (analogues) can be generated, which multiplicity of analogs will include one or more analogs that exhibit the desired binding properties (and any other properties screened for).

In selecting the parental binding domain or template on which to base the variegated amino acid sequences of the library, an important consideration is how the variegated peptide domains will be presented to the target, i.e., in what conformation the peptide analogues will come into contact with the target. In phage display methodologies, for example, the analogs are generated by insertion of synthetic DNA encoding the analogs into phage, resulting in display of the analog on the surfaces of the phage. Such libraries of phage, such as M13 phage, displaying a wide variety of different polypeptides, can be prepared using techniques as described, e.g., in Kay et al., *Phage Display of Peptides and Proteins: A Laboratory Manual* (Academic Press, Inc., San Diego, 1996) and U.S. Pat. No. 5,223,409 (Ladner et al.), incorporated herein by reference.

In isolating the specific polypeptides according to this invention, seven cyclic peptide (or "loop") libraries, designated TN6, TN7, TN8, TN9, TN10, TN11, TN12, and a linear library, designated LN20, were initially screened. Each library was constructed for expression of diversified polypeptides on M13 phage. The seven libraries having a "TN" designation were designed to display a short, variegated exogenous peptide loop of 6, 7, 8, 9, 10, 11 or 12 amino acids, respectively, on the surface of M13 phage, at the amino terminus of protein III. The libraries are designated TN6 (having a potential 3.3×10$^{12}$ amino acid sequence diversity), TN7 (having a potential 1.2×10$^{14}$ amino acid sequence diversity), TN8 (having a potential 2.2×10$^{15}$ amino acid sequence diversity), TN9 (having a potential 4.2×10$^{16}$ amino acid sequence diversity), TN10 (having a potential 3.0×10$^{16}$ amino acid sequence diversity), TN11 (having a potential 1.5×10$^{19}$ amino acid sequence diversity), TN12 (having a sequence diversity of 4.6×10$^{19}$), and LN20 (having a potential 3.8×10$^{25}$ amino acid sequence diversity).

The TN6 library was constructed to display a single microprotein binding loop contained in a 12-amino acid template. The TN6 library utilized a template sequence of Xaa1-Xaa2-Xaa3-Cys-Xaa5-Xaa6-Xaa7-Xaa8-Cys-Xaa10-Xaa11-Xaa12 (SEQ ID NO:612). The amino acids at positions 2, 3, 5, 6, 7, 8, 10, and 11 of the template were varied to permit any amino acid except cysteine (Cys). The amino acids at positions 1 and 12 of the template were varied to permit any amino acid except cysteine (Cys), glutamic acid (Glu), isoleucine (Ile), Lysine (Lys), methionine (Met), and threonine (Thr).

The TN7 library was constructed to display a single microprotein binding loop contained in a 13-amino acid template. The TN7 library utilized a template sequence of Xaa1-Xaa2-Xaa3-Cys-Xaa5-Xaa6-Xaa7-Xaa8-Xaa9-Cys-Xaa11-Xaa12-Xaa13 (SEQ ID NO:613). The amino acids at amino acid positions 1, 2, 3, 5, 6, 7, 8, 9, 11, 12, and 13 of the template were varied to permit any amino acid except cysteine (Cys).

The TN8 library was constructed to display a single microprotein binding loop contained in a 14-amino acid template. The TN8 library utilized a template sequence of Xaa1-Xaa2-Xaa3-Cys-Xaa5-Xaa6-Xaa7-Xaa8-Xaa9-Xaa10-Cys-Xaa12-Xaa13-Xaa14 (SEQ ID NO: 614). The amino acids at position 1, 2, 3, 5, 6, 7, 8, 9, 10, 12, 13, and 14 in the template were varied to permit any amino acid except cysteine (Cys).

The TN9 library was constructed to display a single microprotein binding loop contained in a 15-amino acid template. The TN9 library utilized a template sequence Xaa1-Xaa2-Xaa3-Cys-Xaa5-Xaa6-Xaa7-Xaa8-Xaa9-Xaa10-Xaa11-Cys-Xaa13-Xaa14-Xaa15 (SEQ ID NO:615). The amino acids at position 1, 2, 3, 5, 6, 7, 8, 9, 10, 11, 13, 14 and 15 in the template were varied to permit any amino acid except cysteine (Cys).

The TN10 library was constructed to display a single microprotein binding loop contained in a 16-amino acid template. The TN10 library utilized a template sequence Xaa1-Xaa2-Xaa3-Cys-Xaa5-Xaa6-Xaa7-Xaa8-Xaa9-Xaa10-Xaa11-Xaa12-Cys-Xaa14-Xaa15-Xaa16 (SEQ ID NO:616). The amino acids at positions 1, 2, 15, and 16 in the template were varied to permit any amino acid selected from a group of 10 amino acids: D, F, H, L, N, P, R, S, W, or Y). The amino acids at positions 3 and 14 in the template were varied to permit any amino acid selected from a group of 14 amino acids: A, D, F, G, H, L, N, P, Q, R, S, V, W, or Y). The amino acids at positions 5, 6, 7, 8, 9, 10, 11, and 12 in the template were varied to permit any amino acid except cysteine (Cys).

The TN11 library was constructed to display a single microprotein binding loop contained in a 17-amino acid template. The TN11 library utilized a template sequence Xaa1-Xaa2-Xaa3-Cys-Xaa5-Xaa6-Xaa7-Xaa8-Xaa9-Xaa10-Xaa11-Xaa12-Xaa13-Cys-Xaa15-Xaa16-Xaa17 (SEQ ID NO: 617). The amino acids at positions 1 through 3, 5 through 13, and 15 through 17 in the template were varied to permit any amino acid except cysteine (Cys).

The TN12 library was constructed to display a single microprotein binding loop contained in an 18-amino acid template. The TN12 library utilized a template sequence Xaa1-Xaa2-Xaa3-Cys-Xaa5-Xaa6-Xaa7-Xaa8-Xaa9-Xaa10-Xaa11-Xaa12-Xaa13-Xaa14-Cys-Xaa16-Xaa17-Xaa18 (SEQ ID NO:618). The amino acids at position 1, 2, 17, and 18 in the template were varied to permit any amino acid selected from a group of 12 amino acids: A, D, F, G, H, L, N, P, R, S, W, or Y). The amino acids at positions 3, 5, 6, 7, 8, 9, 10, 11, 12, 13, 14, and 16 were varied to permit any amino acid except cysteine (Cys).

The LN20 library was constructed to display multiple linear peptides on the surface of a phage. Each phage, however, displays multiple copies of the same sequence. Therefore, a single phage will display, for example, five copies of a particular sequence, a different phage will display, for example, five copies of a different sequence, etc. The linear peptides are provided in a 20-amino acid template. The amino acids at each position in the template were varied to permit any amino acid except cysteine (Cys).

The binding polypeptides provided herein can include additions or truncations in the—and/or C-termini. Such modified binding polypeptides are expected to bind cMet. For example, a -GGGK linker (SEQ ID NO:513) can be present at the N-terminus of the binding polypeptides provided herein. Other linkers, such as -GSGK (SEQ ID NO:610), or -GSGSK (SEQ ID NO: 6611) could be used. Binding polypeptides comprising the loop portion of the templates and sequences provided herein are expected to bind cMet and also are encompassed by the present invention. The loop portion of the templates and sequences includes the sequences between and including the two cysteine residues that are expected to form a disulfide bond, thereby generating a peptide loop structure. Furthermore, the binding polypeptides of the present invention can include additional amino acid residues at the—and/or C-termini.

The phage display libraries were created by making a designed series of mutations or variations within a coding sequence for the polypeptide template, each mutant sequence encoding a peptide analog corresponding in overall structure to the template except having one or more amino acid variations in the sequence of the template. The novel variegated (mutated) DNA provides sequence diversity, and each transformant phage displays one variant of the initial template amino acid sequence encoded by the DNA, leading to a phage population (library) displaying a vast number of different but structurally related amino acid sequences. The amino acid variations are expected to alter the binding properties of the binding peptide or domain without significantly altering its structure, at least for most substitutions. It is preferred that the amino acid positions that are selected for variation (variable amino acid positions) will be surface amino acid positions, that is, positions in the amino acid sequence of the domains that, when the domain is in its most stable conformation, appear on the outer surface of the domain (i.e., the surface exposed to solution). Most preferably the amino acid positions to be varied will be adjacent or close together, so as to maximize the effect of substitutions.

As indicated previously, the techniques discussed in Kay et al., *Phage Display of Peptides and Proteins: A Laboratory Manual* (Academic Press, Inc., San Diego, 1996) and U.S. Pat. No. 5,223,409 are particularly useful in preparing a library of potential binders corresponding to the selected parental template. Libraries as discussed above were prepared according to such techniques, and they were screened for cMet binding polypeptides against an immobilized target, as explained in the examples to follow.

In a typical screen, a phage library is contacted with and allowed to bind the target, or a particular subcomponent thereof. To facilitate separation of binders and non-binders, it is convenient to immobilize the target on a solid support.

Phage bearing a target-binding moiety form a complex with the target on the solid support whereas non-binding phage remain in solution and can be washed away with excess buffer. Bound phage are then liberated from the target by changing the buffer to an extreme pH (pH 2 or pH 10), changing the ionic strength of the buffer, adding denaturants, or other known means. To isolate the binding phage exhibiting the polypeptides of the present invention, a protein elution is performed, i.e., some phage are eluted from the target using HGF in solution (competitive elution). Additionally, for example, very high affinity binding phage that could not be competed off during the overnight HGF incubation were captured by using the phage still bound to substrate for infection of *E. coli* cells.

The recovered phage can then be amplified through infection of bacterial cells and the screening process can be repeated with the new pool that is now depleted in non-binders and enriched for binders. The recovery of even a few binding phage is sufficient to carry the process to completion. After a few rounds of selection, the gene sequences encoding the binding moieties derived from selected phage clones in the binding pool are determined by conventional methods, described below, revealing the peptide sequence that imparts binding affinity of the phage to the target. When the selection process works, the sequence diversity of the population falls with each round of selection until desirable binders remain. The sequences converge on a small number of related binders, typically 10-50 out of about $10^9$ to $10^{10}$ original candidates from each library. An increase in the number of phage recovered at each round of selection, and of course, the recovery of closely related sequences are good indications that convergence of the library has occurred in a screen. After a set of binding polypeptides is identified, the sequence information can be used to design other secondary phage libraries, biased for members having additional desired properties.

Formation of the disulfide binding loop is advantageous because it leads to increased affinity and specificity for such peptides. However, in serum, the disulfide bond can be opened by free cysteines or other thiol-containing molecules. Thus, it could be useful to modify the cysteine residues to replace the disulfide cross-link with another less reactive linkage. The —$CH_2$—S—S—$CH_2$— cross-link has a preferred geometry in which the dihedral bond between sulfurs is close to 90 degrees, but the exact geometry is determined by the context of other side groups and the binding state of the molecule. Preferred modifications of the closing cross-link of the binding loop will preserve the overall bond lengths and angles as much as possible. Suitable such alternative cross-links include thioether linkages such as —$CH_2$—S—$CH_2$—$CH_2$—, —$CH_2$—$CH_2$—S—$CH_2$—, —$CH_2$—$CH_2$-S—$CH_2$—$CH_2$—; lactam or amide linkages such as —$CH_2$—NH—CO—$CH_2$— and —$CH_2$—CO—NH—$CH_2$—; ether linkages such as —$CH_2$—$CH_2$—O—$CH_2$—$CH_2$—; alkylene bridges such as —$(CH_2)_n$— (where n=4, 5, or 6); the linkage —$CH_2$—NH—CO—NH—$CH_2$—, and similar groups known in the art.

Although polypeptides containing a stable disulfide-linked binding loop are most preferred, linear polypeptides derived from the foregoing sequences can be readily prepared, e.g., by substitution of one or both cysteine residues, which may retain at least some of the cMet binding activity of the original polypeptide containing the disulfide linkage. In making such substitutions for Cys, the amino acids Gly, Ser, and Ala are preferred, and it also is preferred to substitute both Cys residues, so as not to leave a single Cys that could cause the polypeptide to dimerize or react with other free thiol groups in a solution. All such linearized derivatives that retain cMet binding properties are within the scope of this invention.

Direct synthesis of the polypeptides of the invention can be accomplished using conventional techniques, including solid-phase peptide synthesis, solution-phase synthesis, etc. Solid-phase synthesis is preferred (see, for example, Stewart et al., *Solid-Phase Peptide Synthesis* (W.H. Freeman Co., San Francisco, 1989); Merrifield, J., 1963, *Am. Chem. Soc.*, 85:2149-2154; Bodanszky and Bodanszky, *The Practice of Peptide Synthesis* (Springer-Verlag, New York, 1984)), incorporated herein by reference.

Polypeptides according to the invention can also be prepared commercially by companies providing peptide synthesis as a service (e.g., BACHEM Bioscience, Inc., King of Prussia, Pa.; Quality Controlled Biochemicals, Inc., Hopkinton, Mass.).

Automated peptide synthesis machines, such as manufactured by Perkin-Elmer Applied Biosystems, also are available.

The polypeptide compound is preferably purified after it has been isolated or synthesized by either chemical or recombinant techniques. For purification purposes, there are many standard methods that may be employed, including reversed-phase high pressure liquid chromatography (RP-HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can also be used to separate peptides based on their charge. The degree of purity of the polypeptide can be determined by various methods, including identification of a major large peak on HPLC. A polypeptide that produces a single peak that is at least 95% of the input material on an HPLC column is preferred. Even more preferable is a polypeptide that produces a single peak that is at least 97%, at least 98%, at least 99% or even 99.5% or more of the input material on an HPLC column.

To ensure that the peptide obtained using any of the techniques described above is the desired peptide for use in compositions of the present invention, analysis of the peptide composition can be carried out. Such composition analysis can be conducted using high resolution mass spectrometry to determine the molecular weight of the peptide. Alternatively, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, can also be used to determine the sequence of the peptide.

cMet binding polypeptides according to the present invention also can be produced using recombinant DNA techniques, utilizing nucleic acids (polynucleotides) encoding the polypeptides according to this invention and then expressing them recombinantly, i.e., by manipulating host cells by introduction of exogenous nucleic acid molecules in known ways to cause such host cells to produce the desired cMet binding polypeptides. Such procedures are within the capability of those skilled in the art (see, for example, Davis et al., *Basic Methods in Molecular Biology* (1986)), incorporated by reference. Recombinant production of short peptides, such as those described herein, might not be practical in comparison to direct synthesis, however recombinant means of production can be very advantageous where a cMet binding moiety of this invention is incorporated in a hybrid polypeptide or fusion protein.

In the practice of the present invention, a determination of the affinity of the cMet binding moiety for cMet relative to another protein or target is a useful measure, and is referred to as specificity for cMet. Standard assays for quantitating binding and determining affinity include equilibrium dialysis, equilibrium binding, gel filtration, or the monitoring of numerous spectroscopic changes (such as a change in fluorescence polarization) that result from the interaction of the binding moiety and its target. These techniques measure the concentration of bound and free ligand as a function of ligand (or protein) concentration. The concentration of bound polypeptide ([Bound]) is related to the concentration of free polypeptide ([Free]) and the concentration of binding sites for the polypeptide, i.e., on cMet, (N), as described in the following equation:

$$[Bound]=N\times[Free]/((1/K_a)+[Free]).$$

A solution of the data to this equation yields the association constant, $K_a$, a quantitative measure of the binding affinity. The association constant, $K_a$ is the reciprocal of the dissociation constant, $K_D$. The $K_D$ is more frequently reported in measurements of affinity. Preferred cMet binding polypeptides have a $K_D$ for cMet in the range of, for example, less than 1 nanomolar (nM), 1 nM to 100 micromolar (µM), which includes $K_D$ values of less than 10 nM, less than 20 nM, less than 40 nM, less than 60 nM, less than 80 nM, less than 1 less than 5 µM, less than 10 µM, less than 20 µM, less than 40 µM, less than 60 µM, and less than 80 µM.

Where cMet binding moieties are employed as imaging agents, other aspects of binding specificity become important; imaging agents operate in a dynamic system in that binding of the imaging agent to the target (cMet, e.g., on activated cells) might not be in a stable equilibrium state throughout the imaging procedure. For example, when the imaging agent is initially injected, the concentration of imaging agent and of agent-target complex rapidly increases. Shortly after injection, however, the circulating (free) imaging agent starts to clear through the kidneys or liver, and the plasma concentration of imaging agent begins to drop. This drop in the concentration of free imaging agent in the plasma eventually causes the agent-target complex to dissociate. The usefulness of an imaging agent depends on the difference in rate of agent-target dissociation relative to the clearing rate of the agent. Ideally, the dissociation rate will be slow compared to the clearing rate, resulting in a long imaging time during which there is a high concentration of agent-target complex and a low concentration of free imaging agent (background signal) in the plasma.

Quantitative measurement of dissociation rates can be performed using several methods known in the art, such as fiber optic fluorimetry (see, for example, Anderson and Miller, 1988, *Clin. Chem.*, 34:1417-21), surface plasmon resonance (see, for example, Malmborg et al., 1996, *J. Immunol. Methods*, 198:51-7; and Schuck, 1997, *Curr. Op. Biotechnol.*, 8:498-502), resonant mirror, and grating coupled planar waveguiding (see, for example, Hutchinson, 1995, *Molec. Biotechnol.*, 3:47-54). Automated biosensors are commercially available for measuring binding kinetics: BIAcore surface plasmon resonance sensor (Biacore AB, Uppsala SE), IAsys resonant mirror sensor (Fisons Applied Sensor Technology, Cambridge GB), BIOS-1 grated coupled planar waveguiding sensor (Artificial Sensor Instruments, Zurich CH).

Methods of Screening Polypeptides Identified by Phage Display for Their Ability to Bind to Cells Expressing the Target In another aspect of the invention, methods of screening binding polypeptides identified by phage display for their ability to bind to cells expressing the target (and not to cells that do not express the target) are provided. These methods address a significant problem associated with screening peptides identified by phage display: frequently the peptides so identified do not have sufficient affinity for the target to be screened against target-expressing cells in conventional assays. However, ascertaining that a particular phage-identified peptide binds to cells that express the target (and does not bind to cells that do not) is a critical piece of information in identifying binding peptides that are potential in vivo targeting moieties, whether they are used as monomers or as part of a multimeric construct. The method takes advantage of the increase in affinity and avidity associated with multivalent binding and permit screening of polypeptides with low affinities against target-expressing cells.

The method generally consists of preparation and screening of multimeric constructs including one or more binding polypeptides. For example, polypeptides identified by phage display as binding to a target are biotinylated and complexed with avidin, streptavidin or neutravidin to form tetrameric constructs. These tetrameric constructs are then incubated with cells that express the desired target and cells that do not, and binding of the tetrameric construct is detected. Binding can be detected using any method of detection known in the art. For example, to detect binding the avidin, streptavidin, or neutravidin may be conjugated to a detectable marker (e.g., a radioactive label, a fluorescent label, or an enzymatic label which undergoes a color change, such as HRP (horse radish peroxidase), TMB (tetramethyl benzidine) or alkaline phosphatase).

The biotinylated peptides are preferably complexed with neutravidin-HRP. Neutravidin exhibits lower non-specific binding to molecules than the other alternatives due to the absence of lectin binding carbohydrate moieties and cell adhesion receptor-binding RYD domain in neutravidin (Hiller, Y. et al, 1987. *Biochem. J.*, 248:167-171; Alon, R. et al., 1990. *Biochem. Biophys. Res. Commun.*, 170:1236-41).

The tetrameric constructs can be screened against cells that naturally express the target or cells that have been engineered via recombinant DNA technologies to express the target (e.g., transfectants, transformants, etc.). If cells that have been transfected to express the target are used, mock transfected cells (i.e., cells transfected without the genetic material encoding the target) can be used as a control.

The tetrameric complexes can optionally be screened in the presence of serum. Thus, the assay also can be used to rapidly evaluate the effect of serum on the binding of peptides to the target.

The methods disclosed herein are particularly useful in preparing and evaluating combinations of distinct binding polypeptides for use in dimeric or multimeric targeting constructs that contain two or more binding polypeptides. Use of biotin/avidin complexes allows for relatively easy preparation of tetrameric constructs containing one to four different binding peptides. Furthermore, it has now been found that affinity and avidity of a targeting construct can be increased by inclusion of two or more targeting moieties that bind to different epitopes on the same target. The screening methods described herein are useful in identifying combinations of binding polypeptides that could have increased affinity when included in such multimeric constructs.

In a preferred embodiment, the screening methods described herein can be used to screen cMet binding polypeptides identified by phage display, such as those described herein. These methods can be used to assess the specific binding of cMet binding polypeptides to cells that express cMet or have been engineered to express cMet. Tetrameric complexes of biotinylated cMet binding polypeptides of the invention and, for example, neutravidin-HRP can be prepared and screened against cells transfected to express cMet as well as mock transfected cells, which do not express cMet.

The assay can be used to identify cMet binding polypeptides that bind specifically to cMet-expressing cells (and do not bind to cells that do not express cMet) even when the monodentate $K_D$ of the polypeptide is on the order of 200 nM-300 nM. The assay can be used to screen homotetrameric constructs containing four copies of a single cMet binding polypeptide of the invention as well as heterotetrameric (constructs containing two or more different cMet binding polypeptides). The methods described herein are particularly useful for assessing combinations of cMet binding polypeptides for use in multimeric constructs, particularly constructs containing two or more cMet binding polypeptides that bind to different epitopes of cMet.

The assay also can be used to assess the effect of serum on the cMet binding polypeptides.

Modification or Optimization of cMet Binding Polypeptides

As discussed, modification or optimization of cMet binding polypeptides is within the scope of the invention and the modified or optimized polypeptides are included within the definition of "cMet binding polypeptides". Specifically, a polypeptide sequence identified by phage display can be modified to optimize its potency, pharmacokinetic behavior, stability and/or other biological, physical and chemical properties.

Substitution of Amino Acid Residues

For example, one can make the following isosteric and/or conservative amino acid changes in the parent polypeptide sequence with the expectation that the resulting polypeptides would have a similar or improved profile of the properties described above:

Substitution of alkyl-substituted hydrophobic amino acids: including alanine, leucine, isoleucine, valine, norleucine, S-2-aminobutyric acid, S-cyclohexylalanine or other simple alpha-amino acids substituted by an aliphatic side chain from C1-10 carbons including branched, cyclic and straight chain alkyl, alkenyl or alkynyl substitutions.

Substitution of aromatic-substituted hydrophobic amino acids: including phenylalanine, tryptophan, tyrosine, biphenylalanine, 1-naphthylalanine, 2-naphthylalanine, 2-benzothienylalanine, 3-benzothienylalanine, histidine, amino, alkylamino, dialkylamino, aza, halogenated (fluoro, chloro, bromo, or iodo) or alkoxy (from $C_1$-$C_4$)-substituted forms of the previous listed aromatic amino acids, illustrative examples of which are: 2-,3- or 4-aminophenylalanine, 2-,3- or 4-chlorophenylalanine, 2-,3- or 4-methylphenylalanine, 2-,3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2,3, or 4-biphenylalanine, 2',-3',- or 4'-methyl-2, 3 or 4-biphenylalanine, and 2- or 3-pyridylalanine.

Substitution of amino acids containing basic functions: including arginine, lysine, histidine, ornithine, 2,3-diaminopropionic acid, homoarginine, alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha methyl arginine, alpha methyl 2,3-diaminopropionic acid, alpha methyl histidine, alpha methyl ornithine where alkyl group occupies the pro-R position of the alpha carbon. Also included are the amides formed from alkyl, aromatic, heteroaromatic (where the heteroaromatic group has one or more nitrogens, oxygens or sulfur atoms singly or in combination) carboxylic acids or any of the many well-known activated derivatives such as acid chlorides, active esters, active azolides and related derivatives) and lysine, ornithine, or 2,3-diaminopropionic acid.

Substitution of acidic amino acids: including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids.

Substitution of side chain amide residues: including asparagine, glutamine, and alkyl or aromatic substituted derivatives of asparagine or glutamine.

Substitution of hydroxyl containing amino acids: including serine, threonine, homoserine, 2,3-diaminopropionic acid, and alkyl or aromatic substituted derivatives of serine or threonine. It is also understood that the amino acids within each of the categories listed above can be substituted for another of the same group.

Substitution of Amide Bonds

Another type of modification within the scope of the invention is to substitute the amide bonds within the backbone of the polypeptide. For example, to reduce or eliminate undesired proteolysis, or other degradation pathways that diminish serum stability, resulting in reduced or abolished bioactivity, or to restrict or increase conformational flexibility, one can substitute amide bonds within the backbone of the peptides with functionality that mimics the existing conformation or alters the conformation in the manner desired. Such modifications can produce increased binding affinity or improved pharmacokinetic behavior. It is understood that those knowledgeable in the art of peptide synthesis can make the following amide bond changes for any amide bond connecting two amino acids with the expectation that the resulting peptides could have the same or improved activity: insertion of alpha-N-methylamides or peptide amide backbone thioamides, removal of the carbonyl to produce the cognate secondary amines, replacement of one amino acid with an aza-amino acid to produce semicarbazone derivatives, and use of E-olefins and substituted E-olefins as amide bond surrogates.

Introduction of D-Amino Acids

Another approach within the scope of the invention is the introduction of D-alanine, or another D-amino acid, distal or proximal to the labile peptide bond. In this case it is also understood to those skilled in the art that such D-amino acid substitutions can, and at times, must be made, with D-amino acids whose side chains are not conservative replacements for those of the L-amino acid being replaced. This is because of the difference in chirality and hence side-chain orientation, which could result in the accessing of a previously unexplored region of the binding site of the target that has moieties of different charge, hydrophobicity, steric requirements etc. than that serviced by the side chain of the replaced L-amino acid.

Modifications to Improve Pharmacokinetic or Pharmacodynamic Properties

It also is understood that use of one or more cMet binding polypeptides in a particular application could be benefited by modifications of the peptide or formulations of the peptide to improve pharmacokinetic and pharmacodynamic behavior. It is expected that the properties of the peptide can be changed by attachment of moieties anticipated to bring about the desired physical or chemical properties. Such moieties can be appended to the peptide using acids or amines, via amide bonds or urea bonds, respectively, to the—or C-terminus of the peptide, or to the pendant amino group of a suitably located lysine or lysine derivative, 2,3-diaminopropionic acid, ornithine, or other amino acid in the peptide that possesses a pendant amine group or a pendant alkoxyamine or hydrazine group. Conversely acidic amino acid side-chains such as those of Asp or Glu can be selectively unmasked and amidated with amines bearing the desired modifying functionality, or they can be modified in this manner before incorporation into the peptide chain. The moieties introduced can be groups that are hydrophilic, basic, or nonpolar alkyl or aromatic groups depending on the peptide of interest and the extant requirements for modification of its properties.

Glycosylation of Amino Acid Residues

Yet another modification within the scope of the invention is glycosylation of one or more amino acid residues (e.g., serine or threonine residues) in the cMet binding polypeptide. Glycosylation, which can be carried out using standard conditions, can be used to enhance solubility, alter pharmacokinetics and pharmacodynamics or to enhance binding via a specific or non-specific interaction involving the glycosidic moiety.

Formation of Salts

It also is within the scope of the invention to form different salts that could increase or decrease the water solubility or the ease of formulation of these peptides. These may include, but are not restricted to, N-methylglucamine (meglumine), acetate, oxalates, ascorbates, etc.

Structural Modifications which Retain Structural Features

Yet another modification within the scope of the invention is truncation of cyclic polypeptides. The cyclic nature of many polypeptides of the invention limits the conformational space available to the peptide sequence, particularly within the cycle. Therefore truncation of the peptide by one or more residues distal or even proximal to the cycle, at either the N-terminal or C-terminal region could provide truncated peptides with similar or improved biological activity. A unique sequence of amino acids, even as small as three amino acids, which is responsible for the binding activity, can be identified, as noted for RGD peptides (Plow, E. et al., 1987. *Blood*, 70:110-5; Oldberg, A. et al., 1988. *J. Biol. Chem.*, 263:19433-19436; Taub, R. et al., 1989. *J. Biol. Chem.*, 264:259-65; Andrieux, A. et al., 1989. *J. Biol. Chem.*, 264:9258-65; and U.S. Pat. Nos. 5,773,412 and 5,759,996, each of which is incorporated herein by reference).

It also has been shown in the literature that large peptide cycles can be substantially shortened, eliminating extraneous amino acids, but substantially including the critical binding residues. See, U.S. Pat. No. 5,556,939, incorporated by reference herein.

The shortened cyclic peptides can be formed using disulfide bonds or amide bonds of suitably located carboxylic acid groups and amino groups.

Figure 1B:
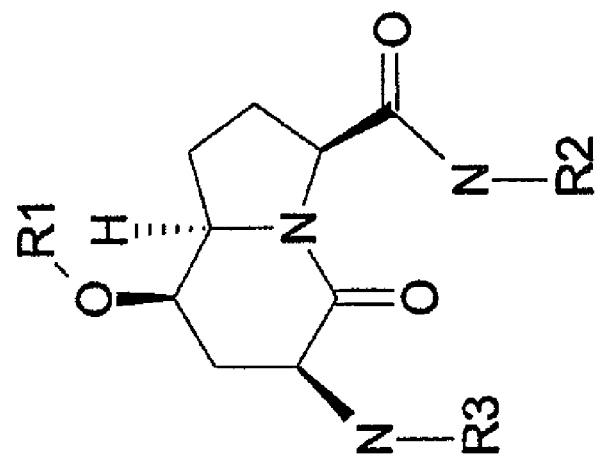
Figure 1C:
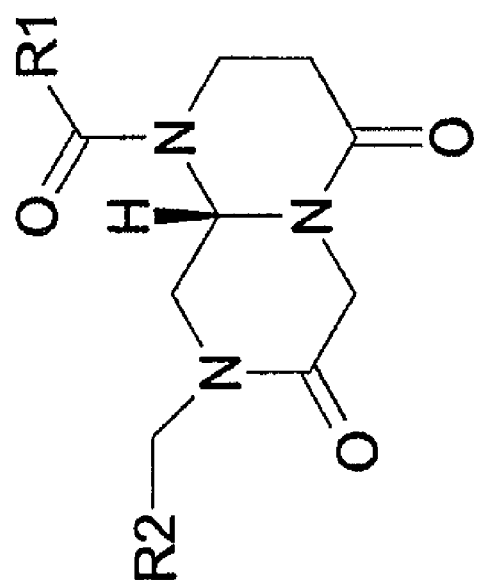

Furthermore, D-amino acids can be added to the peptide sequence to stabilize turn features (especially in the case of glycine). In another approach alpha, beta, gamma or delta dipeptide or turn mimics (such as α, β, γ, or δ turn mimics), some of which are shown in FIGS. 1A-1C, can be employed to mimic structural motifs and turn features in a peptide and simultaneously provide stability from proteolysis and enhance other properties such as, for example, conformational stability and solubility (structure 1A: Hart et al., J. Org. Chem., 64, 2998-2999 (1999); structure 1B: Hanessian et al., "Synthesis of a Versatile Peptidomimetic Scaffold" in Methods in Molecular Medicine, Vol. 23: Peptidomimetics Protocols, W. Kazmierski, Ed. (Humana Press Inc., Totowa, N.J., 1999), Chapter 10, pp. 161-174; structure 1C: WO 01/16135.

Substitution of Disulfide Mimetics

Also within the scope of the invention is the substitution of disulfide mimetics for disulfide bonds within the cMet binding peptides of the invention.

Where disulfide-containing peptides are employed in generating $^{99m}$Tc-based radiopharmaceuticals, or other useful radiopharmaceuticals based on other isotopes, a significant problem is the presence of the disulfide bond. For example, the integrity of the disulfide bond is difficult to maintain during procedures designed to incorporate $^{99m}$Tc via routes that are reliant upon the reduction of pertechnetate ion and subsequent incorporation of the reduced Tc species into substances bearing Tc-specific chelating groups. This is because the disulfide bond is rather easily reduced by the reducing agents commonly used in kits devised for one-step preparation of radiopharmaceuticals. Therefore, the ease with which the disulfide bond can be reduced during Tc chelation may require substitution with mimetics of the disulfide bonds. Accordingly, another modification within the scope of the invention is to substitute the disulfide moiety with mimetics utilizing the methods disclosed herein or known to those skilled in the art, while retaining the activity and other desired properties of the cMet-binding polypeptides of the invention.

1.) Oxime Linker

Figure 2:
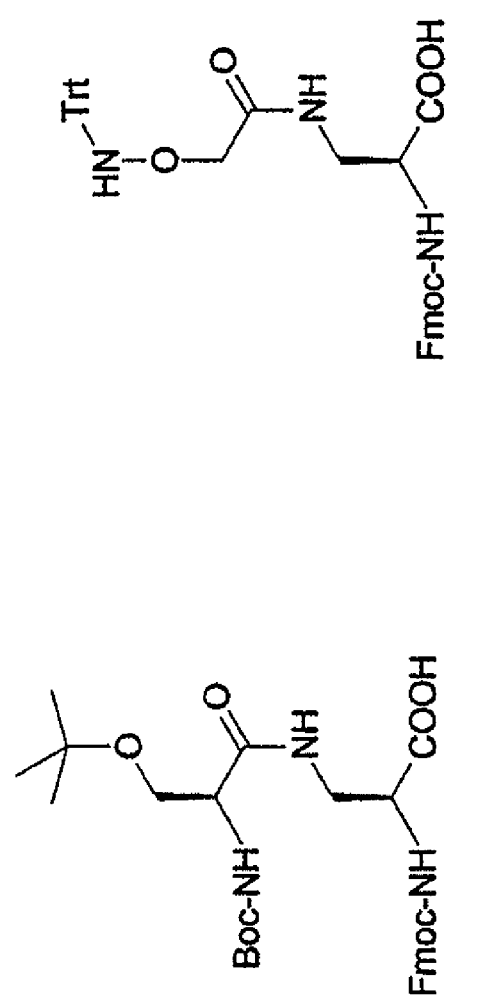
FIG. 2 is a representation of the amino acids (4), containing an aminoalcohol function, and (5) containing an alkoxyamino function.

The oxime moiety has been employed as a linker by investigators in a number of contexts (Wahl, F. and Mutter, M., 1996. *Tetrahedron Lett.*, 37:6861-6864). As shown in FIG. 2, the amino acids 4, containing an aminoalcohol function, and 5 containing an alkoxyamino function, can be incorporated into the peptide chain, not necessarily at the end of the peptide chain. After formation of the peptide the side-chain protecting groups can be removed. The aldehyde group is then unmasked and an oxime linkage is formed.

2.) Lanthionine Linker

Lanthionines are cyclic sulfides, wherein the disulfide linkage (S—S) is replaced by a carbon-sulfur (C—S) linkage. Thus, the lability to reduction is far lower. Lanthionines can be prepared by a number of methods including those discussed below.

1) Preparation of Lanthionines Using Bromoacetylated Peptides

Figure 3:
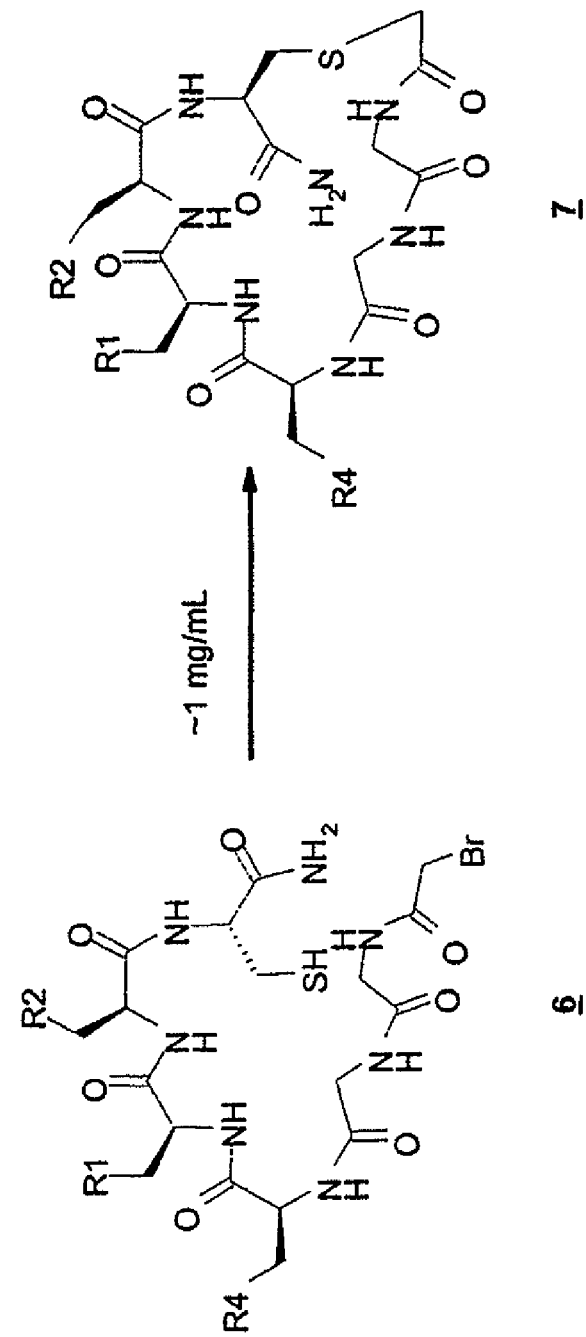
FIG. 3 is a representation depicting the cyclization of Cysteine with a pendant bromoacetamide function (this process is referred to herein as "scheme 1").

Lanthionines can be readily prepared using known methods (Robey, F. and Fields, R., 1989. *Anal. Biochem.*, 177:373-377; Inman, J. et al., 1991. *Bioconjug. Chem.*, 2:458-463; Ploinsky, A. et al., 1992. *J. Med. Chem.*, 35:4185-4194; Mayer et al., "Peptides, Frontiers of Peptide Science", in *Proceedings of the 15th American Peptide Symposium*, Tam and Kaumaya (Eds.), Jun. 14-19, 1995, Nashville, Term. (Klumer Academic Pub., Boston), pp. 291-292; Wakao et al., Jpn. Kokai Tokyo Koho, JP 07300452 A2 (1995)). Preparation of peptides using Boc automated peptide synthesis followed by coupling the peptide terminus with bromoacetic acid gives bromoacetylated peptides in good yield. Cleavage and deprotection of the peptides can be accomplished using HF/anisole. If the peptide contains a cysteine group its reactivity can be controlled with low pH. If the pH of the medium is raised to 6-7 then either polymerization or cyclization of the peptide takes place. Polymerization is favored at high (100 mg/mL) concentration whereas cyclization is favored at lower concentrations (1 mg/mL), e.g., 6 cyclizes to 7 (referred to herein as "scheme 1" as shown in FIG. 3). Inman et al. demonstrated the use of Na-(Boc)-Ne—[N-(bromoacetyl)-β-alanyl]-lysine as a carrier of the bromoacetyl group that could be employed in Boc peptide synthesis thus allowing placement of a bromoacetyl bearing moiety anywhere in a sequence. In preliminary experiments they found that peptides with 4-6 amino acids separating the bromoacetyl-lysine derivative from a cysteine tend to cyclize, indicating the potential utility of this strategy.

2) Preparation of Lanthionines Via Cysteine Thiol Addition to Acrylamides

Several variants of this strategy can be implemented. Resin-bound serine can be employed to prepare the lanthionine ring on resin either using a bromination-dehydrobromination-thiol addition sequence or by dehydration with disuccinimidyl carbonate followed by thiol addition. Conjugate addition of thiols to acrylamides has also been amply demonstrated and a reference to the addition of 2-mercaptoethanol to acrylamide is provided (Wakao et al., Jpn. Kokai Tokyo Koho, JP 07300452 A2, 1995).

3) Diaryl Ether or Diarylamine Linkage From Intramolecular Cyclization of Aryl Boronic Acids and Tyrosine The reaction of arylboronic acids with phenols, amines and heterocyclic amines in the presence of cupric acetate, in air, at ambient temperature, in dichloromethane using either pyridine or triethylamine as a base to provide unsymmetrical diaryl ethers and the related amines in good yields (as high as 98%) has been reported (Evans, D. et al., 1998. Tetrahedron Lett., 39:2937-2940; Chan, D. et al., 1998. *Tetrahedron Lett.,* 39:2933-2936; Lam, P. et al., 1998. *Tetrahedron Lett.,* 39:2941-2944). In the case of N-protected tyrosine derivatives as the phenol component the yields were also as high as 98%. This demonstrates that amino acid amides (peptides) are expected to be stable to the transformation and that yields are high. Precedent for an intramolecular reaction exists in view of the facile intramolecular cyclizations of peptides to lactams, intramolecular biaryl ether formation based on the SNAr reaction and the generality of intramolecular cyclization reactions under high dilution conditions or on resin, wherein the pseudo-dilution effect mimics high dilution conditions.

Figure 4:
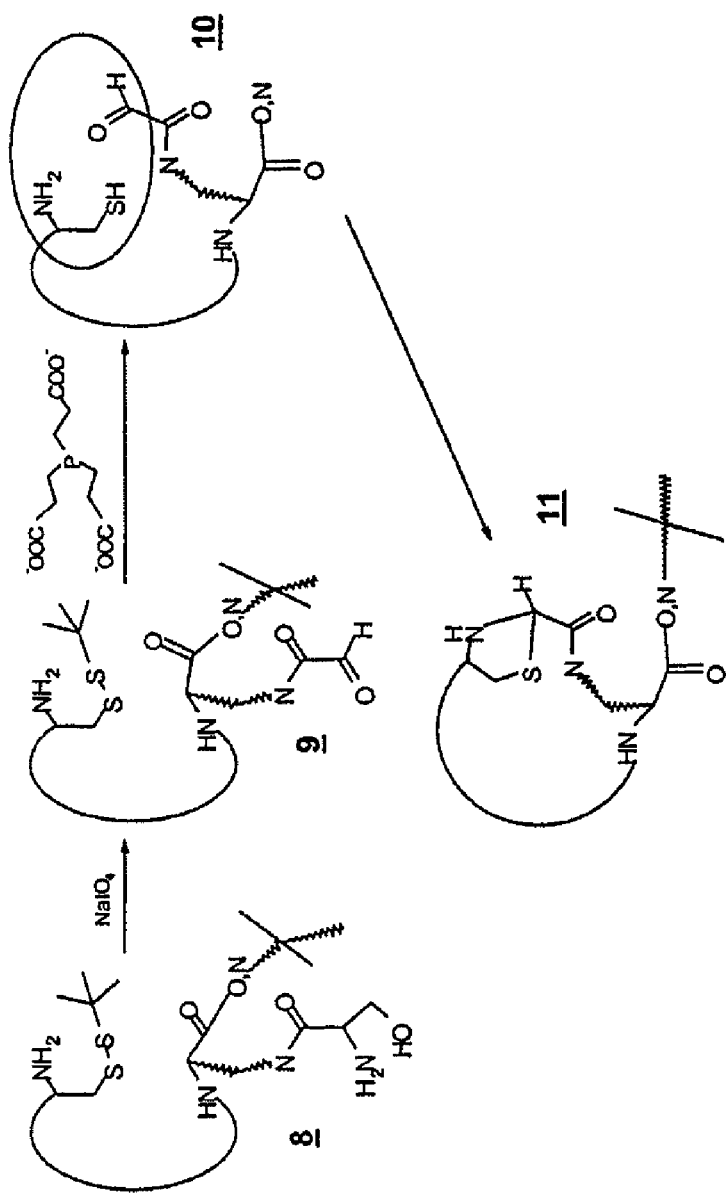
FIG. 4 is a representation showing intramolecular cyclization of suitably located vicinal amino mercaptan functions and aldehyde functions to provide thiazolidines that result in the formation of a bicyclic peptide, one ring of which is that formed by the residues in the main chain, and the second ring being the thiazolidine ring (this process is referred to herein as "scheme 2").

4) Formation of Cyclic Peptides with a Thiazolidine Linkage via Intramolecular Reaction of Peptide Aldehydes with Cysteine Moieties Another approach that may be employed involves intramolecular cyclization of suitably located vicinal amino mercaptan functions (usually derived from placement of a cysteine at a terminus of the linear sequence or tethered to the sequence via a side-chain nitrogen of a lysine, for example) and aldehyde functions to provide thiazolidines that result in the formation of a bicyclic peptide, one ring of which is that formed by the residues in the main chain, and the second ring being the thiazolidine ring. Scheme 2 (FIG. 4) provides an example. The required aldehyde function can be generated by sodium metaperiodate cleavage of a suitably located vicinal aminoalcohol function, which can be present as an unprotected serine tethered to the chain by appendage to a side chain amino group of a lysine moiety. In some cases the required aldehyde function is generated by unmasking of a protected aldehyde derivative at the C-terminus or the N-terminus of the chain (Botti, P. et al., 1996. *J. Am. Chem. Soc.,* 118:10018-10034).

5) Lactams Based on Intramolecular Cyclization of Pendant Amino Groups with Carboxyl Groups on Resin.

Macrocyclic peptides can be prepared by lactam formation by either head-to-tail or by pendant group cyclization. The basic strategy is to prepare a fully protected peptide wherein it is possible to remove selectively an amine protecting group and a carboxy protecting group. Orthogonal protecting schemes have been developed. Of those that have been developed the allyl, trityl and Dde methods have been employed most (Mellor et al., "Synthesis of Modified Peptides", in *Fmoc Solid Phase Synthesis: A Practical Approach,* White and Chan (eds) (Oxford University Press, New York, 2000), Ch. 6, pp. 169-178). The Dde approach is of interest because it utilizes similar protecting groups for both the carboxylic acid function (Dmab ester) and the amino group (Dde group). Both are removed with 2-10% hydrazine in DMF at ambient temperature. Alternately the Dde can be used for the amino group and the allyl group can be used for the carboxyl.

Figure 5:
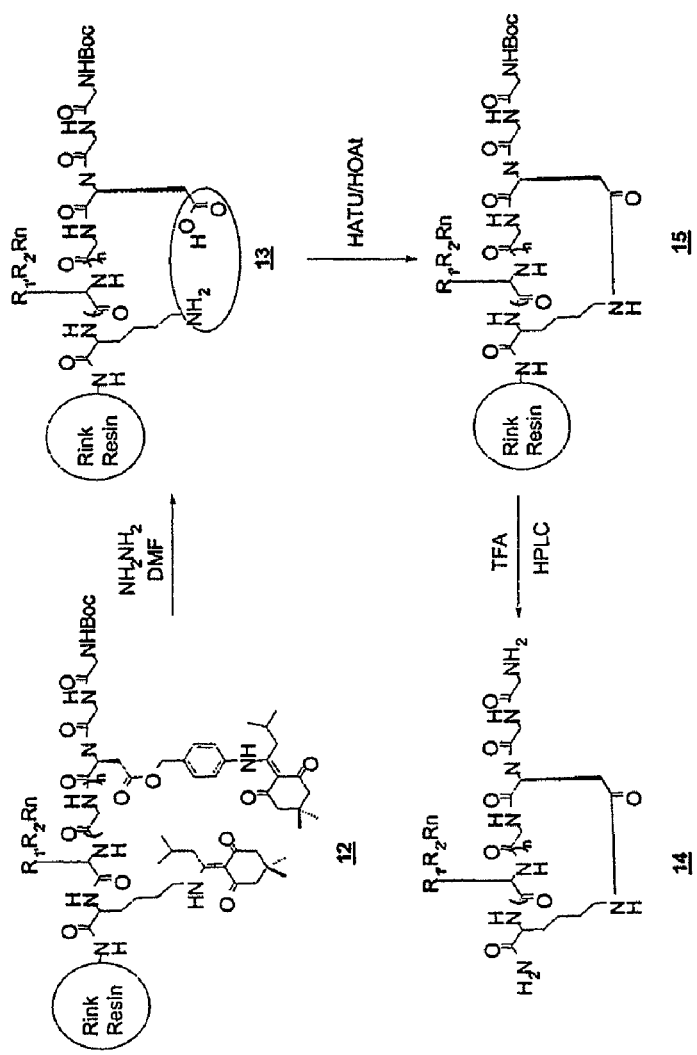
FIG. 5 is a representation showing how a lactam function, available by intramolecular coupling via standard peptide coupling reagents (such as HATU, PyBOP etc) can act as a surrogate for the disulfide bond. The Dde/Dmab approach is shown (and is referred to herein as "scheme 3").

A lactam function, available by intramolecular coupling via standard peptide coupling reagents (such as HATU, PyBOP etc) can act as a surrogate for the disulfide bond. The Dde/Dmab approach is shown in Scheme 3 (FIG. 5).

Thus, a linear sequence containing, for example, the Dde-protected lysine and Dmab ester can be prepared on a Tentagel-based Rink amide resin at low load (~0.1-0.2 mmol/g). Deprotection of both functions with hydrazine is then followed by on-resin cyclization to give the desired products. Subsequently cleavage from resin and purification may also be carried out. For functionalization of the N-terminus of the peptide it is understood that diamino acids such as trans-4-(ivDde)methylaminocyclohexane carboxylic acid or 4-(iv-Dde)methylamino benzoic acid would be required. An alternative scenario is to employ the safety catch method to intramolecular lactam formation during cleavage from the resin.

6) Cyclic Peptides Based on Olefin Metathesis

Figure 6:
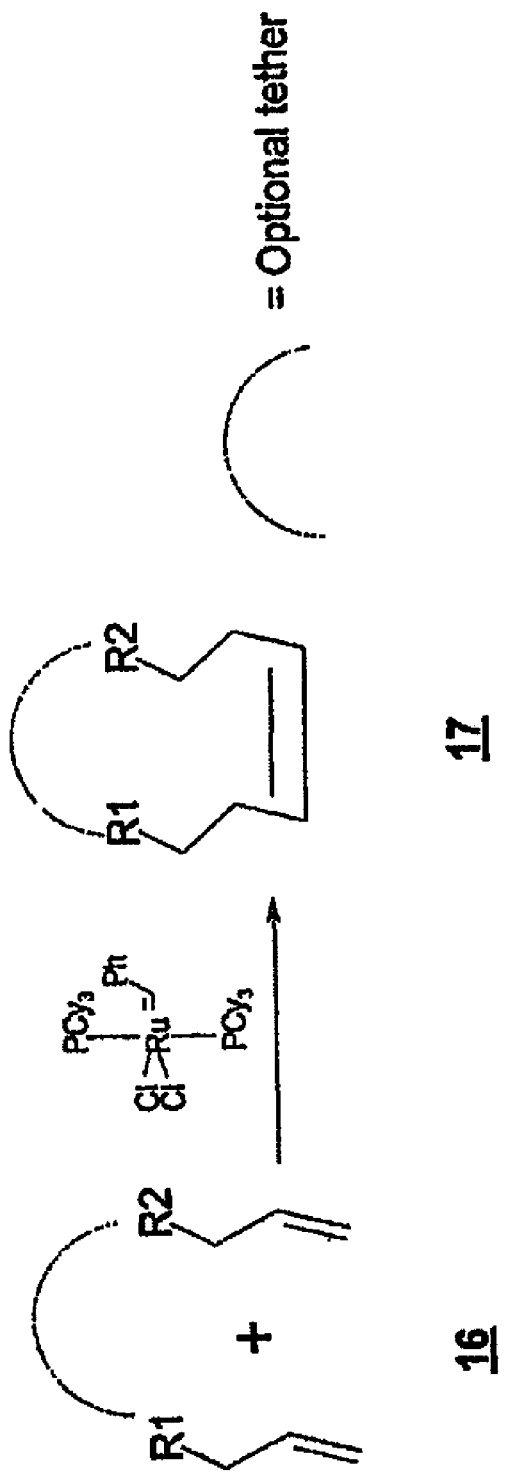
FIG. 6 is a representation showing the Grubbs reaction (referred to herein as "scheme 4").

The Grubbs reaction (Scheme 4, FIG. 6) involves the metathesis/cyclization of olefin bonds (Schuster et al., 1997. *Angew. Chem. Int. Edn Engl.,* 36:2036-2056; Miller et al., 1996. *J. Am. Chem. Soc.,* 118:9606-9614). It is readily seen that if the starting material is a diolefin 16 that the resulting product will be cyclic compound 17. The reaction has been applied to creation of cycles from olefin-functionalized peptides (Pernerstorfer et al., 1997. *Chem. Commun.,* 20:1949-50; Clark et al., 1999. *Chem. Eur. J.,* 5:782-792; Blackwell et al., 1998 *Angew. Chem. Int. Ed.,* 37:3281-3284; Ripka, A. et al., 1998. *Bioorg. Med. Chem. Lett.,* 8:357-360; Miller et al., 1996. *J. Am. Chem. Soc.,* 118:9606-9614; Clark et al., 1995. *J. Am. Chem. Soc.,* 117:12364-12365; Miller et al., 1995. *J. Am. Chem. Soc.,* 117:5855-5856). One can prepare either C-allylated amino acids or possibly N-allylated amino acids and employ them in this reaction in order to prepare carba-bridged cyclic peptides as surrogates for disulfide bond containing peptides.

One also can prepare novel compounds with olefinic groups. Functionalization of the tyrosine hydroxyl with an olefin-containing tether is one option. The lysine ε-amino group is another option with appendage of the olefin-containing unit as part of an acylating moiety, for example. If instead the lysine side chain amino group is alkylated with an olefin containing tether, it can still function as a point of attachment for a reporter as well. The use of 5-pentenoic acid as an acylating agent for the lysine, ornithine, or diaminopropionic side chain amino groups is another possibility. The length of the olefin-containing tether can also be varied in order to explore structure activity relationships.

Manipulation of Peptide Sequences

Other modifications within the scope of the invention include manipulations of peptide sequences, which can be expected to yield peptides with similar or improved biological properties. These include amino acid translocations (swapping amino acids in the sequence), use of retro-inverso peptides in place of the original sequence or a modified original sequence, peptoids and retro-inverso peptoid sequences. Structures wherein specific residues are peptoid instead of peptidic, which result in hybrid molecules, neither completely peptidic nor completely peptoid, are anticipated as well.

Linkers

Additionally, modifications within the invention include introduction of linkers or spacers between the targeting sequence of the binding moiety or binding polypeptide and the detectable label or therapeutic agent. For example, use of such linkers/spacers can improve the relevant properties of the binding peptides (e.g., increase serum stability, etc.). These linkers can include, but are not restricted to, substituted or unsubstituted alkyl chains, polyethylene glycol derivatives, amino acid spacers, sugars, or aliphatic or aromatic spacers common in the art.

For example, suitable linkers include homobifunctional and heterobifunctional cross-linking molecules. The homobifunctional molecules have at least two reactive functional groups, which are the same. The reactive functional groups on a homobifunctional molecule include, for example, aldehyde groups and active ester groups. Homobifunctional molecules having aldehyde groups include, for example, glutaraldehyde and subaraldehyde.

Homobifunctional linker molecules having at least two active ester units include esters of dicarboxylic acids and N-hydroxysuccinimide. Some examples of such N-succinimidyl esters include disuccinimidyl suberate and dithio-bis-(succinimidyl propionate), and their soluble bis-sulfonic acid and bis-sulfonate salts such as their sodium and potassium salts.

Heterobifunctional linker molecules have at least two different reactive groups. Some examples of heterobifunctional reagents containing reactive disulfide bonds include N-succinimidyl 3-(2-pyridyl-dithio)propionate (Carlsson et al., 1978. *Biochem. J.*, 173:723-737), sodium S-4-succinimidyloxycarbonyl-alpha-methylbenzylthiosulfate, and 4-succinimidyloxycarbonyl-alpha-methyl-(2-pyridyldithio)toluene. N-succinimidyl 3-(2-pyridyldithio)propionate is preferred. Some examples of heterobifunctional reagents comprising reactive groups having a double bond that reacts with a thiol group include succinimidyl 4-(N-maleimidomethyl)cyclohexahe-1-carboxylate and succinimidyl m-maleimidobenzoate. Other heterobifunctional molecules include succinimidyl 3-(maleimido)propionate, sulfosuccinimidyl 4-(p-maleimido-phenyl)butyrate, sulfosuccinimidyl 4-(N-maleimidomethyl-cyclohexane)-1-carboxylate, maleimidobenzoyl-5N-hydroxy-succinimide ester.

Furthermore, linkers that are combinations of the molecules and/or moieties described above, can also be employed to confer special advantage to the properties of the peptide. Lipid molecules with linkers may be attached to allow formulation of ultrasound bubbles, liposomes or other aggregation based constructs. Such constructs could be employed as agents for targeting and delivery of a diagnostic reporter, a therapeutic agent (e.g., a chemical "warhead" for therapy), or a combination of these.

Multimeric Constructs of cMet Binding Polypeptides

Constructs employing dimers, multimers or polymers of one or more cMet binding polypeptides of the invention are also contemplated. Indeed, there is ample literature evidence that the binding of low potency peptides or small molecules can be substantially increased by the formation of dimers and multimers. Thus, dimeric and multimeric constructs (both homogeneous and heterogeneous) are within the scope of the instant invention. The polypeptide sequences in the dimeric constructs can be attached at their N- or C-terminus or the N-epsilon nitrogen of a suitably placed lysine moiety (or another function bearing a selectively derivatizable group such as a pendant oxyamino or other nucleophilic group), or can be joined together via one or more linkers (e.g., those discussed herein) employing the appropriate attachment chemistry. This coupling chemistry can include amide, urea, thiourea, oxime, or aminoacetylamide (from chloro- or bromoacetamide derivatives, but is not so limited). For example, methods to prepare dimeric or multimeric constructs of cMet binding polypeptides of the invention include at least those discussed below.

Method A

Fully protected cMet-binding peptides can be built up on Ellman-type safety catch resin using automated or manual Fmoc peptide synthesis protocols (Backes et al., 1996. *J. Am. Chem. Soc.*, 118:3055-56). Separately, using standard methods known in the art of peptide synthesis, a di-lysine derivative can be constructed on 2-chlorotrityl resin (Fields et al., "Principles and Practice of Solid Phase Synthesis" in *Synthetic Peptides, A Users Guide*, Grant, Ed. (W.H. Freeman Co., New York, 1992), Ch. 3, pp. 77-183; Barlos et al., "Convergent Peptide Synthesis" in *Fmoc Solid Phase Peptide Synthesis*, Chan, W. C. and White, P. D., Eds. (Oxford University Press, New York, 2000), Ch. 9, pp. 215-228). Liberation of this from the 2-chlorotrityl resin without removal of the side-chain protecting groups, activation of the carboxyl group and coupling to any amine-functionalized labeling group provides a di-lysine derivative whose protected pendant nitrogen atoms can be unmasked to give two free amino groups. The prior-mentioned safety-catch resin is activated and the desired N-deprotected labeling group-functionalized di-lysine derivative is added to the activated safety-catch resin. The pendant amino groups are acylated by the carboxy-terminus of the safety-catch resin-bound peptide, which is now detached from the resin and represents an integral part of the di-lysine structure. An excess of the safety-catch resin-bound peptide can be employed to insure complete reaction of the amino groups of the di-lysine construct. Optimization of the ratio of the reacting partners in this scheme optimizes the yield. The protecting groups on the cMet-binding peptides are removed employing trifluoroacetic acid based cleavage protocols.

The synthesis of dimeric and multimeric constructs wherein two or more cMet-binding peptides are present in one construct is easily accomplished. Orthogonal protection schemes (such as an allyloxycarbonyl group on one nitrogen and an Fmoc group on the other, or employing the Fmoc group in conjunction with the iV-Dde protecting group on the other, for example) can be employed to distinguish the pendant nitrogen atoms of the di-lysine derivatives described above. Unmasking of one of the amino groups, followed by reaction of the resulting product with an activated safety-catch resin-bound cMet-binding peptide as described above, provides a di-lysine construct having a single cMet-binding peptide attached. Removal of the second protecting group unmasks the remaining nitrogen (Mellor et al., "Synthesis of Modified Peptides" in *Fmoc Solid Phase Peptide Synthesis*, Chan, W. C. and White, P. D., Eds. (Oxford University Press, New York, 2000), Chapt. 6, pp. 169-176). The resulting product can be reacted with a second safety-catch resin bearing another cMet-binding peptide to provide a fully-protected homodimeric construct, which after removal of protecting groups with trifluoroacetic acid, provides the desired material.

Method B

A cMet-binding peptide is assembled on a Rink-amide resin by automated or manual peptide coupling methods, usually employing Fmoc peptide synthesis protocols. The peptide can possess a C-terminus or N-terminus functionalized with a linker or a linker-labeling group construct that may possess an additional nucleophilic group such as the c-amino group of a lysine moiety, for example. Cleavage of the protecting groups is accomplished employing trifluoroacetic acid with appropriate modifiers depending on the nature of the peptide. The fully deprotected peptide is then reacted with a large excess of a bifunctional electrophile such as the commercially available glutaric acid bis-N-hydroxysuccinimide ester (Tyger Scientific, Inc., Princeton, N.J.). The resulting monoamidated, mono-N-hydroxysuccinimidyl ester of glutaric acid is then treated with an additional equivalent of the same peptide, or an equivalent of a different cMet-binding peptide. Purification of the resulting material by HPLC affords the desired homo-dimeric construct bearing a suitable labeling group.

Method C

A modular scheme can be employed to prepare dimeric or higher multimeric constructs bearing suitable labeling groups as defined above. In a simple illustration, fmoc-lysine(iV-Dde) Rink amide resin is treated with piperidine to remove the fmoc moiety. Then a labeling function, such as biotin, 5-carboxyfluorescein or N,N-dimethyl-Gly-Ser(O-t-Bu)-Cys(Acm)-Gly-OH is coupled to the nitrogen atom. The resin is next treated with hydrazine to remove the iV-Dde group. After thorough washing, the resin is treated with cyanuric chloride and a hindered base such as diisopropylethylamine in a suitable solvent such as DMF, NMP or dichloromethane to provide a monofunctionalized dichlorotriazine bound to the resin. Subsequent successive displacement of the remaining chlorine atoms by two equivalents of a cMet-binding peptide provides a resin-bound homo-dimeric labeling group-functionalized construct (Falorni, M. et al., 1998. *Tetrahedron Lett.*, 39:7607-7610; Johnson, C. et al., 1998. *Tetrahedron*, 54:4097-4106; Stankova, M. and Lebl, M., 1996. *Mol. Divers.*, 2:75-80). The incoming peptides can be protected or unprotected as the situation warrants. Cleavage of protecting groups is accomplished employing trifluoroacetic acid-based deprotection reagents as described above, and the desired materials are purified by high performance liquid chromatography.

It is understood that in each of these methods lysine derivatives can be serially employed to increase the multiplicity of the multimers. The use of related, more rigid molecules bearing the requisite number of masked, or orthogonally protected nitrogen atoms to act as scaffolds to vary the distance between the cMet-binding peptides, to increase the rigidity of the construct (by constraining the motion and relative positions of the cMet-binding peptides relative to each other and the reporter) is entirely within the scope of methods A-C and all other methods described herein. The references cited above are incorporated by reference herein in their entirety.

Uses for cMet Binding Polypeptides and Multimeric Peptide Constructs

The cMet binding moieties of the invention also have utility in the treatment of a variety of disease states, including those associated with cellular proliferation (e.g., hyperproliferation, e.g., cancer). The cMet binding moieties of the invention (e.g., polypeptides and multimeric polypeptide constructs) can themselves be used as therapeutics or could be used to localize one or more therapeutic agents (e.g., a chemotherapeutic, a radiotherapeutic, genetic material, etc.) to cMet-expressing cells, including sites of cellular proliferation. Any suitable method of assaying or imaging cMet also can be employed. The cMet binding moieties according to this invention are useful for detection and/or imaging of cMet in vitro or in vivo, and particularly for detection and/or imaging of sites of angiogenesis, in which HGF and cMet are intimately involved, as explained herein.

In Vitro

For detection of HGF or cMet in solution, a binding polypeptide or multimeric polypeptide construct according to the invention can be detectably labeled, e.g., fluorescently labeled, enzymatically labeled, or labeled with a radioactive or paramagnetic metal, then contacted with the solution, and thereafter formation of a complex between the binding polypeptide and the cMet target can be detected. As an example, a fluorescently labeled cMet binding peptide can be used for in vitro cMet or HGF/cMet complex detection assays, wherein the peptide is added to a solution to be tested for cMet or HGF/cMet complex under conditions allowing binding to occur. The complex between the fluorescently labeled cMet binding peptide and cMet or HGF/cMet complex target can be detected and quantified by, for example, measuring the increased fluorescence polarization arising from the cMet or HGF/cMet complex-bound peptide relative to that of the free peptide.

Alternatively, a sandwich-type "ELISA" assay can be used, wherein a cMet binding polypeptide is immobilized on a solid support such as a plastic tube or well, then the solution suspected of containing cMet or HGF/cMet complex target is contacted with the immobilized binding moiety, non-binding materials are washed away, and complexed polypeptide is detected using a suitable detection reagent, such as a monoclonal antibody recognizing cMet or HGF/cMet complex. The monoclonal antibody is detectable by conventional means known in the art, including being detectably labeled, e.g., radiolabeled, conjugated with an enzyme such as horseradish peroxidase and the like, or fluorescently labeled, etc.

For detection or purification of soluble cMet or HGF/cMet complex in or from a solution, binding polypeptides or multimeric polypeptide construct of the invention can be immobilized on a solid substrate such as a chromatographic support or other matrix material, then the immobilized binder can be loaded or contacted with the solution under conditions suitable for formation of a binding polypeptide/cMet complex. The non-binding portion of the solution can be removed and the complex can be detected, for example, using an anti-HGF or anti-HGF/cMet complex antibody, or an anti-binding polypeptide antibody, or the cMet or HGF/cMet complex target can be released from the binding moiety at appropriate elution conditions.

The biology of cellular proliferation and the roles of HGF and cMet in initiating and maintaining it have been investigated by many researchers and continues to be an active field for research and development. In furtherance of such research and development, a method of purifying bulk amounts of cMet or HGF/cMet complex in pure form is desirable, and the binding polypeptides and multimeric polypeptide constructs according to this invention are especially useful for that purpose, using the general purification methodology described above.

In Vivo

Diagnostic Imaging

A particularly preferred use for the polypeptides and multimeric polypeptide constructs according to the present invention is for creating visually readable images of cMet expressing tissue, such as, for example, neoplastic tumors, which exhibit hyperproliferation. The cMet binding polypeptides and multimeric polypeptide constructs disclosed herein can be converted to imaging reagents by conjugating the polypeptides with a label appropriate for diagnostic detection, optionally via a linker. Preferably, a peptide or multimeric polypeptide construct exhibiting much greater specificity for cMet or HGF/cMet than for other serum proteins is conjugated or linked to a label appropriate for the detection methodology to be employed. For example, the cMet or HGF/cMet complex binding polypeptide can be conjugated with or without a linker to a paramagnetic chelate suitable for Magnetic Resonance Imaging (MRI), with a radiolabel suitable for x-ray, Positron Emission Tomography (PET) or scintigraphic imaging (including a chelator for a radioactive metal), with an ultrasound contrast agent (e.g., a stabilized microbubble, a microballoon, a microsphere or what has been referred to as a gas filled "liposome") suitable for ultrasound detection, or with an optical imaging dye.

Suitable linkers can include those discussed herein, including substituted or unsubstituted alkyl chains, amino acid chains (e.g., polyglycine), polyethylene glycols, polyamides, and other linkers known in the art.

In general, the technique of using a detectably labeled cMet binding moiety is based on the premise that the label generates a signal that is detectable outside a patient's body. For example, when the detectably labeled cMet binding moiety is administered to the patient in which it is desirable to detect, e.g., hyperproliferation, the high affinity of the cMet binding moiety for cMet causes the binding moiety to bind to the site of hyperproliferation and accumulate label at the site. Sufficient time is allowed for the labeled binding moiety to localize at the site of proliferation. The signal generated by the labeled peptide is detected by a scanning device that will vary according to the type of label used, and the signal is then converted to an image of the site of proliferation.

In another embodiment, rather than directly labeling a cMet binding polypeptide or multimeric polypeptide construct with a detectable label or radiotherapeutic construct, one or more peptides or constructs of the invention can be conjugated with for example, avidin, biotin, or an antibody or antibody fragment that will bind the detectable label or radiotherapeutic. For example, one or more cMet-binding peptides can be conjugated to streptavidin (potentially generating multivalent binding) for in vivo binding to cMet-expressing cells. After the unbound targeting construct is cleared from the body, a biotinylated detectable label or radiotherapeutic construct (e.g., a chelate molecule complexed with a radioactive metal) can be infused and will rapidly concentrate at the site where the targeting construct is bound. This approach in some situations can reduce the time required after administering the detectable label until imaging can take place. It also can increase signal to noise ratio in the target site, and decrease the dose of the detectable label or radiotherapeutic construct required. This is particularly useful when a radioactive label or radiotherapeutic is used as the dose of radiation that is delivered to normal but radiation-sensitive sites in the body, such as bone-marrow, kidneys, and liver is decreased. This approach, sometimes referred to as pre-targeting or two-step, or three-step approaches was reviewed by S. F. Rosebrough in Q. J. Nuci. Med., 40:234-251 (1996), which is incorporated by reference herein.

A. Magnetic Resonance Imaging

The cMet binding moieties of the present invention can advantageously be conjugated with a paramagnetic metal chelate in order to form a contrast agent for use in MRI. Preferred paramagnetic metal ions have atomic numbers 21-29, 42, 44, or 57-83. This includes ions of the transition metal or lanthanide series which have one, and more preferably five or more, unpaired electrons and a magnetic moment of at least 1.7 Bohr magneton. Preferred paramagnetic metals include, but are not limited to, chromium (III), manganese (II), manganese (III), iron (II), iron (III), cobalt (II), nickel (II), copper (II), praseodymium (III), neodymium (III), samarium (III), gadolinium (III), terbium (III), dysprosium (III), holmium (III), erbium (III), europium (III) and ytterbium (III), chromium (III), iron (III), and gadolinium (III). The trivalent cation, $Gd^{3+}$, is particularly preferred for MRI contrast agents, due to its high relaxivity and low toxicity, with the further advantage that it exists in only one biologically accessible oxidation state, which minimizes undesired metabolysis of the metal by a patient. Another useful metal is $Cr^{3+}$, which is relatively inexpensive. Gd(III) chelates have been used for clinical and radiologic MR applications since 1988, and approximately 30% of MR exams currently employ a gadolinium-based contrast agent.

The practitioner will select a metal according to dose required to detect cellular proliferation and considering other factors such as toxicity of the metal to the subject. See, Tweedle et al., Magnetic Resonance Imaging (2nd ed.), vol. 1, Partain et al., Eds. (W.B. Saunders Co. 1988), pp. 796-797. Generally, the desired dose for an individual metal will be proportional to its relaxivity, modified by the biodistribution, pharmacokinetics and metabolism of the metal.

The paramagnetic metal chelator is a molecule having one or more polar groups that act as a ligand for, and complex with, a paramagnetic metal. Suitable chelators are known in the art and include acids with methylene phosphonic acid groups, methylene carbohydroxamine acid groups, carboxyethylidene groups, or carboxymethylene groups. Examples of chelators include, but are not limited to, diethylenetriaminepentaacetic acid (DTPA), 1,4,7,10-tetraazacyclo-tetradecane-1,4,7,10-tetraacetic acid (DOTA), 1-substituted 1,4,7,-tricarboxymethyl-1,4,7,10-teraazacyclododecane (DO3A), ethylenediaminetetraacetic acid (EDTA), and 1,4,8,11-tetra-azacyclotetradecane-1,4,8,11-tetraacetic acid (TETA). Additional chelating ligands are ethylene bis-(2-hydroxy-phenylglycine) (EHPG), and derivatives thereof, including 5-Cl-EHPG, 5-Br-EHPG, 5-Me-EHPG, 5-t-Bu-EHPG, and 5-sec-Bu-EHPG; benzodiethylenetriamine pentaacetic acid (benzo-DTPA) and derivatives thereof, including dibenzo-DTPA, phenyl-DTPA, diphenyl-DTPA, benzyl-DTPA, and dibenzyl DTPA; bis-2 (hydroxybenzyl)-ethylene-diaminediacetic acid (HEED) and derivatives thereof; the class of macrocyclic compounds which contain at least 3 carbon atoms, more preferably at least 6, and at least two heteroatoms (O and/or N), which macrocyclic compounds can consist of one ring, or two or three rings joined together at the hetero ring elements, e.g., benzo-DOTA, dibenzo-DOTA, and benzo-NOTA, where NOTA is 1,4,7-triazacyclononane N,N',N"-triacetic acid, benzo-TETA, benzo-DOTMA, where DOTMA is 1,4,7,10-tetraazacyclotetradecane-1,4,7,10-tetra(methyl tetraacetic acid), and benzo-TETMA, where TETMA is 1,4, 8,11-tetraazacyclotetradecane-1,4,8,11-(methyl tetraacetic acid); derivatives of 1,3-propylene-diaminetetraacetic acid (PDTA) and triethylenetetraaminehexaacetic acid (TTHA); derivatives of 1,5,10?N,N',N"-tris(2,3-dihydroxybenzoyl)-tricatecholate (LICAM); and 1,3,5-N,N',N"-tris(2,3-dihydroxybenzoyl) aminomethylbenzene (MECAM). A preferred chelator for use in the present invention is DTPA, and the use of DO3A is particularly preferred. Examples of representative chelators and chelating groups contemplated by the present invention are described in WO 98/18496, WO 86/06605, WO 91/03200, WO 95/28179, WO 96/23526, WO 97/36619, PCT/US98/01473, PCT/US98/20182, and U.S. Pat. No. 4,899,755, U.S. Pat. No. 5,474,756, U.S. Pat. No. 5,846,519 and U.S. Pat. No. 6,143,274, all of which are hereby incorporated by reference.

In accordance with the present invention, the chelator of the MRI contrast agent is coupled to the cMet binding polypeptide. The positioning of the chelate should be selected so as not to interfere with the binding affinity or specificity of the cMet binding polypeptide. Preferably, the chelate will be appended either to the N-terminus or the C-terminus, however the chelate also can be attached anywhere within the sequence. In preferred embodiments, a chelator having a free central carboxylic acid group (e.g., DTPA-Asp(β-COOH)—) OtBu) makes it easy to attach at the N-terminus of the peptide by formation of an amide bond. The chelate also can be attached at the C-terminus with the aid of a linker. Alternatively, isothiocyanate conjugation chemistry can be employed as a way of linking the appropriate isothiocyanate group bearing DTPA to a free amino group anywhere within the peptide sequence.

In general, the cMet binding moiety can be bound directly or covalently to the metal chelator (or other detectable label), or it can be coupled or conjugated to the metal chelator using a linker, which can be, without limitation, amide, urea, acetal, ketal, double ester, carbonyl, carbamate, thiourea, sulfone, thioester, ester, ether, disulfide, lactone, imine, phosphoryl, or phosphodiester linkages; substituted or unsubstituted saturated or unsaturated alkyl chains; linear, branched, or cyclic amino acid chains of a single amino acid or different amino acids (e.g., extensions of the N- or C-terminus of the cMet binding moiety); derivatized or underivatized polyethylene glycols (PEGs), polyoxyethylene, or polyvinylpyridine chains; substituted or unsubstituted polyamide chains; derivatized or underivatized polyamine, polyester, polyethylenimine, polyacrylate, poly(vinyl alcohol), polyglycerol, or oligosaccharide (e.g., dextran) chains; alternating block copolymers; malonic, succinic, glutaric, adipic and pimelic acids; caproic acid; simple diamines and dialcohols; any of the other linkers disclosed herein; or any other simple polymeric linkers known in the art (see, for example, WO 98/18497 and WO 98/18496). Preferably the molecular weight of the linker can be tightly controlled. The molecular weights can range in size from less than 100 to greater than 1000. Preferably the molecular weight of the linker is less than 100. In addition, it can be desirable to utilize a linker that is biodegradable in vivo to provide efficient routes of excretion for the imaging reagents of the present invention. Depending on their location within the linker, such biodegradable functionalities can include ester, double ester, amide, phosphoester, ether, acetal, and ketal functionalities.

In general, known methods can be used to couple the metal chelate and the cMet binding moiety using such linkers (WO 95/28967, WO 98/18496, WO 98/18497 and discussion therein). The cMet binding moiety can be linked through an N- or C-terminus via an amide bond, for example, to a metal coordinating backbone nitrogen of a metal chelate or to an acetate arm of the metal chelate itself. The present invention contemplates linking of the chelate on any position, provided the metal chelate retains the ability to bind the metal tightly in order to minimize toxicity. Similarly, the cMet binding moiety can be modified or elongated in order to generate a locus for attachment to a metal chelate, provided such modification or elongation does not eliminate its ability to bind cMet.

MRI contrast reagents prepared according to the disclosures herein can be used in the same manner as conventional MRI contrast reagents. When imaging a site of hyperproliferation, for example, certain MR techniques and pulse sequences can be preferred to enhance the contrast of the site to the background blood and tissues. These techniques include (but are not limited to), for example, black blood angiography sequences that seek to make blood dark, such as fast spin echo sequences (Alexander, A. et al., 1998. *Magn. Reson. Med.,* 40: 298-310) and flow-spoiled gradient echo sequences (Edelman, R. et al., 1990. *Radiology,* 177: 45-50). These methods also include flow independent techniques that enhance the difference in contrast, such as inversion-recovery prepared or saturation-recovery prepared sequences that will increase the contrast between angiogenic tumor and background tissues. Finally, magnetization transfer preparations also can improve contrast with these agents (Goodrich, K. et al., 1996. *Invest. Radiol.,* 31: 323-32).

The labeled reagent is administered to the patient in the form of an injectable composition. The method of administering the MRI contrast agent is preferably parenterally, meaning intravenously, intraarterially, intrathecally, interstitially, or intracavitarilly. For imaging active angiogenesis, intravenous or intraarterial administration is preferred. For MRI, it is contemplated that the subject will receive a dosage of contrast agent sufficient to enhance the MR signal at the site of angiogenesis at least 10%. After injection with the cMet binding moiety-containing MRI reagent, the patient is scanned in the MRI machine to determine the location of any sites of hyperproliferation. In therapeutic settings, upon identification of a site of hyperproliferation (e.g., tumor), a tumoricidal agent or anti-hyperproliferative agent (e.g., inhibitors of HGF) can be immediately administered, if necessary, and the patient can be subsequently scanned to visualize tumor regression or arrest of angiogenesis.

B. Ultrasound Imaging

When ultrasound is transmitted through a substance, the acoustic properties of the substance will depend upon the velocity of the transmissions and the density of the substance. Changes in the acoustic properties will be most prominent at the interface of different substances (solids, liquids, gases). Ultrasound contrast agents are intense sound wave reflectors because of the acoustic differences between the agent and the surrounding tissue. Gas containing or gas generating ultrasound contrast agents are particularly useful because of the acoustic difference between liquid (e.g., blood) and the gas-containing or gas generating ultrasound contrast agent. Because of their size, ultrasound contrast agents comprising microbubbles, microballoons, and the like can remain for a longer time in the blood stream after injection than other detectable moieties; a targeted cMet-specific ultrasound agent therefore could demonstrate superior imaging of sites of hyperproliferation (e.g., cancer) and angiogenesis.

In this aspect of the invention, the cMet binding moiety can be linked to a material that is useful for ultrasound imaging. For example, one or more cMet binding polypeptide or multimeric polypeptide constructs can be linked to materials employed to form vesicles (e.g., microbubbles, microballoons, microspheres, etc.), or emulsions containing a liquid or gas, which functions as the detectable label (e.g., an echogenic gas or material capable of generating an echogenic gas). Materials for the preparation of such vesicles include surfactants, lipids, sphingolipids, oligolipids, phospholipids, proteins, polypeptides, carbohydrates, and synthetic or natural polymeric materials (WO 98/53857, WO 98/18498, WO 98/18495, WO 98/18497, WO 98/18496, and WO 98/18501, incorporated herein by reference in their entirety).

For contrast agents comprising suspensions of stabilized microbubbles (a preferred embodiment), phospholipids, and particularly saturated phospholipids are preferred. Examples of suitable phospholipids include esters of glycerol with one or two (the same or different) fatty acids molecules and with phosphoric acid, wherein the phosphoric acid residue is in turn bonded to a hydrophilic group, such as choline, serine, inositol, glycerol, ethanolamine, and the like groups. Fatty acids present in the phospholipids are in general long chain aliphatic acids, typically containing from 12 to 24 carbon atoms, preferably from 14 to 22, that can be saturated or can contain one or more unsaturations. Examples of suitable fatty acids are lauric acid, myristic acid, palmitic acid, stearic acid, arachidonic acid, behenic acid, oleic acid, linoleic acid, and linolenic acid. Mono esters of phospholipid are also known in the art as the "lyso" forms of the phospholipids. Further examples of phospholipid are phosphatidic acids, i.e., the diesters of glycerol-phosphoric acid with fatty acids, sphingomyelins, i.e., those phosphatidylcholine analogs where the residue of glycerol diester with fatty acids is replaced by a ceramide chain, cardiolipins, i.e., the esters of 1,3-diphosphatidylglycerol with a fatty acid, gangliosides, cerebrosides, etc.

As used herein, the term "phospholipids" includes naturally occurring, semisynthetic or synthetically prepared products that can be employed either singularly or as mixtures.

Examples of naturally occurring phospholipids are natural lecithins (phosphatidylcholine (PC) derivatives) such as, typically, soya bean or egg yolk lecithins. Examples of semisynthetic phospholipids are the partially or fully hydrogenated derivatives of the naturally occurring lecithins.

Figure 7A:
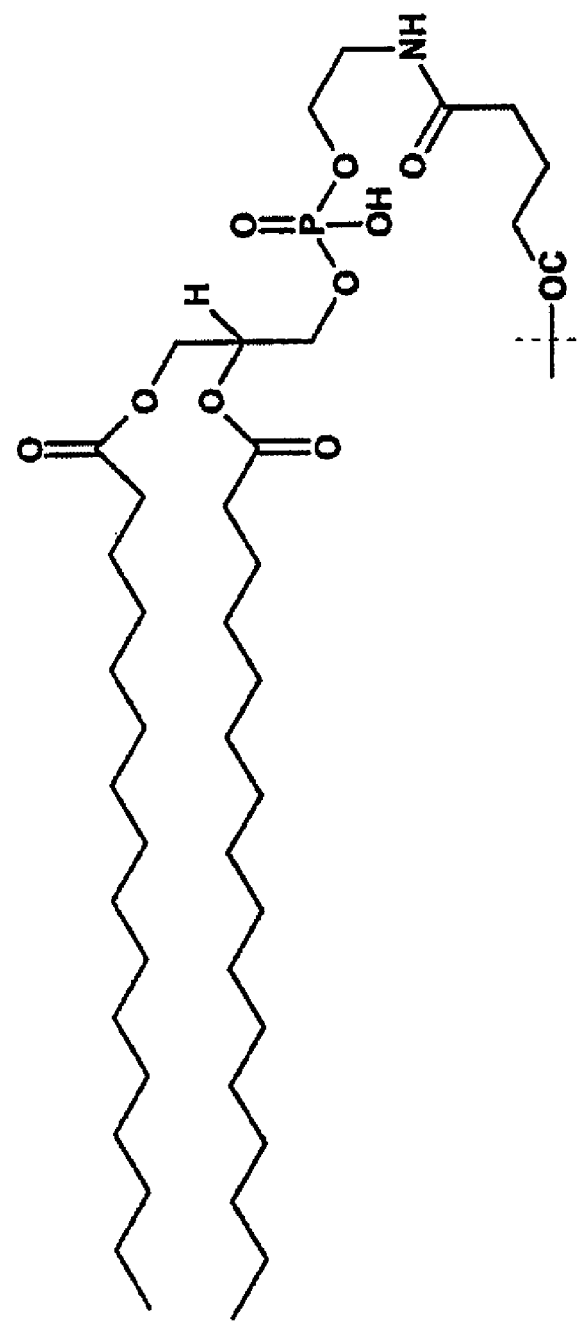
FIGS. 7A and 7B are chemical structures of phospholipid moieties.
Figure 7B:
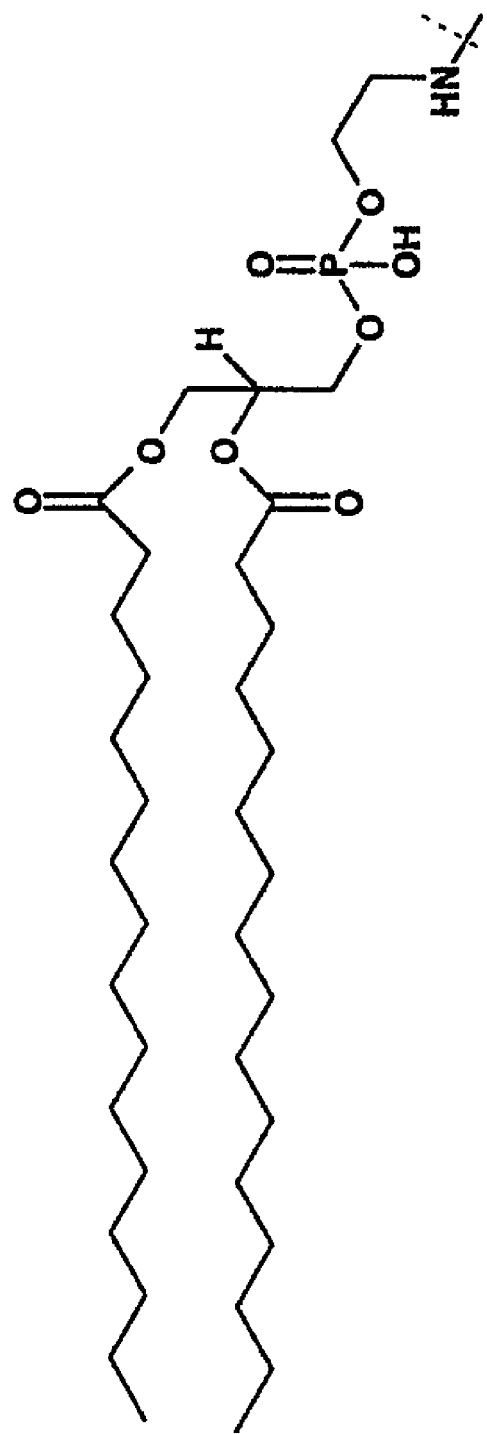

Examples of synthetic phospholipids are, e.g., dilauryloyl-phosphatidylcholine ("DLPC"), dimyristoylphosphatidylcholine ("DMPC"), dipalmitoyl-phosphatidylcholine ("DPPC"), diarachidoylphosphatidylcholine ("DAPC"), distearoyl-phosphatidylcholine ("DSPC"), 1-myristoyl-2-palmitoylphosphatidylcholine ("MPPC"), 1-pahnitoyl-2-myristoylphosphatidylcholine ("PMPC"), 1-palmitoyl-2-stearoylphosphatid-ylcholine ("PSPC"), 1-stearoyl-2-palmitoyl-phosphatidylcholine ("SPPC"), dioleoylphosphatidylycholine ("DOPC"), 1,2 Distearoyl-sn-glycero-3-Ethylphosphocholine (Ethyl-DSPC), dilauryloyl-phosphatidylglycerol ("DLPG") and its alkali metal salts, diarachidoylphosphatidylglycerol ("DAPG") and its alkali metal salts, dimyristoylphosphatidylglycerol ("DMPG") and its alkali metal salts, dipalmitoyl-phosphatidylglycerol ("DPPG") and its alkali metal salts, distearolyphosphatidylg-lycerol ("DSPG") and its alkali metal salts, dioleoylphosphatidylglycerol ("DOPG") and its alkali metal salts, dimyristoyl phosphatidic acid ("DMPA") and its alkali metal salts, dipalmitoyl phosphatidic acid ("DPPA") and its alkali metal salts, distearoyl phosphatidic acid ("DSPA"), diarachidoyl phosphatidic acid ("DAPA") and its alkali metal salts, dimyristoyl phosphatidyl-ethanolamine ("DMPE"), dipalmitoyl phosphatidylethanolamine ("DPPE"), distearoyl phosphatidyl-ethanolamine ("DSPE"), dimyristoyl phosphatidylserine ("DMPS"), diarachidoyl phosphatidylserine ("DAPS"), dipalmitoyl phosphatidylserine ("DPPS"), distearoylphosphatidylserine ("DSPS"), dioleoylphosphatidylserine ("DOPS"), dipalmitoyl sphingomyelin ("DPSP"), and distearoyl sphingomyelin ("DSSP"). In a preferred embodiment, at least one of the phospholipid moieties has the structure shown in FIG. 7A or 7B, and described in U.S. Pat. No. 5,686,060, which is herein incorporated by reference.

Other preferred phospholipids include dipalmitoylphosphatidylcholine, dipalmitoylphosphatidic acid and dipalmitoylphosphatidylserine. The compositions also can contain PEG-4000 and/or palmitic acid. Any of the gases disclosed herein or known to the skilled artisan can be employed; however, inert gases, such as SF6 or fluorocarbons like CF4, C3F8 and C4F10, are preferred.

The preferred gas-filled microbubbles of the invention can be prepared by means known in the art, such as, for example, by a method described in any one of the following patents: EP 554213, U.S. Pat. No. 5,413,774, U.S. Pat. No. 5,578,292, EP 744962, EP 682530, U.S. Pat. No. 5,556,610, U.S. Pat. No. 5,846,518, U.S. Pat. No. 6,183,725, EP 474833, U.S. Pat. No. 5,271,928, U.S. Pat. No. 5,380,519, U.S. Pat. No. 5,531,980, U.S. Pat. No. 5,567,414, U.S. Pat. No. 5,658,551, U.S. Pat. No. 5,643,553, U.S. Pat. No. 5,911,972, U.S. Pat. No. 6,110,443, U.S. Pat. No. 6,136,293, EP 619743, U.S. Pat. No. 5,445,813, U.S. Pat. No. 5,597,549, U.S. Pat. No. 5,686,060, U.S. Pat. No. 6,187,288, and U.S. Pat. No. 5,908,610, which are incorporated by reference herein in their entirety.

The preferred microbubble suspensions of the present invention can be prepared from phospholipids using known processes such as a freeze-drying or spray-drying solutions of the crude phospholipids in a suitable solvent or using the processes set forth in EP 554213; U.S. Pat. No. 5,413,774; U.S. Pat. No. 5,578,292; EP 744962; EP 682530; U.S. Pat. No. 5,556,610; U.S. Pat. No. 5,846,518; U.S. Pat. No. 6,183,725; EP 474833; U.S. Pat. No. 5,271,928; U.S. Pat. No. 5,380,519; U.S. Pat. No. 5,531,980; U.S. Pat. No. 5,567,414; U.S. Pat. No. 5,658,551; U.S. Pat. No. 5,643,553; U.S. Pat. No. 5,911,972; U.S. Pat. No. 6,110,443; U.S. Pat. No. 6,136,293; EP 619743; U.S. Pat. No. 5,445,813; U.S. Pat. No. 5,597,549; U.S. Pat. No. 5,686,060; U.S. Pat. No. 6,187,288; and U.S. Pat. No. 5,908,610, which are incorporated by reference herein in their entirety. Most preferably, the phospholipids are dissolved in an organic solvent and the solution is dried without going through a liposome formation stage. This can be done by dissolving the phospholipids in a suitable organic solvent together with a hydrophilic stabilizer substance or a compound soluble both in the organic solvent and water and freeze-drying or spray-drying the solution. In this embodiment the criteria used for selection of the hydrophilic stabilizer is its solubility in the organic solvent of choice. Examples of hydrophilic stabilizer compounds soluble in water and the organic solvent are, e.g., a polymer, like polyvinyl pyrrolidone (PVP), polyvinyl alcohol (PVA), polyethylene glycol (PEG), etc., malic acid, glycolic acid, maltol, and the like. Such hydrophilic compounds also aid in homogenizing the microbubbles size distribution and enhance stability under storage. Any suitable organic solvent can be used as long as its boiling point is sufficiently low and its melting point is sufficiently high to facilitate subsequent drying. Typical organic solvents include, for example, dioxane, cyclohexanol, tertiary butanol, tetrachlorodifluoro ethylene ($C_2Cl_4F_2$) or 2-methyl-2-butanol. 2-methyl-2-butanol and $C_2Cl_4F_2$ are preferred.

Prior to formation of the suspension of microbubbles by dispersion in an aqueous carrier, the freeze dried or spray dried phospholipid powders are contacted with air or another gas. When contacted with the aqueous carrier the powdered phospholipids whose structure has been disrupted will form lamellarized or laminarized segments that will stabilize the microbubbles of the gas dispersed therein. This method permits production of suspensions of microbubbles, which are stable even when stored for prolonged periods, and are obtained by simple dissolution of the dried laminarized phospholipids, which have been stored under a desired gas, without shaking or any violent agitation.

Unless it contains a hyperpolarized gas, known to require special storage conditions, the lyophilized or freeze-dried residue can be stored and transported without need of temperature control of its environment and in particular it can be supplied to hospitals and physicians for on site formulation into a ready-to-use administrable suspension without requiring such users to have special storage facilities.

Preferably in such a case it can be supplied in the form of a two component kit. The two component kit can include two separate containers or a dual-chamber container. In the former case preferably the container is a conventional septum-sealed vial, wherein the vial containing the lyophilized residue of step b) is sealed with a septum through which the carrier liquid can be injected using an optionally pre-filled syringe. In such a case the syringe used as the container of the second component is also used then for injecting the contrast agent. In the latter case, preferably the dual-chamber container is a dual-chamber syringe and once the lyophilizate/freeze-dried residue has been reconstituted and then suitably mixed or gently shaken, the container can be used directly for injecting the contrast agent. In both cases means for directing or permitting application of sufficient bubble forming energy into the contents of the container are provided. However, as noted above, in the stabilized contrast agents the size of the gas microbubbles is substantially independent of the amount of agitation energy applied to the reconstituted dried product. Accordingly no more than gentle hand shaking is generally required to give reproducible products with consistent microbubble size.

It can be appreciated by one ordinary skilled in the art that other two-chamber reconstitution systems capable of combining the dried powder with the aqueous solution in a sterile manner are also within the scope of the present invention. In such systems, it is particularly advantageous if the aqueous phase can be interposed between the water-insoluble gas and the environment, to increase shelf life of the product. Where a material necessary for forming the contrast agent is not already present in the container (e.g., a cMet binding moiety of the invention to be linked to the phospholipid during reconstitution), it can be packaged with the other components of the kit, preferably in a form or container adapted to facilitate ready combination with the other components of the kit.

No specific containers, vial or connection systems are required; the present invention can use conventional containers, vials and adapters. The only requirement is a good seal between the stopper and the container. The quality of the seal, therefore, becomes a matter of primary concern; any degradation of seal integrity could allow undesirables substances to enter the vial. In addition to assuring sterility, vacuum retention is essential for products stoppered at ambient or reduced pressures to assure safe and proper reconstitution. As to the stopper, it may be a compound or multicomponent formulation based on an elastomer, such as poly(isobutylene) or butyl rubber.

Alternatively, microbubbles can be prepared by suspending a gas in an aqueous solution at high agitation speed, as disclosed, e.g., in WO 97/29783. A further process for preparing microbubbles is disclosed in co-pending European patent application no. 03002373, herein incorporated by reference, which comprises preparing an emulsion of an organic solvent in an aqueous medium in the presence of a phospholipid and subsequently lyophilizing said emulsion, after optional washing and/or filtration steps.

Additives known to those of ordinary skill in the art can be included in the suspensions of stabilized microbubbles. For instance, non-film forming surfactants, including polyoxypropylene glycol and polyoxyethylene glycol and similar compounds, as well as various copolymers thereof; fatty acids such as myristic acid, palmitic acid, stearic acid, arachidonic acid or their derivatives, ergosterol, phytosterol, sitosterol, lanosterol, tocopherol, propyl gallate, ascorbyl palmitate and butylated hydroxytoluene may be added. The amount of these non-film forming surfactants is usually up to 50% by weight of the total amount of surfactants but preferably between 0 and 30%.

In ultrasound applications the contrast agents formed by phospholipid stabilized microbubbles can, for example, be administered in doses such that the amount of phospholipid injected is in the range 0.1 to 200 µg/kg body weight, preferably from about 0.1 to 30 µg/kg.

Other gas containing suspensions include those disclosed in, for example, U.S. Pat. No. 5,798,091, WO 97/29783, also EP 881 915, incorporated herein by reference in their entirety. These agents can be prepared as described in U.S. Pat. No. 5,798,091 or WO97/29783.

Another preferred ultrasound contrast agent comprises microballoons. The term "microballoon" refers to gas filled bodies with a material boundary or envelope. More on microballoon formulations and methods of preparation can be found in EP 324 938 (U.S. Pat. No. 4,844,882); U.S. Pat. No. 5,711,933; U.S. Pat. No. 5,840,275; U.S. Pat. No. 5,863,520; U.S. Pat. No. 6,123,922; U.S. Pat. No. 6,200,548; U.S. Pat. No. 4,900,540; U.S. Pat. No. 5,123,414; U.S. Pat. No. 5,230,882; U.S. Pat. No. 5,469,854; U.S. Pat. No. 5,585,112; U.S. Pat. No. 4,718,433; U.S. Pat. No. 4,774,958; WO 95/01187; U.S. Pat. No. 5,529,766; U.S. Pat. No. 5,536,490; and U.S. Pat. No. 5,990,263, the contents of which are incorporated herein by reference.

The preferred microballoons have an envelope including a biodegradable physiologically compatible polymer or, a biodegradable solid lipid. The polymers useful for the preparation of the microballoons of the present invention can be selected from the biodegradable physiologically compatible polymers, such as any of those described in any of the following patents: EP 458745; U.S. Pat. No. 5,711,933; U.S. Pat. No. 5,840,275; EP 554213; U.S. Pat. No. 5,413,774; and U.S. Pat. No. 5,578,292, the entire contents of which are incorporated herein by reference. In particular, the polymer can be selected from biodegradable physiologically compatible polymers, such as polysaccharides of low water solubility, polylactides and polyglycolides and their copolymers, copolymers of lactides and lactones such as e-caprolactone, γ-valerolactone and polypeptides. Other suitable polymers include poly(ortho)esters (see for instance U.S. Pat. No. 4,093,709; U.S. Pat. No. 4,131,648; U.S. Pat. No. 4,138,344; U.S. Pat. No. 4,180,646); polylactic and polyglycolic acid and their copolymers, for instance DEXON (Heller, J., 1980. *Biomaterials,* 1:51-57); poly(DL-lactide-co-e-caprolactone), poly(DL-lactide-co-γ-valerolactone), poly(DL-lactide-co-γ-butyrolactone), polyalkylcyanoacrylates; polyamides, polyhydroxybutyrate; polydioxanone; poly-β-aminoketones (Polymer, 23:1693 (1982)); polyphosphazenes (Allcock, H., 1976. *Science,* 193:1214-1219); and polyanhydrides. The microballoons of the present invention can also be prepared according to the methods of WO 96/15815, incorporated herein by reference, where the microballoons are made from a biodegradable membrane comprising biodegradable lipids, preferably selected from mono-di-, tri-glycerides, fatty acids, sterols, waxes and mixtures thereof. Preferred lipids are di- or tri-glycerides, e.g. di- or tri-myristin, -palmityn or -stearin, in particular tripalmitin or tristearin.

The microballoons can employ any of the gases disclosed herein of known to the skilled artisan; however, inert gases such as fluorinated gases are preferred. The microballoons can be suspended in a pharmaceutically acceptable liquid carrier with optional additives known to those of ordinary skill in the art and stabilizers.

Microballoons-containing contrast agents are typically administered in doses such that the amount of wall-forming polymer or lipid is from about 10 µg/kg to about 20 µg/kg of body weight.

Other gas-containing contrast agent formulations include microparticles (especially aggregates of microparticles) having gas contained therein or otherwise associated therewith (for example being adsorbed on the surface thereof and/or contained within voids, cavities or pores therein). Methods for the preparation of these agents are as described in EP 0122624; EP 0123235; EP 0365467; U.S. Pat. No. 5,558,857; U.S. Pat. No. 5,607,661; U.S. Pat. No. 5,637,289; U.S. Pat. No. 5,558,856; U.S. Pat. No. 5,137,928; WO 95/21631 or WO 93/13809, incorporated herein by reference in their entirety.

Any of these ultrasound compositions also should be, as far as possible, isotonic with blood. Hence, before injection, small amounts of isotonic agents can be added to any of above ultrasound contrast agent suspensions. The isotonic agents are physiological solutions commonly used in medicine and they comprise aqueous saline solution (0.9% NaCl), 2.6% glycerol solution, 5% dextrose solution, etc. Additionally, the ultrasound compositions can include standard pharmaceutically acceptable additives, including, for example, emulsifying agents, viscosity modifiers, cryoprotectants, lyoprotectants, bulking agents etc.

Any biocompatible gas can be used in the ultrasound contrast agents useful in the invention. The term "gas" as used herein includes any substances (including mixtures) substantially in gaseous form at the normal human body temperature. The gas may thus include, for example, air, nitrogen, oxygen, $CO_2$, argon, xenon or krypton, fluorinated gases (including for example, perfluorocarbons, $SF_6$, $SeF_6$) a low molecular weight hydrocarbon (e.g., containing from 1 to 7 carbon atoms), for example, an alkane such as methane, ethane, a propane, a butane or a pentane, a cycloalkane such as cyclopropane, cyclobutane or cyclopentene, an alkene such as ethylene, propene, propadiene or a butene, or an alkyne such as acetylene or propyne and/or mixtures thereof. However, fluorinated gases are preferred. Fluorinated gases include materials which contain at least one fluorine atom such as $SF_6$, freons (organic compounds containing one or more carbon atoms and fluorine, i.e., $CF_4$, $C_2F_6$, $C_3F_8$, $C_4F_8$, $C_4F_{10}$, $CBrF_3$, $CCl_2F_2$, $C_2ClF_5$, and $CBrClF_2$) and perfluorocarbons. The term perfluorocarbon refers to compounds containing only carbon and fluorine atoms and includes, in particular, saturated, unsaturated, and cyclic perfluorocarbons. The saturated perfluorocarbons, which are usually preferred, have the formula $C_nF_{n+2}$, where n is from 1 to 12, preferably from 2 to 10, most preferably from 3 to 8 and even more preferably from 3 to 6. Suitable perfluorocarbons include, for example, $CF_4$, $C_2F_6$, $C_3F_8C_4F_8$, $C_4F_{10}$, $C_5F_{12}$, $C_6F_{12}$, $C_7F_{14}$, $C_8F_{18}$, and $C_9F_{20}$. Most preferably the gas or gas mixture comprises SF6 or a perfluorocarbon selected from the group consisting of $C_3F_8C_4F_8$, $C_4F_{10}$, $C_5F_{12}$, $C_6F_{12}$, $C_7F_{14}$, $C_8F_{18}$, with $C_4F_{10}$ being particularly preferred. See also WO 97/29783, WO 98/53857, WO 98/18498, WO 98/18495, WO 98/18496, WO 98/18497, WO 98/18501, WO 98/05364, WO 98/17324.

In certain circumstances it can be desirable to include a precursor to a gaseous substance (e.g., a material that is capable of being converted to a gas in vivo, often referred to as a "gas precursor"). Preferably the gas precursor and the gas it produces are physiologically acceptable. The gas precursor can be pH-activated, photo-activated, temperature activated, etc. For example, certain perfluorocarbons can be used as temperature activated gas precursors. These perfluorocarbons, such as perfluoropentane, have a liquid/gas phase transition temperature above room temperature (or the temperature at which the agents are produced and/or stored) but below body temperature; thus they undergo a phase shift and are converted to a gas within the human body.

The gas can comprise a mixture of gases. The following combinations are particularly preferred gas mixtures: a mixture of gases (A) and (B) in which, at least one of the gases (B), present in an amount of between 0.5-41% by vol., has a molecular weight greater than 80 daltons and is a fluorinated gas and (A) is selected from the group consisting of air, oxygen, nitrogen, carbon dioxide and mixtures thereof, the balance of the mixture being gas A.

Since ultrasound vesicles can be larger than the other detectable labels described herein, they can be linked or conjugated to a plurality of cMet binding polypeptides or multimeric polypeptide constructs in order to increase the targeting efficiency of the agent. Attachment to the ultrasound contrast agents described above (or known to those skilled in the art) can be via direct covalent bond between the cMet binding polypeptide and the material used to make the vesicle or via a linker, as described previously. For example, see WO 98/53857 generally for a description of the attachment of a peptide to a bifunctional PEG linker, which is then reacted with a liposome composition (Lanza, G. et al., 1997. Ultrasound Med. Biol., 23:863-870). The structure of these compounds typically comprises:

a) A hydrophobic portion, compatible with the material forming the envelope of the microbubble or of the microballoon, in order to allow an effective incorporation of the compound in the envelope of the vesicle; said portion is typically a lipid moiety (e.g., dipalmitin, distearoil);

b) A spacer (typically PEGs of different molecular weights), which can be optional in some cases (microbubbles may, for instance, prove difficult to freeze dry if the spacer is too long) or preferred in some others (e.g., peptides can be less active when conjugated to a microballoon with a short spacer);

c) A reactive group capable of reacting with a corresponding reactive moiety on the peptide to be conjugated (e.g., maleimido with the —SH group of cysteine).

A number of methods can be used to prepare suspensions of microbubbles conjugated to cMet binding polypeptides. For example, one can prepare maleimide-derivatized microbubbles by incorporating 5% (w/w) of N-MPB-PE (1,2-dipalmitoyl-sn-glycero-3-phosphoethanolamine-4-(p-maleimido-phenyl butyramide), (Avanti Polar-Lipids, Inc., Alabaster, Ala.) in the phospholipid formulation. Then, solutions of mercaptoacetylated cMet-binding peptides (10 mg/mL in DMF), which have been incubated in deacetylation solution (50 mM sodium phosphate, 25 mM EDTA, 0.5 M hydroxylamine.HCl, pH 7.5) are added to the maleimide-activated microbubble suspension. After incubation in the dark, under gentle agitation, the peptide conjugated microbubbles can be purified by centrifugation.

Alternatively, cMet-binding polypeptide conjugated microbubbles can be prepared using biotin/avidin. For example, avidin-conjugated microbubbles can be prepared using a maleimide-activated phospholipid microbubble suspension, prepared as described above, which is added to mercaptoacetylated-avidin (which has been incubated with deacetylation solution). Biotinylated cMet-binding peptides (prepared as described herein) are then added to the suspension of avidin-conjugated microbubbles, yielding a suspension of microbubbles conjugated to cMet-binding peptides.

Ultrasound imaging techniques, which can be used in accordance with the present invention, include known techniques, such as color Doppler, power Doppler, Doppler amplitude, stimulated acoustic imaging, and two- or three-dimensional imaging techniques. Imaging may be done in harmonic (resonant frequency) or fundamental modes, with the second harmonic preferred.

C. Optical Imaging, Sonoluminescence or Photoacoustic Imaging

In accordance with the present invention, a number of optical parameters can be employed to determine the location of cMet or HGF/cMet complex with in vivo light imaging after injection of the subject with an optically-labeled cMet binding polypeptides. Optical parameters to be detected in the preparation of an image may include transmitted radiation, absorption, fluorescent or phosphorescent emission, light reflection, changes in absorbance amplitude or maxima, and elastically scattered radiation. For example, biological tissue is relatively translucent to light in the near infrared (NIR) wavelength range of 650-1000 nm. NIR radiation can penetrate tissue up to several centimeters, permitting the use of the cMet binding polypeptides or multimeric polypeptide constructs of the present invention for optical imaging of cMet or HGF/cMet complex in vivo.

The cMet binding polypeptides or multimeric polypeptide constructs can be conjugated with photolabels, such as, for example, optical dyes, including organic chromophores or fluorophores, having extensive delocalized ring systems and having absorption or emission maxima in the range of 400-1500 nm. The cMet binding polypeptide or multimeric polypeptide construct can alternatively be derivatized with a bioluminescent molecule. The preferred range of absorption maxima for photolabels is between 600 and 1000 nm to minimize interference with the signal from hemoglobin. Preferably, photoabsorption labels have large molar absorptivities, e.g., greater than $10^5$ cm$^{-1}$M$^{-1}$, while fluorescent optical dyes will have high quantum yields. Examples of optical dyes include, but are not limited to those described in WO 98/18497, WO 98/18496, WO 98/18495, WO 98/18498, WO 98/53857, WO 96/17628, WO 97/18841, WO 96/23524, WO 98/47538, and references cited therein. The photolabels can be covalently linked directly to the cMet binding peptide or linked to the cMet binding peptide or multimeric polypeptide construct via a linker, as described previously.

After injection of the optically-labeled cMet binding moiety, the patient is scanned with one or more light sources (e.g., a laser) in the wavelength range appropriate for the photolabel employed in the agent. The light used can be monochromatic or polychromatic and continuous or pulsed. Transmitted, scattered, or reflected light is detected via a photodetector tuned to one or multiple wavelengths to determine the location of cMet or HGF/cMet complex in the subject. Changes in the optical parameter can be monitored over time to detect accumulation of the optically-labeled reagent at the site of hyperproliferation. Standard image processing and detecting devices can be used in conjunction with the optical imaging reagents of the present invention.

The optical imaging reagents described above also can be used for acousto-optical or sonoluminescent imaging performed with optically-labeled imaging agents (see, U.S. Pat. No. 5,171,298, WO 98/57666, and references cited therein).

In acousto-optical imaging, ultrasound radiation is applied to the subject and affects the optical parameters of the transmitted, emitted, or reflected light. In sonoluminescent imaging, the applied ultrasound actually generates the light detected. Suitable imaging methods using such techniques are described in WO 98/57666.

D. Nuclear Imaging (Radionuclide Imaging) and Radiotherapy

The cMet binding moieties can be conjugated with a radionuclide reporter appropriate for scintigraphy, SPECT, or PET imaging and/or with a radionuclide appropriate for radiotherapy. Constructs in which the cMet binding moieties are conjugated with both a chelator for a radionuclide useful for diagnostic imaging and a chelator useful for radiotherapy are within the scope of the invention.

For use as a PET agent a peptide or multimeric polypeptide construct is complexed with one of the various positron emitting metal ions, such as $^{51}$Mn, $^{52}$Fe, $^{60}$Cu, $^{68}$Ga, $^{72}$As, $^{94m}$Tc, or $^{110}$In. The binding moieties of the invention can also be labeled by halogenation using radionuclides such as $^{18}$F, $^{124}$I, $^{125}$I, $^{131}$I, $^{123}$I, $^{77}$Br, and $^{76}$Br. Preferred metal radionuclides for scintigraphy or radiotherapy include $^{99m}$Tc, $^{51}$Cr, $^{67}$Ga, $^{68}$Ga, $^{47}$Sc, $^{51}$Cr, $^{167}$Tm, $^{141}$Ce, $^{111}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{105}$Rh, $^{109}$Pd, $^{117m}$Sn, $^{149}$Pm, $^{161}$Tb, $^{177}$Lu, $^{198}$Au and $^{199}$Au. The choice of metal will be determined based on the desired therapeutic or diagnostic application. For example, for diagnostic purposes the preferred radionuclides include $^{64}$Cu, $^{67}$Ga, $^{68}$Ga, $^{99m}$Tc, and $^{111}$In. For therapeutic purposes, the preferred radionuclides include $^{64}$Cu, $^{90}$Y, $^{105}$Rh, $^{111}$In, $^{117m}$Sn, $^{149}$Pm, $^{153}$Sm, $^{161}$Tb, $^{166}$Dy, $^{166}$Ho, $^{175}$Yb, $^{177}$Lu, $^{186/188}$Re, and $^{199}$Au. $^{99m}$Tc is particularly preferred for diagnostic applications because of its low cost, availability, imaging properties, and high specific activity. The nuclear and radioactive properties of $^{99m}$Tc make this isotope an ideal scintigraphic imaging agent. This isotope has a single photon energy of 140 keV and a radioactive half-life of about 6 hours, and is readily available from a $^{99}$Mo—$^{99m}$Tc generator.

The metal radionuclides may be chelated by, for example, linear, macrocyclic, terpyridine, and $N_3S$, $N_2S_2$, or $N_4$ chelants (see also, U.S. Pat. No. 5,367,080, U.S. Pat. No. 5,364,613, U.S. Pat. No. 5,021,556, U.S. Pat. No. 5,075,099, U.S. Pat. No. 5,886,142), and other chelators known in the art including, but not limited to, HYNIC, DTPA, EDTA, DOTA, DO3A, TETA, and bisamino bisthiol (BAT) chelators (see also U.S. Pat. No. 5,720,934). For example, $N_4$ chelators are described in U.S. Pat. No. 6,143,274; U.S. Pat. No. 6,093, 382; U.S. Pat. No. 5,608,110; U.S. Pat. No. 5,665,329; U.S. Pat. No. 5,656,254; and U.S. Pat. No. 5,688,487. Certain $N_3S$ chelators are described in PCT/CA94/00395, PCT/CA94/00479, PCT/CA95/00249 and in U.S. Pat. No. 5,662,885; U.S. Pat. No. 5,976,495; and U.S. Pat. No. 5,780,006. The chelator also can include derivatives of the chelating ligand mercapto-acetyl-acetyl-glycyl-glycine (MAG3), which contains an $N_3S$, and $N_2S_2$ systems such as MAMA (monoamidemonoaminedithiols), DADS ($N_2S$ diaminedithiols), CODADS and the like. These ligand systems and a variety of others are described in, for example, Liu, S, and Edwards, D., 1999. *Chem. Rev.*, 99:2235-2268, and references therein.

The chelator also can include complexes containing ligand atoms that are not donated to the metal in a tetradentate array. These include the boronic acid adducts of technetium and rhenium dioximes, such as are described in U.S. Pat. No. 5,183,653; U.S. Pat. No. 5,387,409; and U.S. Pat. No. 5,118, 797, the disclosures of which are incorporated by reference herein, in their entirety.

In another embodiment, disulfide bonds of a cMet binding polypeptide of the invention are used as two ligands for chelation of a radionuclide such as $^{99m}$Tc. In this way the peptide loop is expanded by the introduction of Tc (peptide-S—S-peptide changed to peptide-S—Tc—S-peptide). This also has been used in other disulfide containing peptides in the literature (Chen, J. et al., 2001. *J. Nucl. Med.*, 42:1847-1855) while maintaining biological activity. The other chelating groups for Tc can be supplied by amide nitrogens of the backbone, another cystine amino acid or other modifications of amino acids.

Particularly preferred metal chelators include those of Formula 20, 21, 22, 23a, 23b, 24a, 24b and 25, set forth in FIGS. 8A-8F. Formulae 20-22 are particularly useful for lanthanides such as paramagnetic $Gd^{3+}$ and radioactive lanthanides such as $^{177}$Lu, $^{90}$Y, $^{153}$Sm, $^{111}$In, or $^{166}$Ho. Formulae 23a-24b are particularly useful for radionuclides $^{99m}$Tc, $^{186}$Re, or $^{188}$Re. Formula 25 is particularly useful for $^{99m}$Tc. These and other metal chelating groups are described in U.S. Pat. No. 6,093,382 and U.S. Pat. No. 5,608,110, which are incorporated by reference herein in their entirety. Additionally, the chelating group of formula 22 is described in, for example, U.S. Pat. No. 6,143,274; the chelating group of formula 24 is described in, for example, U.S. Pat. No. 5,627,286 and U.S. Pat. No. 6,093,382, and the chelating group of formula 25 is described in, for example, U.S. Pat. No. 5,662,885; U.S. Pat. No. 5,780,006; and U.S. Pat. No. 5,976,495.

Figure 8A:
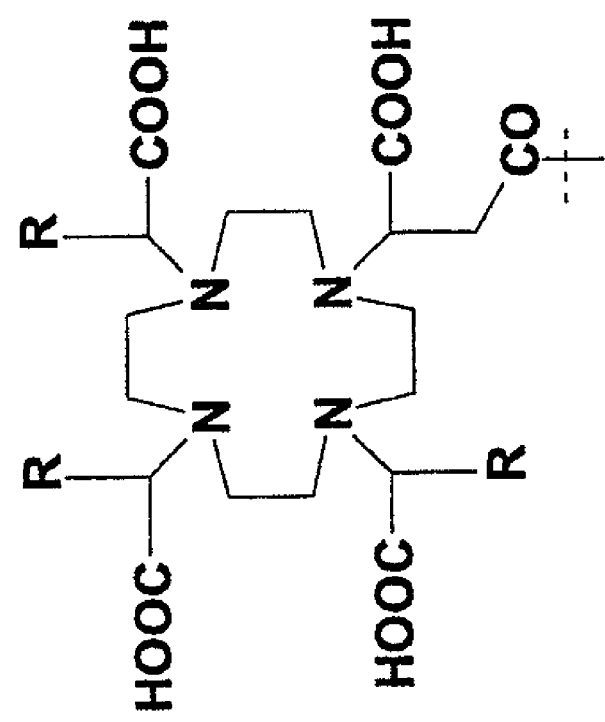
FIGS. 8A-F depict structures of preferred metal chelators.
Figure 8B:
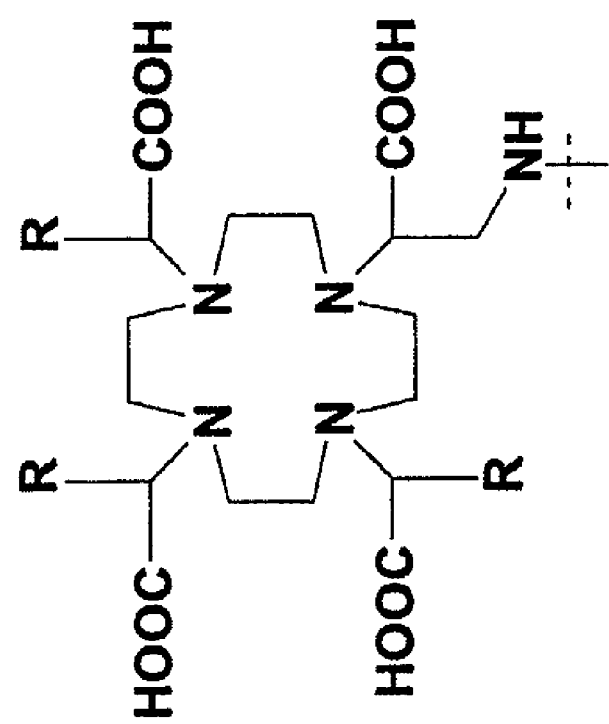
Figure 8C:
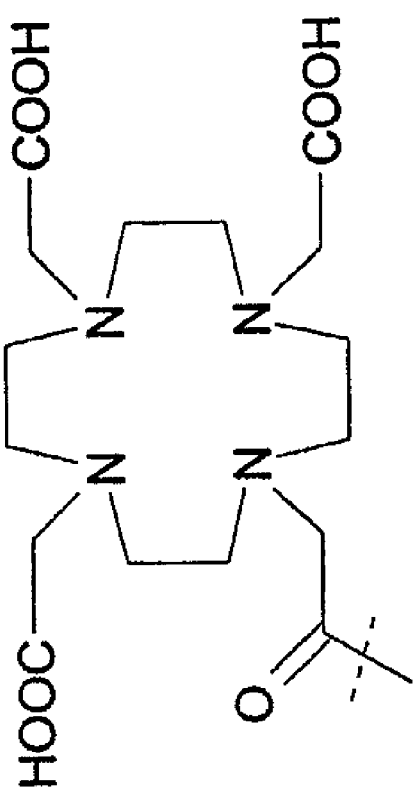
Figure 8D:
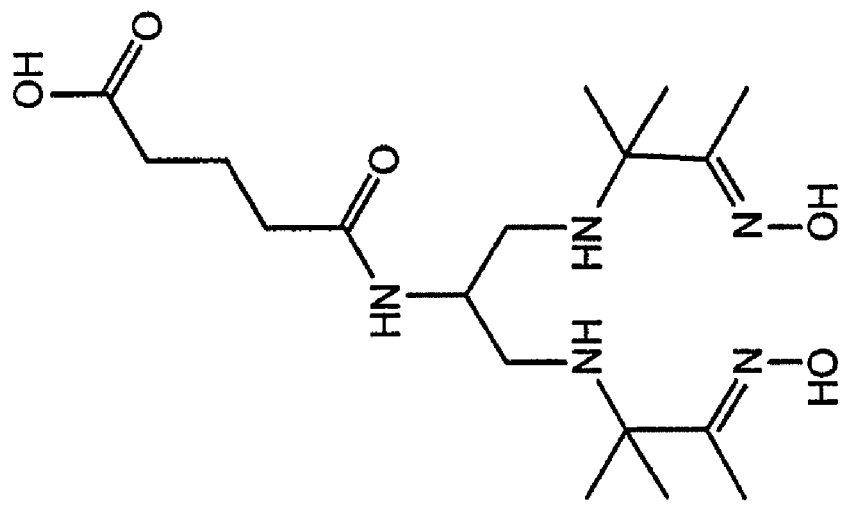
Figure 8D:
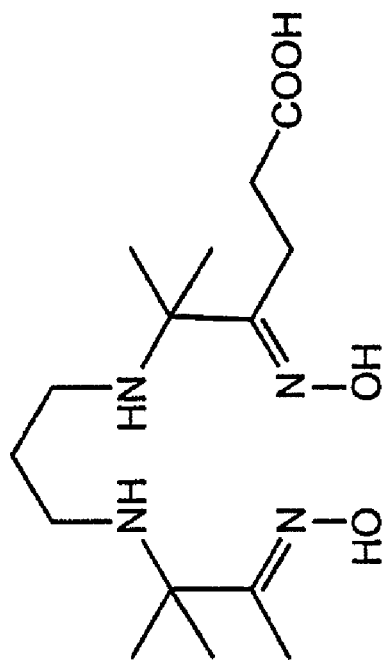
Figure 8E:
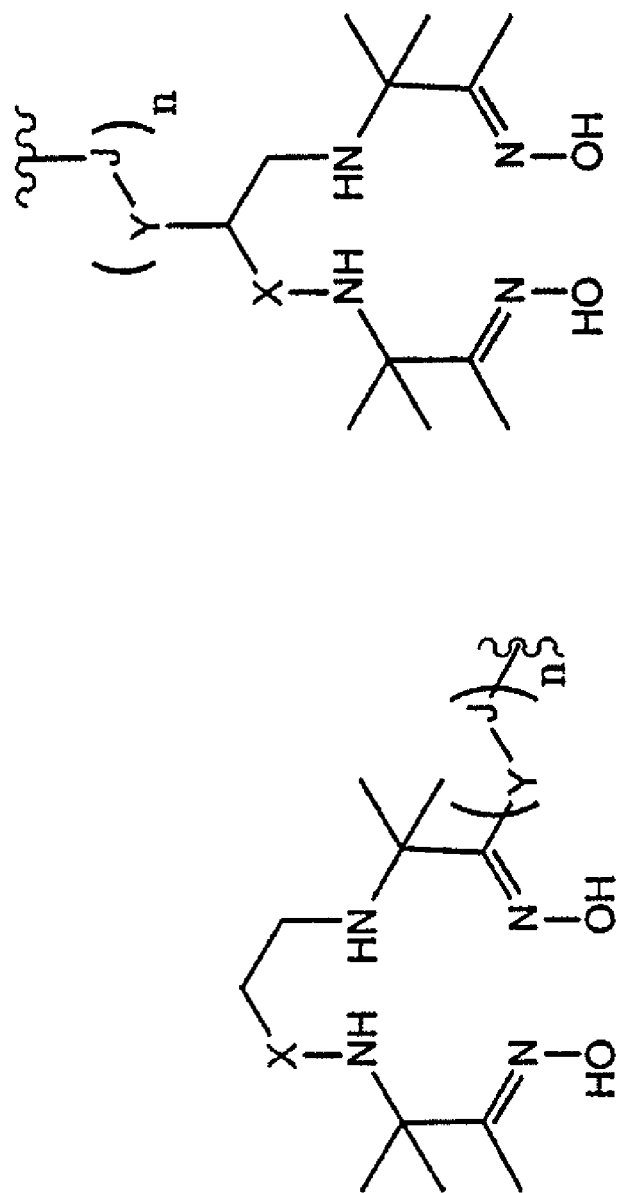
Figure 8F:
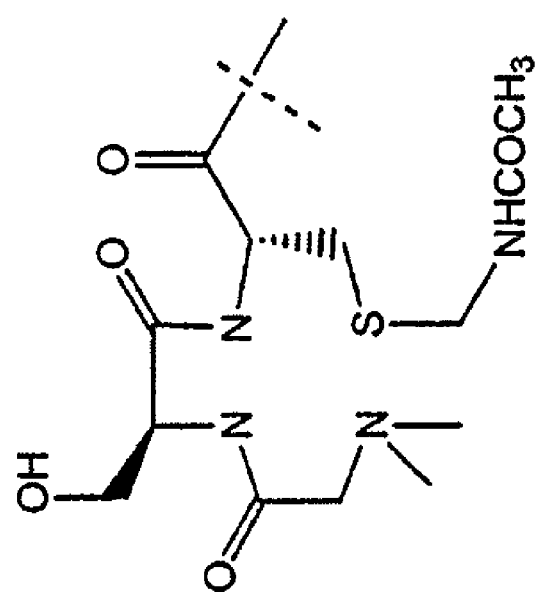

For formulae 24a and 24b of FIG. 8E, X is either $CH_2$ or O; Y is $C_1$-$C_{10}$ branched or unbranched alky, aryl, aryloxy, arylamino, arylaminoacyl, or arylalkyl comprising $C_1$-$C_{10}$ branched or unbranched alkyl groups, hydroxy or $C_1$-$C_{10}$ branched or unbranched polyhydroxyalkyl groups, $C_1$-$C_{10}$ branched or unbranched hydroxy or polyalkoxyalkyl or polyhydroxy-polyalkoxyalkyl groups; J is C(=O)—, OC(=O)—, $SO_2$—, NC(=O)—, NC(=S)—, N(Y), NC(=NCH$_3$)—, NC(=NH)—, N=N—, homopolyamides or heteropolyamines derived from synthetic or naturally occurring amino acids; and n is 1-100. Other variants of these structures are described, for example, in U.S. Pat. No. 6,093,382. The disclosures of each of the foregoing patents, applications and references are incorporated by reference herein, in their entirety.

The chelators can be covalently linked directly to the cMet binding moiety or multimeric polypeptide construct or linked to the cMet binding polypeptide via a linker, as described previously, and then directly labeled with the radioactive metal of choice (see, WO 98/52618, U.S. Pat. No. 5,879,658, and U.S. Pat. No. 5,849,261).

Complexes of radioactive technetium are particularly useful for diagnostic imaging and complexes of radioactive rhenium are particularly useful for radiotherapy. In forming a complex of radioactive technetium with the reagents of this invention, the technetium complex, preferably a salt of $^{99m}$Tc pertechnetate, is reacted with the reagent in the presence of a reducing agent. Preferred reducing agents are dithionite, stannous and ferrous ions; the most preferred reducing agent is stannous chloride. Means for preparing such complexes are conveniently provided in a kit form comprising a sealed vial containing a predetermined quantity of a reagent of the invention to be labeled and a sufficient amount of reducing agent to label the reagent with $^{99m}$Tc. Alternatively, the complex can be formed by reacting a peptide of this invention conjugated with an appropriate chelator with a pre-formed labile complex of technetium and another compound known as a transfer ligand. This process is known as ligand exchange and is well known to those skilled in the art. The labile complex can be formed using such transfer ligands as tartrate, citrate, gluconate or mannitol, for example. Among the $^{99m}$Tc pertechnetate salts useful with the present invention are included the alkali metal salts such as the sodium salt, or ammonium salts or lower alkyl ammonium salts.

Preparation of the complexes of the present invention where the metal is radioactive rhenium can be accomplished using rhenium starting materials in the +5 or +7 oxidation state. Examples of compounds in which rhenium is in the Re(VII) state are $NH_4ReO_4$ or $KReO_4$. Re(V) is available as, for example, $[ReOCl_4](NBu_4)$, $[ReOCl_4](AsPh_4)$, $ReOCl_3(PPh_3)_2$ and as $ReO_2(pyridine)_4^{++}$, where Ph is phenyl and Bu is n-butyl. Other rhenium reagents capable of forming a rhenium complex also can be used.

Radioactively labeled scintigraphic imaging agents provided by the present invention are encompassed having a suitable amount of radioactivity. Generally, the unit dose to be administered has a radioactivity of about 0.01 mCi to about 100 mCi, preferably 1 mCi to 20 mCi. The solution to be injected at unit dosage is from about 0.01 mL to about 10 mL. In forming $^{99m}$Tc radioactive complexes, it is generally preferred to form radioactive complexes in solutions containing radioactivity at concentrations of from about 0.01 mCi to 100 mCi per mL.

Typical doses of a radionuclide-labeled cMet binding imaging agents according to the invention provide 10-20 mCi. After injection of the cMet-specific radionuclide imaging agent into the patient, a gamma camera calibrated for the gamma ray energy of the nuclide incorporated in the imaging agent is used to image areas of uptake of the agent and quantify the amount of radioactivity present in the site. Imaging of the site in vivo can take place in a matter of a few minutes. However, imaging can take place, if desired, in hours or even longer, after the radiolabeled peptide is injected into a patient. In most instances, a sufficient amount of the administered dose will accumulate in the area to be imaged within about 0.1 of an hour to permit the taking of scintiphotos.

Proper dose schedules for the radiotherapeutic compounds of the present invention are known to those skilled in the art. The compounds can be administered using many methods including, but not limited to, a single or multiple IV or IP injections, using a quantity of radioactivity that is sufficient to cause damage or ablation of the targeted cMet-expressing tissue, but not so much that substantive damage is caused to non-target (normal tissue). The quantity and dose required is different for different constructs, depending on the energy and half-life of the isotope used, the degree of uptake and clearance of the agent from the body and the mass of the tumor. In general, doses can range from a single dose of about 30-50 mCi to a cumulative dose of up to about 3 Ci.

The radiotherapeutic compositions of the invention can include physiologically acceptable buffers, and can require radiation stabilizers to prevent radiolytic damage to the compound prior to injection. Radiation stabilizers are known to those skilled in the art, and can include, for example, para-aminobenzoic acid, ascorbic acid, gentistic acid and the like.

A single, or multi-vial kit that contains all of the components needed to prepare the complexes of this invention, other than the radionuclide, is an integral part of this invention.

A single-vial kit preferably contains a chelating ligand, a source of stannous salt, or other pharmaceutically acceptable reducing agent, and is appropriately buffered with pharmaceutically acceptable acid or base to adjust the pH to a value of about 3 to about 9. The quantity and type of reducing agent used would depend on the nature of the exchange complex to be formed. The proper conditions are well known to those that are skilled in the art. It is preferred that the kit contents be in lyophilized form. Such a single vial kit can optionally contain labile or exchange ligands such as glucoheptonate, gluconate, mannitol, malate, citric or tartaric acid and can also contain reaction modifiers such as diethylenetriamine-pentaacetic acid (DPTA), ethylenediamine tetraacetic acid (EDTA), or α, β, or γ cyclodextrin that serve to improve the radiochemical purity and stability of the final product. The kit also can contain stabilizers, bulking agents such as mannitol, that are designed to aid in the freeze-drying process, and other additives known to those skilled in the art.

A multi-vial kit preferably contains the same general components but employs more than one vial in reconstituting the radiopharmaceutical. For example, one vial can contain all of the ingredients that are required to form a labile Tc(V) complex on addition of pertechnetate (e.g., the stannous source or other reducing agent). Pertechnetate is added to this vial, and after waiting an appropriate period of time, the contents of this vial are added to a second vial that contains the ligand, as well as buffers appropriate to adjust the pH to its optimal value. After a reaction time of about 5 to 60 minutes, the complexes of the present invention are formed. It is advantageous that the contents of both vials of this multi-vial kit be lyophilized. As above, reaction modifiers, exchange ligands, stabilizers, bulking agents, etc. can be present in either or both vials.

Therapeutic Applications

The cMet binding polypeptides and multimeric polypeptide constructs of the present invention can be used to present, treat or improve the activity of therapeutic agents such as anti-proliferative or tumoricidal agents against undesired cellular proliferation (such as occurs in neoplastic tumors, e.g., cancer, by providing or improving their affinity for cMet and their residence time at a HGF/cMet complex on proliferating cells, such as, for example, epithelial cells) for diseases associated with cMet, including, but not limited to, diseases related to cMet activity. In this aspect of the invention, hybrid agents are provided by conjugating a cMet binding polypeptide or multimeric polypeptide construct according to the invention with a therapeutic agent. The therapeutic agent can be a radiotherapeutic, discussed above, a drug, chemotherapeutic or tumoricidal agent, genetic material or a gene delivery vehicle, etc. The cMet binding polypeptide moiety portion of the conjugate causes the therapeutic to "home" to the sites of cMet or HGF/cMet complex (i.e., activated epithelial cells), and to improve the affinity of the conjugate for the endothelium, so that the therapeutic activity of the conjugate is more localized and concentrated at the sites of cellular proliferation. In addition, these cMet binding moieties can inhibit HGF-mediated signaling events by preventing HGF from binding to cMet. Such conjugates will be useful in treating hyperproliferative disorders, especially neoplastic tumor growth and metastasis, in mammals, including humans. The method comprises administering to a mammal in need thereof an effective amount of a cMet binding polypeptide or multimeric polypeptide construct according to the invention conjugated with a therapeutic agent. The invention also provides the use of such conjugates in the manufacture of a medicament for the treatment of angiogenesis associated diseases in mammals, including humans.

Suitable therapeutic agents for use in this aspect of the invention include, but are not limited to: antineoplastic agents, such as platinum compounds (e.g., spiroplatin, cisplatin, and carboplatin), methotrexate, adriamycin, mitomycin, ansamitocin, bleomycin, cytosine, arabinoside, arabinosyl adenine, mercaptopolylysine, vincristine, busulfan, chlorambucil, melphalan (e.g., PAM, L-PAM, or phenylalanine mustard), mercaptopurine, mitotane, procarbazine hydrochloride, dactinomycin (actinomycin D), daunorubcin hydrochloride, doxorubicin hydrochloride, taxol, mitomycin, plicamycin (mithramycin), aminoglutethimide, estramustine phosphate sodium, flutamide, leuprolide acetate, megestrol acetate, tamoxifen citrate, testoiactone, trilostane, amsacrine (m-AMSA), aparaginase (L-aparaginase), Erwina aparaginase, etoposide (VP-16), interferon CX-2a, Interferon CX-2b, teniposide (VM-26, vinblastine sulfate (VLB), vincristine sulfate, bleomycin sulfate, adriamycin, and arabinosyl; anti-angiogenic agents such as tyrosine kinase inhibitors with activity toward signaling molecules important in angiogenesis and/or tumor growth such as SU5416 and SU6668 (Sugen/Pharmacia and Upjohn), endostatin (EntreMed), angiostatin (EntreMed), Combrestatin (Oxigene), cyclosporine, 5-fluorouracil, vinblastine, doxorubicin, paclitaxel, daunorubcin, immunotoxins; coagulation factors; antivirals such as acyclovir, amantadine azidothymidine (AZT or Zidovudine), ribavirin and vidarabine monohydrate (adenine arahinoside, ara-A); antibiotics, antimalarials, antiprotozoans such as chloroquine, hydroxychloroquine, metroidazole, quinine and meglumine antimonate; anti-inflammatories such as diflunisal, ibuprofen, indomethacin, meclofenamate, mefenamic acid, naproxen, oxyphenbutazone, phenylbutazone, piroxicam, sulindac, tolmetin, aspirin and salicylates.

In one embodiment of the invention, the therapeutic agent can be associated with an ultrasound contrast agent composition in which cMet binding moieties of the invention are linked to the material employed to form the vesicles as described herein. After administration of the ultrasound contrast agent and the optional imaging of the contrast agent bound to the tissue expressing cMet or HGF/cMet complex, the tissue can be irradiated with an energy beam (preferably ultrasonic, e.g., with a frequency of from 0.3 to 3 MHz), to rupture or burst the microvesicles. The therapeutic effect of the therapeutic agent can thus be enhanced by the energy released by the rupture of the microvesicles, in particular causing an effective delivery of the therapeutic agent to the targeted tissue. For instance, the therapeutic agent can be associated with the targeted ultrasound contrast agent and delivered as described in U.S. Pat. No. 6,258,378, herein incorporated by reference.

The cMet binding polypeptides and multimeric polypeptide constructs of the present invention also can be used to target genetic material to cMet-expressing cells. Thus, they can be useful in gene therapy, particularly for treatment of hyperproliferative disorders. In this embodiment, genetic material or one or more delivery vehicles containing genetic material useful in treating a hyperproliferative disorder can be conjugated to one or more cMet binding moieties of the invention and administered to a patient. The genetic material can include nucleic acids, such as RNA or DNA, of either natural or synthetic origin, including recombinant RNA and DNA and antisense RNA and DNA. Types of genetic material that can be used include, for example, genes carried on expression vectors such as plasmids, phagemids, cosmids, yeast artificial chromosomes (YACs) and defective or "helper" viruses, antigene nucleic acids, both single and double stranded RNA and DNA and analogs thereof, such as phosphorothioate and phosphorodithioate oligodeoxynucleotides. Additionally, the genetic material can be combined, for example, with lipids, proteins or other polymers. Delivery vehicles for genetic material can include, for example, a virus particle, a retroviral or other gene therapy vector, a liposome, a complex of lipids (especially cationic lipids) and genetic material, a complex of dextran derivatives and genetic material, etc.

In a preferred embodiment the constructs of the invention are utilized in gene therapy for treatment of hyperproliferative disorders. In this embodiment, genetic material, or one or more delivery vehicles containing genetic material, e.g., useful in treating a hyperproliferative disorder, can be conjugated to one or more cMet binding polypeptides or multimeric polypeptide constructs of the invention and administered to a patient.

Constructs including genetic material and the cMet-binding moieties of the invention can be used, in particular, to selectively introduce genes into proliferating cancer cells (e.g., epithelial cells), which can be useful to treat cancer.

Therapeutic agents and the cMet binding moieties of the invention can be linked or fused in known ways, optionally using the same type of linkers discussed elsewhere in this application. Preferred linkers will be substituted or unsubstituted alkyl chains, amino acid chains, polyethylene glycol chains, and other simple polymeric linkers known in the art. More preferably, if the therapeutic agent is itself a protein, for which the encoding DNA sequence is known, the therapeutic protein and cMet binding polypeptide can be coexpressed from the same synthetic gene, created using recombinant DNA techniques, as described above. The coding sequence for the cMet binding polypeptide can be fused in frame with that of the therapeutic protein, such that the peptide is expressed at the amino- or carboxy-terminus of the therapeutic protein, or at a place between the termini, if it is determined that such placement would not destroy the required biological function of either the therapeutic protein or the cMet binding polypeptide. A particular advantage of this general approach is that concatamerization of multiple, tandemly arranged cMet binding polypeptides is possible, thereby increasing the number and concentration of cMet binding sites associated with each therapeutic protein. In this manner cMet binding avidity is increased, which would be expected to improve the efficacy of the recombinant therapeutic fusion protein.

Additionally, constructs including cMet binding polypeptides of the present invention can themselves be used as therapeutics to treat a number of diseases associated with cMet activity. For example, where binding of a protein or other molecule (e.g., a growth factor, hormone etc.) is necessary for or contributes to a disease process and a binding moiety inhibits such binding, constructs including such binding moieties could be useful as therapeutics. Similarly, where binding of a binding moiety itself inhibits a disease process, constructs containing such binding moieties also could be useful as therapeutics.

Figure 10:
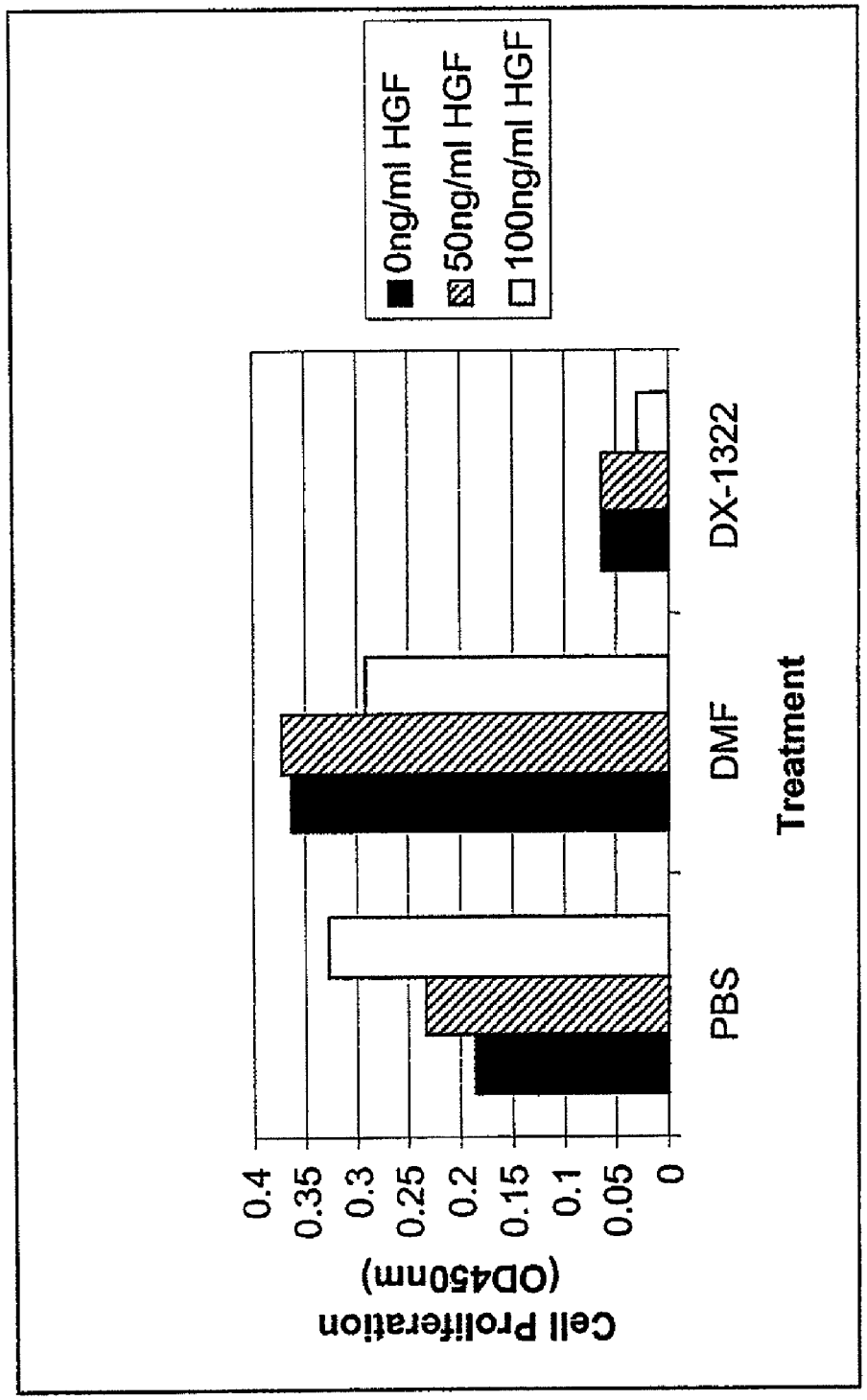
FIG. 10 illustrates the growth inhibitory properties of cMet-binding peptide SEQ ID NO:365.

The binding of HGF to cMet results in the activation of numerous intracellular signal transduction pathways leading to hyperproliferation of various cells. As such, in one embodiment, constructs including cMet binding polypeptides that inhibit the binding of HGF to cMet (or otherwise inhibit activation of cMet) can be used as anti-neoplastic agents. In addition, as binding of HGF and activation of cMet is implicated in angiogenic activity, in another embodiment, constructs including cMet binding polypeptides that inhibit the binding of HGF to cMet, or otherwise inhibit activation of cMet, can be used as anti-angiogenic agents. Certain constructs of the invention including monomers, multimers and heteromultimers that inhibit activation of cMet are also discussed in the Examples, and include, for example, SEQ ID NO:365 (FIG. 10). The binding polypeptides and constructs thereof of the present invention are useful as therapeutic agents for treating conditions that involve endothelial and/or epithelial cells expressing cMet. Because an important function of endothelium is angiogenesis, or the formation of blood vessels, the polypeptides and constructs thereof are particularly useful for treating conditions that involve angiogenesis and/or hyperproliferation. Conditions that involve angiogenesis include, for example, solid tumors, tumor metastases and benign tumors. Tumors caused by cMet activation or through angiogenesis are well known in the art and include, for example, breast, thyroid, glioblastoma, prostate, malignant mesothelioma, colorectal, hepatocellular, hepatobiliary, renal, osteosarcoma and cervical. Additional tumors and related disorders are listed in Table I of U.S. Pat. No. 6,025,331, issued Feb. 15, 2000 to Moses, et al., the teachings of which are incorporated herein by reference. Benign tumors include, for example, hemangiomas, acoustic neuromas, neurofibromas, trachomas, and pyogenic granulomas. Other relevant diseases that involve angiogenesis and/or hyperproliferation include for example, rheumatoid arthritis, psoriasis, and ocular diseases, such as diabetic retinopathy, retinopathy of prematurity, macular degeneration, corneal graft rejection, neovascular glaucoma, retrolental fibroplasia, rebeosis, Osler-Webber Syndrome, myocardial angiogenesis, plaque neovascularization, telangiectasia, hemophiliac joints, angiofibroma and wound granulation. Other relevant diseases or conditions that involve blood vessel growth include intestinal adhesions, atherosclerosis, scleroderma, and hypertropic scars, and ulcers. Furthermore, the binding polypeptides and constructs thereof of the present invention can be used to reduce or prevent uterine neovascularization required for embryo implantation, for example, as a birth control agent.

The binding polypeptides, multimeric polypeptide constructs and constructs conjugates thereof can be administered to an individual over a suitable time course depending on the nature of the condition and the desired outcome. They binding polypeptides and constructs thereof can be administered prophylactically, e.g., before the condition is diagnosed or to an individual predisposed to a condition. The binding polypeptides multimeric polypeptide constructs and conjugates and constructs thereof can be administered while the individual exhibits symptoms of the condition or after the symptoms have passed or otherwise been relieved (such as after removal of a tumor). In addition, they binding polypeptides and constructs thereof of the present invention can be administered a part of a maintenance regimen, for example to prevent or lessen the recurrence or the symptoms or condition. As described below, the binding polypeptides multimeric polypeptide constructs and conjugates and constructs thereof of the present invention can be administered systemically or locally.

The quantity of material administered will depend on the seriousness of the condition. For example, for treatment of a hyperproliferative disorder, e.g., in the case of neoplastic tumor growth, the position and size of the tumor will affect the quantity of material to be administered. The precise dose to be employed and mode of administration must per force, in view of the nature of the complaint, be decided according to the circumstances by the physician supervising treatment. In general, dosages of the agent conjugate polypeptides, multimeric polypeptide constructs and conjugates of the present invention will follow the dosages that are routine for the therapeutic agent alone, although the improved affinity of a binding polypeptide or multimeric polypeptide construct of the invention for its target can allow for a decrease in the standard dosage.

Such conjugate pharmaceutical compositions are preferably formulated for parenteral administration, and most preferably for intravenous or intra-arterial administration. Generally, and particularly when administration is intravenous or intra-arterial, pharmaceutical compositions can be given as a bolus, as two or more doses separated in time, or as a constant or non-linear flow infusion.

As used herein the term "therapeutic" includes at least partial alleviation of symptoms of a given condition. The binding polypeptides, multimeric constructs and constructs conjugates thereof of the present invention do not have to produce a complete alleviation of symptoms to be useful. For example, treatment of an individual can result in a decrease in the size of a tumor or diseased area, or prevention of an increase in size of the tumor or diseased area. Treatment also can prevent or lessen the number or size of metastatic outgrowths of the main tumor(s).

Symptoms that can be alleviated include physiological characteristics such as cMet activity. The binding polypeptides multimeric polypeptide constructs and conjugates and constructs thereof of the present invention can inhibit activity of cMet and its homologs by binding to cMet and inhibiting its activity or by binding to cMet and inhibiting HGF from activating this receptor. Such inhibition can be detected, for example, by measuring the phosphorylation state of the receptor in the presence of or after treatment with the binding polypeptides or constructs thereof. Based on the teachings provided herein, one of ordinary skill in the art would know how and be able to administer a suitable dose of binding polypeptide, multimeric polypeptide constructs and conjugates or construct thereof as provided herein, and measure the effect of treatment on the parameter of interest. For example, the size of the area of interest (e.g., the tumor or lesion) can be measured before and after treatment. Cells or cMet itself can be isolated from the sample and used in assays described herein.

The dosage of the polypeptides multimeric polypeptide constructs and conjugates and constructs thereof can depend on the age, sex, health, and weight of the individual, as well as the nature of the condition and overall treatment regimen. The biological effects of the polypeptides multimeric polypeptide constructs and conjugates and constructs thereof are described herein. Therefore, based on the biological effects of the binding polypeptides multimeric polypeptide constructs and conjugates and constructs provided herein, and the desired outcome of treatment, the preferred dosage is determinable by one of ordinary skill in the art through routine optimization procedures. Typically, the daily regimen is in the range of about 0.1 mg/kg to about 1 mg/kg.

The binding polypeptides moieties and constructs conjugates thereof provided herein can be administered as the sole active ingredient, optionally together with a pharmaceutically acceptable excipient, or can be administered together (e.g., simultaneously or sequentially) with other binding polypeptides and constructs thereof, other therapeutic agents, or combination thereof. In addition, the binding polypeptides moieties and conjugate constructs thereof can be conjugated to therapeutic agents, for example, to improve specificity, residence time in the body, or therapeutic effect. Such other therapeutic agents include, for example, other anti-proliferative compounds, and tumoricidal compounds. The therapeutic agent also can include antibodies. Furthermore, the binding polypeptide multimeric polypeptide constructs and constructs thereof of the present invention can be used as a cancer cell homing device. Therefore, they binding polypeptide or constructs thereof can may be conjugated to nucleic acid encoding, for example, a therapeutic polypeptide, in order to target the nucleic acid to stromal cells. Once exposed to the nucleic acid conjugated binding polypeptide moiety or conjugate thereof, the stromal cells can internalize and express the conjugated nucleic acid, thereby delivering the therapeutic peptide to the target cells.

The binding polypeptides, multimeric polypeptide constructs and conjugates and constructs thereof can be administered locally or systemically by any suitable route. Suitable routes of administration include, but are not limited to, topical application, transdermal, parenteral, gastrointestinal, intravaginal, and transalveolar. Compositions for the desired route of administration can be prepared by any of the methods well known in the pharmaceutical arts, for example, as described in Remington: *The Science and Practice of Pharmacy*, 20th ed., Lippincott, Williams and Wilkins, 2000.

For topical application, the binding polypeptides, multimeric polypeptide constructs and conjugates thereof can be suspended, for example, in a cream, gel or rinse that allows the polypeptides or constructs to penetrate the skin and enter the blood stream, for systemic delivery, or contact the area of interest, for localized delivery. Compositions suitable for topical application include any pharmaceutically acceptable base in which the polypeptides or constructs are at least minimally soluble.

For transdermal administration, the polypeptides, multimeric polypeptide constructs and conjugates thereof can be applied in pharmaceutically acceptable suspension together with a suitable transdermal device or "patch". Examples of suitable transdermal devices for administration of the polypeptides or constructs of the present invention are described, for example, in U.S. Pat. No. 6,165,458, issued Dec. 26, 2000 to Foldvari et al., and U.S. Pat. No. 6,274,166B1, issued Aug. 4, 2001 to Sintov et al., the teachings of which are incorporated herein by reference.

For parenteral administration, the polypeptides, multimeric polypeptide constructs and conjugates thereof can be injected intravenously, intramuscularly, intraperitoneally, or subcutaneously. Typically, compositions for intravenous administration are solutions in sterile isotonic aqueous buffer. Other pharmaceutically acceptable carriers include, but are not limited to, sterile water, saline solution, and buffered saline (including buffers like phosphate or acetate), alcohol, vegetable oils, polyethylene glycols, gelatin, lactose, amylose, magnesium stearate, talc, silicic acid, paraffin, etc. Where necessary, the composition also can include a solubilizing agent and a local anaesthetic such as lidocaine to ease pain at the site of the injection, preservatives, stabilizers, wetting agents, emulsifiers, salts, lubricants, etc. as long as they do not react deleteriously with the active compounds. Similarly, the composition may comprise conventional excipients, i.e. pharmaceutically acceptable organic or inorganic carrier substances suitable for parenteral, enteral or intranasal application which do not deleteriously react with the active compounds. Generally, the ingredients will be supplied either separately or mixed together in unit dosage form, for example, as a dry lyophilized powder or water free concentrate in a hermetically sealed container such as an ampoule or sachette indicating the quantity of active agent in activity units. Where the composition is to be administered by infusion, it can be dispensed with an infusion bottle containing sterile pharmaceutical grade "water for injection" or saline. Where the composition is to be administered by injection, an ampoule of sterile water for injection or saline can be provided so that the ingredients can be mixed prior to administration.

For gastrointestinal and intravaginal administration, the polypeptides, multimeric polypeptide constructs and conjugates thereof can be incorporated into pharmaceutically acceptable powders, pills or liquids, and suppositories for rectal or vaginal administration.

For transalveolar, buccal or pulmonary administration, the polypeptides, multimeric polypeptide constructs and conjugates thereof can be suspended in a pharmaceutically acceptable excipient suitable for aerosolization and inhalation or as a mouthwash. Devices suitable for transalveolar administration such as atomizers and vaporizers also are included within the scope of the invention. Suitable formulations for aerosol delivery of polypeptides, etc. using buccal or pulmonary routes can be found, for example in U.S. Pat. No. 6,312,665B1, issued Nov. 6, 2001 to Pankaj Modi, the teachings of which are incorporated herein by reference.

In addition, the polypeptides, multimeric polypeptide constructs and conjugates thereof of the present invention can be administered nasally or ocularly, where the polypeptide or construct is suspended in a liquid pharmaceutically acceptable agent suitable for drop-wise dosing.

The polypeptides, multimeric polypeptide constructs and conjugates thereof of the present invention can be administered such that the polypeptide, etc. is released in the individual over an extended period of time (sustained or controlled release). For example, the polypeptide, multimeric polypeptide constructs and conjugates thereof can be formulated into a composition such that a single administration provides delivery of the polypeptide, etc. for at least one week, or over the period of a year or more. Controlled release systems include monolithic or reservoir-type microcapsules, depot implants, osmotic pumps, vesicles, micelles, liposomes, transdermal patches and iontophoretic devices. In one embodiment, the polypeptides, multimeric polypeptide constructs and conjugates thereof of the present invention are encapsulated or admixed in a slowly degrading, non-toxic polymer. Additional formulations suitable for controlled release of the polypeptides, multimeric polypeptide constructs and conjugates thereof provided herein are described in U.S. Pat. No. 4,391,797, issued Jul. 5, 1983, to Folkman et al., the teachings of which are incorporated herein by reference.

Another suitable method for delivering the polypeptides of the present to an individual is via in vivo production of the polypeptide. A gene encoding the polypeptide can be administered to the individual such that the encoded polypeptide is expressed. The gene can be transiently expressed. In a particular embodiment, the gene encoding the polypeptide is transfected into cells that have been obtained from the patient, a method referred to as ex vivo gene therapy. Cells expressing the polypeptide are then returned to the patient's body. Methods of ex vivo gene therapy are well known in the art and are described, for example, in U.S. Pat. No. 4,391,797, issued Mar. 21, 1998 to Anderson et al., the teachings of which are incorporated herein by reference.

Isolation of cMet binding moieties polypeptides and preparation and use of cMet binding moieties and conjugates thereof in accordance with this invention will be further illustrated in the following examples. The specific parameters included in the following examples are intended to illustrate the practice of the invention, and they are not presented to in any way limit the scope of the invention.

EXAMPLES

Example 1

Method for Identification of cMet-Binding Polypeptides

A four-pronged selection strategy using a variety of peptide-displaying phage libraries was utilized to screen for cMet-binding polypeptides. Both the extracellular domain of the cMet receptor (expressed as an Fc-fusion protein) and the colorectal cancer cell line, DLD-1, which express high levels of cMet on their cell surface, were used as tools for the selections.

Figure 9:
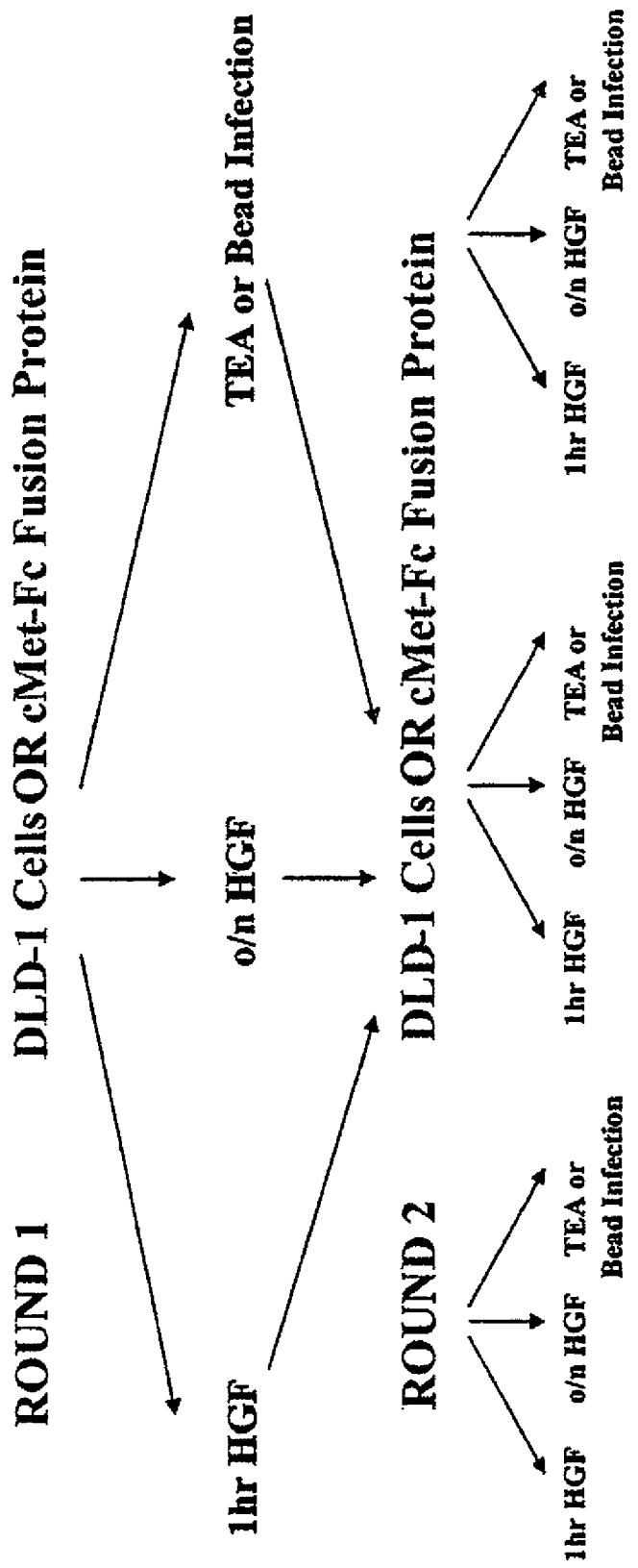
FIG. 9 is a schematic representation of the selection strategy that was employed to identify cMet binding polypeptides. TEA=triethylamine, Bead Infection=capture of non-eluted phage that remained bound to the cMet-Fc/protein-A beads.

Briefly, the selections involved either using the soluble cMet-Fc-fusion protein or DLD-1 cells as the target. Specific elutions with HGF (first for 1 hour and then overnight to identify both low and high affinity cMet binders) were performed. Additionally, while using the soluble cMet receptor, all peptide-displaying phage that remained bound to the receptor were harvested to identify peptides that did not bind to the ligand binding site, but could nevertheless be potentially developed into imaging agents. FIG. 9 illustrates the selection strategy that was employed. Briefly, 21 different selection campaign/elution combinations were performed with each library pool. An additional 10 selection campaigns representing rounds 3 and 4 using the soluble Met-Fc fusion protein were also performed. HGF elutions were at a concentration of 100 ng/mL.

Example 2

Determination of Peptide-Displaying Phage Binding to Soluble cMet-Fc Fusion Protein "Protein Phage ELISAs"

Protein phage ELISAs using peptide-displaying phage isolates from the various selection campaigns were performed to determine specificity of the peptides for cMet versus an unrelated Fc-fusion protein (TRAIL-Fe). Briefly, 384-well plates were coated overnight at 4 C with 0.5 µg/mL of cMet-Fc fusion protein or TRAIL-Fc fusion protein (background). The plates were blocked for 2 hours 37 C with 3% (w/v) BSA in PBS containing 0.05% (v/v) Tween-20 (PBST). The plates were washed with PBST and 100 µL of peptide-displaying phage were added to each well. The plates were incubated for 2 hours at room temperature and washed with PBST. cMet-binding peptide-displaying phage were detected using an HRP-conjugated anti-M13 antibody.

The peptide-displaying phage that demonstrated a >3-fold binding to cMet-Fc fusion protein versus TRAIL-Fc fusion protein are herein referred to as "positive hits". The positive hits identified in the above screen were subjected to DNA sequencing. From subsequent sequence analysis, 187 unique peptide sequences were identified. The corresponding amino acid sequences of the cMet-binding phage-displayed peptides are listed in Table 1 (SEQ ID NO: 001-101, 365-387, 390-404, 449-496).

Example 3

Determination of cMet Binding in a Cellular Model

Whole cell ELISAs were performed to assess whether the positive hits demonstrated specific binding to cell surface-expressed human cMet.

Whole cell ELISAs were performed using 3T3 cells that over-express human cMet. 3T3 cells that do not express cMet ("non-expressing cells") were used as a control cell line. Briefly, 96-well plates were seeded with $10^5$ cells per well. The plates were centrifuged for 5 minutes at 1600 rpm to pellet the cells. The resulting cell layer was fixed with 0.1% (v/v) glutaraldehyde for 12 minutes at 37 C. The cells were washed with PBS and subsequently blocked with 3% BSA in PBST for 1 hour at 37 C. Peptide-displaying phage also were blocked in the above solution for 1 hour at 37 C. 100 µL of blocked phage was then added to each well and the plates were incubated for 1 hour at room temperature. The plates were washed with PBST. cMet-binding peptide-displaying phage were detected using an HRP-conjugated anti-M13 antibody.

Example 4

HGF Competition Protein ELISAs

HGF competition protein ELISAs were performed in an attempt to determine whether any of the cMet-binding peptides compete with HGF for a similar binding site on cMet. This competition ELISA identifies peptides that serve as "HGF antagonistic peptides", peptides that block HGF-mediated signaling events (e.g., proliferation). These assays were conducted using the peptide-displaying phage discovered from the initial selection and screening campaigns using the first generation peptide libraries. Briefly, 96-well plates were coated overnight at 4 C with 0.5 µg/mL of cMet-Fc fusion protein or TRAIL-Fe fusion protein (background). The plates were blocked for 2 hours at 37 C with 3% BSA in PBST. The plates were washed with PBST, and 100 µL of HGF (either at 100 ng/mL or 500 ng/mL in PBST) was added to each well. The plates were incubated for 30 minutes at room temperature after which the plates were washed with PBST and 70 µL of HGF (143 ng/mL or 714 ng/mL) or 70 µL of PBST was added to the respective wells. This was followed by an addition of 30 µL of peptide-displaying phage overnight culture to each well. The plates were incubated for 2 hours at room temperature, washed with PBST and cMet-binding peptide-displaying phage was detected using an HRP-conjugated anti-M13 antibody.

Data for the protein ELISAs, whole cell ELISAs and the HGF competition experiments is presented in Table 7.

Example 5

Peptide Synthesis and Fluorescein Labeling

A select number of cMet-binding peptides corresponding to positive phage isolates were synthesized on a solid phase matrix using 9-fluorenylmethoxycarbonyl protocols. These peptides were purified with reverse phase chromatography. Peptide masses were confirmed by electrospray mass spectrometry, and peptides were quantified by measuring absorbance at 280 nm. For synthesis, two N-terminal and two C-terminal amino acids from the phage vector sequence from which the peptide was excised were retained, and a linker, e.g., -Gly-Gly-Gly-Lys-$NH_2$ (SEQ ID NO:513) was added to the C-terminus of each peptide. Each peptide was N-terminally acetylated. Selected lysine residues were protected with 1-(4,4-dimethyl-2,6-dioxocyclohex-1-ylidene)-3-methylbutyl (ivDde) where appropriate. The protecting group allows for selective coupling to the C-terminal lysine, is not removed during peptide cleavage, but can be removed after coupling with 2% hydrazine in DMF or 0.5 M hydroxylamine, pH 8, in water.

Each peptide was labeled with fluorescein on the C-terminal lysine using fluorescein (N-hydroxysuccinimide ester derivative) or fluorescein isothiocyanate (FITC) in DMF with 2% diisopropylethylamine (DIPEA). In the case where the peptide contained an ivDde protected lysine, the reaction was quenched by the addition of 2% hydrazine, which reacts with all free NHS-fluorescein and removes the internal protecting group. For all other peptides, the reaction was quenched by the addition of an equal volume of 0.5M hydroxylamine, pH 8. The quenched reactions were then diluted with water to less than 10% DMF and then purified using C18 reverse phase chromatography. The peptides were verified by analyzing them for expected mass using an LC-MS system (HP1100 HPLC with in-line SCIEX AP150 single quadrapole mass spectrometer), and the purity of the peptides was determined.

Example 6

Fluorescence Anisotropy Measurements

Fluorescence anisotropy measurements were performed in 384-well microplates in a volume of 104 in binding buffer (PBS, 0.01% Tween-20, pH 7.5) using a Tecan Polarion fluorescence polarization plate reader (Caracas, Venezuela). The concentration of fluorescein-labeled peptide was held constant (20 nM) and the concentration of cMet-Fc fusion protein (or similar target) was varied. Binding mixtures were equilibrated for 10 minutes in the microplate at 30 C before measurement. The observed change in anisotropy was fit to the equation below via nonlinear regression to obtain the apparent $K_D$. This equation (1) assumes that the synthetic peptide and cMet form a reversible complex in solution with 1:1 stoichiometry.

$$r_{obs} = r_{free} + (r_{bound} - r_{free}) \frac{(K_D + cMet + P) - \sqrt{(K_D + cMet + P)2 - 4 \cdot cMet \cdot P}}{2 \cdot P}$$

where $r_{obs}$ is the observed anisotropy, $r_{free}$ is the anisotropy of the free peptide, $r_{bound}$ is the anisotropy of the bound peptide, $K_D$ is the apparent dissociation constant, cMet is the total cMet concentration, and P is the total fluorescein-labeled peptide concentration. $K_D$ was calculated in a direct binding assay ($K_{D,B}$) and therefore these values represent cMet binding to the fluorescein labeled peptide.

Example 7

Peptide Competition Fluorescence Polarization Assays

Peptide competition fluorescence polarization assays were performed to determine which peptides compete with each other for binding to cMet. This would identify potential heteromeric peptide complexes that exhibit higher affinity for the cMet receptor than an individual peptide alone.

Briefly, cross competition of cMet-binding peptides was performed on a Cartesian liquid handler (Irvine, Calif.) in a 3 µL total reaction volume. Flourescein-labeled peptides were diluted to a final concentration of 20 nM and unlabeled competitor peptides were diluted to a final concentration of 10 µM. cMet-Fc fusion protein was diluted to the $K_D$ for each fluorescein-labeled peptide in the reaction. Binding mixtures were equilibrated for 10 minutes on the microplate at 30 C before measuring any changes in anisotropy. From these studies, three pairs of cMet-binding peptides were identified as being non-competitors and represent ideal candidates for heteromeric cMet-binding peptide complexes (see Table 9).

Example 8

General Procedure for Preparation of Heteromeric cMet-Binding Peptide Complexes Each of the dimers consists of a Tc-chelating 6-PnAO ligand bearing sequence (generally referred to as A) and a spacer functionalized (spacer=JJ; J=8-Amino-3,6-dioxaoctanoic acid) portion (generically referred to as B). Compound B was treated with a 10-fold excess of glutaric acid bis NHS ester (Tyger Scientific, Princeton, N.J.) and ~20-fold excess of diisopropylethylamine at ambient temperature in DMF for 30 minutes. The reaction mixture was diluted with ether (15-fold by volume) which led to the precipitation of the mono-NHS ester of the glutarylated peptide. The ether was decanted and the solid washed thrice more with ether, which removed any traces of unreacted glutaric acid bis NHS ester. The resulting solid was resuspended in dry DMF and the compound A (1 equiv) was added followed by diisopropylethylamine (20 equiv) and the mixture was stirred for 24 hours at ambient temperature. The mixture was diluted with water (50-fold) and the mixture was directly loaded onto a reverse-phase HPLC column, which was eluted with a gradient of acetonitrile (0.1% TFA) into water (0.1% TFA). Fractions containing the desired product were combined and lyophilized to provide the desired materials.

Specific Example

Preparation of Heterodimeric cMet-Binding Peptides Complexes

1) Preparation of a PnAOG-Glut Modified SEQ ID NO:514 Peptide (a Type A Compound)

Figure 11:
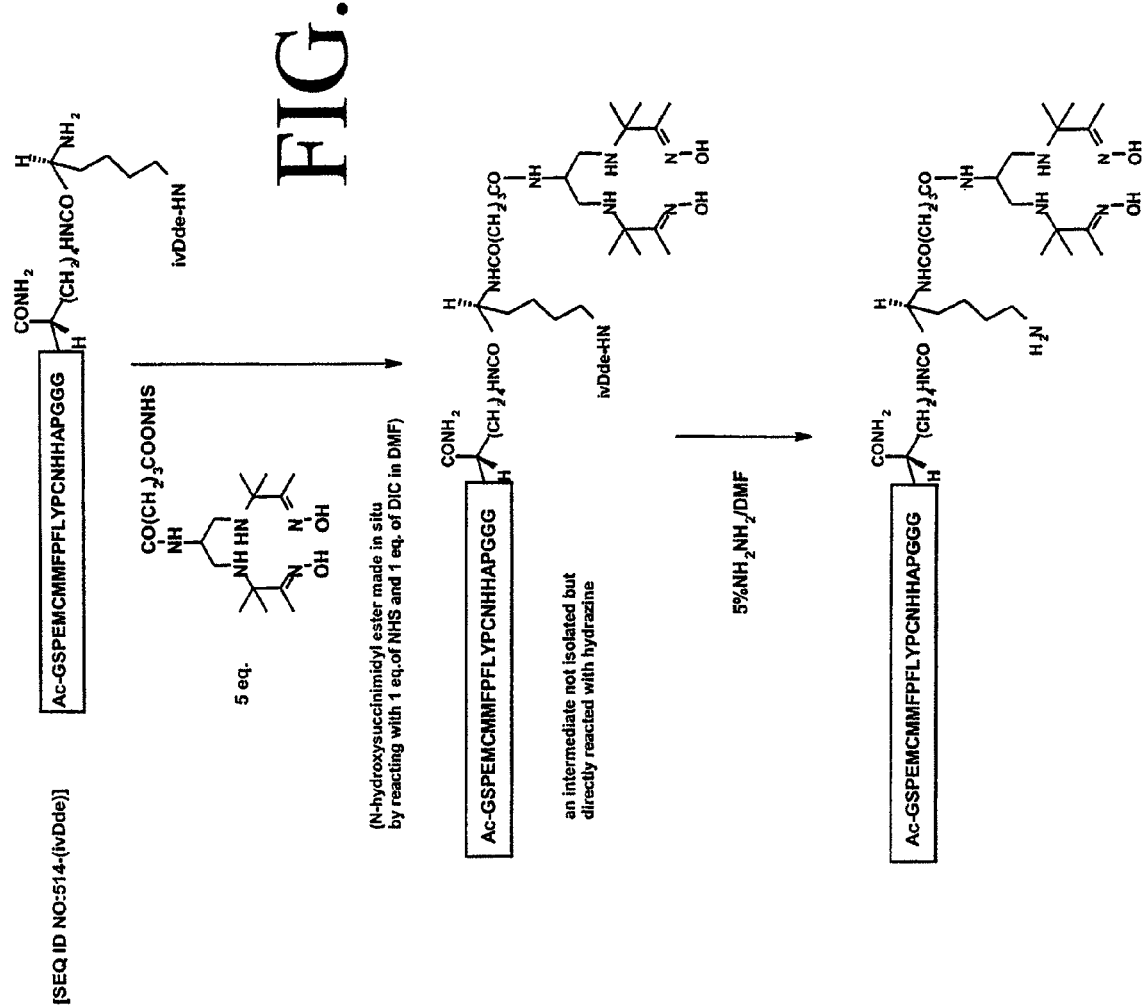
FIG. 11 shows a schematic diagram for the preparation of SEQ ID NO:514 conjugated to a 6-PnAO-Glut moiety, (referred to herein as "scheme 5").

To a solution of 6-Glutaryl-PnAO (40 mg, 0.1 mmol) in dry DMF (0.2 mL) was added N-hydroxysuccinimide (NHS, 14 mg, 0.12 mmol) and diisopropylcarbodiimide (DIC, 15 mg, 0.12 mmol) and stirred for 4 h at room temperature. Ether:hexane (5 mL, 1:1) was added to the reaction mixture. The mixture was stirred and the supernatant solution was removed by decantation, leaving behind the paste in the flask. The paste was washed with ether:hexane (1:1) (3×5 mL) and dissolved in dry DMF (0.2 mL). To this solution were added the K-(ivDde)-modified SEQ ID NO:518 (50 mg, 0.017 mmol) and diisopropylethylamine (DIEA, 10 mg, 0.08 mmol) and the resultant mixture was stirred for 18 hours. Hydrazine (10 µL) was added and the solution was stirred for 30 min. The reaction mixture was diluted with water (20 mL), loaded onto a reversed-phase (C18) HPLC column, and eluted with water (0.1% TFA)-acetonitrile (0.1% TFA) system. Fractions containing the required product (>95% purity) were collected and freeze-dried to provide SEQ ID NO:518-(6-PnAO-Glut)) (see Scheme 5 as shown in FIG. 11) as a colorless fluffy solid. The yield was 25.1 mg (47.4%).

2) Preparation of Dimer Containing SEQ ID NO:514 Linked to SEQ ID NO:515

Figure 12:
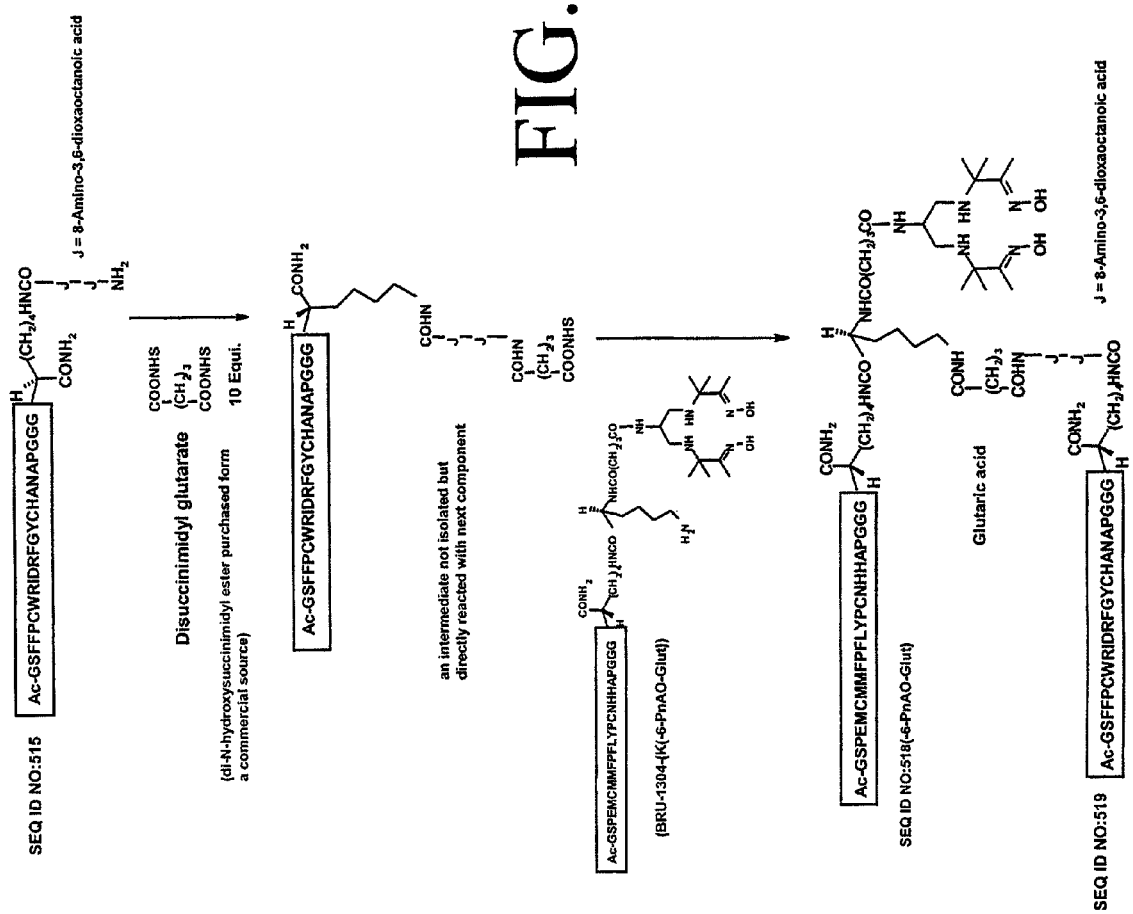
FIG. 12 shows a schematic diagram for the preparation of a heterodimer containing SEQ ID NOS: 514 and 515 joined by a K(PnAO6-Glut) linker (referred to herein as "scheme 5").

To a solution of the peptide containing SEQ ID NO:515 (a type B compound) (10 mg, 0.0034 mmol) and diisopropylethylamine (10 mg, 0.08 mmol) in dry DMF (0.2 mL) was added disuccinimidyl glutarate (10 mg, 0.031 mmol) and stirred at room temperature for 30 min. The reaction mixture was diluted with ether (3 mL) and stirred. The supernatant was decanted, leaving behind the semi-solid in the flask. This process of washing the reaction product was repeated with ether (3×5 mL). The semi-solid thus obtained was dissolved in dry DMF (0.2 mL) and the peptide SEQ ID NO:514-(6-PnAO-Glut)) (10 mg, 0.0032 mmol) and diisopropylethylamine (10 mg, 0.08 mmol) were added and stirred the reaction mixture for 24 h at room temperature. The reaction mixture was diluted with water (10 mL), loaded onto a reversed-phase (C18) HPLC column, and eluted with water (0.1% TFA)-acetonitrile (0.1% TFA) system. Fractions containing the required product (>95% purity) were collected and freeze-dried to provide the heterodimer having SEQ ID NO:514 linked to SEQ ID NO:515 via a 6-PnAO-Glut linkage (see Scheme 6 as shown in FIG. 12) as a colorless fluffy solid.

Figure 13A:
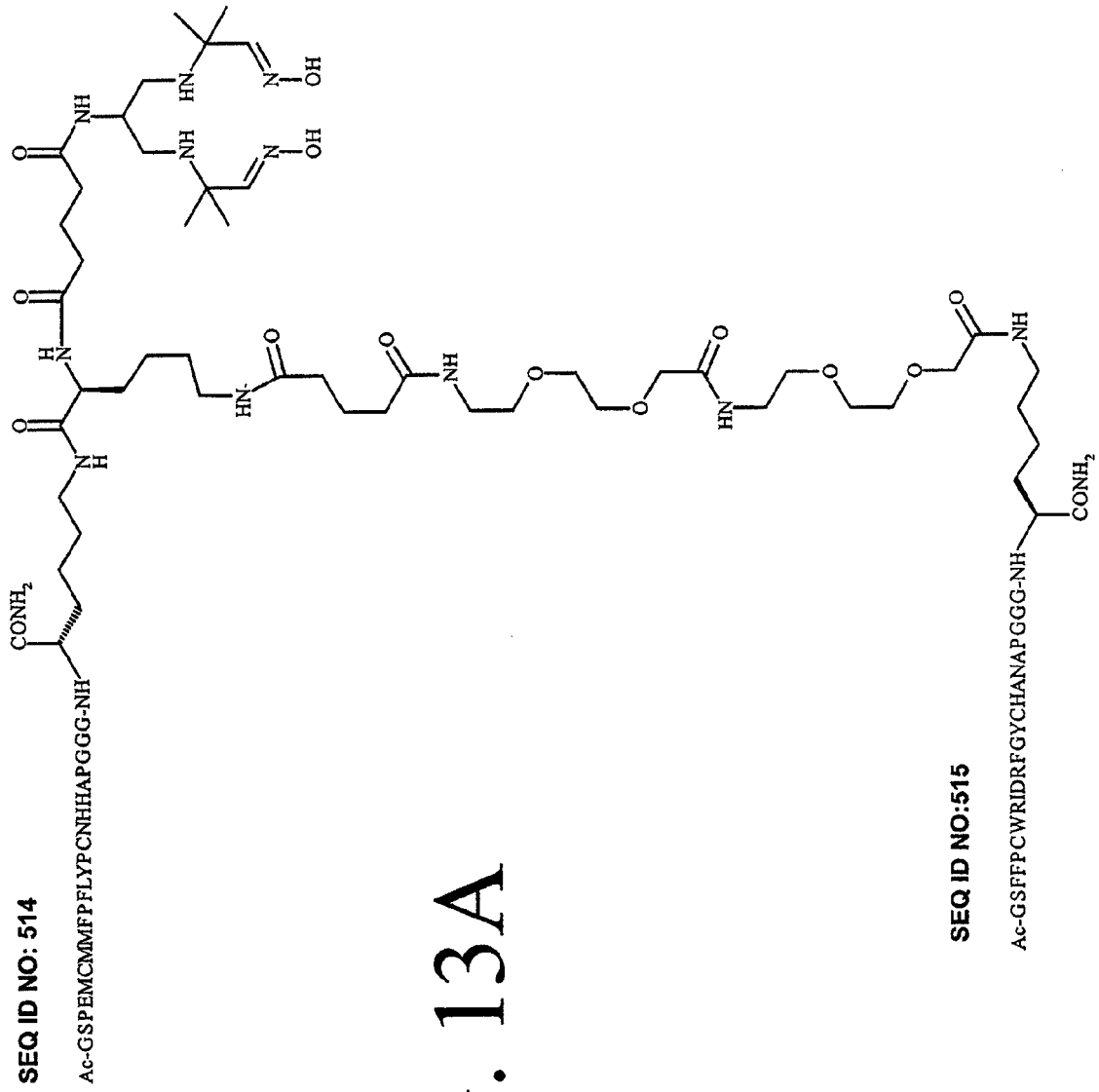
FIGS. 13A-13C show the chemical structures of three heterodimers as follows.
Figure 13B:
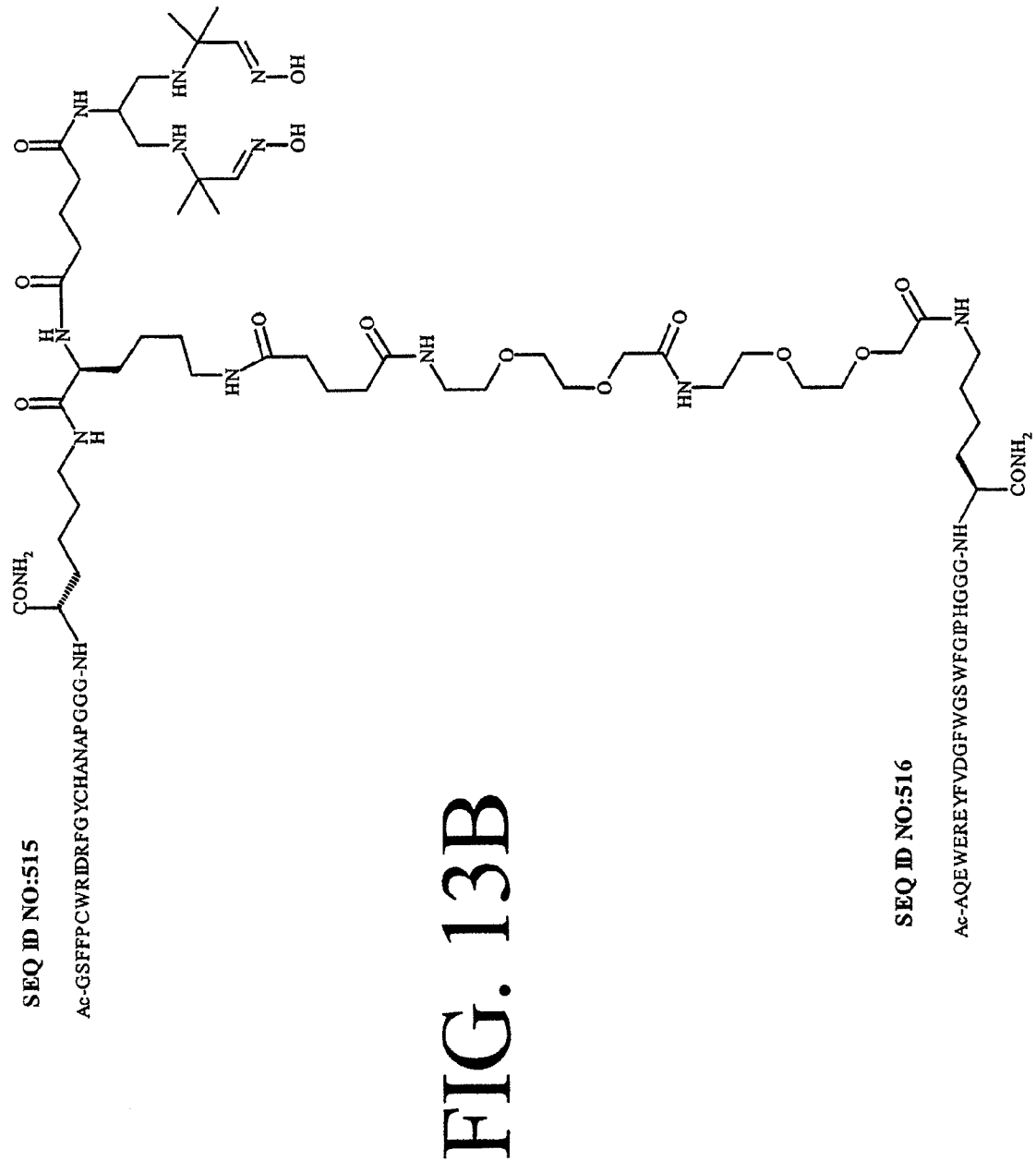
Figure 13C:
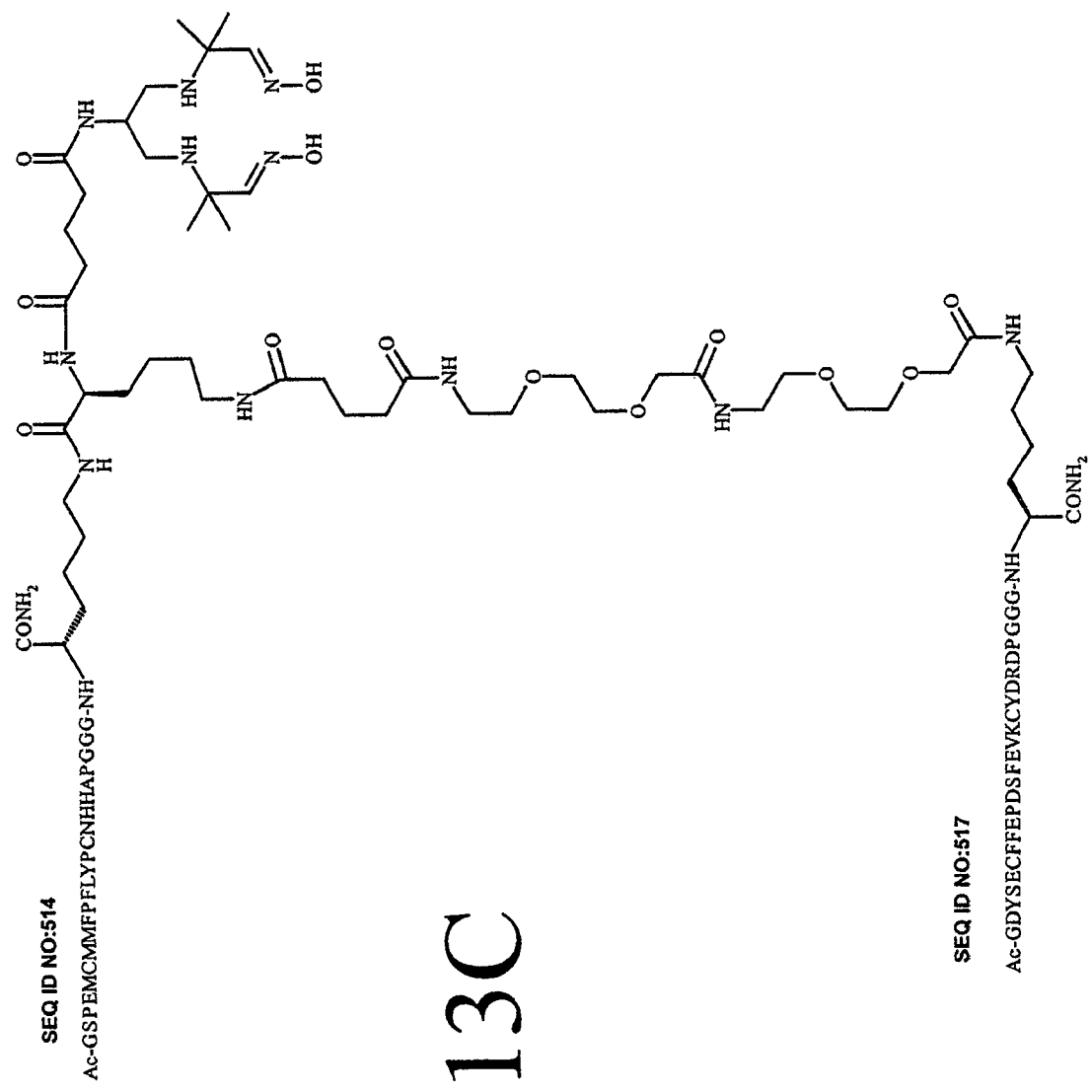

Yield: 6.7 mg (33%). The structures for this and other heterodimers are shown in FIGS. 13A-13C.

Example 9

Cellular Proliferation Assay

Cellular proliferation assays were performed to identify cMet-binding peptides that antagonize HGF-stimulated proliferation. These in vitro studies utilized a leomyosarcoma cell line, SK-LMS-1, in which cells proliferate in response to HGF. SK-LMS-1 cells were seeded on 96-well plates at a density of 2000 cells/well. After a 24 hour incubation at 37 C, the cells were starved in culture media containing 0.1% BSA instead of 10% fetal bovine serum for 36 hours at 37 C. Fresh starvation media with or without a cMet-binding peptide (10 µM) was added to the respective wells and the cells were incubated for 2 hours at 37 C. DMF was used as the control vehicle and did not receive a cMet-binding peptide. HGF was then added at a concentration of either 50 ng/mL or 100 ng/mL and the cells were incubated for an additional 12 hours at 37 C. Proliferation was assessed by measuring the incorporation of BrdU (Calbiochem, San Diego, Calif.) as described by the manufacturer. Results are shown for SEQ ID NO:365 (FIG. 10).

Example 10

Design of a Second Generation cMet-Binding Peptide Library

Initial selection from linear and cyclic peptide libraries identified a number of positive hits for cMet. The TN9 hits contained a highly conserved motif (CxGpPxFxC, SEQ ID NO:512, the 'p' is less strongly selected than are the upper-case amino acids). A library was constructed having both cyclic and linear members and was built in phage having a gene III stump display.

TABLE 1

TN9 and linear components in the second generation library:

Libraries of TN9s for cMet (cMet TN9 2nd lib #1)
E = 0.64A + 0.12C + 0.12G + 0.12T
Q = 0.12A + 0.64C + 0.12G + 0.12T
J = 0.12A + 0.12C + 0.64G + 0.12T
Z = 0.12A + 0.12C + 0.12G + 0.64T

TABLE 1-continued

TN9 and linear components in the second generation library:

Note: $(0.64)^{36} = 1.E-7$
$(0.64)^{39} = 2.5E-8$

Component 1: TN9 consensus with 3 AA left extension (SEQ ID NO: 518)

```
              S   M   G   S   E   T   R   P   T
ctcagcagtcactgtct tCC ATG Ggt tct gaa act cgc cct aca
                  NcoI . . .

e   a   g   s   w   h   C   s   G   P   P   t   F   e   C   w   w   y
jej jqz jjz ejz zjj qez tgt ejz ggt cct cct eqj ttc jej tgc zjj zjj zez G   T   E   P   T   E   A   S
gga acg gag ccg act gaa GCT AGC Gtga ctctgacagtctctgt
                        NheI . . .
``` cMet TN9 2nd lib #2: TN9 consensus with 3 AA right extension.

(SEQ ID NO: 519)

```
              S   M   G   S   E   T   R   P   T
ctcagcagtcactgtct tcc atg ggt tct gAa act cgc cct AcA
                  NcoI . . .

E   A   G   s   w   h   C   s   G   P   P   t   F   e   C   w   w   y
GAG GCT GGT ejz zjj qez tgt ejz ggt cct cct eqj ttc jej tgc zjj zjj zez g   t   e   P   T   E   R   P   S   S   S
jjz eqj jej ccg AcT gAA cgt cct agt GCT AGC Gtga ctctgacagtctctgt
                                    NheI . . .
``` cMet TN9 2nd lib #3 SIQCKGPPWFSCAMY (SEQ ID NO: 537) with 3 AA extension on left (SEQ ID NO: 520)

```
              S   M   G   S   E   T   R   P   T
ctcagcagtcactgtct tcc atg ggt tct gaa act cgc cct AcA
                  NcoI . . .

e   a   g   s   i   q   C   k   G   P   P   w   F   s   C   a   m   y
jej jqz jjz ejz ezz qej tgc eej ggt cct cct zjj ttc ejz tgt jqj ezj zez G   T   E   P   T   E   A   S   A
ggA Acg gAg ccg AcT gAA GCT AGC Gtga ctctgacagtctctgt
                        NheI . . .
``` cMet TN9 2nd lib #4 SIQCKGPPWFSCAMY (SEQ ID NO: 537) with 3 AA extension on right (SEQ ID NO: 521)

```
              S   M   G   S   E   T   R   P   T
ctcagcagtcactgtct tcc atg ggt tct gaa act cgc cct AcA
                  NcoI . . .

E   A   G   s   i   q   C   k   G   P   P   w   F   s   C   a   m   y
gag gcc ggt ejz ezz qej tgc eej ggt cct cct zjj ttc ejz tgt jqj ezj zez g   t   e   P   T   E   R   P   S   S   A
jjz eqj jej ccg AcT gAA cgt cct agt GCT AGC Gtga ctctgacagtctctgt
                                    NheI . . .
``` cMet TN9 5th lib 330-F05 YYGCKGPPTFECQWM (SEQ ID NO: 531)
with 3 AA extension on right
three peptides have the core sequence CKGPPTFEC (SEQ ID NO: 653)

(SEQ ID NO: 522)

```
              S   M   G   S   E   T   R   P   T
ctcagcagtcactgtct tcc atg ggt tct gAa act cgc cct AcA
                  NcoI . . .

E   A   G   y   y   g   C   k   G   P   P   t   F   e   C   q   w   m
GAG GCT GGT zez zez jjz tgc eej ggt cct cct eqz ttc jej tgt qee zjj ezj g   t   e   P   T   E   R   P   S   S   S
jjz eqj jej ccg AcT gAA cgt cct agt GCT AGC Gtga ctctgacagtctctgt
                                    NheI . . .
``` cMet TN9 6th lib: 550-G12 AFFCSGPPTFMCSLY (SEQ ID NO: 536)
with 3 AA extension on right
two peptides have the core sequence CSGPPTFMC (SEQ ID NO: 654)

(SEQ ID NO: 523)

```
              S   M   G   S   E   T   R   P   T
ctcagcagtcactgtct tcc atg ggt tct gAa act cgc cct AcA
                  NcoI . . .
```

TABLE 1-continued

TN9 and linear components in the second generation library:

```
E   A   G   a   f   f   C   s   G   p   P   t   F   m   C   s   l   y
GAG GCT GGT jqz zzq zzq tgt zqz ggt qqj cct eqz ttc ezj tgc ejq qzz zez g   t   e   P   T   E   R   P   S   S   S
jjz eqj jej ccg AcT gAA cgt cct agt GCT AGC Gtga ctctgacagtctctgt
                                    NheI . . .
```

(SEQ ID NO: 524)

cMet TN9 7th lib, three AA to left and let first P of gPP vary.
```
            S   M   G   S   E   T   R   P   T
ctcagcagtcactgtct tCC ATG Ggt tct gaa act cgc cct aca
                  NcoI . . .

e   a   g   q   f   k   C   a   G   p   P   s   F   a   C   w   m   t
jej jqz jjz qej zzq eej tgt jqz ggt qqj ccg ejz ttc jqq tgt zjj ezj eqq G   T   E   P   T   E   A   S
gga acg gag ccg act gaa GCT AGC Gtga ctctgacagtctctgt
                        NheI . . .
```

Example 11

Analysis of 94-E08 and Other Linear Peptides Selected for Binding cMet

The linear isolate 94-E08 (SEQ ID NO:454) has high affinity for cMet yet there were few other peptides isolated that had any homology to 94-E08 and those that did have very limited similarity over very short regions. Thus, three variable oligonucleotides based on 94-E08 were made: (1) vary the first 13 codons, keeping the last 7 constant; (2) vary 13 of the first 18, keeping 5 that showed some similarity to other isolates fixed; and (3) vary the last 13 codons, keeping the first 5 fixed, see table 4 below.

TABLE 4

Component #8 with variation in the first 13 positions (SEQ ID NO: 594).
```
              S   M   G   S   E
5'-tcactgtct tCC ATG Ggt tct gaa-
Scab . . . | NcoI | y   d   t   w   v   f   q   f   i   h
zez jez eqz zjj jzj zzz qej qez ezz qez - e   v   p   G   E   L   V   A   M   Q
jej jzj qqj ggt gag ctg gtt get atg cag -

G   G   S   G   T   E   A   S
ggt ggt agt ggt act gaa GCT AGC Gtga ctctgac-3'
                       | NheI |Scab . . .
```

Component #9 Fix five AAs and extend variegation to position 18 (SEQ ID NO: 595).
```
              S   M   G   S   E
5'-tcactgtct tCC ATG Ggt tct gaa-
   Scab . . . | NcoI | y   D   T   w   v   F   q   f   i   h
zez gat act zjj jzj ttt qej zzz ezz qez -

E   V   p   g   e   l   v   a   M   Q
gag gtt qqj jjz jej qzj jzj jqj atg caa|

G   G   S   G   T   E   A   S
ggt ggt agt ggt act gaa GCT AGC Gtga ctctgac-3'
                       | NheI |Scab . . .
```

Component #10 Fix first seven AAs and vary last 13 (SEQ ID NO: 596).
```
              S   M   G   S   E
```

TABLE 4-continued

```
5'-tcactgtct tCC ATG Ggt tct gaa-
   Scab . . . | NcoI |

Y   D   T   W   V   F   Q   F   i   h
tat gat act tgg gtt ttt caa ttt ezz qez - e   v   p   g   e   l   v   a   m   q
jej jzz qqj jjz jej qzj jzj jqj ezj qzz|

G   G   S   G   T   E   A   S
ggt ggt agt ggt act gaa GCT AGC Gtga ctctgac-3'
                       | NheI |Scab . . .
```

Oligonucleotide design for construction of the second generation peptide library (SEQ ID NOS:553-602; N.B. oligonucleotides marked "[RC]" consist of the reverse complement of the sequence shown):

```
vg#1                    NcoI . . .
(CM2_ZTPSAlt)  5'-tcactgtct tcc atg ggt tct gAa-3'

(CM2_TPLalt)   5-'tcactgtct tcc atg ggttct gAa act
                  cgc cct AcA-3'

(CM2_ZTPS)     5'-ctcagcagtcactgtct tcc at-3'

(CM2_TPLong)   5'-ctcagcagtcactgtct tcc atg ggt
                  tct gAa act cgc cct AcA-3'

(CM2_V1)       5'-tct gAa act cgc cct AcA jej
                  jqz jjz ejz zjj qez tgt ejz ggt cct
                  cct eqj ttc jej tgc zjj zjj zez
                  gga acg gag ccg act gaa get-3'

(CM2_BPL1) [RC] 5'-gga acg gag ccg act gaa GCT
                   AGC Gtga ctctgacagtctctgt-3'

(CM2_XBPS) [RC] 5'-CA Gtga ctctgacagtctctgt-3'

(BPL1_CM2) [RC] 5'-gga acg gag ccg act gaa GCT
                   AGC Gtga ctctgac-3'

(XBPS_CM2) [RC] 5'-act gaa GCT AGC Gtga
                   ctctgac-3'

NheI . . .
vg#2
(CM2_ZTPS)     5'-ctcagcagtcactgtct tcc at-3'
```

```
(CM2_TPLong)   5'-ctcagcagtcactgtct tcc atg ggt
               tct aGa act cgc cct AcA-3'

(CM2_V2)       5'-tct gAa act cgc cct Aca GAG GCT
               GGT ejz zjj qez tgt ejz ggt cct cct
               eqj ttc jej tgt zjj zjj zez jjz eqj
               jej ccg AcT gAA cgt cct agt g-3'

(CM2_2BPL) [Rd] 5'-ccg AcT gAA cgt cct agt GCT AGC
               Gtga ctctgacagtctctgt-3'

(CM2_XBPS) [RC] 5'-CA Gtg actctgacagtctctgt-3'

(BPL2_CM2) [RC] 5'-ccg AcT gAA cgt cct agt GCT AGC
               Gtga ctctgac-3'

(XPL2_CM2) [RC] 5'-ct agt GCT AGC Gtga ctctgac-3' vg#3
(CM2_ZTPS)     5'-ctcagcagtcactgtct tcc at-3'

(CM2_TPLong)   5'-ctcagcagtcactgtct tcc atg ggt tct
               gAa act cgc cct AcA-3'

(CM2_V3)       5'-tct gaa act cgc cct AcA jej jqz
               jjz ejz ezz qej tgc eej ggt cct cct
               zjj ttc ejz tgt jqj ezj ggA Acg gAg
               ccg AcT gAA GC-3'

(CM2_BPL1) [rc] 5'-gga acg gag ccg act gaa GCT AGC
               Gtga ctctgacagtctctgt-3'

(CM2_XBPS) [RC] 5'-CA Gtga ctctgacagtctctgt-3' vg#4
(CM2_ZTPS)     5'-ctcagcagtcactgtct tcc at-3'

(CM2_TPLong)   5'-ctcagcagtcactgtct tcc atg ggt
               tct gAg act cgc cct AcA-3'

(CM2_V4)       5'-tct gaa act cgc cct AcA gag ggc
               ggt ejz ezz qej tgc eej ggt cct
               cct zjj ttc ejz tgt jqj ezj jjz
               eqj jej ccg AcT gAA cgt cct agt GC-
               3'

(CM2_2BPL) [RC] 5'-ccg AcT gAA cgt cct agt GCT AGC
               Gtga ctctgacagtctctgt-3'

(CM2_XBPS) [RC] 5'-CA Gtga ctctgacagtctctgt-3' vg#5
(CM2_ZTPS)     5'-ctcagcagtcactgtct tcc at-3'

(CM2_TPLong)   5'-ctcagcagtcactgtct tcc atg ggt tct
               gAa act cgc cct AcA-3'

(CM2_V5)       5'-tct gAa act cgc cct AcA GAG GCT
               GGT zez zez jjz tgc eej ggt cct cct
               eqz ttc jej tgt qee zjj ezj jjz eqj
               jej ccg AcT gAA cgt cct agt GC-3'

(CM2_2BPL) [RC] 5'-ccg AcT gAA cgt cct agt GCT
               AGC Gtga ctctgacagtctctgt-3'

(CM2_XBPS) [RC] 5'-CA Gtga ctctgacagtctctgt-3' vg#6
(CM2_ZTPS)     5'-ctcagcagtcactgtct tcc at-3'

(CM2_TPLong)   5'-ctcagcagtcactgtct tcc atg ggt
               tct gAa act cgc cct AcA-3'

(CM2_V6)       5'-tct gAa act cgc cct AcA GAG GCT
               GGT jqz zzq zzq tgt zqz ggt qqj cct
               eqz ttc ejz tgc ejq qzz zez jjz eqj
               jej ccg AcT gAA cgt cct agt GC-3'

(CM2_2BPL) [RC] 5'-ccg AcT gAA cgt cct agt GCT AGC
               Gtga ctctgacagtctctgt-3'
```

```
(CM2_XBPS) [RC] 5'-CA Gtga ctctgacagtctctgt-3' vg#7
(CM2_ZTPS)     5'-ctcagcagtcactgtct tcc at-3'

(CM2_TPLong)   5'-ctcagcagtcactgtct tcc atg ggt
               tct gAa act cgc cct AcA-3'

(CM2_V7)       5'-tct gaa act cgc cct aca jej
               jqz jjz qej zzq eej tgt jqz ggt
               qqj ccg ejz zzq jqq tgt zjj ezj
               eqq gga acg gag ccg act gaa GC-3'

(CM2_BPL1) [RC] 5'-gga acg gag ccg act gaa GCT
               AGC Gtgactctgacagtctctgt-3'

(CM2_XBPS) [RC] 5'-CA Gtga ctctgacagtctctgt-3'
```

Component#8 Vary the first 13 positions.

```
(CM2_ZTPSAlt)  5-'tcactgtct tcc atg ggt tct gAa-3'

(CM2C8vg)      5'-tcactgtct tCC ATG Ggt tct gaa
               zez jez eqz zjj jzj jej jzj qqj
               ggt gag ctg gtt gct atg cag ggt
               ggt agt ggt act gaa GCT (L20botamp) [RC] 5-'ggt ggt agt ggt act gaa GCT
               AGC Gtga ctct-3'
```

Component#9 Fix five AAs and extend variegation to position 18.

```
(CM2_ZTPSAlt)        5'-tcactgtct tcc atg ggt tct gAa-3'

(CM2C9vg)            5-'tcactgtct tCC ATG Ggt tct-
                      gaa zez
                     gat act zjj jzj ttt qej zzz ezz qez
                     gag gtt qqj jjz jej qzj jzj jqj atg
                     caa ggt ggt agt ggt act gaa GCT-3'

(L20botamp)[RC]      5'-ggt ggt agt ggt act gaa GCT AGC
                     gTGa ctct-3'
```

Component#10 Fix first seven AAs and vary last 13.

```
(CM2_ZTPSAlt)          5'-tcactgtcttcc atg ggttct
                       gAa-3'

(CM2C10vg)             5'-tcactgtcttCC ATG Ggttct gaa
                       tat gat act tgg gtt ttt caa ttt
                       ezz qez jej jzz qqj jjz jej qzj
                       jzj jqj ezj qzz ggt ggt agt ggt
                       act gaa GCT-3'

(L20botamp) [RC]       5'-ggt ggt agt ggt act gaa GCT
                       AGC gTGa ctct-3'
```

Example 12

Construction of a Second Generation cMet-Binding Peptide Library

The phage vector DY3P82 was digested with NheI and NcoI, cleaned and treated with alkaline phosphatase. The 10 templates, CM2-V1 through CM2-V7, plus CM2-V8vg, CM2-V9vg and CM2-V10vg, were amplified separately, using the primer pairs listed in Table 5 below.

TABLE 5

| Template | Sense | Antisense |
|---|---|---|
| CM2_V1 | CM2_TPLONG | CM2_BPL1 |
| CM2_V2 | CM2_TPLONG | CM2_BPL1 |
| CM2_V3 | CM2_TPLONG | CM2_BPL1 |
| CM2_V4 | CM2_TPLONG | CM2_BPL1 |
| CM2_V5 | CM2_TPLONG | CM2_BPL1 |
| CM2_V6 | CM2_TPLONG | CM2_BPL1 |
| CM2_V7 | CM2_TPLONG | CM2_BPL1 |
| CM2_V8vg | CM2_ZTPSALT | L20BOTAMP |
| CM2_V9vg | CM2_ZTPSALT | L20BOTAMP |
| CM2_V10vg | CM2_ZTPSALT | L20BOTAMP |

Each sample was digested separately with NheI and NcoI, extracted with phenol/chloroform, and mixed in an equimolar ratio prior to performing the ligation. A vector:insert ratio of 1:5 was used. Ligated DNA constructs were electroporated into DH5α cells. The resulting library size was $1.12 \times 10^8$ different transformants.

Example 13

Measurement of Binding of Peptide Dimers to cMet

Using a BIAcore machine, the binding constants were determined for the peptide dimers (shown in FIGS. 13A-13C) binding to immobilized cMet-Fc.

Three densities of cMet-Fc (R&D Systems) were cross-linked to the dextran surface of a CM5 sensor chip by the standard amine coupling procedure (3 μM solution diluted 1:100, 1:50, or 1:20 with 50 mM acetate, pH 5.5). Flow cell 1 was activated and then blocked to serve as a reference subtraction.
Final immobilization levels achieved:
$R_L$ Fc 2 cMet-Fc=2582
$R_L$ Fc 3 cMet-Fc=5048
$R_L$ Fc 4 cMet-Fc=9721
Experiments were performed in PBST buffer (5.5 mM phosphate, pH 7.65, 0.15 M NaCl)+0.05% (v/v) Tween-20). Peptide dimers were dissolved in deionized H$_2$O to 1 mg/mL solutions. Dimers were diluted to 50 nM in PBS. Serial dilutions were performed to produce 25, 12.5, 6.25, and 3.125 nM solutions. All samples were injected in duplicate. For association, dimers were injected at 30 μL/minute for 3 minutes using the kinject program. Following a 10-minute dissociation, any remaining peptide was stripped from the cMet surface with two quick injects of 4M MgCl$_2$ for 2 minutes at 50 μL/minute. Sensorgrams were analyzed using BIAevaluation software 3.1. The heterodimer, Ac-GSPEMCMMFPFLYPC-NHHAPGGGK {PnAO6-Glut-K[Ac-GSFFPCWRLDRF-GYCHANAPGGGKJJ-Glut]-NH$_2$}—NH$_2$ (SEQ ID NO514 linked to SEQ ID NO:515), exhibits a $K_D$ of 0.79 nM.

Example 14

Enhancing the Serum Residence of cMet-Binding Peptides: Conjugation to Maleimide It is known in the art that compounds that contain maleimide and other groups that can react with thiols react with thiols on serum proteins, especially serum albumin, when the compounds are injected. The adducts have serum life times similar to serum albumin, more than 14 days in humans for example.

Methods are available that allow for the direct synthesis of maleimide-labeled linear peptides encompassed by the present invention (Holmes, D. et al., 2000. *Bioconjug. Chem.*, 11:439-444).

Peptides that include disulfides can be derivatized with maleimide in one of several ways. For example, a third cysteine can be added at the carboxy terminus. The added cysteine is protected with protecting group that is orthogonal to the type of groups used for the cysteines that are to form the disulfide. The disulfide is formed by selectively deprotecting the intended cysteines and oxidizing the peptide. The final cysteine is then deprotected and the peptide reacted with a large molar excess of a bismaleimide. The resulting compound has one of the maleimides free to react with serum albumin or other thiol-containing serum proteins.

Alternatively, a cyclic peptide of the present invention is synthesized with a lysine-containing C-terminal extention, such as -GGGK (SEQ ID NO:513). Lysines of the cMet-binding motif are protected with ivDde and the C-terminal lysine is deprotected. This lysine is reacted with a maleimide-containing compound, such as N-[e-maleimidocaproyloxy] succinimide ester (Pierce Biotechnology, Rockford, Ill.) or N-[a-Maleimidoacetoxy]succinimide ester (Pierce Biotechnology).

Example 15

Enhancing the Serum Residence of cMet-Binding Peptides: Conjugation to a Moiety that Binds Serum Albumin Non-Covalently Polypeptides having a molecular weight less than 50-60 kDa are rapidly excreted. Many small molecules, such as fatty acids, bind to serum albumin. Attaching a fatty acid or other serum albumin binding moiety to a peptide causes it to bind non-covalently to serum albumin and can greatly prolong serum residence. Fatty acids attached to peptides of the present invention should contain at least 12 carbons, preferably at least 14 carbons and, more preferably at least 16 carbons. The fatty acid could be straight-chain or branched. The fatty acid could be saturated or unsaturated. Palmate ($CH_3$—$(CH_2)_{14}$—CO— is a preferred fatty acid. This binding in serum can reduce the rate of excretion (Knudsen, L. et al., 2000. *J. Med. Chem.*, 43:1664-1669). Using methods known in the art, serum-albumin-binding moieties can be conjugated to any one of the peptides or multimeric polypeptide binding constructs herein disclosed. The serum-albumin-binding moiety can be joined to the cMet-binding peptide through a linker. The linker can be peptidic or otherwise, such as PEG. Linkers of zero to about thirty atoms are preferred. It is preferred that the linker be hydrophilic. The serum-albumin-binding moiety can be conjugated to the cMet-binding peptide or construct at either end or though a side group of an appended amino acid. Suitable side groups include lysine and cysteine. Such compounds also can comprise, for example, chelators for radionuclides, or other detectable labels or therapeutic constructs, as discussed herein. A cMet peptide or construct joined to a serum-albumin-binding moiety will bind cMet.

Example 16

Enhancing the Serum Residence of cMet-Binding Peptides: Conjugation to PEG

Attachment of PEG to proteins and peptides enhances the serum residence of these molecules. Attachment of PEG (linear or branched) to a cMet-binding peptide or multimeric polypeptide construct is expected give substantial enhancement of serum residence time. The molecular weight of the PEG be at least 10 kDa, more preferably at least 20 kDa, and most preferably 30 kDa or more. The PEG can be attached at the N- or C-terminus. Methods of attaching PEG to peptides are well known in the art. PEG can be attached to reactive side groups such as lysine or cysteine.

Example 17

Enhancing the Serum Residence of cMmet-Binding Peptides: Fusion to Serum Protein Proteins comprising serum albumin (SA) and other proteins have enhanced serum residence times. The amino-acid sequence of human SA (hSA) is shown in Table 10. Table 11 shows a fusion protein comprising of (SEQ ID NO:604), mature hSA, and SEQ ID NO:605. The cMet-binding peptides are separated from mature hSA by linkers that are rich in glycine to allow flexible spacing. One need not use all of hSA to obtain an injectable protein that will have an enhanced serum residence time. Chemical groups, such as maleimide and alpha bromo carboxylates, react with the unpaired cysteine (residue 34) to form stable adducts. Thus, one can attach a single chelator to hSA fusion proteins so that the adduct will bind a radionuclide. One can prepare a chelator with a maleimide group and couple that to hSA or an hSA derivative. Alternatively, hSA or an hSA derivative can be reacted with a bismaleimide and a chelator carrying a reactive thiol could be reacted with the bismaleimide-derivatized hSA.

Construction of genes that encode a given amino-acid sequence are known in the art. Expression of HSA fusions in *Saccharomyces cerevisiae* is known in the art.

Example 18

Pretargeting Radioactivity or Toxins to cMet Expressing Tumors

Conventional radioimmune cancer therapy is plagued by two problems. The generally attainable targeting ratio (ratio of administered dose localizing to tumor versus administered dose circulating in blood or ratio of administered dose localizing to tumor versus administered dose migrating to bone marrow) is low. Also, the absolute dose of radiation or therapeutic agent delivered to the tumor is insufficient in many cases to elicit a significant tumor response. Improvement in targeting ratio or absolute dose to tumor would be of great importance for cancer therapy.

The present invention provides methods of increasing active agent localization at a target cell site of a mammalian recipient. The methods include, for example, a) administering to a recipient a fusion protein comprising a targeting moiety and a member of a ligand-anti-ligand binding pair; b) thereafter administering to the recipient a clearing agent capable of directing the clearance of circulating fusion protein via hepatocyte receptors of the recipient, wherein the clearing agent incorporates a member of the ligand-anti-ligand binding pair; and c) subsequently administering to the recipient an active agent comprising a ligand/anti-ligand binding pair member.

It is known in the art that hexoses, particularly the hexoses galactose, glucose, mannose, mannose-6-phosphate, N-acetylglucosamine, pentamannosyl phosphate, N-acetylgalactosamine, thioglycosides of galactose, and mixtures thereof are effective in causing hepatic clearance. Binding of sugars to hepatic receptors is not, however, the only means of directing a molecule to the liver.

Clearance of carcinoembryonic antigen (CEA) from the circulation is by binding to Kupffer cells in the liver. We have shown that CEA binding to Kupffer cells occurs via a peptide sequence YPELPK (SEQ ID NO:607) representing amino acids 107-112 of the CEA sequence. This peptide sequence is located in the region between the N-terminal and the first immunoglobulin like loop domain. Using native CEA and peptides containing this sequence complexed with a heterobifunctional crosslinking agent and ligand blotting with biotinylated CEA and NCA we have shown binding to an 80 kD protein on the Kupffer cell surface. This binding protein may be important in the development of hepatic metastases. (Thomas, P. et al., 1992. *Biochem. Biophys. Res. Commun.*, 188: 671-677)

To use YPELPK (SEQ ID NO: 607) as a clearance agent, one fuses this sequence via a linker to a moiety that binds the fusion protein (Ab). For example, if the Ab has affinity for DOTA/Re, one would make a derivative having YPELPK attached to DOTA/Re; for example, rvYPELPKpsGGG-DOTA. 'rvYPELPKps' (SEQ ID NO:609) is a fragment of CEA which includes the YPELPK (SEQ ID NO:607) sequence identified by Thomas et al. (supra). Any convenient point on DOTA can be use for attachment. RVYPELP-KPSGGG-DOTA/cold Re (SEQ ID NO:608) would then be used as a clearing agent. The Fab corresponding to the fusion Ab would have affinity for the clearing agent of Kd <100 nM, preferably Kd <10 nM, and most preferably Kd <1 nM.

The therapeutic agent would contain DOTA/$^{185}$Re. In a preferred embodiment, the therapeutic agent would contain two or more DOTA moieties so that the Ab immobilized on the tumor would bind the bis-DOTA compound with high avidity. The two DOTA moieties would preferably be connected with a hydrophilic linker of ten to thirty units of PEG. PEG is a preferred linker because it is not degraded, promotes solubility. Ten to thirty units of PEG is not sufficient to give the bis DOTA compound a very long serum residence time. A half life of 30 minutes to 10 hours is acceptable. The serum half life should be longer than the radioactive half life of the radionuclide used so that most of the radiation is delivered to the tumor or to the external environment.

In one embodiment, a "fusion protein" of the present invention comprises at least one cMet-binding peptide fused to the amino terminus or the carboxy terminus of either the light chain (LC) or the heavy chain (HC) of a human antibody. Optionally and preferably, two or more cMet-binding peptides are fused to the antibody. The antibody is picked to have high affinity for a small molecule that can be made radioactive or have a toxin attached. Preferably, the affinity of the Fab corresponding to the Ab has affinity for the small molecule with IQ less than 100 nM, more preferably less than 10 nM, and most preferably less than 1 nM. The small molecule could be a chelator capable of binding a useful radioactive atom, many of which are listed herein. The small molecule could be a peptide having one or more tyrosines to which radioactive iodine can be attached without greatly affecting the binding property of the peptide.

Any cMet-binding peptide (CMBP) of the present invention can be fused to either end of either chain of an antibody that is capable of binding a small radioactive compound. Useful embodiments include:
1) CMBP#1::link::LC/HC,
2) LC::link::CMBP#1/HC,
3) LC/CMBP#1::link::HC,
4) LC/HC::link::CMBP#1,
5) CMBP#1::link1::LC::link2::CMBP#2/HC,
6) LC/CMBP#1::link1::HC::link2::CMBP#2,
7) CMBP#1::link1::LC/CMBP#2::link2::HC,
8) CMBP#1::link1::LC/HC::link2::CMBP#2,
9) LC::link1::CMBP#1/CMBP#2::link2::HC,
10) LC::link1::CMBP#1/HC::link2::CMBP#2, 11) CMBP#1::link1::LC::link2::CMBP#2/CMBP#3::link3::HC,
12) CMBP#1::link1::LC::link2::CMBP#2/HC::link3::CMBP#3,
13) CMBP#3::link3::LC/CMBP#1::link1::HC::link2::CMBP#2,
14) LC::link3::CMBP#3/CMBP#1::link1::HC::link2::CMBP#2, and
15) CMBP#1::link1::LC::link2::CMBP#2/CMBP#3::link3::HC::link4::CMBP#4.

In cases (5)-(15), the linkers (shown as "link1", "link2", "link3", and "link4") can be the same or different or be absent. These linkers, if present, are preferably hydrophilic, protease resistant, non-toxic, non-immunogenic, and flexible. Preferably, the linkers do not contain glycosylation sites or sequences known to cause hepatic clearance. A length of zero to fifteen amino acids is preferred. The cMet-binding peptides (CMBP#1, #2, #3, and #4) could be the same or different. If the encoded amino-acid sequences are the same, it is preferred that the DNA encoding these sequences is different.

Since antibodies are dimeric, each fusion protein will present two copies of each of the fused peptides. In case (15), there will be eight CMBPs present and binding to cMet-displaying cells should be highly avid. It is possible that tumor penetration will be aided by moderate cMet affinity in each of the CMBPs rather than maximal affinity.

The fusion protein is produced in eukaryotic cells so that the constant parts of the HC will be glycosylated. Preferably, the cells are mammalian cells, such as CHO cells.

The fusion proteins are injected into a patient and time is allowed for the fusion protein to accumulate at the tumor. A clearing agent is injected so that fusion protein that has not become immobilized at the tumor will be cleared. In previous pretargeting methods, the antibody combining site has been used to target to the tumor and biotin/avidin or biotin/streptavidin has been used to attach the radioactive or toxic agent to the immobilized antibody. The biotin/avidin or streptavidin binding is essentially irreversible. Here we fuse a target-binding peptide to the antibody which is picked to bind a radioactive or toxic agent. Because the fusion protein contains 2, 4, 6, or 8 CMBPs, binding of the fusion protein to the tumor is very avid. A clearing agent that will cause fusion protein not immobilized at the tumor to clear can be administered between 2 and 48 hours of the injection of the fusion protein. Because the clearance agent is monomeric in the moiety that binds the antibody, complexes of clearance agent and immobilized fusion protein will not have very long life times. Within 4 to 48 hours of injecting clearance agent, the immobilized antibody will have lost any clearance agent that binds there. The active agent is, preferably, dimeric in the moiety that binds the fusion protein. The active agent is injected between 2 and ~48 hours of injection of clearance agent.

Example 19

Binding of cMet Binding Peptides/Avidin HRP Complex to MDA-MB-231 Cells

The spacer length requirements for the binding of a biotinylated derivative of a cMet binding peptide, SEQ ID NO:514, to cMet expressing MDA-MB-231 cells were determined. In order to decide the spacer length to be placed in between peptide and biotin, derivatives were synthesized with no spacer, a single spacer, J, and two spacers, JJ. These three different derivatives of cMet-binding peptide SEQ ID NO:514 and a control peptide that does not bind to cMet, were tested as tetrameric complexes with neutravidin HRP for their ability to bind cMet expressing MB-231 cells. All three tetrameric complexes of cMet-binding peptides bound to the MB231 cells as compared to control peptide; however, the peptide with the JJ spacer exhibited the best $K_D$ (12.62 nM). This suggests that inclusion of two spacers (JJ) between the cMet-binding peptide and the biotin is better than one or no spacer.

Cell Culture: MDA-MB231 cells were obtained from ATCC and grown as monolayer culture in their recommended media plus 1 mL/L pen/strep (InVitrogen, Carlsbad, Calif.). Cells were split the day before the assay, 35000 cells were added to each well of a 96-well plate.

Binding of Peptide/Neutravidin HRP to MDA-MB-231 Cells

Figure 14:
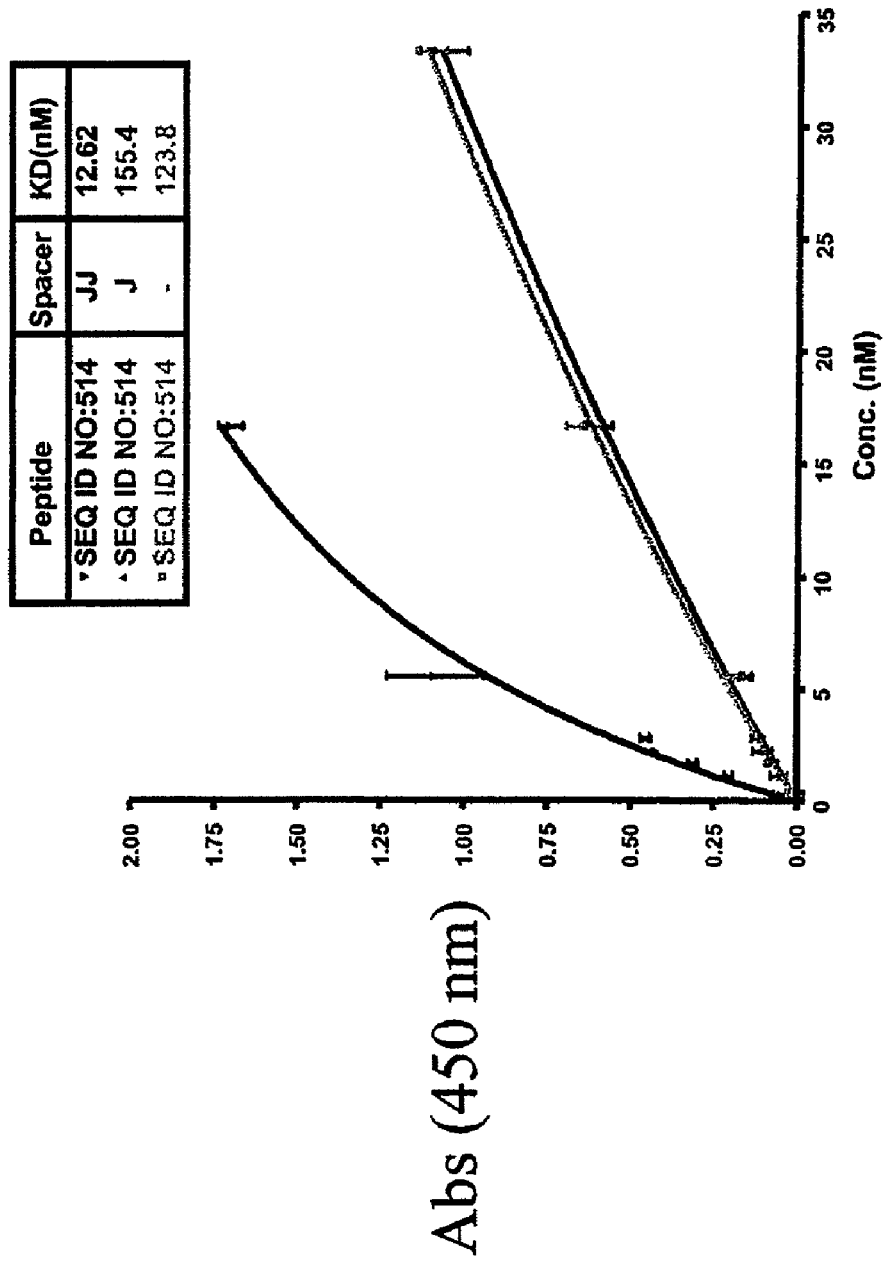
FIG. 14 is a graphical representation of data showing binding of derivatives of SEQ ID NO:514 with different spacer length and biotin. Derivatives have none, one J and two J spacers respectively in between the targeting sequence and biotin.

Complexes of control peptide, and the SEQ ID NO:514 derivatives described above, with neutravidin-HRP, were prepared as described above and tested for their ability to bind MDA-MB-231 cells. During the peptide/neutravidin-HRP complex preparation, a 7.5-fold excess of biotinylated peptides over neutravidin-HRP was used to make sure that all four biotin binding sites on neutravidin were occupied. After complex formation, the excess of free biotinylated peptides was removed using soft release avidin-sepharose to avoid any competition between free biotinylated peptides and neutravidin HRP-complexed biotinylated peptides. The experiment was performed at several different concentrations of peptide/neutravidin-HRP, from 0.28 nM to 33.33 nM, to generate saturation binding curves for derivatives without a J spacer and with a single J spacer (FIG. 14), and 0.28 nM to 16.65 nM to generate a saturation binding curve for the derivative with the JJ spacer (FIG. 14). In order to draw the saturation binding curve, the background binding of the control peptide/neutravidin HRP complex was subtracted from the binding of the SEQ ID NO:514 derivatives in complex with neutravidin-HRP for each concentration tested. Therefore, absorbance on the Y-axis of FIG. 14 is differential absorbance (cMet-binding peptide minus control peptide) and not the absolute absorbance. Analysis of the saturation binding data in FIG. using Graph Pad Prism software (version 3.0) yielded a $K_D$ of 12.62 nM (+1-3.16) for the tetrameric derivative with the JJ spacer, 155.4 nM (+/−86.56) for the tetrameric derivative with the J spacer and 123.8 nM (+/−37.71) for the tetrameric derivative without a spacer peptide complexes. These binding constants are, as expected, lower than that measured by FP for the related monodentate peptide SEQ ID NO:514 (880 nM).

Results: It is evident from FIG. 14 that the derivative with the JJ spacer showed much better binding to cMet on MDA-MB-231 cells than either of the other two derivatives, with a $K_D$ of 12.62 nM after subtracting binding of control peptide as background binding (n=1). This suggests that a certain minimum spacer length may be required to be able to reach multiple different binding sites on cells and thus achieve multimeric binding. This minimum spacer length could depend on the spacing between different target molecules on cells. As was the case where the binding target was KDR, the neutravidin-HRP assay with biotinylated peptides identified with phage display was useful for identifying peptides capable of binding to an immobilized target even when the affinity of the monomeric binding sequence is too low for an ELISA-type assay (with washing steps after binding) to work well.

TABLE 6 cMet-binding peptide sequences

CLASS I
TN6:

| SEQ ID NO: | Isolate | Sequence |
|---|---|---|
| SEQ ID NO: 001 | 571-005, | GSWIICWWDNCGSSAP |
| SEQ ID NO: 002 | 465-A06, | GSYYDCREFQCNKPAP |
| SEQ ID NO: 003 | 465-D09, | GSSHLCNPEFCHFTAP |
| SEQ ID NO: 004 | 569-H10, | GSMLMCELWWCRFLAP |
| SEQ ID NO: 005 | 470-E11, | GSLIFCPYGECMMYAP |
| SEQ ID NO: 006 | 452-F01, | GSEYSCRTSRCIFSAP |
| SEQ ID NO: 007 | 569-C03, | GSFILCWWTFCDTNAP |
| SEQ ID NO: 008 | 574-H03, | GSSTICPGTACVDHAP |
| SEQ ID NO: 009 | 567-C08, | GSLIICWWSWCDKQAP |
| SEQ ID NO: 010 | 561-C08, | GSFNICPYQWCTLWAP |

Consensus Motif: G-S-X1-X2-X3-C-X4-X5-X6-X7-C-X8-X9-X10-A-P-G-G-K (SEQ ID NO: 525); where X1 is F, L, S, W, Y, or M; X2 is I, Y, H, T, or N; X3 is I, L, D, M, F, or S, preferably I; X4 is P, R, W, N, or E, preferably W or P; X5 is W, Y, E, P, L, T, or G; X6 is S, T, D, F, E, W, G, or Q; X7 is F, W, N, Q, E, R, or A; X8 is G, N, H, R, M, I, D, V, or T; X9 is S, K, F, M, T, D, or L; and X10 is S, P, T, L, Y, N, H, Q, or W.

CLASS II
TN8:

| SEQ ID NO: | Isolate | Sequence |
|---|---|---|
| SEQ ID NO: 011 | 573-F04, | AGGFACGPPWDICWMFGT |
| SEQ ID NO: 012 | 570-E07, | AGAWNCEYPTFICEWQGA |
| SEQ ID NO: 013 | 456-E04, | AGNWICNLSEMRCYPKGT |
| SEQ ID NO: 014 | 434-E12, | AGDGWCMAWPEICEWLGT |
| SEQ ID NO: 015 | 489-A04, | AGLYLCDLSIMYCFFQGT |
| SEQ ID NO: 016 | 484-D08, | AGWWSCQWELNVCIWQGT |
| SEQ ID NO: 017 | 482-D02, | AGYYHCIDDFPQCKWMGT |
| SEQ ID NO: 018 | 437-A09, | AGWFECEFGFWGCNWLGT |
| SEQ ID NO: 019 | 352-E04, | AGTVYCSWESSECWWVGT |
| SEQ ID NO: 020 | 376-E05, | AGVWICRVWDDECFFQGT |
| SEQ ID NO: 021 | 482-A12, | AGDHYCWEEWWFCWDSGT |
| SEQ ID NO: 022 | 423-C11, | AGVLQCIGFEWFCDIWGT |
| SEQ ID NO: 023 | 499-C09, | AGVIVCNLSMMYCLYPGT |
| SEQ ID NO: 024 | 457-A09, | AGYPECKDNYHWCEWKGT |
| SEQ ID NO: 025 | 573-E07, | AGWTWCDLSMMSCIFHGT |
| SEQ ID NO: 026 | 465-F08, | AGVTNCNLSTMFCFLHGT |
| SEQ ID NO: 027 | 465-E09, | AGTLSCSEEYKSCQLQGT |
| SEQ ID NO: 028 | 444-B08, | AGTIRCNLAMMVCMFEGT |
| SEQ ID NO: 029 | 465-E11, | AGQYLCTQAALGCPEWGT |
| SEQ ID NO: 030 | 465-D12, | AGQMWCAEKNSKCYQWGT |
| SEQ ID NO: 031 | 470-A02, | AGQAVCEWGPFWCQMQGT |
| SEQ ID NO: 032 | 465-C01, | AGPYSCHSESHDCKLMGT |
| SEQ ID NO: 033 | 448-H02, | AGPLFCFEWPSLCHWGGT |
| SEQ ID NO: 034 | 465-D01, | AGNLPCHWNMSVCDHQGT |
| SEQ ID NO: 035 | 571-C11, | AGMDFCEGFWFLCIGNAT |
| SEQ ID NO: 036 | 465-B11, | AGLLGCWDMPMECTGEGT |
| SEQ ID NO: 037 | 442-E08, | AGKYMCEGFEWFCEMWGT |
| SEQ ID NO: 038 | 465-C11, | AGKTVCQKWESVCSGMGT |
| SEQ ID NO: 039 | 465-F10, | AGKQWCVVWEETCDQLGT |
| SEQ ID NO: 040 | 471-A11, | AGIWFCNNEEKSCWAYGT |
| SEQ ID NO: 041 | 465-C07, | AGHTICQHKALGCPANGT |
| SEQ ID NO: 042 | 465-D04, | AGHFECPKHQYMCDMPGT |
| SEQ ID NO: 043 | 445-E04, | AGGNWCSFYEELCEWLGT |
| SEQ ID NO: 044 | 465-B06, | AGGHWCLELKHLCPPYGT |
| SEQ ID NO: 045 | 470-C02, | AGFWDCGWMMQDCHMHGT |

TABLE 6-continued cMet-binding peptide sequences

SEQ ID NO: 046    458-B05,  ADAWMCEYFQWNCGDKGT

SEQ ID NO: 047    545-E08,  GDGFLCRWENGWCEFWDP

Consensus Motif: A-G-X1-X2-X3-C-X4-X5-X6-X7-X8-X9-C-X10-X11-X12-G-T-G-G-G-K (SEQ ID NO 526); where
X1 is any amino acid other than C, preferably G, V, W, T, K, Q;

X2 is any amino acid other than C, preferably W, Y, L, F, T;

X3 is any amino acid other than C, preferably W, E, F, I, L, S

X4 is any amino acid other than C, preferably E, N, Q;

X5 is any amino acid other than C, preferably W, L, E;

X6 is any amino acid other than C, preferably E, S, Y;

X7 is any amino acid other than C, preferably E, M, P;

X8 is any amino acid other than C, preferably M, S, W;

X9 is any amino acid other than C, preferably F, L, V;

X10 is any amino acid other than C, preferably E, D, W;

X11 is any amino acid other than C, preferably W, F, M;
and

X12 is any amino acid other than C, preferably Q, W, L.

CLASS III
TN9 #1:

SEQ ID NO:    Isolate   Sequence

SEQ ID NO: 048    325-H05,  AGSIQCKGPPWFSCAMYGT

SEQ ID NO: 049    330-F05,  AGYYGCKGPPTFECQWMGT

SEQ ID NO: 050    333-F09,  AGQFKCAGPPSFACWMTGT

SEQ ID NO: 051    336-G04,  AGWFQCKGPPSFECERHGT

SEQ ID NO: 052    334-G06,  AGWTHCIGPPTFECIPMGT

SEQ ID NO: 053    330-B07,  AGSFACKGPPTFACVEFGT

SEQ ID NO: 054    330-C10,  AGNYFCAGSPSFSCYFMGT

SEQ ID NO: 055    331-G04,  AGSWHCAGPPSFECWEFGT

SEQ ID NO: 056    548-F06,  AGWISCAGPPTFACWPGGT

SEQ ID NO: 057    538-F08,  AGFVNCKGPPTFECILTGT

SEQ ID NO: 058    547-H07,  AGDWICHGPPMFECEWVGT

SEQ ID NO: 059    323-A11,  AGYTSCVGPPSFECTPYGT

SEQ ID NO: 060    333-H03,  AGYFECKGPPTFECWLSGT

SEQ ID NO: 061    329-D02,  AGHAWCSGPPRFECWPPGT

SEQ ID NO: 062    550-C09,  AGHYWCAGPPTFICMGPGT

SEQ ID NO: 063    548-E08,  AGETTCLGWPTFVCVDYGT

SEQ ID NO: 064    332-A05,  AGHGTCRGWPTFECIYFGT

SEQ ID NO: 065    330-C01,  AGDWHCQGPPAFMCWMIGT

SEQ ID NO: 066    545-A09,  AGLPKCSGPPWFSCYYGGT

SEQ ID NO: 067    334-C08,  AGGWECTGPPWFQCGYYGT

SEQ ID NO: 068    333-C05,  AGDIVCTGHPYFECWSWGT

SEQ ID NO: 069    551-B02,  AGTWHCAGPPWFTCYMDGT

SEQ ID NO: 070    551-G12,  AGSWECTGPPSFHCQWYGT

SEQ ID NO: 071    330-G09,  AGHWICVGPPTFSCQWHGT

SEQ ID NO: 072    331-F01,  AGEWWCHGPPEFLCYWTGT

SEQ ID NO: 073    274-B07,  AGETVCYWLNGWFCVDDGT

SEQ ID NO: 074    335-D11,  AGSIQCVGPPSFECTPYGT

SEQ ID NO: 075    336-D07,  AGYSVCKGYPSFECAFFGT

SEQ ID NO: 076    332-C03,  AGVNSCLGPPTFECYQMGT

SEQ ID NO: 077    331-D03,  AGYWHCKGPPHFACEFHGT

SEQ ID NO: 078    331-G06,  AGNWICTGPPSFGCWYHGT

SEQ ID NO: 079    552-G03,  AGYWSCAGPPMFMCTWQGT

SEQ ID NO: 080    552-G11,  AGYWDCKGPPHFFCEWHGT

SEQ ID NO: 081    550-G08,  AGYFHCSGSPWFQCDYYGT

SEQ ID NO: 082    550-G12,  AGWYNCSGENFWNCKWIGT

TABLE 6-continued cMet-binding peptide sequences

SEQ ID NO: 083   552-A01,   AGWSDCLGPPQFTCVHWGT

SEQ ID NO: 084   548-C06,   AGTMYCLGPPTFICQQYGT

SEQ ID NO: 085   545-B12,   AGSYWCSGPPTFMCRYEGT

SEQ ID NO: 086   549-F06,   AGSTDCRGHPTFECWGWGT

SEQ ID NO: 087   552-F01,   AGSSPCKGWPTFECYFYGT

SEQ ID NO: 088   547-H12,   AGSIACTGWPYFSCIDLGT

SEQ ID NO: 089   550-F11,   AGQFYCSGPPTFQCIMIGT

SEQ ID NO: 090   548-D08,   AGPWKCTGPPTFSCIQFGT

SEQ ID NO: 091   549-D02,   AGNYWCSGPPSFICHAVGT

SEQ ID NO: 092   552-F02,   AGMTLCAGPPTFECYEVGT

SEQ ID NO: 093   545-E04,   AGETKCSGPPYFYCWMEGT

SEQ ID NO: 094   545-E05,   AGETFCVGNPSFECWSWGT

SEQ ID NO: 095   547-H03,   AGETFCSGWPTFECMQWGT

SEQ ID NO: 096   552-G09,   AGEIFCVGPPTFTCMWTGT

SEQ ID NO: 097   550-A08,   AGDFICQGPPSFVCTNIGT

SEQ ID NO: 098   550-G07,   AGAFFCSGPPTFMCSLYGT

SEQ ID NO: 099   551-A05,   AGWGWCSGPPMFMCTEYGT

SEQ ID NO: 100   548-C10,   GSEFECTGWPEFRCYEYAP

SEQ ID NO: 101   465-C10,   GSILYCINRNDPQCPYTAP

Consensus Motif: G-X1-X2-X3-C-X4-G-X5-P-X6-F-X7-C-X8-X9-X10-G-T (SEQ ID NO: 527); where:
X1 is any amino acid other than C, preferably E, S, Y, or W;

X2 is any amino acid other than C, preferably W, T, or F;

X3 is any amino acid other than C, preferably W, H, or F;

X4 is any amino acid other than C, preferably A, K, S, or T;

X5 is any amino acid other than C, preferably P or W;

X6 is any amino acid other than C, preferably T or S;

X7 is any amino acid other than C, preferably E or S;

X8 is any amino acid other than C, preferably W, Y, or I;

X9 is any amino acid other than C, preferably W, Y, M, or E; and

X10 is any amino acid other than C, preferably Y.

CLASS IV
TN9 #2:

SEQ ID NO:   Isolate   Sequence

SEQ ID NO: 102   605-G10,   SETRPTEAGDLICSGPPTFICTLYHTEPTE

SEQ ID NO: 103   593-C01,   SETRPTQAVRSQCSGPPTFECWYFGTEPTE

SEQ ID NO: 104   592-C01,   SETRPTEGGSWYCSGPPAFECWWYGTEPTE

SEQ ID NO: 105   591-E01,   SETRPTVASRWHCNGPPTFECWRYGTEPTE

SEQ ID NO: 106   590-E01,   SETRPTEAGTFHCSGPPTFECWSYGPKPTE

SEQ ID NO: 107   589-B01,   SETRPTEAGSLWCMGPPWFCCVIYGTQPTE

SEQ ID NO: 108   607-A02,   SETRPTEAGILHCSGPPTFECWWNYTEPTE

SEQ ID NO: 109   590-F01,   SETRPTESGRVHCPGPPWFRCARNGTEPTE

SEQ ID NO: 110   589-C01,   SETRPTAAGRILCTGPPWFSCAMYGTEPTE

SEQ ID NO: 111   606-B11,   SETRPTEAADWLCSGPPTFECWWFGTEPTE

SEQ ID NO: 112   593-E01,   SETRPTQVGRWQCDGPPTFACRSYGTEPTE

SEQ ID NO: 113   592-F12,   SETRPTEAGSTKCSGPPTFECWWFDTEPTE

SEQ ID NO: 114   590-F07,   SETRPTVAGSWHCSGPPTFECWWYGTEPTE

SEQ ID NO: 115   588-D02,   SETRPTEAGRNHCKGPPGFRCAMTDTEPTE

SEQ ID NO: 116   607-H09,   SETRPTETDFVYCRGPPTFECWWYGTEPTE

SEQ ID NO: 117   590-H01,   SETRPTSSGSRHCKGPPTFECWGYGTEPTE

SEQ ID NO: 118   589-F01,   SETRPTEAGSWRCSGPPTFECWWYETSPTE

SEQ ID NO: 119   608-F11,   SETRPTDAIRSYCSGPPTFECWWFGTEPTE

SEQ ID NO: 120   606-D11,   SETRPTEAGSWNCSGPPAFECWWYGSEPTE

SEQ ID NO: 121   604-D04,   SETRPTEAGSWQCSGPPTFECWSFGTEPTE

TABLE 6-continued cMet-binding peptide sequences

SEQ ID NO: 122   602-A11,   SETRPTEAGSWHCNGPPTFECWWYDMEPTE

SEQ ID NO: 123   593-F02,   SETRPTEAGRVSCLGPPTFECWWFVPEPTE

SEQ ID NO: 124   591-H05,   SETRPTDAGSWRCAGPPTFECWWFGTEPTE

SEQ ID NO: 125   590-H06,   SETRPTEPVTWQCTGPPTFECWWLGTEPTE

SEQ ID NO: 126   588-F10,   SETRPTDAVSTHCNGPPTFECYIYGTEPTE

SEQ ID NO: 127   608-G03,   SETRPTVAESWYCVGPPSFECWWYGTEPTE

SEQ ID NO: 128   604-D09,   SETRPTEAGSWNCSGPPTFECWSYQTEPTE

SEQ ID NO: 129   602-A12,   SETRPTEAGSGHCNGPPTFKCWWYDMEPTE

SEQ ID NO: 130   592-G11,   SETRPTDQDSWQCSGPPTFECWWYGTEPTE

SEQ ID NO: 131   588-G01,   SETRPTESTQVQCAGPPSFACWMTGTEPTE

SEQ ID NO: 132   606-E05,   SETRPTEVESWHCSGPPTFECWWYGTEPTE

SEQ ID NO: 133   594-C07,   SETRPTEAGSFHCSGPPTFECWLYWTDPTE

SEQ ID NO: 134   592-H01,   SETRPTEAGQFGCKGPPPFECKLMGRVPTE

SEQ ID NO: 135   605-C05,   SETRPTDTVTWHCNGPPTFECWWYGTEPTE

SEQ ID NO: 136   594-E08,   SETRPTEADRWHCDGPPTFECWWYGTEPTE

SEQ ID NO: 137   593-B11,   SETRPTEAGSIQCVGPPWFSCRMYVTEPTE

SEQ ID NO: 138   590-C01,   SETRPTVSGSWQCVGPPTFECWSYGTEPTE

SEQ ID NO: 139   612-G11,   SETRPTENGSWHCNGPPTFECWWYGTEPTE

SEQ ID NO: 140   612-E08,   SETRPTEAGSWHCSGPPIFECWWYDMEPTE

SEQ ID NO: 141   612-A02,   SETRPTVDGGWHCNGPPTFECWMYGTEPTE

SEQ ID NO: 142   611-G01,   SETRPTDAGTWNCTGPPSFECWWFGTEPTE

SEQ ID NO: 143   610-G04,   SETRPTWDGKWHCSGPPTFECWWYGTEPTE

SEQ ID NO: 144   610-E06,   SETRPTEAGSWRCSGPPTFECWWYYTEPTE

SEQ ID NO: 145   610-C06,   SETRPTEAGNWLCSGPPTFECWWYVTGPTE

SEQ ID NO: 146   610-A04,   SETRPTEGGNWHCSGPPTFECWLYGTEPTE

SEQ ID NO: 147   612-D02,   SETRPTEAGGWHCSGPPTFECWWFNMEPTE

SEQ ID NO: 148   612-A12,   SETRPTEVISWHCSGPPTFECYRYGTEPTE

SEQ ID NO: 149   611-D03,   SETRPTEVGSWHCNGPPTFECWWYGTEPTE

SEQ ID NO: 150   610-G10,   SETRPTLASTWYCSGPPTFECWWYGTEPTE

SEQ ID NO: 151   610-A11,   SETRPTEAGGWYCKGPPTFECWWDGTEPTE

SEQ ID NO: 152   612-H02,   SETRPTEAGGWFCSGPPTFECWWYDTVPTE

SEQ ID NO: 153   612-B01,   SETRPTEAATWQCSGPPTFECWGYGTEPTE

SEQ ID NO: 154   610-C12,   SETRPTEAGDYVCVGPPTFECYLMDAEPTE

SEQ ID NO: 155   610-B01,   SETRPTEAGGWYCSGPPSFECWSYGTEPTE

SEQ ID NO: 156   612-H04,   SETRPTESSSWHCSGPPTFECWRFGTEPTE

SEQ ID NO: 157   612-B09,   SETRPTEAGSWYCSGPPTFECWWYYAEPTE

SEQ ID NO: 158   611-G07,   SETRPTLAGNWQCSGPPTFECWWYGTEPTE

SEQ ID NO: 159   611-E10,   SETRPTEAGSWHCNGPPTFECWQYGTEPTE

SEQ ID NO: 160   610-H02,   SETRPTEAGSWECHGPPSFECWWYGTEPTE

SEQ ID NO: 161   610-D03,   SETRPTEAGSWRCSGPPTFECWWYDAEPTE

SEQ ID NO: 162   610-B03,   SETRPTEAGSWNCAGPPTFECWWYGTEPTE

SEQ ID NO: 163   612-H05,   SETRPTEAGSFYCSGPPTFECWQYVPEPTE

SEQ ID NO: 164   612-F05,   SETRPTEAGSWMCSGPPTFECWQYFTEPTE

SEQ ID NO: 165   612-B10,   SETRPTEAGSLHCSGPPTFECWWWETEPTE

SEQ ID NO: 166   611-E11,   SETRPTEEGVWHCNGPPTFECWWYGTEPTE

SEQ ID NO: 167   610-F08,   SETRPTEAGRWNCSGPPTFECWWYSTEPTE

SEQ ID NO: 168   610-D05,   SETRPTEAGSWRCSGPPTFECWWFGTEPTE

SEQ ID NO: 169   610-B04,   SETRPTQAVSSYCSGPPTFECWSFGTEPTE

SEQ ID NO: 170   612-B12,   SETRPTEAGRSYCSGPPTFECWWYATEPTE

SEQ ID NO: 171   611-H01,   SETRPTVVAKVHCAGPPTFECWTYGTEPTE

SEQ ID NO: 172   610-H05,   SETRPTEPGSWHCSGPPTFVCWWWGTEPTE

SEQ ID NO: 173   610-F10,   SETRPTEAGRWHCSGPPTFECWWHDTEPTE

TABLE 6-continued cMet-binding peptide sequences

SEQ ID NO: 174  612-H07, SETRPTEAGSWQCTGPPTFECWGYVEEPTE

SEQ ID NO: 175  612-G09, SETRPTEAGSWQCGPPTFECWWYYTGPTE

SEQ ID NO: 176  612-F08, SETRPTEAGSWYCTGPPTFECWLYETYPTE

SEQ ID NO: 177  611-H08, SETRPTAAWSGSCSGPPSFECWNYGTEPTE

SEQ ID NO: 178  610-E01, SETRPTEAGSWQCSGPPTFACWWYGTEPTE

SEQ ID NO: 179  610-B09, SETRPTEAGILHCSGPPTFECWWEVMEPTE

SEQ ID NO: 180  612-E07, SETRPTEAGRVACSGPPTFECWSYDEEPTE

SEQ ID NO: 181  612-C11, SETRPTEAGNWECQGPPTFECWWFGTEPTE

SEQ ID NO: 182  610-E04, SETRPTLASNGYCNGPPTFECWHYGTEPTE

SEQ ID NO: 183  610-B12, SETRPTEAGSFHCSGPPTFECIWYGSEPTE

SEQ ID NO: 184  616-B11, SETRPTEAGSWYCSGPPTFACWWDGTEPTE

SEQ ID NO: 185  615-H08, SETRPTQGDNWNCSGPPTFECWWYGTEPTE

SEQ ID NO: 186  615-B11, SETRPTEAGRWHCNGPPTFECWRYDYDPTE

SEQ ID NO: 187  614-C07, SETRPTEAYSWECTGPPMFECWWYGTEPTE

SEQ ID NO: 188  613-H12, SETRPTEVVDWHCSGPPQFECWWYGTEPTE

SEQ ID NO: 189  613-F02, SETRPTEAGSWNCSGPPTFECWWYGSEPTE

SEQ ID NO: 190  613-D05, SETRPTASGSWHCSGPPTFECWIFGTEPTE

SEQ ID NO: 191  612-H12, SETRPTEAGAWYCMGPPTFECWWYDRGPTE

SEQ ID NO: 192  616-D05, SETRPTEAGGLHCSGPPTFECWWYDTEPTE

SEQ ID NO: 193  615-C01, SETRPTVGGSWDCKGPPTFECWSYGTEPTE

SEQ ID NO: 194  614-E09, SETRPTEAGAWSCLGPPTFECWWYGTEPTE

SEQ ID NO: 195  614-A03, SETRPTEAGSLHCSGPPTFECWWFDTEPTE

SEQ ID NO: 196  616-C02, SETRPTAGRSWECSGPPTFECWVFGTEPTE

SEQ ID NO: 197  615-C04, SETRPTDNGSWHCNGPPTFECWWYGTEPTE

SEQ ID NO: 198  614-C12, SETRPTEAGSWQCKGPPTFECWWYGTEPTE

SEQ ID NO: 199  615-C11, SETRPTEVGNYKCSGPPTFECWWYGTEPTE

TABLE 6-continued cMet-binding peptide sequences

SEQ ID NO: 200  614-H08, SETRPTEAGSWHCVGPPTFECWGYVTEPTE

SEQ ID NO: 201  614-E11, SETRPTEAGSFVCKGPPTFECYWFGQDPTE

SEQ ID NO: 202  616-E10, SETRPTEAGSWHCSGPPTFECWWYGPDPTE

SEQ ID NO: 203  615-D02, SETRPTEAERWHCSGPPTFECWWYGTEPTE

SEQ ID NO: 204  614-F04, SETRPTEAGSWHCSGPPTFECWFYVKEPTE

SEQ ID NO: 205  614-D06, SETRPTEAGSWDCSGPPTFECWWFGTEPTE

SEQ ID NO: 206  614-B08, SETRPTEPAGWECRGPPSFECLWYGTEPTE

SEQ ID NO: 207  613-H01, SETRPTDAGPWNCTGPPSFECWWYGTEPTE

SEQ ID NO: 208  613-E04, SETRPTEARGWHCSGPPTFECWLWGTEPTE

SEQ ID NO: 209  613-808, SETRPTEAGRWNCSGPPTFECWQYEMDPTE

SEQ ID NO: 210  615-D04, SETRPTEAGSWYCSGPPTFECFWYDTEPTE

SEQ ID NO: 211  615-A05, SETRPTESGSWHCSGPPTFECWWFGTEPTE

SEQ ID NO: 212  614-E04, SETRPTEAGSWLCTGPPTFECWWFDTDPTE

SEQ ID NO: 213  613-E06, SETRPTEPSHWHCVGPPTFACWWYVTDPTE

SEQ ID NO: 214  613-C05, SETRPTEAGSWYCSGPPMFECYLFVTEPTE

SEQ ID NO: 215  616-C07, SETRPTEAVNWHCLGPPSFECWQFGTEPTE

SEQ ID NO: 216  615-G02, SETRPTEAGSWHCSGPPTFECWWYGTDPTE

SEQ ID NO: 217  615-E06, SETRPTEAGSWHCSGPPTFECWSFVSLPTE

SEQ ID NO: 218  615-A08, SETRPTEGSEWSCIGPPSFECWWYGTEPTE

SEQ ID NO: 219  614-G01, SETRPTEDGYWNCSGPPTFECWWHGTEPTE

SEQ ID NO: 220  613-D01, SETRPTEAGSWSCSGPPTFECWPYYTEPTE

SEQ ID NO: 221  614-G02, SETRPTEAGSWYCSGPPTFECWWYWPEPTE

SEQ ID NO: 222  614-E06, SETRPTDDGRWSCAGPPTFECWRYGTEPTE

SEQ ID NO: 223  620-E11, SETRPTEGGSWSCGGPPTFECWWFGTEPTE

SEQ ID NO: 224  620-A11, SETRPTVTGSWYCSGPPTFECWWYGTEPTE

SEQ ID NO: 225  618-F04, SETRPTEASSWYCTGPPAFECWWYGTEPTE

TABLE 6-continued cMet-binding peptide sequences

| SEQ ID NO: 226 | 617-G06, | SETRPTEAGSWLCSGPPTFECWWYGTEPTE |
| --- | --- | --- |
| SEQ ID NO: 227 | 616-G06, | SETRPTESVRWYCSGPPTFECWWYGTEPTE |
| SEQ ID NO: 228 | 620-F10, | SETRPTEAGRLVCSGPPTFMCRTYATDPTE |
| SEQ ID NO: 229 | 619-G04, | SETRPTEAGSWECTGPPWFVCRQYAIEPTE |
| SEQ ID NO: 230 | 618-F12, | SETRPTEAGYLYCSGPPTFECWWYDTMPTE |
| SEQ ID NO: 231 | 618-B06, | SETRPTEAGSWHCSGPPTFECWWFGTEPTE |
| SEQ ID NO: 232 | 617-E09, | SETRPTEAGNWHCLGPPTFECWWYGTEPTE |
| SEQ ID NO: 233 | 616-F10, | SETRPTEAGSWHCSGPPTFECWWYDTEPTE |
| SEQ ID NO: 234 | 620-B11, | SETRPTESGGWYCSGPPAFECWWYGTEPTE |
| SEQ ID NO: 235 | 619-G07, | SETRPTVAGAVSCSGPPTFECWWYGTEPTE |
| SEQ ID NO: 236 | 619-E11, | SETRPTEAGRWYCSGPPTFECWWFLPDPTE |
| SEQ ID NO: 237 | 619-B12, | SETRPTEAGGWHCSGPPSFECWWFDTVPTE |
| SEQ ID NO: 238 | 618-G11, | SETRPTGVGGWYCSGPPSFECWLYGTEPTE |
| SEQ ID NO: 239 | 618-B11, | SETRPTQADYLHCSGPPTFECFWYGTEPTE |
| SEQ ID NO: 240 | 617-F01, | SETRPTGDGNWHCNGPPTFECWRFGTEPTE |
| SEQ ID NO: 241 | 617-B01, | SETRPTEASNYHCIGPPTFECFWYGTEPTE |
| SEQ ID NO: 242 | 616-G12, | SETRPTEAGDWLCKGPPTFECWWQVTDPTE |
| SEQ ID NO: 243 | 620-G01, | SETRPTEAGSWHCNGPPTFECWWYSSDPTE |
| SEQ ID NO: 244 | 620-C10, | SETRPTEDGGWRCSGPPTFECWWYGTEPTE |
| SEQ ID NO: 245 | 619-G09, | SETRPTEAGRIECKGPPWFSCVIYGTEPTE |
| SEQ ID NO: 246 | 619-F06, | SETRPTGGGSWNCSGPPTFECWWYGTEPTE |
| SEQ ID NO: 247 | 618-C03, | SETRPTEAGSLYCSGPPTFECWWYITHPTE |
| SEQ ID NO: 248 | 617-F02, | SETRPTEAGRWHCSGPPRFECWWYDTEPTE |
| SEQ ID NO: 249 | 616-H01, | SETRPTEYGSWHCSGPPTFECWYHGTEPTE |
| SEQ ID NO: 250 | 618-D01, | SETRPTEAGNWHCSGPPSFECWWYATEPTE |
| SEQ ID NO: 251 | 617-F03, | SETRPTEQGSWHCKGPPTFECWSYGTEPTE |
| SEQ ID NO: 252 | 616-H03, | SETRPTDAANYHCSGPPTFECWWYGTEPTE |
| SEQ ID NO: 253 | 616-G02, | SETRPTEAGSWYCSGPPMFECWWLAEEPTE |
| SEQ ID NO: 254 | 620-G09, | SETRPTEAGGWYCSGPPAFECWWYATEPTE |
| SEQ ID NO: 255 | 620-D12, | SETRPTEAGIWSCSGPPTFECWWYESSPTE |
| SEQ ID NO: 256 | 619-A09, | SETRPTEEGLRVCSGPPTFECWWYGTEPTE |
| SEQ ID NO: 257 | 618-D06, | SETRPTEAGSWLCFGPPTFECWSFGTEPTE |
| SEQ ID NO: 258 | 617-H12, | SETRPTVAGSWDCSGPPTFECWWYGTEPTE |
| SEQ ID NO: 259 | 616-H05, | SETRPTKADNWHCSGPPTFECWWYGTEPTE |
| SEQ ID NO: 260 | 619-H10, | SETRPTEAGIVYCSGPPTFECWWFGTEPTE |
| SEQ ID NO: 261 | 619-D03, | SETRPTEAGYWHCLGPPTFECWWYVKEPTE |
| SEQ ID NO: 262 | 618-D12, | SETRPTEPGLLHCSGPPTFECWWYGTEPTE |
| SEQ ID NO: 263 | 620-E04, | SETRPTEASSWYCSGPPSFECWWYGTEPTE |
| SEQ ID NO: 264 | 620-A05, | SETRPTEAGSWHCLGPPTFECWWYVKEPTE |
| SEQ ID NO: 265 | 619-D04, | SETRPTEAGIILCKGPPWFSCDIYDTGPTE |
| SEQ ID NO: 266 | 618-A11, | SETRPTAAGNWHCSGPPTFECWAYGTEPTE |
| SEQ ID NO: 267 | 617-D07, | SETRPTVGGSWYCSGPPTFECWSYGTEPTE |
| SEQ ID NO: 268 | 627-A10, | SETRPTEDGWLDCKGPPTFECWWYGTEPTE |
| SEQ ID NO: 269 | 626-H02, | SETRPTEDGNWHCSGPPTFECWSYGTEPTE |
| SEQ ID NO: 270 | 626-F06, | SETRPTEAGSWHCSGPPTFECWYYWPEPTE |
| SEQ ID NO: 271 | 624-D02, | SETRPTEAGSLYCSGPPMFECWWYDWYPTE |
| SEQ ID NO: 272 | 622-D09, | SETRPTEAGGWYCMGPPAFECWWYASEPTE |
| SEQ ID NO: 273 | 621-F11, | SETRPTNAGSWYCSGPPTFECWWYGTEPTE |
| SEQ ID NO: 274 | 621-B11, | SETRPTEASRWHCNGPPTFECWWYGTEPTE |
| SEQ ID NO: 275 | 627-B03, | SETRPTEAGSFVCSGPPTFECWWYNTGPTE |
| SEQ ID NO: 276 | 626-H03, | SETRPTEAGSWHCSGPPTFECWSYGTEPTE |
| SEQ ID NO: 277 | 626-F07, | SETRPTESDIWLCSGPPTFECWWYGTEPTE |

TABLE 6-continued cMet-binding peptide sequences

SEQ ID NO: 278  626-D02, SETRPTDADPWHCSGPPTFECWWFGTEPTE

SEQ ID NO: 279  625-B03, SETRPTEAGVVLCSGPPTFECWWYDTEPTE

SEQ ID NO: 280  622-D10, SETRPTEVGSVHCSGPPTFECWWFGTEPTE

SEQ ID NO: 281  621-G02, SETRPTEAGRWLCSGPPTFECWEYDTEPTE

SEQ ID NO: 282  621-E04, SETRPTDAGWLQCSGPPTFECWWYGTEPTE

SEQ ID NO: 283  621-B12, SETRPTEASRRHCNGPPTFECWRYGTEPTE

SEQ ID NO: 284  626-H04, SETRPTEAGRWYCSGPPTFECWLFVEEPTE

SEQ ID NO: 285  626-F11, SETRPTAADSWQCSGPPTFECWSFGTEPTE

SEQ ID NO: 286  626-D03, SETRPTEAGSWHCGGPPTFECWMYVTEPTE

SEQ ID NO: 287  626-A02, SETRPTDDGSWYCSGPPTFECWWYGTEPTE

SEQ ID NO: 288  623-E07, SETRPTEAGYWHCLGPPTFECWWYDMEPTE

SEQ ID NO: 289  622-G09, SETRPTEAGILRCSGPPTFECWYYETEPTE

SEQ ID NO: 290  622-E05, SETRPTEDVSVHCAGPPTFECWLYGTEPTE

SEQ ID NO: 291  622-812, SETRPTEEGVFQCVGPPTFECWWYGTEPTE

SEQ ID NO: 292  621-G07, SETRPTEDGGFFCSGPPTFECWWYGTEPTE

SEQ ID NO: 293  621-E07, SETRPTEPGSWHCSGPPTFECWWYGTEPTE

SEQ ID NO: 294  621-C01, SETRPTEAGSWHCSGPPTFECWWYDRAPTE

SEQ ID NO: 295  626-A05, SETRPTEAGTWYCSGPPTFECWYYATEPTE

SEQ ID NO: 296  623-G02, SETRPTEAGSLYCSGPPAFECWYGTVPTE

SEQ ID NO: 297  622-H11, SETRPTDPGVLHCSGPPTFECWWFGTEPTE

SEQ ID NO: 298  622-C04, SETRPTEAGTWYCLGPPTFECWSFWQDPTE

SEQ ID NO: 299  621-G11, SETRPTEAGRWGCSGPPTFECWWYVAEPTE

SEQ ID NO: 300  621-C07, SETRPTEAGIWHCAGPPTFICWLYETEPTE

SEQ ID NO: 301  627-C03, SETRPTEAGSWHCSGPPSFECWQYSTEPTE

SEQ ID NO: 302  626-D12, SETRPTEAGSWQCSGPPTFECWVYETEPTE

SEQ ID NO: 303  626-A06, SETRPTEAGSWYCSGPPTFECWWYDVGPTE

SEQ ID NO: 304  623-H02, SETRPTDEVSWECRGPPTFECWWYGTEPTE

SEQ ID NO: 305  623-B05, SETRPTEGGSWVCSGPPTFECWWYGTEPTE

SEQ ID NO: 306  622-E10, SETRPTEYGSWYCSGPPTFECWWLGTEPTE

SEQ ID NO: 307  622-C06, SETRPTEAGVWLCSGPPTFECWWYDTDPTE

SEQ ID NO: 308  621-H03, SETRPTMAGSYYCSGPPTFECWVYGTEPTE

SEQ ID NO: 309  621-E11, SETRPTEAGYVQCYGPPSFVCHPMVPDPTE

SEQ ID NO: 310  621-C08, SETRPTEDGFVLCKGPPWFSCEMYGTEPTE

SEQ ID NO: 311  627-C04, SETRPTEAGGWNCSGPPTFECWWYVTEPTE

SEQ ID NO: 312  626-A07, SETRPTEDGSWECFGPPTFECWSYGTEPTE

SEQ ID NO: 313  623-H08, SETRPTDAVSYVCKGPPTFECWWYGTEPTE

SEQ ID NO: 314  622-F05, SETRPTEARSWHCSGPPTFECWWYGTEPTE

SEQ ID NO: 315  627-A04, SETRPTASVSWHCSGPPTFECWSYGTEPTE

SEQ ID NO: 316  626-G05, SETRPTEAGSWYCSGPPTFECWYYDMDPTE

SEQ ID NO: 317  623-H11, SETRPTEAGSWLCSGPPTFECWWFGTEPTE

SEQ ID NO: 318  622-F11, SETRPTGDGSWYCSGPPTFECWWLGTEPTE

SEQ ID NO: 319  621-F03, SETRPTEAGSWYCSGPPTFECWWYFLDPTE

SEQ ID NO: 320  626-F01, SETRPTEAGGWYCSGPPTFECWWFATEPTE

SEQ ID NO: 321  621-F04, SETRPTEAGDLDCLGPPTFICRIYGTEPTE

SEQ ID NO: 322  630-F06, SETRPTEAGSWQCVGPPTFECWSFGTEPTE

SEQ ID NO: 323  630-A03, SETRPTEADSWYCSGPPTFECWLFGTEPTE

SEQ ID NO: 324  629-F10, SETRPTQADSWYCSGPPTFECWWWGTEPTE

SEQ ID NO: 325  629-D11, SETRPTEAFSWDCSGPPTFECWWFGTEPTE

SEQ ID NO: 326  629-B06, SETRPTEAGSWQCSGPPVFECWWYDTEPTE

SEQ ID NO: 327  628-H01, SETRPTEAGNVQCSGPPTFECWWFDTEPTE

SEQ ID NO: 328  628-F03, SETRPTEAGSVVCSGPPRFECWAFVTEPTE

SEQ ID NO: 329  627-G02, SETRPTEDGTLHCSGPPTFACWWYGTEPTE

TABLE 6-continued cMet-binding peptide sequences

SEQ ID NO: 330   629-E01, SETRPTDAEVWVCNGPPTFECWWYGTEPTE

SEQ ID NO: 331   628-H09, SETRPTEDVTFHCSGPPTFECWLYGTEPTE

SEQ ID NO: 332   628-A05, SETRPTSDFDWHCKGPPTFECWSYGTEPTE

SEQ ID NO: 333   627-G04, SETRPTEADSWYCSGPPTFECWWYVPEPTE

SEQ ID NO: 334   630-A05, SETRPTDDGNWYCSGPPTFECWWYGTEPTE

SEQ ID NO: 335   629-E03, SETRPTEAGSWYCSGPPTFECWRYDTDPTE

SEQ ID NO: 336   629-C02, SETRPTEAGPWSCSGPPTFECWWFDTEPTE

SEQ ID NO: 337   628-H10, SETRPTEAGMFLCSGPPAFECWWYDTEPTE

SEQ ID NO: 338   628-F12, SETRPTEAGSLYCSGPPTFECWLYDVEPTE

SEQ ID NO: 339   627-D12, SETRPTEAGQWNCSGPPTFECWWYDIEPTE

SEQ ID NO: 340   630-G02, SETRPTEAGSWYCSGPPTFECWWFETEPTE

SEQ ID NO: 341   629-E06, SETRPTEAGSFVCSGPPTFECWGYVTEPTE

SEQ ID NO: 342   628-D07, SETRPTQDGTWFCSGPPTFECWWYGTEPTE

SEQ ID NO: 343   627-E06, SETRPTEGDSWHCAGPPTFECWWYGTEPTE

SEQ ID NO: 344   629-E07, SETRPTEAGSWSCSGPPTFECWSYGTEPTE

SEQ ID NO: 345   629-C11, SETRPTEAGRIQCSGPPTFECWWYDEEPTE

SEQ ID NO: 346   629-A03, SETRPTEAGTIVCKGPPWFSCEIYETEPTE

SEQ ID NO: 347   628-A12, SETRPTEAGDWYCSGPPAFECWEYLGEPTE

SEQ ID NO: 348   627-E08, SETRPTEAGSWFCSGPPSFECWSYVTEPTE

SEQ ID NO: 349   629-E08, SETRPTEAGSWHCSGPPAFECWWYDNEPTE

SEQ ID NO: 350   629-B02, SETRPTEAGRWTCSGPPTFECWWYVSDPTE

SEQ ID NO: 351   628-E06, SETRPTEAGEWYCGGPPTFECWWFDTAPTE

SEQ ID NO: 352   627-G09, SETRPTEAGSWHCSGPPSFECWWFDTGPTE

SEQ ID NO: 353   631-A11, SETRPTEAGSFICSGPPTFECWWYGTEPTE

SEQ ID NO: 354   630-C10, SETRPTEDVRWYCSGPPTFECWWFGTEPTE

SEQ ID NO: 355   628-B08, SETRPTEAGSWYCSGPPTFECWWYVPEPTE

SEQ ID NO: 356   629-F03, SETRPTEAGNWLCSGPPAFECWWFVAEPTE

SEQ ID NO: 357   632-A09, SETRPTEAGSWYCSGPPTFECWWYGTEPTE

SEQ ID NO: 358   632-G07, SETRPTEAGDWLCAGPPTFECWWWGTDPTE

SEQ ID NO: 359   631-F12, SETRPTEAGSWHCVGPPTFECWWFDTEPTE

SEQ ID NO: 360   633-A02, SETRPTEAGEWSCSGPPTFECWWWDMEPTE

SEQ ID NO: 361   633-B06, SETRPTYYVSWYCSGPPTFECWSYGTEPTE

SEQ ID NO: 362   632-D11, SETRPTEDGSWYCSGPPTFECWWYGTEPTE

SEQ ID NO: 363   631-D10, SETRPTEDGTWYCSGPPTFECWWYGTEPTE

SEQ ID NO: 364   633-F09, SETRPTETDSWVCSGPPTFECWWYGTEPTE

Consensus Motif#1: G-X1-X2-X3-C-X4-G-P-P-X5-F-X6-C-X7-X8-X9-X10-X11-X12-P-T-E (SEQ ID NO: 528), where:

X1 is any amino acid other than C, preferably S, R, I, D, or N;

X2 is any amino acid other than C, preferably W, L, F, V, or I;

X3 is any amino acid other than C, preferably H, Y, L, Q, N, or V;

X4 is any amino acid other than C, preferably S, K, or L;

X5 is any amino acid other than C, preferably T, S, A, or W;

X6 is any amino acid other than C, preferably E or S;

X7 is any amino acid other than C, preferably W;

X8 is any amino acid other than C, preferably W, S, or L;

X9 is any amino acid other than C, preferably Y or F;

X10 is any amino acid other than C, preferably D, G, V, or E;

X11 is any amino acid other than C, preferably T, P, M, or S; and

X12 is any amino acid other than C, preferably E or G.

Motif#2: T-X1-X2-X3-X4-X5-X6-C-X7-G-P-P-X8-F-X9-C-X10-X11-X12-G (SEQ ID NO: 529), where:

X1 is any amino acid other than C, preferably E, D, or V;

X2 is any amino acid other than C, preferably A, D, G, S, or V;

X3 is any amino acid other than C, preferably G, V, D, or S;

X4 is any amino acid other than C, preferably S,

TABLE 6-continued cMet-binding peptide sequences

N, R, T, or G;

X5 is any amino acid other than C, preferably W;

X6 is any amino acid other than C, preferably H or Q;

X7 is any amino acid other than C, preferably S, N, or K;

X8 is any amino acid other than C, preferably T;

X9 is any amino acid other than C, preferably E;

X10 is any amino acid other than C, preferably W;

X11 is any amino acid other than C, preferably W or S;
and

X12 is any amino acid other than C, preferably Y or F.

---

CLASS V
TN10:

| SEQ ID NO: | Isolate | Sequence |
|---|---|---|
| SEQ ID NO: 365 | 545-C02, | GSWRFCGGEYSFQVCQDVAP |
| SEQ ID NO: 366 | 546-E02, | GSHHTCLDGFAGWRCTEVAP |
| SEQ ID NO: 367 | 545-C11, | GSFAPCGWPSFAIDCIAEAP |
| SEQ ID NO: 368 | 549-G01, | GSTKVCHEKWNQLFCHNQAP |
| SEQ ID NO: 369 | 548-F07, | GSPEMCMMFPFLYPCNHHAP |
| SEQ ID NO: 370 | 551-H10, | GSFFPCWRIDRFGYCHANAP |

Consensus Motif: S-X1-X2-X3-C-X4-X5-X6-X7-X8-X9-X10-X11-C-X12-X13-X14-A-P (SEQ ID NO: 530), where
X1 is one of W, H, F, T, or P;

X2 is one of R, H, A, K, E, or F;

X3 is one of F, T, P, V, or M;

X4 is one of F, L, H, M, or W;

X5 is one of G, D, W, E, M, or R;

X6 is one of E, G, P, K, F, or I;

X7 is one of Y, F, S, W, P, or D;

X8 is one of S, A, F, N, or R;

X9 is one of F, G, A, Q, or L;

X10 is one of Q, W, I, L, Y, or G;

X11 is one of V, R, D, F, P, or Y;

X12 is one of Q, T, I, H, or N;

X13 is one of D, E, A, N, or H;
and

X14 is one of V, E, Q, H, or N

---

TABLE 6-continued cMet-binding peptide sequences

CLASS VI
TN11 #1:

| SEQ ID NO: | Isolate | Sequence |
|---|---|---|
| SEQ ID NO: 371 | 443-H10, | GSQQICDRKEYRFQACLSDAP |
| SEQ ID NO: 372 | 557-A12, | GSTMSCWRWGRDAYSCNQMAP |
| SEQ ID NO: 373 | 465-A03, | GSSQICAVYLDDTHNCERHAP |
| SEQ ID NO: 374 | 446-E12, | GSSHCNQMITPWQNCGMRAP |
| SEQ ID NO: 375 | 445-E06, | GSSARCDELINDFHSCLVMAP |
| SEQ ID NO: 376 | 452-A03, | GSRFHCWQGDLMQTYCMPMAP |
| SEQ ID NO: 377 | 465-C06, | GSQNNCEYGSRGSSFCLAMAP |
| SEQ ID NO: 378 | 441-H01, | GSMNMCDTTDEISPTCHPSAP |
| SEQ ID NO: 379 | 443-D04, | GSMLGCLFEHQNKYDCYVLAP |
| SEQ ID NO: 380 | 445-G12, | GSLYRCLGEASPTPPCAYEAP |
| SEQ ID NO: 381 | 442-E03, | GSGMGCHQVNISTGDCAEDAP |
| SEQ ID NO: 382 | 453-A05, | GSGDPCSPGPSINGHCSVMAP |
| SEQ ID NO: 383 | 445-E07, | GSFWNCTTDLGAMSDCGFFAP |
| SEQ ID NO: 384 | 451-B12, | GSFTACNKTSTTRQPCNPYAP |
| SEQ ID NO: 385 | 465-B07, | GSELFCFYHHQGYEGCDVLAP |
| SEQ ID NO: 386 | 451-C06, | GSDMNCTVLAQDQIFCFREAP |
| SEQ ID NO: 387 | 445-E11; | GSAGWCYTMNYVDQLCTYMAP |

Consensus Motif: S-X1-X2-X3-C-X4-X5-X6-X7-X8-X9-X10-X11-X12-C-X13-X14-X15-A-P (SEQ ID NO: 532), where
X1 is any amino acid other than C, preferably S, F, G, M, or Q;

X2 is any amino acid other than C, preferably M, L, N, or Q;

X3 is any amino acid other than C, preferably N, G, H, I, or R;

X4 is any amino acid other than C, preferably D, L, N, T, or W;

X5 is any amino acid other than C, preferably Q, T, R, V, or Y;

X6 is any amino acid other than C, preferably G, E, L, M, or T;

TABLE 6-continued cMet-binding peptide sequences

X7 is any amino acid other than C, preferably A, D, H, I, L, N, or S;

X8 is any amino acid other than C, preferably Q, R, S, T, or Y;

X9 is any amino acid other than C, preferably D, G, I, or P;

X10 is any amino acid other than C, preferably T, F, or Q;

X11 is any amino acid other than C, preferably Q, F, H, P, S, or Y;

X12 is any amino acid other than C, preferably D, F, N, P, or S;

X13 is any amino acid other than C, preferably L, A, G, N, or S;

X14 is any amino acid other than C, preferably V, P, R, or Y;
and

X15 is any amino acid other than C, preferably M, D, E, or L.

CLASS VII
TN11 #2

| SEQ ID NO: | Isolate | Sequence |
|---|---|---|
| SEQ ID NO: 388 | 593-G11, | SETRPTEAGMCACRGPPAFVCQWYGSEPTE |
| SEQ ID NO: 389 | 631-E12, | SETRPTEAGSCHCSGPPTFECWSYVTEPTE |

CLASS VIII
TN12:

| SEQ ID NO: | Isolate | Sequence |
|---|---|---|
| SEQ ID NO: 390 | 546-G02, | GDYDYCDFDLETYIPECHSYDP |
| SEQ ID NO: 391 | 333-C03, | GDDFHCEFIDDYQSEICYFNDP |
| SEQ ID NO: 392 | 549-G05, | GDLLVCKFDDKFWTETCEWADP |
| SEQ ID NO: 393 | 546-B01, | GDSYNCSWDSKTFEVTCLYADP |
| SEQ ID NO: 394 | 551-D02, | GDASWCDENSPAAWFYCELWDP |
| SEQ ID NO: 395 | 334-F05, | GDLLGCGYQEKGGEYKCRFNDP |
| SEQ ID NO: 396 | 330-G02, | GDPWWCFEKDSFIPFACWHHDP |
| SEQ ID NO: 397 | 316-F08, | GDYYQCQFSKDMYSERCWPYDP |
| SEQ ID NO: 398 | 332-H09, | GDNRFCSWVYNVDDWWCVDNDP |
| SEQ ID NO: 399 | 545-H12, | GDYSECFFEPDSFEVKCYDRDP |
| SEQ ID NO: 400 | 548-G05, | GDYRMCQISDMWGNYECSSDDP |
| SEQ ID NO: 401 | 547-C09, | GDPDECQLNRETFEVWCPWHDP |
| SEQ ID NO: 402 | 545-F04, | GDHRKCEISAKTHEVTCYDNDP |
| SEQ ID NO: 403 | 552-F06, | GDHLTCEFRDDGWKEHCWWSDP |
| SEQ ID NO: 404 | 531-E11, | GDASMCYDGLALRWDQCWPHDP |

Consensus Motif: D-X1-X2-X3-C-X4-X5-X-6-X7-X8-X9-X10-X11-X12-X13-C-X14-X15-X16-D-P (SEQ ID NO: 533),
where
X1 is any amino acid other than C, preferably Y, A, H, L, or P;

X2 is any amino acid other than C, preferably L, R, S, D, or Y;

X3 is any amino acid other than C, preferably E, M, or W;

X4 is any amino acid other than C, preferably E, Q, D, F, or S;

X5 is any amino acid other than C, preferably F, I, W, or E;

X6 is any amino acid other than C, preferably D, S, or N;

X7 is any amino acid other than C, preferably D, S, or L;

X8 is any amino acid other than C, preferably D, K, or E;

X9 is any amino acid other than C, preferably T, F, or G;

X10 is any amino acid other than C, preferably F, W, Y, or G;

X11 is any amino acid other than C, preferably E, S, or W;

X12 is any amino acid other than C, preferably E, V, F, or Y;

X13 is any amino acid other than C, preferably T, E, K, or V;

X14 is any amino acid other than C, preferably W or E;

X15 is any amino acid other than C, preferably D, W, F, P, or S;
and

X16 is any amino acid other than C, preferably N, I, or A.

CLASS IX
TN9 #3:

| SEQ ID NO: | Isolate | Sequence |
|---|---|---|
| SEQ ID NO: 405 | 606-B08, | SETRPTEAGSCHCSGPPTFQCWCYEVEPTE |
| SEQ ID NO: 406 | 602-G12, | SETRPTEAGSCHCSGPPTFECWCYGTEPTE |

TABLE 6-continued cMet-binding peptide sequences

SEQ ID NO: 407    603-E09, SETRPTGESDCHCSGPPTFECYCYGTEPTE

SEQ ID NO: 408    606-C12, SETRPTESGNCYCSGPPWFECWCYGTEPTE

SEQ ID NO: 409    603-H03, SETRPTEAGACRCSGPPTFECYCYDMAPTE

SEQ ID NO: 410    604-G01, SETRPTEAGSCYCSGPPRFECWCYETEPTE

SEQ ID NO: 411    602-G04, SETRPTEAGSCHCSGPPSFECWCFGTEPTE

SEQ ID NO: 412    611-G11, SETRPTVSVSCSCGGPPTFECWCFGTEPTE

SEQ ID NO: 413    611-F02, SETRPTEAGSCHCNGPPTFECFCFGTEPTE

SEQ ID NO: 414    610-G02, SETRPTEAGSCYCGGPPSFECWCYGTEPTE

SEQ ID NO: 415    614-E08, SETRPTEAGSCHCSGPPTFECWCYGSNPTE

SEQ ID NO: 416    615-A01, SETRPTEAGSCHCSGPPAFECWCYRAEPTE

SEQ ID NO: 417    617-H02, SETRPTEAGSCDCSGPPTFECWCFGTEPTE

SEQ ID NO: 418    616-F12, SETRPTEAGKCHCGGPPSFECWCYATEPTE

SEQ ID NO: 419    620-G06, SETRPTEAGKCHCSGPPTFECTCYHTDPTE

SEQ ID NO: 420    627-B04, SETRPTEAGFCQCSGPPAFECWCYDTEPTE

SEQ ID NO: 421    627-B06, SETRPTEAVSCECKGPPTFECWCFGTEPTE

SEQ ID NO: 422    626-H05, SETRPTEAGDCHCSGPPTFECWCYGTEPTE

SEQ ID NO: 423    626-D11, SETRPTEAGACDCIGPPTFECWCYDTYPTE

SEQ ID NO: 424    626-E05, SETRPTEAGNCLCSGPPTFECACYHSEPTE

SEQ ID NO: 425    621-D01, SETRPTEAGSCHCSGPPTFQCWCYSTEPTE

SEQ ID NO: 426    622-A10, SETRPTEAGICHCSGPPTFECWCYATEPTE

SEQ ID NO: 427    630-D09, SETRPTEEGSCHCSGPPTFECWCFGTEPTE

SEQ ID NO: 428    628-D01, SETRPTEAGICNCSGPPTFECWCYSMGPTE

SEQ ID NO: 429    628-F11, SETRPTQGGNCHCSGPPTFECWCYGTEPTE

SEQ ID NO: 430    628-D04, SETRPTEAGSCNCSGPPTFECYCYTLDPTE

SEQ ID NO: 431    630-G01, SETRPTDNGSCQCSGPPTFECWCFGTEPTE

SEQ ID NO: 432    627-G06, SETRPTESGSCHCSGPPTFECWCYGTEPTE

SEQ ID NO: 433    630-G05, SETRPTEAGSCNCSGPPSFECWCYVTEPTE

SEQ ID NO: 434    630-C03, SETRPTEGGSCYCGGPPTFECWCYGTEPTE

SEQ ID NO: 435    627-G07, SETRPTEAGRCHCSGPPTFECWCYVQEPTE

SEQ ID NO: 436    630-H10, SETRPTESGSCLCSGPPQFECWCYGTEPTE

SEQ ID NO: 437    628-B01, SETRPTETDSCHCIGPPTFECWCYGTEPTE

SEQ ID NO: 438    630-F01, SETRPTEAGFCRCSGPPTFECWCYDTEPTE

SEQ ID NO: 439    629-D01, SETRPTEHGSCNCYGPPTFECWCYGTEPTE

SEQ ID NO: 440    633-G02, SETRPTALGGCLCSGPPTFECWCYGTEPTE

SEQ ID NO: 441    631-F07, SETRPTEGGSCECSGPPTFECWCYGTEPTE

SEQ ID NO: 442    633-G08, SETRPTEEGSCHCSGPPAFECWCYGTEPTE

SEQ ID NO: 443    632-H07, SETRPTEAGTCYCSGPPTFECWCYGTEPTE

SEQ ID NO: 444    631-D03, SETRPTEDGSCHCSGPPRFECWCYGTEPTE

SEQ ID NO: 445    633-G12, SETRPTEAGSCHCSGPPTFECWCYSTEPTE

SEQ ID NO: 446    633-H03, SETRPTEAGSCYCSGPPTFECWCYAEEPTE

SEQ ID NO: 447    632-F05, SETRPTEAGSCHCSGPPTFECWCFEPEPTE

Motif13-1 G-X1-C-X2-C-X3-G-P-P-X4-F-X5-C-X6-C-X7-X8-X9-X10-P (SEQ ID NO: 534), where
X1 is any amino acid other than C, preferably S;

X2 is any amino acid other than C, preferably H, Y, or N;

X3 is any amino acid other than C, preferably S or G;

X4 is any amino acid other than C, preferably T;

X5 is any amino acid other than C, preferably E;

X6 is any amino acid other than C, preferably W;

X7 is any amino acid other than C, preferably Y;

X8 is any amino acid other than C, preferably G, D, A, E, or S;

X9 is any amino acid other than C, preferably T or S;
and

X10 is any amino acid other than C, preferably E or D.

Motif13-2 is T-X1-X2-X3-X4-C-X5-C-X6-G-P-P-X7-F-E-C-X8-C-X9-G (SEQ ID NO: 535) where:
X1 is any amino acid other than C, preferably E;

X2 is any amino acid other than C, preferably A,

TABLE 6-continued cMet-binding peptide sequences

S, E, or G;

X3 is any amino acid other than C, preferably G;

X4 is any amino acid other than C, preferably S;

X5 is any amino acid other than C, preferably H;

X6 is any amino acid other than C, preferably S;

X7 is any amino acid other than C, preferably T;

X8 is any amino acid other than C, preferably W, Y, or F;
and

X9 is any amino acid other than C, preferably Y or F.

CLASS X

| SEQ ID NO: | Isolate | Sequence |
| --- | --- | --- |
| SEQ ID NO: 448 | 606-E11, | SEYPTWVSKEFHECAGELVAMQGGSGTE |

CLASS XI
Linear #1:

| SEQ ID NO: | Isolate | Sequence |
| --- | --- | --- |
| SEQ ID NO: 449 | 525-A07, | AQQASRFTFTDGDSYWWFEDF |
| SEQ ID NO: 450 | 528-F05, | AQIQGIQKTEQGEFYWFNWPA |
| SEQ ID NO: 451 | 524-E09, | AQREVEEPYWYLDFLSSWRMHE |
| SEQ ID NO: 452 | 96-H12, | AQRPEAHYKLAMSYPIIPRTKT |
| SEQ ID NO: 453 | 118-A08, | AQRWSSPGMSQSFVLEWKWNDN |
| SEQ ID NO: 454 | 94-E08, | AQYDTWVFQFIHEVPGELVAMQ |
| SEQ ID NO: 455 | 119-F06, | AQMYQTPDGVIGKFVDWMFN |
| SEQ ID NO: 456 | 95-A11, | AQVGSPMLPSWFSFEANWSS |
| SEQ ID NO: 457 | 94-H04, | AQNAVVPPPMLWSIYWDYGREG |
| SEQ ID NO: 458 | 94-F07, | AQPYYELQDADMLLVVALLSTG |
| SEQ ID NO: 459 | 103-G08, | AQVGTAEAIMFSDVEDTGVHKF |
| SEQ ID NO: 460 | 118-C07, | AQFPLEFDVPNFSYHWLVSFNP |
| SEQ ID NO: 461 | 104-C09, | AQDLKPWTAGWEPPWLWTDRGP |
| SEQ ID NO: 462 | 117-F08, | AQHQYGQMMVLHIQYDMGEFIP |
| SEQ ID NO: 463 | 76-D09, | AQSPYIFPIDDSGRQIFVIQWG |

TABLE 6-continued cMet-binding peptide sequences

| SEQ ID NO: 464 | 93-C08, | AQVPDWLSAVVIEKLIEYGMMV |
| --- | --- | --- |
| SEQ ID NO: 465 | 92-B05, | AQFDRYWHFAWMDVSFSSGQSG |
| SEQ ID NO: 466 | 116-H02, | AQKETWEFFDIVYGSGWKFNSP |
| SEQ ID NO: 467 | 02-B08, | AQHSVQRQMDVWMPVQFMAGFT |
| SEQ ID NO: 468 | 117-F03, | AQEWQTWTWNMIEVISENKTP |
| SEQ ID NO: 469 | 127-A07, | AQGFELWVDHTRNFFIAISP |
| SEQ ID NO: 470 | 94-B08, | AQAYEWWADESIFNHGYYWGHQ |
| SEQ ID NO: 471 | 115-G02, | AQDPGFSKHSMGHGYPSKMNWG |
| SEQ ID NO: 472 | 130-E10, | AQEWEREYFVDGFWGSWFGIPH |
| SEQ ID NO: 473 | 136-D01, | AQMGHHWDVQWDYKLFHVARGD |
| SEQ ID NO: 474 | 15-D02, | AQELFQILEKQMWSDFMEWATP |
| SEQ ID NO: 475 | 79-B02, | AQHWDYDSGSDFWFPVFFLEHH |
| SEQ ID NO: 476 | 94-A06, | AQHGYLSPLKQYQMSHVEFWTY |
| SEQ ID NO: 477 | 94-G02, | AQFSGLVMYGRTHEVQWTFGSM |
| SEQ ID NO: 478 | 75-B12, | AQAEWVITSEEFYWKMADFGPP |
| SEQ ID NO: 479 | 117-F04, | AQWPHDGLVHWGEVIMLRF |
| SEQ ID NO: 480 | 151-B08, | AQWNQWDEFMWFLNPPPIGLMW |
| SEQ ID NO: 481 | 117-E09, | AQDNTADQMFNGFHVLAMYMV |
| SEQ ID NO: 482 | 93-B10, | AQSDHDHAHWGVKHWPFRRYQ |
| SEQ ID NO: 483 | 98-F05, | AQLFQYLWHDDPQGAFFQLSMW |
| SEQ ID NO: 484 | 118-B12, | AQHVVTLTLIQMPFAFNFEPRM |
| SEQ ID NO: 485 | 27-D10, | AQVGESLDDGWTFFSDKWFDFF |
| SEQ ID NO: 486 | 122-D07, | AQFMYEKEHYVMSISLPGLWFY |
| SEQ ID NO: 487 | 149-E06, | AQHMDPAEWDWFIRIYSPVVNP |
| SEQ ID NO: 488 | 166-H04, | AQMWHRVHDPGYTFEVTWLWDN |
| SEQ ID NO: 489 | 96-D06, | AQWNWDMGFMWTTDSAQVQPSM |

TABLE 6-continued cMet-binding peptide sequences

| SEQ ID NO: 490 | 103-C04, | AQKTWFLEADLFQMFQEVTWQF |
|---|---|---|
| SEQ ID NO: 491 | 527-E08, | AQWGAVDNDWYDWEMEQIWMFE |
| SEQ ID NO: 492 | 524-H02, | AQVEDMATVHFKFNPATHEVIW |
| SEQ ID NO: 493 | 523-A04, | AQRDYLFYWNDGSYQPWQVFVG |
| SEQ ID NO: 494 | 524-D07, | AQQWMFQIHQSMAWPYEWIDSY |
| SEQ ID NO: 495 | 522-H03, | AQGIAWQLEWSYMPQSPPSFDR |
| SEQ ID NO: 496 | 527-A10, | AQGGRYPFYDTDWFKWEMYVL |

CLASS XII
Linear #2

| SEQ ID NO: | Isolate | Sequence |
|---|---|---|
| SEQ ID NO: 497 | 594-F01, | SEEDTWLFWQIIEVPVGQVLMQGGSGTE |
| SEQ ID NO: 498 | 592-E11, | SEYDTLLFQRTGEVVGKLGSMQGGSGTE |
| SEQ ID NO: 499 | 591-G09, | SEYDTWVFQFMLEVPGSWMARLGGSGTE |
| SEQ ID NO: 500 | 601-G11, | SEYDTWIFQFYREVPGVPGAMQGGSGTE |
| SEQ ID NO: 501 | 592-G01, | SEVDTGVQLLTHEGPGELVAMQGGSGTE |
| SEQ ID NO: 502 | 591-H01, | SESDTWVFQLIHEVPASVVAMQGGSGTE |
| SEQ ID NO: 503 | 592-G05, | SEYDTWVFQFRHGVKAQLVAMRGGSGTE |
| SEQ ID NO: 504 | 606-D12, | SEYDSRVFQYAPEVAGQVEAMQGGSGTE |
| SEQ ID NO: 505 | 592-B01, | SEDESRVVQFQHEVSGELVAMQGGSGTE |
| SEQ ID NO: 506 | 591-A06, | SEQDTFVFMYNGEVSGDMVAMQGGSGTE |
| SEQ ID NO: 507 | 588-H01, | SEYDTWVFQFRRQVPGVLETMLGGSGTE |
| SEQ ID NO: 508 | 589-A01, | SEQETLVFAVIDGDPGELVAMQGGSGTE |
| SEQ ID NO: 509 | 619-F10, | SEYDTWVFQFIHVARGEMEGTLGGSGTE |
| SEQ ID NO: 510 | 592-B01, | SEDESRVVQFQHEVSGELVAMQGGSGTE |
| SEQ ID NO: 511 | 591-A06, | SEQDTFVFMYNGEVSGDMVAMQGGSGTE |

TABLE 7

| SEQ ID NO: | Isolate | Protein ELISA | WC ELISA | HGF 100 ng/mL | HGF 500 ng/mL |
|---|---|---|---|---|---|
| CLASS I | | | | | |
| SEQ ID NO: 001 | 571-C05 | 4.9 | 1.30 | 102% | 74% |
| SEQ ID NO: 002 | 465-A06 | 4.4 | 1.33 | 56% | 32% |
| SEQ ID NO: 003 | 465-D09 | 3.2 | 1.30 | 90% | 70% |
| SEQ ID NO: 004 | 569-H10 | 3.4 | 1.27 | 98% | 83% |
| SEQ ID NO: 005 | 470-E11 | 3.5 | 1.33 | 55% | 127% |
| SEQ ID NO: 006 | 452-F01 | 3.2 | 1.33 | 117% | 110% |
| SEQ ID NO: 007 | 569-C03 | 3.4 | 1.30 | 95% | 89% |
| SEQ ID NO: 008 | 574-H03 | 3.2 | 1.27 | 88% | 18% |
| SEQ ID NO: 009 | 567-C08 | 3.8 | 1.27 | 85% | 94% |
| SEQ ID NO: 010 | 561-C08 | 3.0 | 1.37 | 92% | 96% |
| CLASS II | | | | | |
| SEQ ID NO: 011 | 573-F04 | 5.6 | 1.30 | 76% | 71% |
| SEQ ID NO: 012 | 570-E07 | 4.5 | 1.27 | 81% | 71% |
| SEQ ID NO: 013 | 456-E04 | 3.9 | 1.40 | 82% | 81% |
| SEQ ID NO: 014 | 434-E12 | 4.8 | 1.33 | 117% | 41% |
| SEQ ID NO: 015 | 489-A04 | 4.3 | 1.33 | 30% | 13% |
| SEQ ID NO: 016 | 484-D08 | 4.1 | 1.33 | 105% | 90% |
| SEQ ID NO: 017 | 482-D02 | 3.9 | 1.37 | 66% | 44% |
| SEQ ID NO: 018 | 437-A09 | 3.9 | 1.13 | 89% | 78% |
| SEQ ID NO: 019 | 352-E04 | 3.9 | 1.37 | 88% | 74% |
| SEQ ID NO: 020 | 376-E05 | 3.7 | 1.37 | 122% | 121% |
| SEQ ID NO: 021 | 482-A12 | 3.5 | 1.37 | 98% | 79% |
| SEQ ID NO: 022 | 423-C11 | 3.4 | 1.40 | 132% | 75% |
| SEQ ID NO: 023 | 499-C09 | 3.2 | 1.33 | 91% | 70% |
| SEQ ID NO: 024 | 457-A09 | 14.5 | 1.30 | 27% | 67% |
| SEQ ID NO: 025 | 573-E07 | 3.2 | 1.37 | 77% | 82% |
| SEQ ID NO: 026 | 465-F08 | 3.8 | 1.30 | 68% | 116% |
| SEQ ID NO: 027 | 465-E09 | 3.6 | 1.30 | 60% | 77% |
| SEQ ID NO: 028 | 444-B08 | 3.6 | 1.43 | 111% | 93% |
| SEQ ID NO: 029 | 465-E11 | 4.3 | 1.23 | 33% | 124% |
| SEQ ID NO: 030 | 465-D12 | 3.2 | 1.27 | 34% | 0% |
| SEQ ID NO: 031 | 470-A02 | 3.2 | 1.30 | 78% | 62% |
| SEQ ID NO: 032 | 465-C01 | 3.2 | 1.27 | 267% | 23% |
| SEQ ID NO: 033 | 448-H02 | 3.8 | 1.43 | 113% | 92% |
| SEQ ID NO: 034 | 465-D01 | 3.3 | 1.30 | 235% | 134% |
| SEQ ID NO: 035 | 571-C11 | 3.5 | 1.23 | 107% | 72% |
| SEQ ID NO: 036 | 465-B11 | 3.6 | 1.27 | 97% | 89% |
| SEQ ID | 442-E08 | 4.1 | 1.43 | 81% | 75% |

TABLE 7-continued

| SEQ ID NO: | Isolate | Protein ELISA | WC ELISA | HGF 100 ng/mL | HGF 500 ng/mL |
|---|---|---|---|---|---|
| SEQ ID NO: 037 | 465-C11 | 3.1 | 1.30 | 41% | 4% |
| SEQ ID NO: 038 | 465-F10 | 3.7 | 1.33 | 61% | 42% |
| SEQ ID NO: 039 | 471-A11 | 3.0 | 1.37 | 85% | 80% |
| SEQ ID NO: 040 | 465-C07 | 3.1 | 1.27 | 102% | 138% |
| SEQ ID NO: 041 | 465-D04 | 3.1 | 1.23 | 77% | 31% |
| SEQ ID NO: 042 | 445-E04 | 4.2 | 1.37 | 127% | 102% |
| SEQ ID NO: 043 | 465-B06 | 4.1 | 1.23 | 89% | 57% |
| SEQ ID NO: 044 | 470-C02 | 3.9 | 1.33 | 340% | 227% |
| SEQ ID NO: 045 | 458-B05 | 4.5 | 1.33 | 201% | 247% |
| SEQ ID NO: 046 | 545-E08 | 4.7 | 1.30 | 81% | 57% |
| CLASS III | | | | | |
| SEQ ID NO: 048 | 325-H05 | 15.9 | 1.47 | 41% | 32% |
| SEQ ID NO: 049 | 330-F05 | 13.8 | 1.33 | 51% | 27% |
| SEQ ID NO: 050 | 333-F09 | 14.8 | 1.43 | 52% | 32% |
| SEQ ID NO: 051 | 336-G04 | 5.4 | 1.33 | 46% | 23% |
| SEQ ID NO: 052 | 334-G06 | 8.0 | 1.30 | 56% | 43% |
| SEQ ID NO: 053 | 330-B07 | 18.1 | 1.27 | 58% | 40% |
| SEQ ID NO: 054 | 330-C10 | 13.4 | 1.33 | 48% | 25% |
| SEQ ID NO: 055 | 331-G04 | 18.3 | 1.47 | 56% | 36% |
| SEQ ID NO: 056 | 548-F06 | 14.3 | 1.23 | 76% | 18% |
| SEQ ID NO: 057 | 538-F08 | 12.3 | 1.23 | 55% | 43% |
| SEQ ID NO: 058 | 547-H07 | 15.9 | 1.17 | 60% | 45% |
| SEQ ID NO: 059 | 323-A11 | 21.2 | 1.43 | 41% | 18% |
| SEQ ID NO: 060 | 333-H03 | 8.1 | 1.43 | 55% | 37% |
| SEQ ID NO: 061 | 329-D02 | 3.2 | 1.27 | 53% | 31% |
| SEQ ID NO: 062 | 550-C09 | 10.2 | 1.40 | 25% | 25% |
| SEQ ID NO: 063 | 548-E08 | 5.3 | 1.27 | 102% | 50% |
| SEQ ID NO: 064 | 332-A05 | 6.0 | 1.40 | 40% | 21% |
| SEQ ID NO: 065 | 330-C01 | 4.7 | 1.30 | 58% | 43% |
| SEQ ID NO: 066 | 545-A09 | 13.5 | 1.30 | 44% | 22% |
| SEQ ID NO: 067 | 334-C08 | 8.0 | 1.47 | 70% | 57% |
| SEQ ID NO: 068 | 333-C05 | 6.3 | 1.33 | 83% | 66% |
| SEQ ID NO: 069 | 551-B02 | 9.0 | 1.30 | 69% | 43% |
| SEQ ID NO: 070 | 551-G12 | 3.9 | 1.37 | 88% | 46% |
| SEQ ID NO: 071 | 330-G09 | 13.5 | 1.40 | 42% | 26% |
| SEQ ID NO: 072 | 331-F01 | 12.6 | 1.47 | 77% | 73% |
| SEQ ID NO: 073 | 274-B07 | 7.8 | 1.10 | 342% | 296% |
| SEQ ID NO: 074 | 335-D11 | 6.7 | 1.37 | 56% | 37% |
| SEQ ID NO: 075 | 336-D07 | 5.8 | 1.33 | 44% | 37% |
| SEQ ID NO: 076 | 332-C03 | 5.7 | 1.20 | 37% | 95% |
| SEQ ID NO: 077 | 331-D03 | 5.5 | 1.40 | 64% | 55% |
| SEQ ID NO: 078 | 331-G06 | 4.7 | 1.40 | 59% | 51% |
| SEQ ID NO: 079 | 552-G03 | 10.7 | 1.27 | 101% | 83% |
| SEQ ID NO: 080 | 552-G11 | 7.4 | 1.23 | 55% | 41% |
| SEQ ID NO: 081 | 550-G08 | 9.1 | 1.40 | 79% | 58% |
| SEQ ID NO: 082 | 550-G12 | 14.3 | 1.43 | 61% | 79% |
| SEQ ID NO: 083 | 552-A01 | 3.9 | 1.33 | 76% | 81% |
| SEQ ID NO: 084 | 548-C06 | 13.0 | 1.23 | 94% | 77% |
| SEQ ID NO: 085 | 545-B12 | 17.1 | 1.27 | 51% | 42% |
| SEQ ID NO: 086 | 549-F06 | 5.2 | 1.30 | 96% | 40% |
| SEQ ID NO: 087 | 552-F01 | 4.8 | 1.30 | 56% | 37% |
| SEQ ID NO: 088 | 547-H12 | 5.6 | 1.10 | 92% | 81% |
| SEQ ID NO: 089 | 550-F11 | 12.4 | 1.23 | 58% | 23% |
| SEQ ID NO: 090 | 548-D08 | 19.5 | 1.23 | 97% | 62% |
| SEQ ID NO: 091 | 549-D02 | 8.9 | 1.27 | 47% | 36% |
| SEQ ID NO: 092 | 552-F02 | 12.3 | 1.23 | 60% | 40% |
| SEQ ID NO: 093 | 545-E04 | 16.3 | 1.23 | 48% | 17% |
| SEQ ID NO: 094 | 545-E05 | 10.3 | 1.27 | 70% | 32% |
| SEQ ID NO: 095 | 547-H03 | 16.2 | 1.23 | 109% | 53% |
| SEQ ID NO: 096 | 552-G09 | 9.7 | 1.27 | 98% | 68% |
| SEQ ID NO: 097 | 550-A08 | 8.4 | 1.27 | 52% | 51% |
| SEQ ID NO: 098 | 550-G07 | 6.2 | 1.27 | 63% | 36% |
| SEQ ID NO: 099 | 551-A05 | 4.0 | 1.30 | 68% | 42% |
| SEQ ID NO: 100 | 548-C10 | 8.4 | 1.20 | 69% | 57% |
| SEQ ID NO: 101 | 465-C10 | 3.0 | 1.27 | 95% | 71% |
| CLASS V | | | | | |
| SEQ ID NO: 365 | 545-C02 | 26.3 | 1.33 | 54% | 31% |
| SEQ ID NO: 366 | 546-E02 | 10.4 | 1.33 | 74% | 54% |
| SEQ ID NO: 367 | 545-C11 | 7.7 | 1.30 | 77% | 50% |
| SEQ ID NO: 368 | 549-G01 | 7.0 | 1.27 | 62% | 18% |
| SEQ ID NO: 369 | 548-F07 | 27.5 | 2.43 | 54% | 37% |
| SEQ ID NO: 370 | 551-H10 | 13.3 | 1.87 | 88% | 49% |
| CLASS VI | | | | | |
| SEQ ID NO: 371 | 443-H10 | 3.4 | 1.40 | 124% | 143% |
| SEQ ID NO: 372 | 557-A12 | 4.6 | 1.37 | 87% | 62% |
| SEQ ID NO: 373 | 465-A03 | 4.0 | 1.30 | 33% | 17% |
| SEQ ID NO: 374 | 446-E12 | 3.3 | 1.37 | 73% | 83% |

TABLE 7-continued

| SEQ ID NO: | Isolate | Protein ELISA | WC ELISA | HGF 100 ng/mL | HGF 500 ng/mL |
|---|---|---|---|---|---|
| SEQ ID NO: 374 | | | | | |
| SEQ ID NO: 375 | 445-E06 | 4.3 | 1.33 | 83% | 73% |
| SEQ ID NO: 376 | 452-A03 | 3.0 | 1.30 | 140% | 112% |
| SEQ ID NO: 377 | 465-C06 | 6.4 | 1.23 | 184% | 104% |
| SEQ ID NO: 378 | 441-H01 | 3.6 | 1.40 | 91% | 69% |
| SEQ ID NO: 379 | 443-D04 | 3.2 | 1.43 | 69% | 73% |
| SEQ ID NO: 380 | 445-G12 | 4.0 | 1.37 | 85% | 52% |
| SEQ ID NO: 381 | 442-E03 | 3.9 | 1.43 | 130% | 81% |
| SEQ ID NO: 382 | 453-A05 | 4.5 | 1.33 | 51% | 28% |
| SEQ ID NO: 383 | 445-E07 | 3.1 | 1.37 | 82% | 64% |
| SEQ ID NO: 384 | 451-B12 | 3.1 | 1.37 | 61% | 27% |
| SEQ ID NO: 385 | 465-B07 | 4.8 | 1.27 | 111% | 79% |
| SEQ ID NO: 386 | 451-C06 | 3.0 | 1.37 | 108% | 86% |
| SEQ ID NO: 387 | 445-E11 | 3.7 | 1.43 | 69% | 79% |
| CLASS VIII | | | | | |
| SEQ ID NO: 390 | 546-G02 | 16.1 | 1.27 | 32% | 19% |
| SEQ ID NO: 391 | 333-C03 | 12.4 | 1.37 | 52% | 43% |
| SEQ ID NO: 392 | 549-G05 | 23.7 | 1.47 | 28% | 21% |
| SEQ ID NO: 393 | 546-B01 | 8.4 | 1.20 | 95% | 77% |
| SEQ ID NO: 394 | 551-D02 | 13.4 | 1.37 | 91% | 70% |
| SEQ ID NO: 395 | 334-F05 | 13.5 | 1.40 | 58% | 29% |
| SEQ ID NO: 396 | 330-G02 | 7.4 | 1.30 | 37% | 31% |
| SEQ ID NO: 397 | 316-F08 | 7.0 | 1.30 | 72% | 38% |
| SEQ ID NO: 398 | 332-H09 | 6.2 | 1.30 | 50% | 43% |
| SEQ ID NO: 399 | 545-H12 | 11.3 | 1.30 | 74% | 60% |
| SEQ ID NO: 400 | 548-G05 | 6.1 | 1.30 | 110% | 47% |
| SEQ ID NO: 401 | 547-C09 | 4.3 | 1.23 | 50% | 32% |
| SEQ ID NO: 402 | 545-F04 | 5.2 | 1.17 | 143% | 114% |
| SEQ ID NO: 403 | 552-F06 | 11.1 | 1.23 | 82% | 32% |
| SEQ ID NO: 404 | 531-E11 | 3.4 | 1.30 | 61% | 33% |
| CLASS XI | | | | | |
| SEQ ID NO: 449 | 525-A07 | 7.0 | 1.17 | 93% | 88% |
| SEQ ID NO: 450 | 528-F05 | 4.3 | 1.10 | 84% | 81% |
| SEQ ID NO: 451 | 524-E09 | 8.2 | 1.33 | 100% | 93% |
| SEQ ID NO: 452 | 96-H12 | 35.3 | 1.37 | 88% | 64% |
| SEQ ID NO: 453 | 118-A08 | 11.3 | 1.30 | 85% | 74% |
| SEQ ID NO: 454 | 94-E08 | 8.9 | 1.23 | 102% | 74% |
| SEQ ID NO: 455 | 119-F06 | 8.0 | 1.33 | 4% | 27% |
| SEQ ID NO: 456 | 95-A11 | 7.0 | 1.30 | 109% | 108% |
| SEQ ID NO: 457 | 94-H04 | 7.0 | 1.37 | 150% | 101% |
| SEQ ID NO: 458 | 94-F07 | 6.1 | 1.20 | 106% | 104% |
| SEQ ID NO: 459 | 103-G08 | 5.7 | 1.33 | 140% | 95% |
| SEQ ID NO: 460 | 118-C07 | 5.6 | 1.27 | 100% | 84% |
| SEQ ID NO: 461 | 104-C09 | 5.0 | 1.30 | 64% | 50% |
| SEQ ID NO: 462 | 117-F08 | 4.5 | 1.27 | 102% | 270% |
| SEQ ID NO: 463 | 76-D09 | 4.4 | 1.23 | 79% | 87% |
| SEQ ID NO: 464 | 93-C08 | 4.4 | 1.37 | 101% | 96% |
| SEQ ID NO: 465 | 92-B05 | 4.3 | 1.20 | 94% | 94% |
| SEQ ID NO: 466 | 116-H02 | 4.0 | 1.23 | 84% | 72% |
| SEQ ID NO: 467 | 02-B08 | 3.9 | 1.30 | 84% | 96% |
| SEQ ID NO: 468 | 117-F03 | 3.8 | 1.40 | 104% | 93% |
| SEQ ID NO: 469 | 127-A07 | 3.8 | 1.20 | 101% | 107% |
| SEQ ID NO: 470 | 94-B08 | 3.8 | 1.20 | 111% | 121% |
| SEQ ID NO: 471 | 115-G02 | 3.7 | 1.27 | 59% | 0% |
| SEQ ID NO: 472 | 130-E10 | 3.7 | 1.80 | 100% | 92% |
| SEQ ID NO: 473 | 136-D01 | 3.7 | 1.23 | 85% | 149% |
| SEQ ID NO: 474 | 15-D02 | 3.6 | 1.23 | 97% | 118% |
| SEQ ID NO: 475 | 79-B02 | 3.5 | 1.30 | 102% | 86% |
| SEQ ID NO: 476 | 94-A06 | 3.5 | 1.17 | 84% | 96% |
| SEQ ID NO: 477 | 94-G02 | 3.5 | 1.30 | 108% | 76% |
| SEQ ID NO: 478 | 75-B12 | 3.4 | 1.23 | 95% | 108% |
| SEQ ID NO: 479 | 117-F04 | 3.3 | 1.37 | 93% | 91% |
| SEQ ID NO: 480 | 151-B08 | 3.3 | 1.23 | 102% | 368% |
| SEQ ID NO: 481 | 117-E09 | 3.3 | 1.37 | 109% | 102% |
| SEQ ID NO: 482 | 93-B10 | 3.1 | 1.20 | 0% | 0% |
| SEQ ID NO: 483 | 98-F05 | 3.1 | 1.23 | 88% | 57% |
| SEQ ID NO: 484 | 118-B12 | 3.1 | 1.30 | 98% | 112% |
| SEQ ID NO: 485 | 27-D10 | 3.0 | 1.17 | 111% | 131% |
| SEQ ID NO: 486 | 122-D07 | 3.0 | 1.63 | 102% | 92% |
| SEQ ID NO: 487 | 149-E06 | 3.0 | 1.80 | 80% | 86% |
| SEQ ID NO: 488 | 166-H04 | 3.0 | 1.27 | 77% | 85% |
| SEQ ID NO: 489 | 96-D06 | 3.0 | 1.37 | 154% | 151% |
| SEQ ID NO: 490 | 103-C04 | 3.0 | 1.40 | 73% | 86% |
| SEQ ID NO: 491 | 527-E08 | 3.2 | 1.23 | 98% | 95% |
| SEQ ID NO: 492 | 524-H02 | 3.2 | 1.53 | 26% | 25% |
| SEQ ID NO: 493 | 523-A04 | 5.5 | 1.30 | 133% | 143% |
| SEQ ID NO: 494 | 524-D07 | 3.9 | 1.23 | 105% | 104% |

TABLE 7-continued

| SEQ ID NO: | Isolate | Protein ELISA | WC ELISA | HGF 100 ng/mL | HGF 500 ng/mL |
|---|---|---|---|---|---|
| SEQ ID NO: 495 | 522-H03 | 4.5 | 1.17 | 107% | 94% |
| SEQ ID NO: 496 | 527-A10 | 3.8 | 1.30 | 84% | 78% |

Note:
Protein ELISAs were measured as fold over background (cMet-Fc vs. TRAIL-Fc)
Whole Cell ELISAs were measured as fold over background (3T3 cells expressing human cMet vs. non-expressing 3T3 cells)
HGF competition ELISA measured as a % of binding in the absence of HGF.

TABLE 8

Fluorescence polarization analysis of select peptides from first generation peptide library positive hits

| SEQ ID NO: | Isolate | Kd (human) | Kd (mouse) |
|---|---|---|---|
| CLASS I | | | |
| SEQ ID NO: 001 | 571-C05 | 0.20 | 3.50 |
| CLASS III | | | |
| SEQ ID NO: 048 | 325-H05 | 3.50 | NT |
| SEQ ID NO: 051 | 336-G04 | 3.20 | NT |
| SEQ ID NO: 052 | 334-G06 | 2.70 | NT |
| SEQ ID NO: 053 | 330-B07 | 2.90 | NT |
| SEQ ID NO: 055 | 331-G04 | 0.90 | 1.10 |
| SEQ ID NO: 056 | 548-F06 | 2.70 | NT |
| SEQ ID NO: 059 | 323-A11 | 4.30 | NT |
| SEQ ID NO: 061 | 329-D02 | 5.20 | NT |
| SEQ ID NO: 067 | 334-C08 | 1.65 | NT |
| SEQ ID NO: 068 | 333-C05 | 2.80 | NT |
| SEQ ID NO: 071 | 330-G09 | 1.85 | NT |
| SEQ ID NO: 072 | 331-F01 | 0.98 | NT |
| SEQ ID NO: 074 | 335-D11 | 3.30 | NT |
| SEQ ID NO: 078 | 331-G06 | 2.90 | NT |
| CLASS V | | | |
| SEQ ID NO: 369 | 548-F07 | 0.88 | NB |
| SEQ ID NO: 370 | 551-H10 | 0.22 | NB |
| CLASS VIII | | | |
| SEQ ID NO: 390 | 546-G02 | 1.50 | NT |
| SEQ ID NO: 391 | 333-C03 | 1.80 | NT |
| SEQ ID NO: 399 | 545-H12 | 1.15 | NB |
| CLASS XI | | | |
| SEQ ID NO: 449 | 525-A07 | 6.90 | NT |
| SEQ ID NO: 450 | 528-F05 | 2.70 | NT |
| SEQ ID NO: 451 | 524-E09 | 2.00 | NT |
| SEQ ID NO: 452 | 96-H12 | >2.00 | NT |
| SEQ ID NO: 453 | 118-A08 | >2.00 | NT |
| SEQ ID NO: 454 | 94-E08 | 0.93 | NT |
| SEQ ID NO: 456 | 95-A11 | 2.30 | NT |
| SEQ ID NO: 458 | 94-F07 | 3.75 | NT |
| SEQ ID NO: 459 | 103-G08 | >2.00 | NT |
| SEQ ID NO: 461 | 104-C09 | >2.00 | NT |
| SEQ ID NO: 462 | 117-F08 | >2.00 | NT |
| SEQ ID NO: 463 | 76-D09 | >2.00 | NT |
| SEQ ID NO: 464 | 93-C08 | >2.00 | NT |
| SEQ ID NO: 466 | 116-H02 | >2.00 | NT |
| SEQ ID NO: 467 | 02-B08 | >2.00 | NT |
| SEQ ID NO: 469 | 127-A07 | 2.40 | NT |
| SEQ ID NO: 472 | 130-E10 | 2.60 | 7.65 |
| SEQ ID NO: 475 | 79-B02 | 1.90 | NT |
| SEQ ID NO: 479 | 117-F04 | 1.70 | NT |
| SEQ ID NO: 492 | 524-H02 | 0.80 | NT |

Kd values are in μM. NB = no binding, NT = not tested

TABLE 9 cMet-binding heteromeric peptide complexes

| SEQ ID NO: | Isolate | CLASS |
|---|---|---|
| PAIR I | | |
| SEQ ID NO: 472 | 130-E10 | XI |
| SEQ ID NO: 370 | 551-H10 | V |
| PAIR II | | |
| SEQ ID NO: 369 | 548-F07 | V |
| SEQ ID NO: 370 | 551-H10 | V |
| PAIR III | | |
| SEQ ID NO: 370 | 551-H10 | V |
| SEQ ID NO: 399 | 545-H12 | VIII |

TABLE 10

Amino-acid sequence of Mature HSA from GenBank entry AAN17825

(SEQ ID NO: 603)
DAHKSEVAHR FKDLGEENFK ALVLIAFAQY LQQCPFEDHV

KLVNEVTEFA KTCVADESAE NCDKSLHTLF GDKLCTVATL

RETYGEMADC CAKQEPERNE CFLQHKDDNP NLPRLVRPEV

DVMCTAFHDN EETFLKKYLY EIARRHPYFY APELLFFAKR

YKAAFTECCQ AADKAACLLP KLDELRDEGK ASSAKQRLKC

ASLQKFGERA FKAWAVARLS QRFPKAEFAE VSKLVTDLTK

VHTECCHGDL LECADDRADL AKYICENQDS ISSKLKECCE

KPLLEKSHCI AEVENDEMPA DLPSLAADFV ESKDVCKNYA

EAKDVFLGMF LYEYARRHPD YSVVLLLRLA KTYKTTLEKC

CAAADPHECY AKVFDEFKPL VEEPQNLIKQ NCELFEQLGE

YKFQNALLVR YTKKVPQVST PTLVEVSRNL GKVGSKCCKH

PEAKRMPCAE DYLSVVLNQL CVLHEKTPVS DRVTKCCTES

LVNRRPCFSA LEVDETYVPK EFNAETFTFH ADICTLSEKE

RQIKKQTALV ELVKHKPKAT KEQLKAVMDD FAAFVEKCCK

ADDKETCFAE EGKKLVAASR AALGL

TABLE 11

Amino-acid Sequence of SEQ ID NO: 604::HSA::SEQ ID NO: 603

(SEQ ID NO: 605)
GSFFPCWRIDRFGYCHANAP GSGGSGG DAHKSEVAHR FKDLGEENFK

ALVLIAFAQY LQQCPFEDHV KLVNEVTEFA KTCVADESAE

NCDKSLHTLF GDKLCTVATL RETYGEMADC CAKQEPERNE

CFLQHKDDNP NLPRLVRPEV DVMCTAFHDN EETFLKKYLY

EIARRHPYFY APELLFFAKR YKAAFTECCQ AADKAACLLP

KLDELRDEGK ASSAKQRLKC ASLQKFGERA FKAWAVARLS

QRFPKAEFAE VSKLVTDLTK VHTECCHGDL LECADDRADL

AKYICENQDS ISSKLKECCE KPLLEKSHCI AEVENDEMPA

TABLE 11-continued

Amino-acid Sequence of SEQ ID NO: 604::HSA::SEQ ID NO: 603

DLPSLAADFV ESKDVCKNYA EAKDVFLGMF LYEYARRHPD

YSVVLLLRLA KTYKTTLEKC CAAADPHECY AKVFDEFKPL

VEEPQNLIKQ NCELFEQLGE YKFQNALLVR YTKKVPQVST

PTLVEVSRNL GKVGSKCCKH PEAKRMPCAE DYLSVVLNQL

CVLHEKTPVS DRVTKCCTES LVNRRPCFSA LEVDETYVPK

EFNAETFTFH ADICTLSEKE RQIKKQTALV ELVKHKPKAT

KEQLKAVMDD FAAFVEKCCK ADDKETCFAE EGKKLVAASR AALGL

GSGGEGGSG GSWIICWWDNCGSSAP

While this invention has been particularly shown and described with references to preferred embodiments thereof, it will be understood by those skilled in the art that various changes in form and details may be made therein without departing from the scope of the invention encompassed by the appended claims.

What is claimed is:

1. A polypeptide or multimeric polypeptide comprising the amino acid sequence: Gly-X1-Cys-X2-Cys-X3-Gly-Pro-Pro-X4-Phe-X5-Cys-X6-Cys-X7-X8-X9-X10-Pro (SEQ ID NO:534), wherein
X1 is Ser;
X2 is His, Tyr or Asn;
X3 is Ser or Gly;
X4 is any amino acid other than Cys;
X5 is Glu;
X6 is Trp;
X7 is Tyr;
X8 is Gly, Asp, Ala, Glu or Ser;
X9 is Thr or Ser; and
X10 is Glu or Asp.

2. The polypeptide or multimeric polypeptide according to claim 1, comprising the amino acid sequence of SEQ ID NO:405, 406, 408-411, 413-420, 422-436, or 438-447.

3. The polypeptide or multimeric polypeptide according to claim 1, comprising the amino acid sequence of SEQ ID NO:410.

4. The polypeptide or multimeric polypeptide according to claim 1, consisting of the amino acid sequence of SEQ ID NO:410.

* * * * *

UNITED STATES PATENT AND TRADEMARK OFFICE
CERTIFICATE OF CORRECTION

PATENT NO. : 8,044,175 B2  Page 1 of 1
APPLICATION NO. : 12/012011
DATED : October 25, 2011
INVENTOR(S) : Daniel T. Dransfield et al.

It is certified that error appears in the above-identified patent and that said Letters Patent is hereby corrected as shown below:

Title Page, Item (63) should read:

-- (63) Continuation of application No. 10/792,582,
filed on Mar. 3, 2004, now abandoned --.

Signed and Sealed this
Twenty-ninth Day of November, 2011

David J. Kappos
*Director of the United States Patent and Trademark Office*